US009708625B2

(12) United States Patent
Li et al.

(10) Patent No.: US 9,708,625 B2
(45) Date of Patent: Jul. 18, 2017

(54) METHODS OF CONTROLLING SEED SIZE IN PLANTS

(71) Applicant: Institute of Genetics and Developmental Biology Chinese Academy of Sciences, Beijing (CN)

(72) Inventors: Yunhai Li, Beijing (CN); Wenjuan Fang, Beijing (CN); Zhibiao Wang, Beijing (CN); Rongfeng Cui, Beijing (CN)

(73) Assignee: Institute of Genetics and Developmental Biology Chinese Academy of Sciences, Beijing (CN)

( * ) Notice: Subject to any disclaimer, the term of this patent is extended or adjusted under 35 U.S.C. 154(b) by 214 days.

(21) Appl. No.: 14/372,582

(22) PCT Filed: Jan. 15, 2013

(86) PCT No.: PCT/GB2013/050072
§ 371 (c)(1),
(2) Date: Jul. 16, 2014

(87) PCT Pub. No.: WO2013/108017
PCT Pub. Date: Jul. 25, 2013

(65) Prior Publication Data

US 2014/0366221 A1 Dec. 11, 2014

Related U.S. Application Data

(60) Provisional application No. 61/588,792, filed on Jan. 20, 2012.

(30) Foreign Application Priority Data

Feb. 9, 2012 (GB) .................................. 1202258.8

(51) Int. Cl.
*C12N 15/87* (2006.01)
*C12N 15/82* (2006.01)
*C12N 9/02* (2006.01)

(52) U.S. Cl.
CPC ....... *C12N 15/8261* (2013.01); *C12N 9/0071* (2013.01); *C12N 9/0077* (2013.01); *C12N 15/827* (2013.01)

(58) Field of Classification Search
None
See application file for complete search history.

(56) References Cited

U.S. PATENT DOCUMENTS

2003/0092014 A1* 5/2003 Coleman ............. C12N 9/0073 435/6.12

FOREIGN PATENT DOCUMENTS

| | | |
|---|---|---|
| KR | 100877729 | 1/2009 |
| WO | 02/099063 | 12/2002 |
| WO | 2009/047525 | 4/2009 |

OTHER PUBLICATIONS

International Search Report for PCT/GB2013/050072 mailed Jun. 26, 2013.

Adamski et al., "Local Maternal Control of Seed Size by Kluh/CYP78A5-Dependent Growth Signaling", Proceedings of the National Academy of Science of the United States of America, vol. 106. No. 47, Nov. 2009, pp. 20115-20120.

Fang et al., "Maternal Control of Seed Size by EOD3/CYP78A6 in Arabidopsis Thaliana", Plant Journal vol. 70, No. 6, Jun. 2012, pp. 929-939.

Zondlo et al., "CYP78AS Encodes a Cytochrome P450 That Marks the Shoot apical meristem boundary in Arabidopsis" The Plant Journal, vol. 19, No. 3, Aug. 1999, pp. 259-268.

Ito, Toshiro et al., "Overexpression of a Gene Encoding a Cytochrome P450, CYP78A9, Induces Large and Seedless Fruit in Arabidopsis", The Plant Cell, vol. 12, 1541-1550, Sep. 2000.

Ma, Meng et al., "Expression of TaCYP78A3, a gene encoding cytochrome P450 CYP78A3 protein in wheat (*Triticum aestivum* L.), affects seed size", The Plant Journal, (2015) 83, 312-325.

Ma, Meng et al., "TaCYP78A5 regulates seed size in wheat (*Triticum aestivum*)", Journal of Experimental Botany, vol. 27, No. 5 pp. 1397-1410, 2016.

Wang, Xiaobo et al., "Evolution and association analysis of GmCYP78A10 gene with seed size/weight and pod number in soybean", Mol Biol Rep (2015) 42:489-496.

Yang, Weibing et al., "Control of Rice Embryo Development, Shoot Apical Meristem Maintenance, and Grain Yield by a Novel Cytochrome P450", Molecular Plant, vol. 6, No. 6, pp. 1945-1960, Nov. 2013.

Zhang, Xiangqian et al., "Epigenetic Mutation of RAV6 Affects Leaf Angle and Seed Size in Rice", Plant Physiology, Nov. 2015, vol. 169, pp. 2118-2128.

Zhao, Boatian et al., Arabidopsis KLU homologue GmCYP78A72 regulates seed size in soybean, Plant Mol Biol (2016) 90:33-47.

* cited by examiner

*Primary Examiner* — Stuart F Baum

(74) *Attorney, Agent, or Firm* — McKee, Voorhees & Sease, PLC

(57) ABSTRACT

This invention relates to the identification of a regulator protein (termed CYP78A6, or EOD3) which controls the size of plant seeds and organs in *Arabidopsis* and other plants. Manipulation of CYP78A protein expression may useful, for example, in improving crop yield and increasing plant biomass.

9 Claims, 19 Drawing Sheets

A Col-0 *eod3-ko1*

LP+RP RP+LB2 LP+RP RP+LB2

B Col-0 *eod3-ko2*

LP+RP RP+LB2 LP+RP RP+LB2

C Col-0 *cyp78a9-ko1*

LP+RP RP+LBa1 LP+RP RP+LBa1

SEQUENCE LISTING

<160> NUMBER OF SEQ ID NOS: 131

<210> SEQ ID NO 1
<211> LENGTH: 1593
<212> TYPE: DNA
<213> ORGANISM: Arabidopsis thaliana

<400> SEQUENCE: 1
atggctacga aactcgaaag ctccttaatc tttgcccttt tgtccaaatg cagcgttcta 60
agccaaacca accttgcctt ctccctcctc gccgtcacaa tcatctggct cgccatatct 120
ctcttcttat ggacctatcc cggtggacct gcttggggga aatacctctt cggccggtta 180
atatccggtt catacaaaac cggaaacgtt attcccggtc caaaaggctt ccctttggtt 240
ggaagcatgt cactcatgtc aagcactcta gctcaccgac gaatcgctga tgcagctgag 300

```
aaattcggag ccaagaggct catggctttc agcttaggag agactcgcgt gatcgtcacg    360
tgcaatcccg acgtagcgaa agagattctg aatagcccgg tttttgctga tcgaccggtt    420
aaagaatcgg cttactcact gatgtttaac agagcaattg gttttgcacc acacggtgtt    480
tactggcgaa cgcttcgccg tatcgcttcg aaccatctct ttagtacaaa acaaatcaga    540
agagccgaga cgcaacgacg agtgatctca agccagatgg ttgagtttct tgaaaaacag    600
agtagtaacg aaccctgttt tgttcgtgag ttgcttaaaa cggcgtcgct taacaacatg    660
atgtgctctg tattcggaca agagtatgag cttgaaaaaa accatgttga gttacgtgaa    720
atggtcgaag aaggttatga tttgctcgga acgttgaatt ggactgatca ccttccttgg    780
ctatcggagt ttgatcctca aagactccgg tctagatgtt ccacactcgt accaaaggta    840
aaccggtttg tatcccggat tatatccgaa caccgtaatc aaaccggtga tttgcctcgt    900
gatttcgtcg acgttttgct ctccctccat ggttcagata aattatccga cccggacata    960
atcgccgttc tttgggagat gatattcaga ggaacagaca cagttgcggt cttaatcgag   1020
tggatcctcg ctaggatggt ccttcatcca gatatgcaat caacggtaca aaacgagctg   1080
gatcaagtag tcgggaaatc aagagcccta gatgaatctg acttggcttc acttccatat   1140
ctaacggctg tggtgaaaga agtattgagg cttcatcctc caggcccact tctatcatgg   1200
gcccgtttgg ccataacaga cacgatcgtt gatggtcgtc ttgttccggc agggaccaca   1260
gcaatggtga acatgtgggc cgtatcgcat gatccacacg tgtgggttga tcctttggag   1320
tttaaacctg agaggttcgt ggcaaaagaa ggtgaggtgg agttttcggt tcttgggtcg   1380
gatttgagac ttgcaccttt cgggtcgggt cgtcggattt gccccgggaa gaatcttggt   1440
tttactaccg ttatgttttg gacggcgatg atgttacatg agtttgaatg ggaccgtcc    1500
gatggtaacg gcgttgactt atctgagaaa ctgaggcttt cttgcgagat ggctaatcct   1560
cttcctgcta aattgcgccg taggcgcagt taa                                1593
```

<210> SEQ ID NO 2
<211> LENGTH: 1668
<212> TYPE: DNA
<213> ORGANISM: Arabidopsis thaliana

<400> SEQUENCE: 2

```
atggccacca agctcgacac cagtagctta cttttggccc tcttgtccaa atgtagcctc     60
cttactcaaa ccaatcttgc tctctctctc ctcgtagcct ccctagcttc tctcgctctt    120
tctctcttct tctggtctca tcccggagga cccgcatggg gaaagtactt cctccaccgc    180
cgccgtcaaa ccaccgtgat acccgggcca agaggcttac cttttgtcgg aagcatgtct    240
ctcatgtcaa acactctggc tcaccgttgc atagccgcaa ccgcagagaa atttagagcc    300
gaacggttaa tggcgtttag tttgggagaa actcgcgtga tcgtcacgtg caatcctgat    360
gtagctaaag agattctaaa cagtccggtt ttcgctgacc gcccggttaa ggaatcagct    420
tattccctca tgtttaaccg tgctatcggt ttcgctcctt acggcgttta ctggcgaacc    480
ttgagaaaaa tcgcgtctaa tcatcttttc agcccgaaac agattaaacg ttccgaaacg    540
cagagaagcg tgatcgcgaa tcaaatcgtg aagtgtctca caaaacagag taacaccaaa    600
ggtctctgtt tcgcacgtga cttgatcaaa acggcatcgc ttaataacat gatgtgctct    660
gttttcggaa aagaatacga gcttgaggaa gagcatgaag aagtgagtga gctacgtgaa    720
ttggtggaag aaggttatga tttactcggt acactgaatt ggaccgatca tctcccatgg    780
ctctctgaat ttgatcctca aagaatccgg tctagatgct ctaatctcgt cccaaaagta    840
```

```
aaccggtttg tgaaccggat tatctctgac caccgtgaac aaactcgtga ctcaccgagt    900
gacttcgttg acgtattgct ctctctcgat ggtcctgata aattatccga ccctgatatc    960
atcgccgttc tatgggaaat gatattcaga ggaactgaca cggtggctgt tttgatcgag   1020
tggattcttg ctaggatggt ccttcatcca gatattcaat cgacggttca caatgagctt   1080
gatcaaatcg tgggacgatc aagggctgtc gaagagtctg acgtggtgtc tctagtatat   1140
ctaacggctg tggtgaaaga agtcttgagg cttcacccgc caggcccact actctcatgg   1200
gcccgtttag caatcacaga cacgatcatc gacggtcgtc gtgttccggc ggggaccacc   1260
gcaatggtga acatgtgggc tattgcacac gatccacacg tgtgggagaa tccgttggag   1320
tttaaacccg aacgttttgt agccaaggaa ggtgaggttg agttctcggt tcttgggtct   1380
gatttgaggc ttgcaccgtt cgggtccggt cgtcgggttt gccccgggaa gaatcttggt   1440
ttgaccaccg tgacgttttg gactgcgacg cttttgcatg agtttgaatg gctgacgccg   1500
tccgatgaga agaccgttga cttgtccgag aaactgaggc tctcgtgtga gatggctaat   1560
cctcttgctg ctaaattacg ccccaggcgc agttttagtc aaaagaataa aataaagaac   1620
aaagaaagta aaggaaacaa aaaaaaagaa tcatacaaaa aatactaa                1668
```

<210> SEQ ID NO 3
<211> LENGTH: 1608
<212> TYPE: DNA
<213> ORGANISM: Arabidopsis thaliana

<400> SEQUENCE: 3

```
atgagaaccg aaatagaaag tttgtgggta tttgctcttg catcaaaatt caatatttac     60
atgcaacaac attttgcttc ccttctcgtc gccattgcta tcacttggtt taccataacc    120
atcgtatttt ggtctactcc gggtggaccg gcttggggaa aatacttctt cactcgccgg    180
tttatttctc tcgattacaa ccgaaaatac aagaatctca ttcccggtcc tagagggttt    240
ccacttgtgg gaagcatgag ccttaggtca agccacgtgg ctcatcagcg catagcgtct    300
gtggctgaga tgagtaacgc caagcggctc atggcgttta gcctcggtga tactaaggtg    360
gtggtgacgt gtcatcctgc cgtggcaaag gagatactaa acagttcggt ttttgctgac    420
cgaccggttg acgaaaccgc ttacggtttg atgtttaacc gagccatggg atttgctccc    480
aatggtactt attggcgtac gctgcgtcgg ttaggctcga accatctttt taacccgaag    540
caaatcaaac aatcggagga tcagagacgg gtgatagcga ctcagatggt gaatgcgttt    600
gcacgtaacc ctaaatccgc gtgtgcagtg cgtgatttgc tcaaaacagc gtcgttgtgt    660
aacatgatgg gtttggtttt cgggagagag tatgaattgg agtcaaataa caacttggaa    720
tctgaatgct taaagggttt ggttgaagaa gggtacgatc ttctaggtac gttaaattgg    780
accgaccatc ttccttggtt agccggttta gatttccaac aaatccggtt taggtgctcg    840
cagctcgtac cgaaagtaaa tctgttattg agccgtatca tacatgaaca acgtgctgcc    900
acgggtaact ttcttgacat gttactttct cttcaaggtt cagaaaaatt atcagaatcc    960
gacatggttg ctgttctttg ggaaatgata tttaggggaa cggacactgt tgcggttttg   1020
gtcgagtggg tgctagcgag gattgtgatg catcccaaag ttcaattaac ggtccacgat   1080
gagcttgacc gagtcgttgg cagatcaaga accgtggatg agtcagacct tccatcactc   1140
acgtatctaa cggctatgat caaagaagtg ttgaggctgc atccaccagg tccactgctt   1200
tcttgggcac gactgtctat aacagacact tccgtagatg gatatcacgt gccggctggg   1260
```

```
accaccgcga tggtcaacat gtgggctata gcacgtgacc cacacgtgtg ggaggatcct   1320

ttagagttta agcctgagag gttcgtggct aaagagggtg aagctgagtt ctctgttttc   1380

gggtcggatc tgaggttggc accgttcggg tcgggtaaga gggtttgccc tggaaagaat   1440

ttgggactta caacggtgtc gttttgggtt gcaacgctct tgcatgagtt tgagtggctt   1500

cctagcgtcg aagctaaccc tccagatctc tcggaggttt tgaggctctc gtgtgagatg   1560

gcttgtccac tcatcgttaa cgtaagctca aggcgtaaga taatgtaa                1608


<210> SEQ ID NO 4
<211> LENGTH: 1611
<212> TYPE: DNA
<213> ORGANISM: Arabidopsis thaliana

<400> SEQUENCE: 4

atggagttga tgaatttggc ttcaaaagaa acaagctatt ggatgattgc actgcctgcc     60

ggttttggat cccaaaacct acatgatgtt tccaccctag gctatctatt ccttgccgtc    120

gtttttctct ctatagtcac gtgggctctc gccggaggcg gtggtgtcgc ttggaagaac    180

ggccgtaacc ggttgggtcg tgtcgcgatc cctggtcctc gtggcatacc agtattcggc    240

agtcttttca ctctcagccg aggcttggct catcggacgt tagcagccat ggcttggagc    300

cgagccaaca ctgagattat ggcttttagc cttggttcaa cgccggttat cgtggcttct    360

gaaccaaaca tagctcgtga gattctgatg tcgcctcact tcgcggaccg gccggttaag    420

cagtctgcta agagcctcat gttcagccga gccataggtt tcgccccaaa cgggacttac    480

tggcgcatgt taagaaggat cgcatcgact cacctatttg ctcctcggcg tatcttagca    540

cacgaagctg ggcgccagct agactgcgct gaaatggtga aagctgtgtc agtggagcaa    600

aacggcgctg gatcagtcgt tttaaggaaa cacttacaac tagccgcctt gaacaacatc    660

atgggaagtg tttttgggag aagatacgat cctctggctc agaaagagga tcttgatgag    720

cttacatcaa tggttaggga agggttcgag cttttgggtg cttttaattg gtctgattat    780

cttccatggc tcggttattt ctacgactca attcgtttaa accaacgttg ctcagatctc    840

gtccctcgaa ttagaaccct cgtcaagaaa atcatcgacg aacatcgagt tagtaactct    900

gagaagaaaa gagacattgg agattttgtt gatgtcttat tgtctttaga cggtgatgag    960

aaacttcaag aagatgacat gatcgccgtt ttatgggaga tgatttttcg agggacagat   1020

acaacggcgt tattaacgga gtggaccatg gccgagctag tactgaaccc taacgtgcaa   1080

accaagttac gagacgagat tttaactgct gtgggcgacg gcgccgacgg agacgtggca   1140

gatgctgacc tggcaaaact cccgtaccta aacgcagtgg tgaaggaaac tctaaggctg   1200

catcctcctg gaccactgct ttcatgggct cgtctttcca cgtcagacgt ccagctcagc   1260

aatggcatgg tgattccaaa gggaactaca gcgatggtca acatgtgggc tataacccac   1320

gaccagactg tatggtccga cccgctaaag tttgacccgg agagattcac tgggaatgct   1380

gacatggata ttcgtggtgg ggatctaagg cttgcaccgt ttggagccgg taggagagtg   1440

tgtccgggga agaacatggg gctagctact gtgactcggt gggtggctga gttggtacga   1500

cggttcgagt ggggtcagga tcagaccgag ccagttgatc ttggtgaggt cttgaagctt   1560

tcttgtgaga tggagcatcc gttacgtgcc gttgtaacgg aaatatttta a            1611


<210> SEQ ID NO 5
<211> LENGTH: 1554
<212> TYPE: DNA
<213> ORGANISM: Arabidopsis thaliana
```

<400> SEQUENCE: 5

```
atgtctccgg aagcttacgt tctgttcttt aacagtttta acctcgtaac cttcgaagcc     60
tttgcttcag tctcacttat catagccaca gttgctttct tgctctcacc aggtgggctc    120
gcatgggcct ggaccgggtc atccaagagt cgggtttcga ttccaggacc atctggttct    180
ctttccgtct tctccggctc caatccccac cgtgttctcg ccgctcttgc taaacgcttc    240
aaggcctctc cgttgatggc gttctcagtt gggttttcgc gtttcgttat ctctagtgaa    300
ccggagacgg ctaaagagat tttgagcagc tctgcttttg ctgaccggcc ggttaaggag    360
tcagcttacg agcttttgtt tcaccgtgcc atgggattcg caccgtatgg tgagtattgg    420
aggaatctga ggagaatctc ctccactcat cttttcagtc caagaagaat cgcgagtttt    480
gagggtgtta gagttggcat cggtatgaag atggtcaaga agattaaaag ccttgttacg    540
tctgatgctt gtggtgaagt tgaagtgaaa aagatcgttc actttggttc tttgaataat    600
gtaatgacga cagtgtttgg tgaaagctac gattttgatg aagttaatgg aaaagggtgt    660
tttttggaga ggctggtgag tgaaggctac gagttgcttg ggatttttaa ctggagtgat    720
cacttttggt ttcttcgttg gtttgacttc caaggagtga ggaagaggtg tagagctttg    780
gtctctgaag tcaacacttt tgtcggcgga ataattgaga aacacaagat gaagaagggt    840
aataatctca atggagagga aaatgacttc gttgatgtct tgcttggctt gcaaaaggat    900
gaaaagttgt ctgattctga catgattgct gttctttggg aaatgatatt tagagggaca    960
gatacagttg cgattctagt ggaatgggtg cttgcaagaa tggttttgca tcaagacatc   1020
caagataaac tctacagaga gatagcttct gctacaagta acaatattag atccttgtct   1080
gattccgaca tcccaaaact gccgtacctt caagctattg tcaaagaaac cctaaggctc   1140
caccccccctg gtccacttct ctcttgggct cgtctcgcta tccatgacgt ccacgtaggt  1200
cctaaccttg tccctgctgg aaccatagct atggtcaaca tgtggtccat cacacacaac   1260
gctaaaatct ggaccgaccc tgaagcgttt atgcctgaaa ggttcattag tgaggatgtg   1320
agcatcatgg gctcggatct tagattggct ccattcggat ccggtcgtcg ggtttgtccc   1380
ggtaaagcaa tgggtctagc tactgttcat ctctggattg gtcaactaat tcagaatttt   1440
gaatgggtga agggttcttg tgatgttgag ctcgctgagg ttctgaagct gtctatggag   1500
atgaagaatc cgttgaagtg caaggctgtt ccaaggaatg ttggtttcgc ttga         1554
```

<210> SEQ ID NO 6
<211> LENGTH: 1614
<212> TYPE: DNA
<213> ORGANISM: Arabidopsis thaliana

<400> SEQUENCE: 6

```
atgactattg atatgtatct ttccttcgct tctcgttctg gatcttctcc atttccaagt     60
ctcgagcttt gtctcagcat tttcctcttc atctcccttt tcgttttctg gttgactcca    120
ggtggctttg cttgggcact ctacaaagct cgtttccata cccgacctga gtccaaaacc    180
ggacctgcca ttcccggccc gtctggtctc cccatctttg gcctcctctt ggcttttgtc    240
aacaacgcct taacacacag aatcctcgcc aatattgctg acacttgcaa agcaaaagct    300
ctcatggcgt tctccgtagg gtcaacccgg tttgttataa ccagcgaacc agagaccgcg    360
aaagagcttc taaacagctc tgcttttgca gaccggccag tgaaagagtc tgcttacgag    420
ctgctctttg atagagccat ggggtttgct cccctttggtg attactggag agagttgagg   480
```

```
agaatctctt ctacccatct cttcagccct aagaggatct tcagttctgg cgagtcccgc    540
cgaaaaatcg ggcaaaacat ggtaggagag atcaagaacg caatggagtg ttatggagaa    600
gtgcatataa aaaagatctt gcatttcgga tcactcaaca acgtgatgtc tagcgttttc    660
ggtaaaacat acaacttcaa cgaaggtatt gtctactcga aagagagcaa tgagttggag    720
catttggtgt ctgaaggcta tgagctgctc ggaatcttca actggagtga tcatttccct    780
ggaatgagat ggttagattt acaaggtgtg aggagaagat gtcgtagttt ggtcggtaga    840
gtgaatgtgt tcgtcggtaa gataatcaat gaccacaaat caaagaggtc acttcgtgat    900
aatcctgaag agagcactta tgatgatgac tttgtagatg tcttacttgg catgcacggc    960
aacagcaaac tttctgactc cgatatgatc gcagtccttt gggaaatgat tttagggga   1020
acagacacgg tggcgattct cttggaatgg atccttgcga ggatggttct tcaccctgac   1080
attcaagcca aggcgcaggc cgagatcgat tgtatcgtgg gtgactcggg acgtcaagtc   1140
acagactcag acctccccaa gctcccatac gttcgtgcca ttgtcaagga aaccctaagg   1200
atgcacccac ctggtcctct cctctcatgg gctcgtctct ccattcacga tactcagatc   1260
gggactcact ttatacccgc aggaaccact gcgatggtta acatgtgggc tataacccac   1320
gatgaaaagg tctggccgga agctcatgag tataaaccag agaggtttct tggtgcgcaa   1380
gaaagtaata acttccccat catgggatct gatctgaggc ttgctccctt cggtgctgga   1440
cgtagggtct gtcccggcaa gtcaatgggt ctagccaccg tggagctatg gctagctcag   1500
ttgctaggaa gctataagtg ggtctcatgt ggtgaagtgg atttgagtga gactttgaag   1560
ctatctttgg agatgaagaa cactcttgtc tgcaaggcaa tccctagggg ttaa         1614
```

<210> SEQ ID NO 7
<211> LENGTH: 1668
<212> TYPE: DNA
<213> ORGANISM: Oryza sativa

<400> SEQUENCE: 7

```
atggcaatgg ccaccgccac cgcctcctcc tgcgtcgacg ccacgtggtg ggcgtacgcc     60
ctcccggcgc tcctcggcgc cgacaccctc tgcgcccacc cggcgctgct cgccggcgcc    120
gtcctcctgg ccttcgccac cgccgcggtg ctcgcctggg ccgcgtcccc cggcgggccg    180
gcgtgggcgc acggccgcgg ccgcctcggc gcgacgccca tcgaggggcc ccgggggctc    240
cccgtgttcg gcagcatctt cgcgctctcc cggggcctcc cgcaccgcgc gctcgacgcg    300
atgtcgcgcg acgcggcggc gccacgggcg agggagctca tggcgttctc cgtcggggag    360
acgccggcgg tggtgtcgtc gtgcccggcg acggcgaggg aggtgctcgc gcacccgtcg    420
ttcgccgacc gcccgctgaa gcgctcggcg cgggagctgc tgttcgcgcg cgccatcggg    480
ttcgccccca gcggcgagta ctggcgcctc ctccgccgca tcgcctccac ccacctcttc    540
tcccctcgcc gcgtcgccgc gcacgagccg gggcgccagg ccgacgccac ggcgatgctg    600
tccgccatgg ccgccgagca gtccgccacc ggcgccgtcg tgctccgccc ccacctccag    660
gccgccgcgc tcaacaacat catgggcagc gtgttcggcc ggcgctacga cgtctcctcc    720
tcctccggcg ccgccgccga cgaggccgag cagctcaaga gcatggtgcg cgaggggttc    780
gagctcctcg gcgcgttcaa ctggtccgac cacctcccat ggctcgccca cctctacgac    840
cccaaccacg tcgcccgccg ctgcgccgcg ctcgtccccc gcgtccaggc gttcgtccgc    900
ggcgtcatcc gcgaccaccg cctccgccgc gactcctcct ccaccgccgc cgacaatgcc    960
gacttcgtcg acgtcctcct ctccctcgag gcccacgaga acctcgccga ggacgacatg   1020
```

```
gtcgccgtcc tctgggagat gatatttcgt gggacggaca cgacggcgtt ggtgacggag   1080

tggtgcatgg cggaggtggt gaggaacccg gcggtgcagg cgaggctgag ggcggaggtg   1140

gacgcggcgg tgggcggcga cgggtgtccc agcgacggcg acgtggcgcg gatgccgtac   1200

ctgcaggcgg tggtgaagga gacgctgagg gcgcacccgc cggggccgct gctgagctgg   1260

gcgcggctgg ccaccgccga cgtggggctc gccaacggca tggtggtgcc ggcgggcacg   1320

acggcgatgg tgaacatgtg ggccatcacc cacgacggcg aggtgtgggc cgacccggag   1380

gcgttcgcgc cggagcggtt catcccgtcg gagggcggcg ccgacgtcga cgtccgcgac   1440

ggcgacctcc gcctggcgcc gttcggcgcc gggcgccgcg tctgccccgg caagaacctc   1500

ggcctcgcca ccgtctccct ctgggtcgcc cgcctcgtcc acgccttcga ctggttcctc   1560

cccgacggct cgccgccggt gtccctcgac gaggtcctca agctctccct cgagatgaag   1620

acccctctcg ccgccgccgc caccccccgc cgccgccgcg ccgcctga                1668
```

```
<210> SEQ ID NO 8
<211> LENGTH: 2133
<212> TYPE: DNA
<213> ORGANISM: Zea mays

<400> SEQUENCE: 8

acccattcac tcactcatct caaggcctag gtagcaccgt agcagctact agaagcagct     60

agccagaaca actcgtccat ggcgatggcc tccgcggctt gctcatgcac ggacggcacg    120

tggtgggtgt acgcgctccc ggcgctgctc ggctccgaca ccctgtgcgc ccacccggcc    180

ctcctggctg gcctgatctt tctggccacc gtctcggtgg ctctgctggc gtgggccacg    240

tcgccgggcg gtccggcgtg gacgaacggc cgcggccgcc tcggcgtcac tcctatcgtg    300

ggaccccgtg gtctgcccgt gttcggcagc atcttcgcgc tgtcccgcgg gctgccgcac    360

cgcgccctcg ccgagatggc ccgcgccgca gggccccggg ccaaggagct catggcgttc    420

tccgtcggtg acacgcccgc ggtcgtgtcg tcctgcccgg ccacggcacg tgaggtgctc    480

gcgcacccgt cattcgccga ccgccctgtg aagcggtcgg cccgggagct catgttcgcg    540

cgtgccatcg ggttcgcgcc caacggcgag tactggcgcc gcctccgccg cgtcgcgtcc    600

acgcacctct tttccccgcg ccgggtcgcc tcgcacgagc cgggacgcca aggtgacgcg    660

gaggccatgc tccgctccat cgccgccgag cagtcggcct ctggcgccgt cgccctccgc    720

ccgcacctcc aggccgccgc tctcaacaac atcatgggca gcgtcttcgg cacgcggtac    780

gacgtcacat caggcgccgg cgccgcggag gccgagcatc tcaagagcat ggtgcgcgag    840

gggttcgagc tcctcggcgc cttcaactgg tccgaccacc tcccctggct cgcccacctg    900

tacgacccaa gcaacgtcac ccgccggtgc gccgcgctcg tgccgcgcgt ccagaccttc    960

gtccgtggcg tcatcgacga gcaccggcgc cgccgccaaa actccgccgc cctcaacgac   1020

aatgctgact tcgtcgacgt gctcctctcc ctcgagggtg acgagaagct cggcgacgac   1080

gacatggtcg ccatcctctg ggagatggtc ttccgcggta cggacacgac gacgcttctg   1140

accgagtggt gcatggcgga gctggtgcgc cacccggcgg tgcaggcgag ggtgcgcgcc   1200

gaggtcgacg cggctgtcgg tgccggaggt tgccccaccg acgccgacgt ggcgcgcatg   1260

ccgtacctgc aggcggttgt gaaggagacg ctgcgcgccc acccgcctgg cccgctgctg   1320

agctgggctc gcctcgccac cgccgacgtg ccactctgca acggcatggt ggtcccggct   1380

ggcaccacgg cgatggtgaa tatgtgggcc ataacccacg atgccgccgt gtgggccgac   1440
```

```
ccggacgcgt tcgcgccgga gcggttcctg ccctccgggg gcggcgccga cgtggacgtc   1500

cgcggcgtcg acctccgcct ggccccgttc ggcgccgggc gtcgcgtctg ccccggcaag   1560

aacctgggcc tcaccaccgt gggcctctgg gttgcccgcc tcgtgcacgc cttccagtgg   1620

gccctgcctg acggcgcggc ggccgtttgc ctcgacgagg tcctcaagct ctccctggag   1680

atgaagacgc cgctcgtcgc cgcagccatc cccgcaccg cctgatccgt cctgccgccg    1740

acgcgtcacg tcacgcgttg tttgcatgga tgatggtatc tttgtctgtc tgtgtggtct   1800

tcgctaaagt ttgcttcttc tcgatcgtcg gttcgttcgt gcctccacct tagcctaggg   1860

tttggtttct tgcaaggtag tgagtgtgtc ttagtctcac catcaccggg gctccaattt   1920

tggaaagctg cgtgttagga gttaacccct agacatgttt gcgtcttgat cgccaccacc   1980

catcagtatc agcgcagaaa ctacatatag atcagtgttt gtcgaccagt catggaagtc   2040

gtgtgctctc aagtctgatg tattatatac atatatatgt attgtaatgt gattatcaag   2100

aaccgtgcta tttacaaaaa aaaaaaaaaa aaa                                2133
```

<210> SEQ ID NO 9
<211> LENGTH: 1799
<212> TYPE: DNA
<213> ORGANISM: Phalaenopsis sp. SM9108

<400> SEQUENCE: 9

```
cggcaccact cctctctgtt cctctaatat ctggttaaaa atgacaatgt catccatgga     60

ttcatcttca ataatattaa cttatctctc cccaacactt tctccagcta tcgccgcttc    120

tatcatcatc atctcagctc tactactctt tcccggcggt ctggcgtggg ccctttccct    180

caagcgccca acattctccg ggcccaccgg aattgttttt gctctcgcca gctctgctgc    240

tcataagtca cttgccgccc tagctcgctc cgttcgacgc cctccgcctc atggctttct    300

cggtcggcct cactcgcttc atcgtttcaa gccacccgaa aaccgcaaaa gagattcttt    360

caagcccagc cttcgctgat cggcccatta aagaatcagc atacgaactt ctgtttaatc    420

gcgctatggg ttttgcccca tttggggatt actggagaaa cctgagaaag atttcgtcca    480

catatctttt cagtccgcgg cgagtttcat cgttcgagaa gcaacggagt gagattggcg    540

aaggaatggt gcgggatatg aaaagaatga tggagagaaa tggagttgta gaagtgagga    600

gaatgttgca ctacgggtct ttgaataaca tcatgttgac tgtttttggg aaaaagtttg    660

attttgcaaa ggatgagggg ttggagcttg agttgatcct taaggaagga tatgagttac    720

ttgggatctt caactggggt gatcatttgc ctcttttggg atggttagat ttgcaaggtg    780

tgaggagaag atgcagaaca cttgtggcta aggtcaatgt atttgtgaag aagatcatag    840

acgagcataa gaggagagcc aacggcgtag ggattgatga gggtgaaggt gaagattttg    900

ttgatgtgct tcttggtttg gaggagaaag atagactctc agaatctgat atggtcgcag    960

ttctttggga aatgatcttt agaggaactg atactgttgc catcctattg gaatggacgt   1020

tggctagaat ggttcttcat cctgatattc aatcgaaggc acaagttgag attgattctg   1080

tcgttgactc ttcaaggcca gtattggatt ctgatatcca acgacttcct tatctccaat   1140

ctatagtaaa agaaaccctt cgaatgcatc ctcctgggcc tctattgtca tgggctcgcc   1200

tagctatcca tgacgttcct gttgatggtc acatgattcc tgctgggacg actgcaatgg   1260

tgaacatgtg ggcaataaca catgacgaat gcaactgggc tgagcctaac aaattcaatc   1320

ctgatcgatt catcgatgaa gatgtcaata ttcttggttc cgatttaagg ttggcaccct   1380

ttggctccgg taaaagagtt tgccctggca aaacgatggc attggctgca gttcatcttt   1440
```

```
ggttggctca gttgctgaaa agcttcaaat tgcttccttc gagaaatggt gtagatttgt   1500

ctgagtgcct aaagatgtct ctcgagatga agaatccttt ggtatgtgtg gctgttccaa   1560

ggttcgagta gtcctgctaa gatgacgtct agttataaga aatttgttct ttgcaaattg   1620

tggccaacat aaatgatttc gtaagctagc aacttatgga taatgtcggt acatgttcgt   1680

ttaaagtgtc aactttgttt ggttgaattt taaaatttga cattgtaata aagattctct   1740

ggttctatgt aaatattgta attcagctta taatataaga aagaaatgaa tttgttgct    1799
```

<210> SEQ ID NO 10
<211> LENGTH: 1611
<212> TYPE: DNA
<213> ORGANISM: Glycine max

<400> SEQUENCE: 10

```
aagcactatc cctcccacca tgacaagcca cattgacgac aacctctgga taatagccct     60

gacctcgaaa tgcacccaag aaaaccttgc atgggtcctt ttgatcatgg gctcactctg    120

gttaaccatg actttctatt actggtcaca ccccggtggt cctgcctggg gcaagtacta    180

cacctactct cccccccttt caatcattcc cggtcccaaa ggcttccctc ttattggaag    240

catgggcctc atgacttccc tggcccatca ccgtatcgca gccgcggccg ccacatgcag    300

agccaagcgc ctcatggcct ttagtctcgg cgacacacgt gtcatcgtca cgtgccaccc    360

cgacgtggcc aaggagattc tcaacagctc cgtcttcgcc gatcgtcccg tcaaagaatc    420

cgcatacagc ctcatgttta accgcgccat cggcttcgcc tcttacggag tttactggcg    480

aagcctcagg agaatcgcct ctaatcacct cttctgcccc cgccagataa aagcctctga    540

gctccaacgc tctcaaatcg ccgcccaaat ggttcacatc ctaaataaca agcgccaccg    600

cagcttacgt gttcgccaag tgctgaaaaa ggcttcgctc agtaacatga tgtgctccgt    660

gtttggacaa gagtataagc tgcacgaccc aaacagcgga atggaagacc ttggaatatt    720

agtggaccaa ggttatgacc tgttgggcct gtttaattgg gccgaccacc ttccttttct    780

tgcacatttc gacgcccaaa atatccggtt caggtgctcc aacctcgtcc ccatggtgaa    840

ccgtttcgtc ggcacaatca tcgctgaaca ccgagctagt aaaaccgaaa ccaatcgtga    900

ttttgttgac gtcttgctct ctctcccgga acctgatcaa ttatcagact ccgacatgat    960

cgctgtactt tgggaaatga tattcagagg aacggacacg gtagcggttt tgatagagtg   1020

gatactcgcg aggatggcgc ttcatcctca tgtgcagtcc aaagttcaag aggagctaga   1080

tgcagttgtc ggaaaagcac gcgccgtcgc agaggatgac gtggcagtga tgacgtacct   1140

accagcggtg gtgaaggagg tgctgcggct gcacccgccg ggcccacttc tatcatgggc   1200

ccgcttgtcc atcaatgata cgaccattga tgggtatcac gtacctgcgg ggaccactgc   1260

tatggtcaac acgtgggcta tttgcaggga cccacacgtg tggaaggacc cactcgaatt   1320

tatgcccgag aggtttgtca ctgcgggtgg agatgccgaa ttttcgatac tcgggtcgga   1380

tccaagactt gctccatttg ggtcgggtag gagagcgtgc ccagggaaga ctcttggatg   1440

ggctacggtg aacttttggg tggcgtcgct cttgcatgag ttcgaatggg taccgtctga   1500

tgagaagggt gttgatctga cggaggtgct gaagctctct agtgaaatgg ctaaccctct   1560

caccgtcaaa gtgcgcccca ggcgtggata agagagagtt gaagctttta t             1611
```

<210> SEQ ID NO 11
<211> LENGTH: 1885
<212> TYPE: DNA

<213> ORGANISM: Glycine max

<400> SEQUENCE: 11

```
ggcactcact gaagcactat ccctcccacc atgacaagcc acattgacga caacctctgg     60
ataatagccc tgacctcgaa atgcacccaa gaaaaccttg catgggtcct tttgatcatg    120
ggctcactct ggttaaccat gactttctat tactggtcac accccggtgg tcctgcctgg    180
ggcaagtact acacctactc tcccccccctt tcaatcattc ccggtcccaa aggcttccct    240
cttattggaa gcatgggcct catgatttcc ctggcccatc accgtatcgc agccgcggcc    300
gccacatgca gagccaagcg cctcatggcc tttagtctcg gcgacacacg tgtcatcgtc    360
acgtgccacc ccgacgtggc caaggagatt ctcaacagct ccgtcttcgc cgatcgtccc    420
gtcaaagaat ccgcatacag cctcatgttt aaccgcgcca tcggcttcgc ctcttacgga    480
gtttactggc gaagcctcag gagaatcgcc tctaatcact tcttctgccc ccgccagata    540
aaagcctctg agctccaacg ctctcaaatc gccgcccaaa tggttcacat cctaaataac    600
aagcgccacc gcagcttacg tgttcgccaa gtgctgaaaa aggcttcgct cagtaacatg    660
atgtgctccg tgtttggaca agagtataag ctgcacgacc caaacagcgg aatggaagac    720
cttggaatat tagtggacca aggttatgac ctgttgggcc tgtttaattg ggccgaccac    780
cttccttttc ttgcacattt cgacgcccaa aatatccggt tcaggtgctc caacctcgtc    840
cccatggtga accgtttcgt cggcacaatc atcgctgaac accgagctag taaaaccgaa    900
accaatcgtg attttgttga cgtcttgctc tctctcccgg aacctgatca attatcagac    960
tccgacatga tcgctgtact ttgggaaatg atattcagag gaacggacac ggtagcggtt   1020
ttgatagagt ggatactcgc gaggatggcg cttcatcctc atgtgcagtc caaagttcaa   1080
gaggagctag atgcagttgt cggaaaagca cgcgccgtcg cagaggatga cgtggcagtg   1140
atgacgtacc taccagcggt ggtgaaggag gtgctgcggc tgcacccgcc gggcccactt   1200
ctatcatggg cccgcttgtc catcaatgat acgaccattg atgggtatca cgtacctgcg   1260
gggaccactg ctatggtcaa catgtgggct atttgcaggg acccacacgt gtggaaggac   1320
ccactcgaat ttatgcccga gaggtttgtc actgcgggtg gagatgccga attttcgata   1380
ctcgggtcgg atccaagact tgctccattt gggtcgggta ggagagcgtg cccagggaag   1440
actcttggat gggctacggt gaacttttgg gtggcgtcgc tcttgcatga gttcgaatgg   1500
gtaccgtctg atgagaaggg tgttgatctg acggaggtgc tgaagctctc tagtgaaatg   1560
gctaaccctc tcaccgtcaa agtgcgcccc aggcgtggat aagagagagt tgaagctttt   1620
attaaaaagg gaacaagaaa aaaagaaaat gaaatatata gaaataaaac agacaagaaa   1680
gtaaagtaaa gattatgcat gttgctgcat gtaggttggt ggttggtggc aggtgtgcag   1740
ccacacaatg gtaatatggt ggaagggatg ggttaggctc tcttttttttt ttttagtggt   1800
caagtattaa gtcttctcag cttgtcttct tattacaaaa aaagtactgt tgccagtgta   1860
aataaactta atacgttttt agttg                                        1885
```

<210> SEQ ID NO 12
<211> LENGTH: 1686
<212> TYPE: DNA
<213> ORGANISM: Glycine max

<400> SEQUENCE: 12

```
atgtcaaccc acattgaaag cctgtgggtg ttggccttag cctcaaaatg cattcaagag     60
aacattgcat ggtcactctt gatcatcatg gtcactctct ggctcaccat gaccttcttc    120
```

```
tactggtctc accctggtgg tcctgcttgg ggcaaatact actactttaa ttactggaaa    180
aaaaccacct caaccaacac aaacatcaac cttaaaatga ttatccctgg tcctagaggc    240
taccctttca ttgggagtat gagtctcatg acatccctcg cacaccaccg tattgctgcg    300
gcgggggaag catgcaacgc caccaggctc atggcttttt ccatgggtga cacacgcgcc    360
atagtaacgt gcaaccccga tgtcgctaaa gagattctca atagttccac ttttgctgat    420
cgtcccataa aggaatcagc ttacagcctc atgttcaacc gcgccatcgg cttcgcccct    480
tacggcgtct actggcgtac cctccgccgc atcgccgcca cgcacctctt ctgccccaaa    540
caaatcaaag cctccgagct ccagcgcgct gaaatcgccg cccaaatgac aaactcattc    600
cgaaatcacc gttgcagcgg cggtttcgga atccgcagcg tgctcaagag agcgtcactg    660
aacaacatga tgtggtcggt gtttggacaa aagtacaacc ttgacgagat aaacaccgca    720
atggacgagc tatccatgtt ggtggaacaa ggctatgact tgttgggcac ccttaattgg    780
ggagaccata tccctttcct gaaagacttt gacctacaga aaatccggtt cacctgctcc    840
aaattagtcc ctcaagtgaa ccggttcgtt ggttcaatca tcgccgacca ccaggccgac    900
acaacccaaa ccaaccgcga tttcgttcat gttttgctct ctctccaagg tcccgataaa    960
ttgtctcact ccgacatgat tgctgtcctc tgggaaatga tatttagggg gaccgacacg   1020
gtggcggttt tgattgagtg gatactggcg aggatggtgc ttcatccgga ggtgcaaagg   1080
aaggtacaag aggagttgga cgcggtggtt aggggtggcg ctttgacgga ggaggtcgtg   1140
gcggcgacgg cgtatcttgc ggcggtggtg aaagaggttc tgaggctgca cccgccgggc   1200
ccgcttctct cgtgggcccg cttggccatc actgatacga ccattgatgg gtatcacgtg   1260
cctgcgggga ccaccgctat ggttaatatg tgggccatag caagggaccc ggaggtgtgg   1320
ctggacccac ttgagttcaa gcccgagagg ttcatgggtc tggaaaacga gttttctgtt   1380
ttcgggtcgg atctgagact cgctccattc ggttcgggtc ggagaacatg ccccgggaag   1440
actttgggtt tgagcaccgt aaccttctgg gtggcttggc ttttgcatga gtttgaatgg   1500
ctaccgtctg atgaagccaa ggttgatcta acggaggtgc tgaggctctc gtgtgaaatg   1560
gctaacccac tcattgttaa agttcgccct aggcatggat taagcactta atgataatat   1620
aattaagcct atctacgtta ttaacttgaa atgttttaat gggaaggaaa aaaaaaaaaa   1680
agagag                                                              1686
```

<210> SEQ ID NO 13
<211> LENGTH: 2100
<212> TYPE: DNA
<213> ORGANISM: Oryza sativa

<400> SEQUENCE: 13

```
aactcaaact gcacttccct tttcagctct tctccaacct caatttcacc ccatttttcc     60
atatcctctc tgcacacgta cgtacaggta aacgtgcctg atcatggaca tggactcgtc    120
gccgtcgaca caggactgtg gcggctggct gctgtacgtc tccctcgctg ccaaatgcgg    180
cggcgaccct tgccgcgtcg tcggcttcgt cgccgttgcc gtcgtcgcct tcgccgtcac    240
gtcgctcctg cactggctgt cgcccggtgg cccggcgtgg gggaggtatt ggtggaacag    300
gaggggtggt ctgggcattg ctgccgccat tcctgggccc cgtgggttgc ccgtgctcgg    360
cagcatgtcg ctcatggcgg gactcgcgca ccggaagctc gccgcggcgg cgggggggctc    420
gccggcgagg cggcgcctca tggcgctgtc tctcggggag acacgggtgg tggtcaccgc    480
```

```
cgaccccggc gtcgcgcggg agctcctcgc cagcgcggcg ttcgccgacc ggccggtgaa    540

ggagtccgcg tacgggatgc tgttccaccg cgccatcggg ttcgcgccct acggcacgta    600

ctggcgcgcg ctccgccgcg tcgcgtccac gcacctcttc tcgccgaggc aggtgtccgc    660

ctccgccgcg cagcgcgcgg tgatcgcgcg ccagatggtg gaggccatga ggtccgccgc    720

cgccgccgcc gccggtggcg gcgtggcggc gaggccgttc ctgaagcgcg cgtcgctgca    780

caacgtgatg tggtcggtgt tcgggaggaa gtacgagctg gcggcgccgg agagcgagga    840

gacggcggag ctgaggagca tggtggacga aggctacgac ctcctcggcc agctcaactg    900

gtccgaccac ctcccatggc tcgcaccctt tgacctcaag aagacgcggt caaggtgctc    960

gtcccttgtc ccccgcgtca accgcttcgt cacccgcatc atcgacgagc accgtgctcg   1020

cctcagcctc gccgtcgacg ccgccgtcga cttcaccgac gtccttctct ccctccacgg   1080

cggcgacaag ctctccgacg ccgacatggt cgccgtcctc tgggagatga tctttcgagg   1140

gacggacacg gtggcggtcc tgatcgagtg ggtggcggcg aggctggtgc tgcaccagga   1200

cgtgcaggcc agggtccatg acgagctgga ccgagtggtc gggtcggacc gggcagtgac   1260

cgagtcggac gcgtccaagc tggtctacct ccaagcggtg atcaaagagg tcctgcgcct   1320

ccacccgccg ggcccactgc tctcgtgggc acgcctcgcc acgtcggatg tacacgtcgg   1380

cgggttcctc ataccctctg ggaccaccgc catggtgaac atgtgggcca taacccatga   1440

ccctgccgtt tggcccgacc cgaacgagtt caaaccagag aggttcgtcg cagggccctc   1500

gtcggaccag gccacggagt ttccgataat ggggtcggat ctcaggctcg cgccgttcgg   1560

gtcaggaagg cgaagctgcc ccggcaagtc gctcgccatc gccactgtcg gattctgggt   1620

tgccacgttg ctacacgagt tcgattggct tcccttgtca gataagtcgc gcggcgtcga   1680

tctgtcggag gtgctgaagc tgtcgtgcga gatggcaacc ccgctggagg caaggctaag   1740

gccgcgacgc aaggtgtgat gacgtgtcac caccgtcacg tgggactaag acgaggagag   1800

ggaagccgac ttccacttcc ttctagtgct tgttgagatg tgtaaatgtc cctaaatgta   1860

aagtgttacg ctttgagtag aaatgcccct acgttgtagt gcgtagtatt gtacacttgt   1920

agtatgtaat gcttgtattt ttgtgtgttt tgcacgtcct aagtagtgga gtagtagctg   1980

ataatagtta gttaattact ctgctattta gtcatagtta actacctacc tgcaggtgat   2040

gagagtgaca gttttttttt gtttaattaa ctgcaggtga tgagtgtaga atagctcggt   2100
```

```
<210> SEQ ID NO 14
<211> LENGTH: 1861
<212> TYPE: DNA
<213> ORGANISM: Brachypodium distachyon

<400> SEQUENCE: 14

atggcgaccc ctgaggactg tggcagctgg ttgctgtacc tgtcgctggc cgccaaatgc     60

ggcggcgacg gcgaccaccc gcgccgcctg gccgggctcc ttgccgtctg cgccgccgct    120

ttcctcgtca cctgcctcct gcactggtgc ttcccccggcg ggccggcgtg gggccgctgg    180

tggtggacgc ggcggggcct gggccgcggg cccgtcgtcc ctgggccgag gggcctgccg    240

gtgatcggca gcatgtggct catgactggc ctcgcccacc gcaagctcgc cgcggaggct    300

gcccgcctgc gaggcggcgg gcgccggctg atggccttct ccctcggcga gacgcgcgtg    360

gtcgtggcgg gccatcccga cgtggcccgg gagatcctga ccagcccggc cttcgccgac    420

cggcccgtca aggagtccgc ctacgggctc atgttccacc gcgccatcgg cttcgcgcgc    480

cacggcgcct actggcgcgc gctccgccgc gttgcttcca cgcacctctt ctcgccctgg    540
```

```
caggtcgccg cgtccggcgc ccagcgcgcg gtgatcgcgc gccagatggt ggccgccctc    600
gccgggggcg ccgaggtccg gcgcgtcctg cgtcgcgcgt cgctgcacaa cgtgatgtgg    660
tcggtgttcg gccgccgcta cgacctggag ctggaccctg gcaaggaggt ccgcgagctg    720
ggccagctcg tggacgaagg ctacgacctg ctgggccagc tcaactggtc cgaccacctc    780
ccctggctcg cccgcttcga cctgcagggc acccgggccc ggtgcgccag cctagtgccc    840
cgcgtgaacc gcttcgtcgg cggcatcatc gatgaccacc gggtcaaagc tccgtccgcc    900
gtcaaggact tcacggacgt cctgctgggc ctgcaaggcg gcgacaggct cgccgactcc    960
gacatggtcg cggtgctctg ggagatggtg ttccgtggca cggacacggt ggccgtgctg   1020
atggagtggg tgctggcccg gctcgtgctg caccaggacg tgcaggcccg ggtgcacgag   1080
gagctggacc gcgtcgtcgg gcgcgaccgg gccgtggccg agtccgacgc ggcctcgctc   1140
gcctacctcc acgccgtggt caaggaggtc ctgcgcctcc acccgccagg cccgctgctg   1200
tcctgggccc gcctggccac gtcggacgtg cacgtggacg ggttcctcat ccccgctggc   1260
accaccgcca tggtgaacat gtgggccatc acccacgacg gcgacgtctg ggccgagccc   1320
atggagttcc ggcccgagcg gttcgtcggg ccgggggctg aggagttctc cgtcatgggc   1380
tctgatctcc ggctggcgcc gtttggggcc ggccggagga gctgccccgg gaagagcctg   1440
gccatggcga ccgtggcgtt ctggctcgcc acgctgctcc acgagttcga cctgcttcct   1500
tcctccgacc cggcacgtgg cgtgcaactg tcggagaccc tgaggctgtc gtgcgagatg   1560
gccaccccgc tggccctgac gccgagggct cgtcgacgcc cggcggtttg aatttgaatt   1620
gatgacgtat catgcctacg ccaccactgg ctagctagct agaaccctag tattgttgct   1680
gctttgtttt tgagacgttg tcgcctaccg gtcggccgcc ggctcgctac cacgcacgca   1740
cgtacgggca taacgctggc ttatctcgtc cagagctagc aaatgaatcg tttggacttt   1800
tatatatcga gacgtgccag ctgatgacag cgatgttttt tgccttcttg ttcccccggt   1860
c                                                                   1861
```

<210> SEQ ID NO 15
<211> LENGTH: 1755
<212> TYPE: DNA
<213> ORGANISM: Glycine max

<400> SEQUENCE: 15

```
atgacaaccc acattgataa cctgtgggtg ttggccttgg tctcaaaatg cacacaagag     60
aacattgcat ggtcactctt gaccatcatg gtcactctct ggctctccat gaccttcttc    120
tgctggtctc atcccggtgg tcctgcttgg ggcaagtact actcctttca ttactggaaa    180
aaaacaacca caaccacaac ctcaacctca aacaacacaa actccaacaa ccttaaaatg    240
attcccggtc ccaaaggcta tcctttcatt ggaagcatga gcctcatgac atcccttgca    300
caccaccgta ttgctgccgc tgctcaagca tgcaaagcca ccaggctcat ggccttctcc    360
atgggtgaca cgcgtgtcat cgtcacgtgc cacccccacg tggccaagga gattcttaac    420
agctccgtct tcgccgatcg tcccataaag gaatcagcct acagcctcat gttcaaccgc    480
gccatcggct ttgcccctta cggcgtttac tggcgcaccc tccgccgcat cgccgccacg    540
cacctcttct gccccaaaca aatcaaggcc tcggagctcc agcgcgccga aatcgccgcc    600
cagatgaccc actcgttccg aaaccgccgc ggcggtttcg gaatccgcag cgttctcaag    660
agagcgtcgc tcaacaacat gatgtggtcg gtgtttggac aaagatatga ccttgacgag    720
```

```
acaaacactt cagtggacga gttatcccgg ttagtggaac aaggctatga cttgttgggt    780
acccttaatt ggggagacca tatccctttt ctgaaagact ttgaccttca aaaaatccgg    840
tttacctgct ccaaactcgt cccccaagtg aaccggttcg taggttcaat catcgccgac    900
caccaaaccg acacaaccca aaccaaccgc gatttcgttc atgttttgct ctctctccaa    960
ggtcccgata aattgtctca ctccgacatg attgctgtcc tctgggaaat gatatttagg   1020
gggaccgaca cggtggcggt tttgattgag tggattatgg caaggatggt gcttcatccg   1080
gaggtacaaa ggagggtgca agaggagctg gacgcggtgg ttggaggtgg tgcgcgcgct   1140
ttgaaggagg aggacgtggc ggcgacggcg tatcttctgg cggtggtgaa ggaggttctg   1200
aggctgcacc ctccaggccc gcttctctcg tgggcccgct tggccatcac cgatacgacc   1260
attgatgggt ataacgtgcc cgcgggaacc accgccatgg ttaatatgtg ggccatagga   1320
agggacccgg aggtgtggct ggacccactt gatttcaagc ccgagaggtt catgggcctg   1380
gaggcggagt tttctgttct cgggtcggat ctgaggctgg ctccattcgg gtcgggtaga   1440
agaacctgcc ccggaaagac tttgggtttg agcaccgtga ctttctgggt ggcgaggctt   1500
ttgcacgagt ttgaatggct accatctgat gaggggaagg ttgatctaac ggaggtgctg   1560
aggctctcgt gtgaaatggc taacccgctc tatgttaaag ttcgccctag gcgtggatta   1620
agtacttaat aataataata ataataataa taataataat aataatgtta agtagcaggt   1680
gcatggccct ttggagccac taaatgttaa gtgaatccat gaatcaaggt agaaagtttg   1740
agttggctct gtctc                                                    1755
```

<210> SEQ ID NO 16
<211> LENGTH: 1662
<212> TYPE: DNA
<213> ORGANISM: Oryza sativa

<400> SEQUENCE: 16

```
atggcgactc cggaggacac tggcagctgg ctgctctacc tctccttggc ggctaaatgc     60
tccggcgatg gcgacggcca gcctcaccgg cttcttgggt tcgtcgtggt ttgcgccgtc    120
gctggtctgg ttacatgtct gctgcactgg tccttccccg gagggccggc gtgggggagg    180
tggtggtgga cgcggcggcg gcgtcggggg tcgccgtgcg gtgtggcggc tgttcctggg    240
ctgagggggc tgccggtgat cggcagcatg tggctcatga ccgggctggc gcaccggaag    300
ctcgccgcgg cggcggaggc ggcgggggcg gggcggctga tggcgctgtc gctcggggag    360
acgcgggtgg tcgtggcggc gcacccggac gtggcgaggg agatcctgca cggcgcggcg    420
ttcgccgacc gccccgtgaa ggagtccgcg tacgggctgc tgttccaccg cgccatcggg    480
ttcgcgcccc acggcgcgta ctggcgcgcg ctgcggcggg tggcgtccac gcacctcttc    540
tccccgtggc aggtcgcggc gtccgcgccc cagcgcgcgg tcatcgcgcg ccagatggtc    600
cgcgccatca agctgcagca gcggagccgg agcggcgatt ccgccgccgg cgccgccgtc    660
gaggtccgcc gcgtcctgcg ccgcgcgtcg ctccacaacg tgatgtggtc ggtgttcggc    720
cggcggtacg agctgcagct ggaccccggc aaggagagcg acgaggtccg ggagctgagg    780
gccctcgtcg acgaaggcta cgacctgctc ggccagctca actggtccga ccacctccca    840
tggctcgccc gcttcgacct gcagagcacc cgcgcccgct gctcccgcct cgtcccccgc    900
gtcaaccgct tcgtcacccg catcatcgac gagcatcgct catctgctcc cgtcgcagcc    960
gccatcgact tcaccgacgt cttgctctcc ctgcagggca gcgacaagct cgccgactcc   1020
gacatggtcg ccgttctctg ggagatggtg tttcgcggga cggacacggt ggccgtgctg   1080
```

```
atcgagtggg tcttagcccg gctcgtgctg cagcaggacg tgcaggctcg ggtgcacgac   1140

gagctgggcc gggtggttgg gctggaccgg gacgtgaccg agtccgacac ggcctcactc   1200

gtctacctcc acgccgtcat caaggagacg ctgaggctgc acccaccggg cccactcctc   1260

tcatgggccc gcctggccac gtcggacgta cacgtggacg ggtacctgat ccccgctggc   1320

accaccgcga tggtgaacat gtgggccata gcacacgacc ccgacgtgtg ggccgagccg   1380

atggagtttc ggcccgagcg gttcatcggg aaggcggcgg agttcagtgt aatgggttcg   1440

gatctcaggc tcgcgccgtt cggatcgggt cggcggagct gccccgggaa gagcctcgcc   1500

atggccacgg tggcattctg gcttgccacg ctgttgcacg agttcgccct cctcccctcg   1560

cccgacccgg cacacggcgt cgacttgtcg gaggtgctaa ggctgtcgtg cgagatggcc   1620

accccgctgg cggtgacagc gtggcctcgg cgtgtggtgt ga                      1662
```

```
<210> SEQ ID NO 17
<211> LENGTH: 1672
<212> TYPE: DNA
<213> ORGANISM: Glycine max

<400> SEQUENCE: 17

acaccatcca ctactcttct tagttccagc acaacaagct cttcatttct cccacacttt     60

cttttctttc accaaaaatg tcaccagatt tcacactttt gttcttcccg gaactcatgc    120

agtcccctat gatcactttc caagccaccc tctgcgtcct tctcttcacc ctcatgttca    180

cgctgctctt cactcctggt gggcttcctt gggcctgggc ccggcccaga cccatcatcc    240

ctggcccagt aactgccctg ttagggatct ttactggctc cacgcctcac cgtgctttat    300

ccaaactcgc ccgtaattac cacgcggaaa aactcatggc tttctccatc ggtttaaccc    360

gtttcgtcat ctccagcgaa ccggagaccg ctaaggagat tctcggcagc cccagtttcg    420

ctgataggcc ggtgaaggaa tccgcctatg agcttctctt ccaccgcgca atgggttttg    480

caccgtatgg ggagtactgg aggaatttga ggagaatctc agccctacat ctcttctccc    540

cgaagagaat caccggctct gaatccttca ggagcgaggt tggattaaaa atggttgaac    600

aagttaagaa aaccatgagt gagaaccaac atgttgaggt taagaaaatt ctacacttta    660

gttcgttgaa caatgtgatg atgacggtgt ttggtaagtc ttatgagttt tacgagggtg    720

agggtttgga gcttgagggt ttggtgagtg aagggtatga gttgttgggt gtttttaact    780

ggagtgacca ttttccggtt ttggggtggt tggatttgca gggtgtgagg aagaggtgta    840

ggtgtttggt tgaaaaggtt aatgtttttg ttggaggggt tattaaggag catagggtga    900

agagggagag gggtgagtgt gtgaaggatg aaggaactgg ggattttgtt gatgttttgc    960

ttgatttgga gaaggaaaac aggctcagtg aagctgacat gatcgctgtt ctttgggaaa   1020

tgatatttag gggaactgac acggtggcaa ttctgctaga gtggactctg gctcggatgg   1080

ttctccaccc tgaaatccaa gcaaaggcac agcgcgaaat agacttcgtt tgcggatcct   1140

ccaggcccgt atccgaagca gacattccga acctgcgcta ccttcagtgc atagtaaaag   1200

aaacccttcg tgtgcaccca ccaggcccgc tactctcgtg ggctcgcctt gctgtgcacg   1260

acgttaccgt gggcggcaag cacgtgattc ccaagggcac caccgcgatg gtgaacatgt   1320

gggccataac ccacgacgag agggtgtggg ccgagcccga gaagtttagg cccgagcggt   1380

ttgtggagga ggatgtgagc ataatggggt ctgatttgag gttggcacct ttcgggtctg   1440

gaagaagagt gtgccctggg aaggcccttg gtttggcctc ggttcatctt tggctcgctc   1500
```

```
agttgcttca aaattttcat tgggtttcat ctgatggtgt ttctgtggag ttggatgagt   1560

ttcttaagct ttctatggag atgaagaagc cactgtcttg caaggctgtg cctagggttt   1620

ctgtttaggt ttatgtgtgt tgttgggttg agttggtttg gtttgtctgc tt           1672


<210> SEQ ID NO 18
<211> LENGTH: 1635
<212> TYPE: DNA
<213> ORGANISM: Glycine max

<400> SEQUENCE: 18

tcagcacaac ctcttcatct ctcccaggct ttcttttctt tgcaacaaca ctaccaaaaa     60

tgtcaccaga tttcacactt ttgttctccc cggaactcat gcagtcccct atcatcactt    120

tccaagccac tttctgtgtc cttctcttca ccctcatgtt cacgccgttc ttcactcctg    180

gtgggcttcc ttgggcctgg gcccggccca gaaccatcat ccctggccca gtaactgccc    240

tgctcggggt cttcacgggt tccacacctc acagcgcttt atccaaactg gcccgcactt    300

atcacgcgga aaagctcatg gctttctcca tcggtttaac ccggttcgtt atctccagcg    360

aaccggaaac cgcaaaggag attctcggca gccccggttt tgcggacagg ccggtgaagg    420

aatccgccta tgagcttctc ttccaccgtg caatgggttt cgcaccgtac ggagagtact    480

ggagaaacct gaggagaatc tcagccctac atctcttctc cccgaagaga atcaccagct    540

ctgagtcctt caggagcaag gttgggttaa aaatggttga acaagttaag aaaaccatga    600

gtgagaacca acacgtcgag gttaagaaaa ttctacactt tagttcgttg aacaatgtga    660

tgatgacggt gtttggtaag tgttatgagt tttacgaggg tgagggtttg gagcttgagg    720

gtttggtgag tgaagggtat gagttgttgg gtgtttttaa ctggagtgac catttttccgg   780

ttttggggtg gttggatttg caggggggtga ggaagaggtg taggtgtttg gttgaaaagg   840

ttaatgtttt tgttggaggg gttattaagg agcatagggt gaagagggag aggggtgact    900

gtgtgaagga tgaaggagct gaggattttg ttgatgtttt gcttgatttg gagaaggaaa    960

acaggctcag tgaagctgac atgattgctg ttctttggga aatgatattc aggggaactg   1020

acacggtagc aattctgcta gagtggattc tggctcgcat ggttctccac cctgaaatcc   1080

aagcaaaggc acagcgcgaa atagacttcg tttgcggatc ctccaggctc gtatccgaag   1140

cagacattcc gaacctgcgc taccttcagt gcatagtaaa agaaaccctc cgtgtgcacc   1200

caccaggccc gctactctcg tgggctcgcc ttgctgtgca cgacgttacg gttggcggca   1260

agcacgtgat tcccaagggc accaccgcga tggtgaacat gtgggccata acccacgacg   1320

agagggtgtg ggccgagccc gagaagttta ggcccgagcg gtttgtggaa gaggatgtga   1380

gcataatggg gtctgatttg aggttggcac ctttcgggtc tggaagaaga gtgtgtcctg   1440

ggaaggccct tggtttggcc tcggttcatc tttggctcgc tcagttgctt caaaattttc   1500

attgggtttc atctgatggt gtttctgtgg aattggatga gtttctcaag ctttctatgg   1560

agatgaagaa gccactgtct tgcaaggctg tgcctagggt ttctgtttag gtttatgtgt   1620

gttgttgggt tgagg                                                    1635


<210> SEQ ID NO 19
<211> LENGTH: 2158
<212> TYPE: DNA
<213> ORGANISM: Zea mays

<400> SEQUENCE: 19

cccgaatcgg gagtagtagt agtagtgcat ccaatcgaca cacacacaaa aaaaaaggtt     60
```

```
agttagccat ggcgccgcca acagaggact gcggctggct gctgtacctt tccctggccg    120
ccaaatgcgg cgaccctcag cgcctgctcg gcttcgccgc ggtcttcgtc gcggcctgcg    180
tagtcacgtc gctcctgcac tgggcgtccc cgggcggccc cgcctggggg tggtactggt    240
ggaccaggcg ggccgggctg ggcatcgtcc gtgccgccat cccgggaccc cggggcctgc    300
cggtggtcgg cagcatgggc ctgatgaccg gcctggcgca ccgcaagctc tcggcggcgg    360
ccgagagaca ggccagcagg cgccgcctca tggcgttctc gcttggcgag acccgggtgg    420
tggtcaccgc cgaccccgac gtcgcgcggg agctgctcgc cagcgccgcc ttcgccgacc    480
gccccgtcaa ggagtccgcg tacgggctcc tgttccaccg cgccatcggc tttgccccgc    540
acggcgccta ctggcgcgcg ctccggcgcg tcgcgtccgc gcacctcttc tcgccgcgcc    600
agatcgcggc ctccgcggcg cagcgcgcgg ccatcgcgcg ccagatggtg gacgccacga    660
cgaccgccgc ggcccacgcc cccgtcgtcg tggcgcgccg gttcctgaag cgcgcgtcgc    720
tgcacaacgt catgtggtcg gtgttcggcc gcaggtacga cctgatggcg gacagccggg    780
aggccgagga gctcaaggcc ctggtagacg aaggctacga cctgcttggg cagctcaact    840
ggtccgacca cctcccgtgg ctcgcccgct tcgacctgca gaagacccgg gccaggtgct    900
gcgcgctcgt cccgcgggtg aaccgcttcg ttggcaacat catcggcgag caccgtgccc    960
gcctcggccg cggcgtcgac accgccgtca tggacttcac ggacgtcctg ctctccctcc   1020
agggcgacga caagctctcc gacgccgaca tgatcgccgt tctgtgggag atgatcttcc   1080
gaggcacgga cacggtggca gtcctgatcg agtgggtgct ggcccgtctg gtgctgcacc   1140
aggacgtgca gagcaaggtc caggaggagc tggaccgggt ggtcgggctg ggccaggccg   1200
tgacggagtc ggacacggcc tcgctgccct acctccaggc ggtcatcaag gaagtgctac   1260
gcctgcaccc gccaggccca ctgctctcct gggcgcgcct cgccacctca gacgtgcacg   1320
taggcgggta ccttgtgccc gcgggcacca ccgccatggt gaacatgtgg gccataaccc   1380
atgaccccag cctgtggcct gagccaatgg agttcaggcc cgagaggttc atgggccctg   1440
ccgccgagga cgtcccgata atgggttcgg atctccggct cgcgcctttc gggtccggca   1500
ggcggagctg ccccggcaag tcactcgcgg tggctaccgt cggattctgg gtcgccaccc   1560
tgctgtacga gttcaaatgg ctgccgccgt ccgacgagcc acgcggcggc ggcgtcgacc   1620
tatccgaagt gctgaggctg tcgtgtgaga tggctgcacc gctggaggcg agggtggtgc   1680
cacgtcacgc ggtgtgctga gggggctgag acacgtggcc tgcaggggtg gggatcagag   1740
gaggaaagct cgaccgatcg tcttctagct tctactacta cgtaatacct taccttgtag   1800
cagaacgtaa cgtggtcgat atgagatgtg taaagaaaga aaaaaaaaga acgcccagtt   1860
gcaccatgca tgctagctgc tggtgtggag tcagtacgta gtagcagcac ccggtttgat   1920
cgatgcttat gtgtgtaatg taatacctac ctgcagttgc aagtaaatgt gtgcctgtta   1980
ttagtctagc taggtagtgt agtgtagtgt accggatggt gagcgagcgt gacagttacc   2040
tttccttttc agtactgcct agctagctag acctagatgt attattatat attgtgtact   2100
cccttcttac gtacgtgcgt tccataataa atgtattctg tagttgtctt tttctact     2158
```

<210> SEQ ID NO 20
<211> LENGTH: 2176
<212> TYPE: DNA
<213> ORGANISM: Sorghum bicolor

<400> SEQUENCE: 20

-continued

```
cactcaaccc gagcgccact tctccaaagc atcagcgaac gagcgagctg agggagcgag      60
agagagaaaa ggatagtgaa acacgagaga gctaggagcc atggcggtgg cggcgacccc     120
cgatgactgc ggcagctggt tgctgtacct gtccctagcc gccaaatgcg ccggcggcga     180
ccagcctcac cgcctggccg gtttcctggc ggtctgcgcc gtggccttcg tcgtcacttg     240
cctcctccac tggtgcttcc ctggaggtcc ggcgtgggga aggtggtggt ggacgacgca     300
ggcgcggcgg gtcgcggcgg ccgccgttcc ggggccgagg ggcctgcccg tggtcgggag     360
catgtggctc atgacgggcc tggcgcaccg caagctggcg gcggcggcgg acagcctccg     420
cgccaggcgc ctgatggcgt tctccctcgg cggcacgcgg gtggtggtgg ccgcgcaccc     480
ggacgtggcg cgggagatcc tcaacagccc ggcgttcgcg gaccgtccca tcaaggagtc     540
cgcgtacggg ctcctgttcc accgcgccat cggcttcgcg ccctacggcg cctactggcg     600
cgcgctccgc cgcgtggcgt ccacgcacct cttctccccg tggcaggtcg ccgcctccgc     660
cgcgcagcgc gccgtcatcg cgcgccagat ggtcgccgcc atgaagcagg agctgtcgtc     720
gtcgtcgtcg gcctcggccg gcttcgaggt ccgccgcgtc ctgcgccgcg ggtccctgca     780
caacgtgatg tggtcggtgt tcggccggcg gtacgacctg gagctggacc cggccaagga     840
gagccccgag acgcgggagc tgaggagcct cgtggacgaa ggctacgacc tgctgggcca     900
gctcaactgg tccgaccacc tcccctggct cgcgcgcttc gacctgcaga gcaccaggtc     960
caggtgcgac cgcctcgtcc cgctcgtgaa ccgcttcgtc ggcggcatca tcgacgcgca    1020
ccgcgcccgg aacgacctcc gctccgctcc accacacgcc gtcatggact tcaccgacgt    1080
gctcctctcg ctgccggccg acgacaggct caccgactct gacatgatcg ccgtcctctg    1140
ggaaatggtg ttccgtggaa ctgacaccgt tgccgtgctg atcgagtggg tgctggcgag    1200
gctcgtgctg caccctgacg tgcaggcccg tgtccacgac gagctggacc gcgtggtcgg    1260
gcgtgaccgg gccgtgaccg agtccgactc ggggtcactg gtctacctgc acgccgtgat    1320
caaggaggtg ctcaggatgc acccgccggg cccactgctg tcgtgggcgc gcctggccac    1380
gtcggacgtg caggtggacg ggcacctcat ccccgccggc accaccgcca tggtgaacat    1440
gtgggccata acgcacgacc cggacgtgtg ggcggagccg gcggagttcc agccggagag    1500
gttcatggga tccaccaccg gcggcgagtt cccgataatg ggtcggacc tgaggctcgc     1560
gccgttcggg gcgggccggc gcagctgccc cgggaagagc ctcgccatgg ccaccgtggc    1620
tctctggctc gcgacgctgc tgcacgagtt cgagctgctc ccggcgcgcg gcgtctacct    1680
gtcggaggtg ctcaagctgt cgtgcgagat ggccgtcccg ctggccgtga cggcgaggcc    1740
ccggcaagcg gtgtgatgac gcgtcacggc ggctgggacg acggagcagg caggcaggca    1800
gtcagttggg gtatcagtct cactgtgagc attataccac aactactagt agtactacta    1860
ctgtacacgg aatggaaaag cgcttgtgct tttgggagac gttgctaccg gtcacagctt    1920
gcaagttgct actactgggt cgacatgggg tatatgcttt tcatgttact atcttcgata    1980
tgtatcgaga tcaggttgcc gaatgtgata ctttggcttg tactgttagc ttttgtctgg    2040
gtgctctttt attgcttttt ttttaagtag taatcgctgt aagactcgta aaatgtatat    2100
gctggtttgg atggttttgg attgtagctc acaaactagt attacgcagt tcaatgcctt    2160
aatatgctat ctgttc                                                    2176
```

<210> SEQ ID NO 21
<211> LENGTH: 1587
<212> TYPE: DNA
<213> ORGANISM: Glycine max

<400> SEQUENCE: 21

```
atgtcatcat cggaactctc ctctttcttt cttctccgtc tatcagacat actcagtttc     60
gatgttttgc tcggagttat gtttctagtt gccgtgttcg gctactggct ggttcccggc    120
ggtcttgctt gggctttttc caagttcaag cccgcgattc ccgggccttc cggttacccg    180
gtggtgggtc tggtttgggc tttcataggg cctcttactc acagggtcct tgctaagttg    240
gctgaaacct ttgatgcaaa gcccttgatg gcgttctctg tggggttcac tcgtttcatc    300
atctcttctc accccgacac cgccaaagag atcttgaaca gttccgcttt cgcggatcgt    360
cccgttaagg aatctgctta tgaacttctc tttcaccgtg cgatggggtt tgcaccctac    420
ggtgagtact ggaggaacct gaggaggatc tccgcaactc acatgttctc tccgaggaga    480
atcgcagccc aaggagtgtt tcgggcccgg attggagccc aaatggtgag agacatcgtg    540
ggcctgatgg ggagggacgg tgtggtggag gtgaggaagg tgttgcattt tgggtcgttg    600
aataacgtga tgaagagcgt gtttgggagg agttatgtgt ttggtgaggg gggtgatggg    660
tgtgagctcg aggggttggt gagcgagggg tatcatttgc ttggggtgtt taactggagt    720
gaccactttc cactcttggg ttggttggat ttgcaaggtg tgaggaagag ctgtaggagt    780
ttggttgata gagtgaatgt ttatgttggg aaaatcattt tggagcatag agtgaagagg    840
gttgctcaag gtgaggataa taaggccatt gatactgata gttctggtga ctttgttgat    900
gtgctgctgg atttggagaa agagaatagg ctaaaccact ctgatatggt tgctgttttg    960
tgggaaatga tatttagagg gactgatacg gtagctatcc ttctagagtg gattctagca   1020
agaatggttc ttcatccaga aatacaagca aaggcacaat ctgaaataga ctctgtggtt   1080
gggtctgggc gtagtgtgag tgatgatgac cttccaaacc ttccttacgt tcgagccata   1140
gtgaaggaaa ccttaaggat gcacccacca ggccctcttc tttcatgggc cagactttct   1200
attcatgaca cacaaattgg caatcacttt gttccagctg gcaccactgc tatggtaaac   1260
atgtgggcca taactcacga ccaagaagtg tggtatgagc caaaacagtt caagccggag   1320
cgtttttga aggacgagga cgtgccaatc atgggatctg atcttaggtt ggcacctttt   1380
ggctctggga ggagagtgtg ccctggaaaa gccatgggct tggccactgt tgagctttgg   1440
cttgctatgt tcttacaaaa attcaaatgg atgccctgtg atgattctgg tgttgacttg   1500
tctgagtgtt tgaagctctc catggagatg aaacactctc tcaaaaccaa agttgttgca   1560
aggcctgtag tttctcttgc aatgtaa                                       1587
```

<210> SEQ ID NO 22
<211> LENGTH: 2074
<212> TYPE: DNA
<213> ORGANISM: Zea mays

<400> SEQUENCE: 22

```
aaagacttga accacgcaac cctctctggt ctctggtcgt cctactttct tccacagcag     60
aaggaaactt gagtcgtgag cgcagtggtg catccaatcc acaaagagct gaggttagtc    120
agccatggcg gcaccgccga ccgaggactg cggctggctg ctgtacctct ccctggccgc    180
caaatgcggc gaccctagcc gcctgctcgg cttggcggcg gtcttcgtcg gcgcctgcgt    240
cgtaacgtcg ctcctgcact gggcgtgccc gggcggcccc gcctgggggc ggtactggtg    300
gaccaggcga ggcgggctgg gcatcgtccg cgccgccatc ccgggacccc ggggcctgcc    360
agtggtcggc agcatggggc tgatgaccgg cctggcgcac cgcaagctcg cggcggcggc    420
```

```
ggcggcggcc gggggtcagg gcagcagcag gcgccgccgt ctcatggcgc tctccctcgg    480

cgagacccgg gcggtggtga ccggcgaccc ggacgtcgcg agggagctgc tcggcagcgc    540

cgccttcgcc gaccgccccg tcaaggagtc cgcgtacggg ctcctcttcc accgcgccat    600

cggcttcgcc ccgcacggcg cctactggcg cgcgctccgc cgcgtggcgt cggcgcacct    660

cttctcgccg cgccaggtcg cggcctcctc cgcgcagcgc gcggtcatcg cgcgccagat    720

ggtggacgcc gtgaccacgg ccgcccccgc ccccgccccc gccgtcgtgg tggcgcgccg    780

gttcctgaag cgcgcgtcgc tgcacaacgt catgtggtcg gtgttcgggc gcaggtacga    840

cctgctgctg ctggcggcgg acggcgagga gctgaaggcg ctggtggacg aaggctacga    900

cctcctcggg cagctgaact ggtccgacca cctcccgtgg ctggcccgct tcgacctgca    960

gaggacccgg gccaggtgct ccgcgctcgt cccgcgggtg aaccgcttcg ttggcaacat   1020

catcgacgag caccgtgcgc gcctcggcct cggcgacacc ggcggcgtca cggacttcac   1080

cgacgtcctg ctctccctcc agggcgtcga caagctctcc gacgccgaca tggtcgccgt   1140

tctctgggag atgatcttcc gaggcacgga cacggtggcc gtcctaatgg agtgggtgct   1200

ggcgcgtctc gtgctgcacc aggacgtgca gagcaaggtc caggaggagc tggaccgggt   1260

ggtggggcca ccgggccagg ccgcatccgt gacggagtcg gacaccgcct cgctcgtcta   1320

cctccaggcg gtcatcaagg aagtgctgcg cctgcacccg ccaggcccgc tgctctcctg   1380

ggcgcgcctg gccacgtcgg acgcgcgcgt aggcgggtac cacgtgcccg cgggcaccac   1440

cgccatggtg aacatgtggg ccataacgca tgaccccagc gtgtgggccg agccgacgga   1500

gttcaggccc gagaggttcg tgggcgcctc tgctggtgct ggtgctggtg ctggtgccga   1560

ggacgttccg atgataatgg gctcggatct ccggctcgcg cccttcgggt ccggcaggcg   1620

gagctgcccc ggcaagtcgc tcgcgctggc taccgtcggg ttctgggtgg ccaccctgct   1680

ccacgagttc aaatggttgc cgccgtgccg cggcgtcgac ctgtccgagg tgctgaggct   1740

gtcgtgtgag atggctgcac cgctggaggc gagggtggtt ccacgtcacg cggtgtgaga   1800

tgacgaggat gagacacgtg gcctggggat aggagaagtt gcccgatcgt ctgtctagat   1860

tgtactgtac tatatatctt atcttagctt tccttacctt gtagcagaga acgtaacgtg   1920

gcccggcggc gatggatgat gagaatgaga tgtgtaaaag aagaaaaaga gcatgcccga   1980

gtgccatatg ctttagagtg gactgtgtat atatgatgat gctattgcta aaaaaaaaaa   2040

aaaaaaaaaa aaaaaaaaaa aaaaaaaaaa aaaa                               2074
```

<210> SEQ ID NO 23
<211> LENGTH: 2061
<212> TYPE: DNA
<213> ORGANISM: Brachypodium distachyon

<400> SEQUENCE: 23

```
atggcgccgg cgacttctgc ttccgaggac tgcgcggggt ggctgctgta cgcgtccctg     60

gccgcgagat gcaacgacgg cggtgaggcc taccgggccg ccgtcttcgc catggccctg    120

ctggccacca gtttcatcct cacctcgctc ctccactggg cctccacccc cggcggcccg    180

gcctggggac gctaccgctg gacttccacc acctctcggg ccgccattag cactagccct    240

cgcatccccg gcccgcgcgg gctgccggtg gtcggcagca tgggcctcat gacgggcctg    300

gcccaccgca agctcgccgc ggctgtcgcc gccgggggag acgacgaaga ggagaggtcc    360

cagcggaggc ggctgatggc gttctcgatg ggcgagacgc gggccgtggt gagctcggac    420

ccggccgtgg cccgcgagct gctgtcgagc ccggcgttcg cggaccggcc cgtcaaggag    480
```

```
tccgcctacg ggctcctctt ccaccgcgcc atcggcttcg cgccccacgg cgcctactgg    540
cgctccctcc gccgcgtcgc ctcggcgcac ctcttctcgc cgcgccaggt cgccgcctcc    600
gccgcccacc gcgccgccat cgcccgcagc atggttggct ccgtctccgc catcgccatg    660
ggctccggcg aggtcgaggt ccgccggttc ctgaagcggg cggcgctgca cggggtcatg    720
tggtccgtgt tcggccggag gtacgacggc acggcggcgc cggagctggg gaagaaggag    780
gaggaagagc tgaggagcat ggtggaagaa ggatacgagc tcctcggcaa gctcaactgg    840
gccgaccacc tgccatggct ggcccgcttc gacctccagg ggatacgggc ccggtgcgcc    900
gccctcgtgc cacgcgtcaa ccgcttcgtc ggcaagatcg tcgacgacca ccgcgccgct    960
gctgccgccg acgccggcga tcgtgtcgtg gacttcaccg acgttctgct atcccttcaa   1020
ggcgccgaca agctctccga cgccgacatg atcgcggttc tctgggagat ggtgttccgt   1080
ggcacggaca cgatggcggt ggtgatggag tgggtgctgg cccggctggt gatgcaccag   1140
gacgtgcagg ccagggtcca ggaggagctg gaccgggtgg tcgggccggg ccaagccgtc   1200
tccgaatcgg acgcggcccg gctcgtctac ctccaggccg ttattaagga gacgatgcgg   1260
ctgcacccgc caggcccccct gctctcatgg gcccggctcg ccacatcgga cgttcatgtg   1320
ggcgggttcc tcgtgccagc tggcaccacc gccatggtta acatgtgggc catcacccat   1380
gacccgaccg tgtgggcgga tccgctggag ttcaaccccg acaggttcat tgtcggagcc   1440
gttccgttgt cggaaggtca tcataatgcc gttccgggcg ctgagttctc cataatgggc   1500
tcggatctca ggctcgcgcc attcggatcg ggcaggcgga tctgccccgg gaagccactg   1560
gcgatggcca gcatcgggtt ttgggtcgcg acgctcctcc atgagttcaa gtggacctcg   1620
gcgccacgtg gtgacgtcga cctgtcggag gtgctgaggc tgtcatgcga gatggccgcc   1680
ccgctcaagg cgaggctcac accaaggcgc cctgtgtgat gatatgccgg agccaccgac   1740
cacttcttca ccggactagt cctgtctatc ttctttgctt attttctctc taccgatgcc   1800
tgtagtgaaa aaaaagaagt aatgtcccgg tttggaaacg tgcctgctgc tataataggt   1860
ccggtcctgg tcgtacttct ctagtccttt tgctgtactt agcttagcta aaagagatgc   1920
taaattaggt acttatgaac tactagtatt ataaggaaat gagtgtgaca gttttcttgt   1980
gtgttttccc tttgctgcct agctagaggt ttctatgcat gtaaatacct ttatatttcc   2040
caatgcaagc ctttgtttgc t                                               2061
```

<210> SEQ ID NO 24
<211> LENGTH: 1716
<212> TYPE: DNA
<213> ORGANISM: Glycine max

<400> SEQUENCE: 24

```
acaccacagt ttcaaagccc ttctaaaacg ccttactctg tatcttcttt catcatccaa     60
aaaaaaccat tcacacaaag aaaacctttg ggtttcccaa gatgtcatca tcggaactct    120
cttctttctt tctcctgccc ctatcagcca tactcagttt cgatgctttg ctcggagtta    180
tgtttctagt ggccgtgttc ggctactggc tggttcccgg tggtcttgct tgggctttgt    240
ccaaattcaa gcctgcgatt cccgggcctt gcggttaccc ggtggtgggc ctggtttggg    300
ctttcatagg gcctcttact cacagggtcc ttgcaaagtt ggctgaaacc ttcgatgcaa    360
agcccctgat ggcattctcg gtagggttta ctcgctttat catctcttct caccccgaca    420
ctgccaaaga gatcttgaac agttctgctt ttgcggatcg tcctgttaag gaatccgctt    480
```

```
atgagcttct ctttcaccgc gcaatggggt tcgcacccta cggtgagtac tggaggaatc    540
tgaggaggat ttcagcgact cacatgttct ctccgaagag aattgcggcc caaggagtgt    600
tccgggcccg ggttggggcc caaatggtga gagaaatcgt gggcctgatg ggaagaatg     660
atgtcgtgga ggtgagaaag gtgttgcatt ttggatcgtt gaataacgtg atgaagagtg    720
tgtttgggag gagctatgtg tttggtgagg ggggtgatgg gtgtgagctt gaggagttgg    780
tgagtgaggg gtatgatttg cttgggctgt ttaactggag tgaccacttt cctctcttgg    840
gttggttgga ttttcaagga gtgaggaaga ggtgcaggag tctggtggat agagtgaatg    900
tttttgttgg gaaaatcatt atggagcata gagtgaagag ggatgctgaa agtggtgact    960
ttgttgatgt gctgttggat ttggagaaag aggataggct aaaccactct gatatggttg   1020
ctgttttgtg ggaaatgata tttaggggga ctgatacagt ggcaattctt ctagagtgga   1080
ttctagcaag gatggtactg catccagaaa tacaagcaaa ggctcagtgt gaaatagact   1140
ctgtggttgg gtctgggtgc agtgtgactg atgatgacct tcctaacctc ccttacgtgc   1200
gagctatagt gaaggaaacc cttaggatgc acccaccggg ccctcttctt tcatgggcca   1260
ggctttccat tcacgagaca caaattggca accactttgt tccagctggc acaactgcta   1320
tggtcaactt gtgggccatc actcatgacc aacaagtgtg gtccgagcca gaacaattca   1380
agcccgagcg gtttctgaag gacgaggacg tgccaatcat ggggtctgat cttaggttgg   1440
caccttttgg cgctggtagg agagtgtgcc ctggaaaagc catgggcttg gccactgttg   1500
agctttggct tgctgtgttc cttcaaaagt tcaaatggat gccttgtgat gattctggtg   1560
tggacttgtc tgagtgcttg aagctctcca tggagatgaa acactccctc atcaccaaag   1620
ctgttgcaag gcctacatct tctcttgcaa tgtaatgggt tggagtatcc catcatttta   1680
ctccccttaa taataatatt tctttccttt taaaaa                             1716
```

<210> SEQ ID NO 25
<211> LENGTH: 1578
<212> TYPE: DNA
<213> ORGANISM: Oryza sativa

<400> SEQUENCE: 25

```
atggcgctct cctccatggc cgcggcgcaa gagagctccc tcctcctctt cctcctcccg     60
acgtcggccg cctccgtgtt cccgccgctc atctccgtgg tcgtcctcgc cgcgctcctc    120
ctgtggctct cgccgggtgg ccccgcgtgg gcgctgtccc gttgccgtgg cacgccgccg    180
ccgccgggcg tggcgggggg cgcggccagc gcgctgtccg gccctgccgc gcaccgcgtg    240
ctcgccggga tttcgcgcgc cgtcgagggc ggcgcggcgg tgatgtcgct ctccgtcggc    300
ctcacccgcc tcgtcgtggc gagccggccg gagacggcga gggagatcct cgtcagcccg    360
gcgttcggcg accgccccgt gaaggacgcg gcgaggcagc tgctgttcca ccgcgccatg    420
gggttcgccc cgtcgggcga cgcgcactgg cgcgggctcc gccgcgcctc cgcggcgcac    480
ctcttcggcc cgcgccgcgt ggccgggtcc gcgcccgagc gcgaggccat cggcgcccgc    540
atagtcggcg acgtcgcctc cctcatgtcc cgccgcggcg aggtccccct ccgccgcgtc    600
cttcacgccg cgtcgctcgg ccacgtcatg gcgaccgtct tcggcaagcg gcacggcgac    660
atctcgatcc aggacggcga gctcctggag gagatggtca ccgaagggta cgacctcctc    720
ggcaagttca actgggccga ccacctgcca ttgctcaggt ggctcgacct ccagggcatc    780
cgccgccggt gcaacaggct agtccagaag gtggaggtgt tcgtcggaaa gatcatacag    840
gagcacaagg cgaagcgagc tgccggaggc gtcgccgtcg ccgacggcgt cttgggcgac    900
```

```
ttcgtcgacg tcctcctcga cctccaggga gaggagaaga tgtcagactc cgacatgatc     960
gctgttcttt gggagatgat ctttagaggg acggacacgg tggcgatctt gatggagtgg    1020
gtgatggcga ggatggtgat gcacccggag atccaggcga aggcgcaggc ggaggtggac    1080
gccgccgtgg ggggacgccg cggccgcgtc gccgacggcg acgtggcgag cctcccctac    1140
atccagtcca tcgtgaagga gacgctgcgc atgcacccgc cgggcccgct cctgtcgtgg    1200
gcgcgcctcg ccgtgcacga cgcgcgcgtc ggtggccacg ccgtccccgc cgggacgacg    1260
gcgatggtga acatgtgggc gatcgcccac gacgccgccg tctggccgga gccggatgcg    1320
ttccgcccgg agcgcttctc ggagggggag gacgtcggcg tgctcggcgg cgacctccgc    1380
ctcgcgccgt tcggcgccgg ccgccgcgtc tgccctggca ggatgctggc gctcgccacc    1440
gcccacctct ggctcgccca gctgctgcac gccttcgact ggtcccccac cgccgccggc    1500
gtcgacctgt ccgagcgcct cggcatgtcg ctggagatgg cggcgccgct cgtgtgcaag    1560
gccgtggcta gggcctga                                                  1578
```

<210> SEQ ID NO 26
<211> LENGTH: 1611
<212> TYPE: DNA
<213> ORGANISM: Glycine max

<400> SEQUENCE: 26

```
atgtcaccag attttacact cttgttcttc ccggaactca tccaaccccc tatcgtcacc      60
ctccaagccg ccctatgcat ccttctctta accttcctcc tcacgttttt cctcactcca     120
ggcgggcttg cgtgggcctg ggccaccaag tcctcgaccc ggcccatcat tccgggccca     180
gtaatggccc tgctcagcgt cttcaccggc tccaccccgc accgcaggtt atccatgctc     240
gcccgctctt accacgcaga aaagctcatg gctttttcaa tcggtctgac ccggttcgtc     300
atctcgagtg aaccggaaac cgcaaaggag attctcggca gccccggttt tgctgacaga     360
ccagtgaagg aatcggccta ccagcttctc ttccaccgcg caatggggtt tgcaccatac     420
ggagaatact ggagaaacct gaggagaatc tccgcccttc atctcttctc tcccaagaga     480
atcaccggct cggaagcctt taggaacgag gtggggttga aaatggtaga tgaagttaag     540
aaggttatga aggataaccg acacgtggag gttaagagga ttttgcacta cgggtcgttg     600
aacaatgtga tgatgacggt gttcggtaag tgttatgagt tctacgaggg tgagggtgtt     660
gagcttgagg ctttggtgag cgaagggtat gagctgttgg gtgtttttaa ctggagcgac     720
cattttccgg ttctggggtg gttggatttg cagggtgtga ggaagaggtg taggtgtttg     780
gttgaaaagg ttaatgcgtt tgttgggggt gttattgagg agcatagagt gaagagggtg     840
agaggtgggt gtgtgaagga tgaagggact ggggattttg ttgatgtttt gcttgatttg     900
gagaacgaga acaagcttag tgaggctgac atgatcgctg ttctttggga aatgatattt     960
aggggaactg acacggtggc aattctgctg gagtggatct tggctcggat ggttctccac    1020
cccgacatcc aagccaaagc acagcgcgaa atagactccg tctgcggacc ctacaggctc    1080
gtatccgaag cagacatgcc gaacctgcgc taccttcagg gcatagtaaa agaaactctc    1140
cgcgtgcacc ctccaggccc gctactctcg tgggctcgcc tggcggtgca cgacgttacc    1200
gtgggcggca agcacgtgat tcccaagggc accaccgcga tggtgaacat gtgggccata    1260
acgcacgacg agaggttttg ggccgagccc gagaggttca ggcccgagcg gtttgtggag    1320
gaggaggatg tgaacataat ggggtctgat ttgaggttgg cacctttcgg gtctgggaga    1380
```

```
agagtgtgcc ctgggaaggc cttgggcttg gcctcggttc atctttggct cgctcagttg   1440

ctacaaaatt ttcattgggt tcaatttgat ggtgtctctg ttgagttgga tgagtgtctt   1500

aagctttcta tggagatgaa gaagccactt gcttgcaagg ctgtgcctag ggttgctgtt   1560

tagtttatgg gtgttgttgg gttacttggg tgggtttggg ttatttgcta a            1611
```

<210> SEQ ID NO 27
<211> LENGTH: 1603
<212> TYPE: DNA
<213> ORGANISM: Sorghum bicolor

<400> SEQUENCE: 27

```
ccttctcacc tccctccccc acgccgtcgc catggacgcc accacccagg actccctcct     60

cttcctcttc ccggccgccg ccaccttcct ctccccgctc ctcgccgtgc tcctcgtagc    120

gctctcgctg ctctggctcg tcccaggcgg gcccgcgtgg gcgctcatct ccacctccag    180

gtcccgcgcg accccgccgc cgggcgcgcc gggcgtggtc accgcgctct cgggccccgc    240

agcgcaccgc gccctggcgt ccctgtcgcg gtcgcttccc ggcggcgccg cgctgtcggc    300

gttctccgtc ggactcacgc gcctcgtcgt tgccagccag ccggacacgg cgcgggagct    360

cctggccagc gccgccttcg ccgaccgccc cgtcaaggac gcggcccggg ggctcctctt    420

ccaccgcgcc atgggcttcg caccctccgg cgactactgg cgcgcgctgt gccgcatcag    480

ctccgcctac ctcttcagcc cgcgcagcga gtccgccacg gcacccogac gcgtcaccat    540

cggcgagcgc atgctgcgtg acctctccga cgccatcggc cgcctgaggc ggagcctggt    600

gagcagggtg aacgtgttcg tggcgaggat catcgaagag cacaggcaga agaagaagga    660

cgacgtcgcc aacaatggcg agtcggccgc cggagacttc gtcgacgtct tgctcggact    720

ggagggcgag gagaagctgt cggactccga catgatcgct gtcctctggg agatgatctt    780

tcgagggacc gacacggtgg cgatcctgct ggagtgggtg atggcgcgga tggtgctgca    840

cccggggatc cagtccaagg cgcaggcgga gctggacgcc gtcgtgggcc gcggcggcgc    900

cgtctccgac gccgacgtgt cccggctgcc ctacctgcag cgcgtcgtga aggagacgct    960

ccgcgtgcac ccgccgggcc cgctgctgtc gtgggcgcgc ctcgccgtgc acgacgcggt   1020

ggtcggcggc cacctcgtcc cggcgggcac cacggccatg gtcaacatgt gggccatcgc   1080

gcgcgacccc gcggtgtggg cggaccccac cgcgttccgg cccgagcggt tcgaggagga   1140

ggacgtgagc gtgctgggcg gggacctccg gctcgcgccg ttcggcgccg ggcggcgcgt   1200

gtgccccggc aagacgctgg cgctcgccac cgtccacctc tggctcgcgc agctgctgca   1260

ccgcttccag tgggcgccgg cagacggcgg cgtcgacctg gcggagcgcc tcggcatgtc   1320

gctggagatg gagaagccgc tcgtgtgcaa gcccacgccg aggtggtgat ccctgaaagc   1380

acaaccgagt tccaatgcat gatcatgtta ctattactag cgtttcatta cgccgcataa   1440

tttgtttctt ctgagtcgag tggatcggtg ttcaatctgc ataagtggtt ttgtctatgt   1500

tattgtttct gtttgtgatt gatgggatta ggtgaagagt gttcacagtg ctccatttgt   1560

taggagtacc agaaatatgt gaaaaacgcc tgatgagaaa cta                     1603
```

<210> SEQ ID NO 28
<211> LENGTH: 1647
<212> TYPE: DNA
<213> ORGANISM: Oryza sativa

<400> SEQUENCE: 28

```
atggatgcca ctctcggcgc ctccactacc catggctacc tcctcctcct cccggccaac     60
```

```
tccaccacct tcttctcccc gctcctcgct gccctcctcg ccgtcacctc gctgctctgg    120
ctcgtcccgg gcggccccgc gtgggcgctc tcccgctgcc gccggccccc gcccggcgcg    180
ccgggcgcgc tcgccgcgct cgccggcccc gccgcgcacc gcgcgctcgc ggccatgtcg    240
aggtccgtgc ctggcggcgc cgccctggcg tccttctccg tcggcctcac gcgtttcgtc    300
gtggccagcc gccccgacac ggcgcgggag ctcctgtcca gcgccgcgtt cgccgaccgc    360
cccgtgaagg acgcggcgcg gggtttgctc ttccaccgcg ccatggggtt cgcgccctcc    420
ggcgactact ggcgcgcgct ccgccgcgtc agcgccaacc acctcttcac ccctcgccgc    480
gtcgccgcct cggccccgcg acgcctcgcc atcggcgagc gcatgctaga ccgcctgtcc    540
gccctcgccg gcggcgagat cggcatgagg cgcgtgctcc acgcggcgtc cctggaccac    600
gtcatggaca ccgtcttcgg gacgcgctac gacggcgaca gccaggaggg cgccgagctc    660
gaggccatgg tgaaggaagg gtacgacctc ctcgggatgt tcaactgggg agaccacctg    720
ccgctgctca aatggctcga cctgcaaggc gtgaggagga ggtgcaggac gctggtgcaa    780
cgagtcgacg tgttcgtccg aagcatcatc gacgagcaca ggcagaggaa gcgccgcacc    840
ggcggcaatg gcggaggcga ggagctcccc ggcgacttcg tcgacgtgtt gctcgggttg    900
caggggggagg agaagatgac ggagtccgac atggtcgccg ttctctgggt aaccaaggat    960
ccatctgaca tgcatgcatc tattcgatcg atcttgtgca ttgcgatcaa cggattcatg   1020
gatatatttg atcttgcgcg cgtgcaggag atgatctttc gggggacgga cacggtggcg   1080
attctgctgg aatggatcat ggcgaggatg gtgctgcacc cggacatcca ggcgaaggcg   1140
caggcggagc tcgacgccgt cgtcggccgc gggcgcgccg tgtcggacgg cgacgtcgcc   1200
ggcctgcgct acctccagtg cgtcgtgaag gaggcgctcc gcgtgcaccc gccgggcccg   1260
ctcctgtcgt gggcgcgcct cgccgtgcgc gacgcgcacg tcggcggcca cgtggtcccc   1320
gcgggcacca cggccatggt caacatgtgg gccatcgcgc acgacccgga gctctggccg   1380
gagcccgacg agttccggcc ggagcggttc gcggaggagg acgtcagcgt gctcggcggc   1440
gacctccgcc tcgcgccgtt cggcgcgggg cggcgcgcct gcccgggcaa gacgctcgcg   1500
ctcgccaccg tccacctctg gctcgcgcag ctgctgcacc gcttcgagtg ggcaccggtc   1560
ggcggcggcg tccacttgtt ggagcgcctg aacatgtcgc tggagatgga gaagcctctc   1620
gtgtgcaagg ctaaacctag gtggtga                                       1647
```

<210> SEQ ID NO 29
<211> LENGTH: 1905
<212> TYPE: DNA
<213> ORGANISM: Glycine max

<400> SEQUENCE: 29

```
cattagtatc atcttccctc gtatacttcc cctcctcaac tttgttttgt ttttcatgta     60
cgctttttga atcatcttac gtgctcctaa tcatgattcc aacacttgtt tgtattggca    120
caacaatatt ccaaagcacc ctctcttctt actcattgtc tttcatctct ctttttctct    180
ccacgtcact cgcccttctt gctatttccc tcaactattg gcttgtcccc ggaggttttg    240
catggaggaa atatcacagt cgttacaaag gccatgcaaa agtctctggc ccaatgggct    300
ggcccatatt gggaacttta cctgcgatgg gccctctagc ccacaggaaa cttgctgcca    360
tggccacttc accaaaagca aaaaagctca tgacattgag tctaggaaca aatccagttg    420
ttatcagcag tcacccagaa accgcaagag aaattctttg tgggtcgaac ttcgctgacc    480
```

```
gacccgttaa agaatcggcc cgaatgctca tgtttgagcg tgccattgga tttgctccat    540
atgggactta ttggcgccac ctacgtaaag tggcaatcac ccacatgttc tctccaagga    600
ggatttctga cttggagagt ctccgacaac atgtggttgg tgaaatggtg atgaggatat    660
ggaaggagat gggggacaaa ggggtggtag aggttcgagg catattgtat gaagggtctt    720
tgagccacat gttggagtgt gtgtttggta ttaataattc tctaggatca caaacaaagg    780
aggcgttggg tgatatggtt gaggaagggt atgacttgat tgccaagttt aattgggcag    840
actattttcc tttcgggttt ttggactttc acggggtcaa gagaaggtgt cacaaattgg    900
caactaaggt caatagtgtg gtgggtaaaa ttgtggaaga aagaaaaaat tcagggaagt    960
acgttggaca aaatgatttt cttagtgcct tgttattgtt gcctaaagag gaaagcatag   1020
gtgattcaga tgtagtggct atcttatggg aaatgatatt tcggggaaca gacacaattg   1080
ctatactttt agaatggatc atggccatga tggttttaca ccaagacgta caaatgaaag   1140
ctcgtcaaga gatcgactca tgcatcaagc aaaacggtta catgcgagac tcagacattc   1200
caaacctccc ttacctccag gccatagtga aggaggttct ccgattgcac ccaccaggcc   1260
cattactttc ctgggctcgc ctcgcaatcc atgatgtcca cgtggacaag gtcatcgtgc   1320
cagctggcac aactgcaatg gttaacatgt gggctatatc acatgactca tccatttggg   1380
aggacccgtg ggcctttaag cccgaaagat tcatgaaaga agatgtgtcg atcatggggt   1440
cggacatgag acttgcacca tttggtgcag gacgtagggt gtgcccagga aaaacattag   1500
gcttagccac agttcatcta tggcttgcac aacttcttca ccatttcata tggattccag   1560
tgcaacccgt ggatctttca gaatgcctaa agctctcgct cgaaatgaaa aagcctttac   1620
gatgccaagt gattcgcagg ttcaacacca taagctcttg aactcaacaa gataaattaa   1680
tgcacaataa aggatatcat tatcgatgta actgttgtga taaaaaaaaa ttaaagtctt   1740
tgatttgggt ggaagttatg taatgttgta aaaatatatc aagtatgtag tatgcgttga   1800
gctcaagata gtccaagaaa tgggctaatg aatggattga tactatctct ctttgaaagt   1860
acaccacgta caatattgga tctaataaag tcgcatggtt tttgt                   1905
```

<210> SEQ ID NO 30
<211> LENGTH: 1894
<212> TYPE: DNA
<213> ORGANISM: Zea mays

<400> SEQUENCE: 30

```
ggagagatca gctgagagct ggtgggtgct tcccatgacc ttgataccgg ccatctccgg     60
cgagcaacac ggtaacatgg caaccgtagc cactagcttc gcctacctcg ccatcttcgc    120
atgcctcgca tgggtgggcg cgtccctgct ctactgggct cacccaggcg gccctgcgtg    180
gggcaagtac tggagggcga gggggaagaa gccgtcggcg gcgatcccgg ggcctaaggg    240
gctcccggtg gtcggcagcc tcggcctcat gtccgggctg gcgcaccgct cgctggccga    300
cgaggcgtcg cgccgcccgg gggccaagcg gctcatggcg ctgtcgctcg gccccgtccg    360
cgcggtcgtc acgtcccacc cggacgtggc caaggagatc cttgatagcc cggcgttcgc    420
cgcccgcccc ctgaaccacg ccgcgtacgg cctcatgttc caccgctcca tcggcttcgc    480
cgagcacggc ccgtactggc gcgcgctccg gcgcgtcgcc gcgggccacc tgttcggccc    540
gaggcaggtc gaagccttcg cgccgtaccg cgcggccgtc gccgagggca tcgtcgcggc    600
cctgctgcgc gccggctccg gcggcgccgt cgtccaggtg cgcggcctcc tgcggcgggc    660
gtcgctctac tacatcatgc ggttcgtgtt cggcaaggag tacgacgtgt cacgcgtggt    720
```

```
gccgccgtcc ggcggggagg aggtggagga gctgctcgag atggtgcacg aggggtacga    780
gctcctgggc atggagaacc tgtgcgacta cttcccgggg ctcgccgccc tcgacccgca    840
gggcgtgggc gcacgatgcg ccgagctcat gccgcgggtg aaccggttcg tgcacggcgt    900
catccaggag caccgtgcca aggcggtcgc cggtggagac gcgcgtgact tcgtcgacat    960
cttgctctcc ctgcaggaga gtgaggggct cgccgacgcc gacatagcct ctgtgctctg   1020
ggagatgatc ttcagaggaa cggacgccat ggcggtgctc atggagtgga ccctagctcg   1080
cctcgtcctc caccgcgacg tccaagccaa ggcgcaccgt gagctcgaca aggtcgtcgg   1140
cgcggacagc cagaccaccg agtccgcggc gccgtacctg caggcgttgc taaaggaggc   1200
tctccggatg cacccgccgg ggcccctcct gtcgtggcgc cacagggcca tatccgacac   1260
gtacgtcgac ggccacctcg tcccggcggg caccacggcc atggtgaacc agtgggccat   1320
cagccgcgac cccgaggtgt gggacgcgcc gctcgagttc cggcccgagc ggttcctccc   1380
cggcggcgag ggccaggacg tgtccgtgct cggcgccgac ggccgcctcg tgccgttcgg   1440
gtccggcagg aggagctgcc ccggaaagtc cctggccatg accaccgtga cctcctggat   1500
ggccacgctg ctgcacgagt tcgagtggct gccagcgtca gacgacacag gcgacgtcga   1560
cctctcggag gtgctccgtc tgtcctgcga gatggcagtg ccgctggagg tccgcgtgcg   1620
cccgaggagc agcgtgtgaa tgaagtgctg cctgccgata gccatgacac acccccattg   1680
tgcaatgtgt agcagtgagc ctaagcgttc tgttagtgaa ctgtgaataa gcagctggtg   1740
aggactgtgc acaccagctc agctcagcct ttggttcagg gtttcaactt gcccgtgtat   1800
atcgtatatt tagtgtgacc gtgagtatta agttatccgc aaaaggtgta caaatcacaa   1860
aagctatcga atgaagattg tgtgaagtgg tgtc                               1894
```

<210> SEQ ID NO 31
<211> LENGTH: 1914
<212> TYPE: DNA
<213> ORGANISM: Glycine max

<400> SEQUENCE: 31

```
tttcgataaa caccattttt tctcttcctc ttttgaccaa acatgaaacc cacggcaaca     60
ttcttctttc tcctatccac aacaacactc cttgtttgtc tttgcctcgg aacaacaacg    120
ttccaaacca ctctctttat aaccttcttc actatttccc ttaactactg gcttgtccct    180
ggaggctttg catggagaaa ctatcactct tatcacacca acgaaaaacc aaacaaaaaa    240
cttactgggc ctatgggctg gcccatactt gggtctctgc ctctcatggg ctctttagcc    300
caccaaaaac tcgctgcctt agccgcgacg ttaaacgcga agaggttaat ggcactgagt    360
ctgggaccca ctcccgttgt tataagcagc caccccgaga ccgccagaga aatcttactc    420
ggttcctcgt tttcggatcg tccgataaaa gaatccgcac gcgctctcat gttcgagcgt    480
gccattggct tcgctccatc cggaacctac tggcgacacc tacgtaggat cgcggcgttc    540
cacatgttct ctccgaggag gattcagggc ctggagggtc tccgacagcg cgtgggtgac    600
gacatggtga agagcgcgtg gaaggagatg gagatgaaag gcgtggtgga ggttcgcggt    660
gtgtttcagg aagggtctct ttgtaatatt ctggaaagtg tttttgggag taatgataag    720
agtgaggagt tgggggatat ggttagggaa gggtacgagc tgattgcgat gttgaacttg    780
gaggattatt ttcctttgaa gtttttggac tttcatgggg tgaagagaag gtgccacaag    840
ttggcggcta aggttggtag cgtggtgggg caaattgtgg aggatcgaaa aagagaaggg    900
```

```
agttttgttg tcaagaatga ttttcttagc actttgctat ccttgcccaa agaagaaagg    960
ttggctgatt cagatatggc ggctattttg tgggaaatgg tgtttcgagg aacagacaca   1020
gttgcaatac tccttgaatg ggtcatggcc aggatggttt tacaccaaga cgtacaaaag   1080
aaagcccgcg aagaaatcga cacgtgcatc ggccaaaaca gtcacgtgcg agactcggat   1140
attgcaaatc tcccatacct ccaggctata gtaaaagaag ttctccggct gcacccaccc   1200
ggcccactcc tatcatgggc ccgtcttgca gtcaatgatg tccacgttga caaagttctt   1260
gtgccagctg gtacaacagc aatggttaac atgtgggcca tatcacatga ctcatccatc   1320
tgggaagacc catgggcttt caagcccgag aggttcctca aagaagatgt ttctatcatg   1380
ggatcggact tgaggcttgc acccttcggg gctggacgta gggtgtgtcc gggccgggcc   1440
ttgggtttgg ccacgaccca tctctggctc gcgcaacttc ttcgccactt catatggctt   1500
cccgcgcaac ccgtggatct ttcggagtgt cttaggcttt ccatggaaat gaagacacct   1560
ctgcgatgtc tagttgttcg tagataaaaa atataataac gtaagccttt tagctgaact   1620
atgtttgatg tgcaattata gaatgatcga gcttgtatct gatgtttgat gttaaagatg   1680
gtactcaaat atttagtgaa atatttagag atgagttatc gtataattat ggaacttatc   1740
tctaagcttt atttcacttt atttttaagg gtatcaaatt attaaaataa atatctagtg   1800
ccaggactag aggtggatgt aagaaaagat tggatcgatt aagaaggttt tatgtctctt   1860
taaatcgtaa aatgtaaatt gctgtaatgt aatgaagttg cttccgtacg tatg         1914
```

<210> SEQ ID NO 32
<211> LENGTH: 1310
<212> TYPE: DNA
<213> ORGANISM: Sorghum bicolor

<400> SEQUENCE: 32

```
atggacttca ccgacgtcct gctctccctc aacggcgacg acaagctctc cgacgccgac     60
atgatcgccg tcctctggga gatgatcttc cgaggcacgg acacggtggc ggtgctgatc    120
gagtgggtgc tggcacgtct ggtgctgcac caggacgtgc agcgcaaggt gcacgacgag    180
ctggaccggg tggtcgggcc gggcgaggcc gtgacggagt cggacaccgc ctcactggtg    240
tacctgcagg cggtcatcaa ggaagtgctg cgcctgcacc cgccgggccc actgctgtcc    300
tgggcgcggc tggccacgtc ggacgtgaac gtcggcgggc acctggtccc cgcgggcacc    360
accgccatgg tgaacatgtg ggccataacc cacgacgcca gcgtgtggcc tgagccgacg    420
gagttcaggc ccgagaggtt cgtcgccgcc gccggcggcg aggacgtcgt cccgataatg    480
ggttcggacc tccggctcgc gccgttcggg tccggcaggc ggagctgccc cgggaagtcg    540
ctcgcggtgg ccaccgtcgg gttctgggtc gccaccctgc tgcacgagtt cgaatggttg    600
ccgtgcggcg gcggcggcgg cgtggacctg tccgaagtgc tgaggctgtc gtgtgagatg    660
gccgcgccgc tggaggcgag ggtggtgcca cgtcgtcacg cggtgtgatg atgacgaggc    720
agctgagaca cacgtggacg tggctgggga gaggggacgg agtggctagc ttcttctact    780
actactacct taccaccttc tagcagaacg taacgtacgt ggccccggac gacgatcgat    840
gagcgagatg cgtaaaaaaa aaatcgccca agtgccatgc tttagagctg atgctggtgt    900
ggacttccag taatttcctg tgtatgatgg taggtgctgg tggaaggact acgtagtaac    960
caccagccgg tttgatgctt aattatgtgt gtgtgtgtgt gtgtgtgtgt gtgtgtgtgt   1020
gtgtgtgtgt gtgtgtgtgt gtgtgtgtgt gtgtgtgtgt gtgtgtgtgt gtgtgtgtgt   1080
gtgtgtaatg taacttacta gctgctgctg ctgcatgtaa tatctgcctg ctgttagtcg   1140
```

```
actactaggt agtgtagtgt accagatgat gagtgtgaca gttatctttt ccttttcagt   1200

aatgcgtagc tagctagagc tagatgtgta ttattgtgta ataataatcc tatgtgtgta   1260

tatatctctc tatagtttct atcctaatgc aagcgtgcgt gtgtgtacgt              1310


<210> SEQ ID NO 33
<211> LENGTH: 1852
<212> TYPE: DNA
<213> ORGANISM: Glycine max

<400> SEQUENCE: 33

atgaaaccca cggcaacatt cttctttctc cttccttcaa caacactcgt tgtttgtctt     60

tgccttggaa ttggaacaac caccctcttt ataaccctcc tcgcaatttc ccttaactac    120

tggcttgtcc ctggaggctt tgcatggaga aactatgact attatcaaac caaaaaaaaa    180

cttactgggc ctatgggctg gcccatactc gggactctgc ctctcatggg ctctttagct    240

caccaaaaac ttgcggcttt agccacttcg ctgaacgcaa agaggttaat ggcgctgagt    300

ctgggcccca ctcccgttgt tataagcagc caccccgaga ccgctagaga aatcttgttg    360

ggttcatcgt tttcggatcg tccgataaaa gaatcggcac gcgctctcat gttcgagcgt    420

gccattggtt tcgctcattc aggaacctac tggcggcacc tacgtaggat cgcggcgttt    480

catatgttct ctccgaggag gattcatggc ttggagggtc tccgacaacg cgtaggtgac    540

gacatggtga agagcgcgtg gagggagatg gggagaaagg gggtggtgga ggttcggagg    600

gtatttcagg aagggtcact ttgtaatatt ttggagagtg tttttggaag taacgataag    660

agtgaggagt tgagggatat ggttagggaa gggtacgagt tgattgcgat gtttaacttg    720

gaggattatt ttcccttcaa gtttttggat tttcatgggg tgaagagaag gtgccacaag    780

ttggcggcta aggttggtag tgtggtgggc caaattgtgg aggaacgaaa aagagatggt    840

ggttttgttg ggaagaatga ttttcttagc actttgctat ccttgcccaa agaagaaaga    900

ttggctgatt cagatctggt ggctattctg tgggaaatgg tatttcgagg aacagacaca    960

gttgcaatac tccttgaatg ggttatggca aggatggttt tacaccaaga cttacaaaag   1020

aaagcccgcg aagaaatcga cacgtgcgtc ggccaaaaca gtcacgtgcg agactcggat   1080

attgcgaatc tcccttacct ccaggccata gtgaaagaag ttctccggct gcacccacca   1140

ggcccgctac tatcatgggc tcgccttgcg gtccatgatg tccatgcgga caaagtcctc   1200

gtgccagctg gcacaacagc aatggttaac atgtgggcca tttcgcatga ctcgtccatc   1260

tgggaagacc catgggcttt caagcccgag aggttcctca aagaagatgt ttccatcatg   1320

ggatcggact tgaggcttgc acccttcggg gctggacgta gggtgtgtcc gggccgggcc   1380

ttgggcttgg ccacggccca tctctggctc gcgcaacttc ttcgccactt catatggctt   1440

cccgcacaaa ccgtggatct ttccgaatgc cttaggcttt ccatggaaat gaagacacct   1500

ctgcgatgcc tagtggttcg tagataaata aataaaaaat cgtaagccct tgaaccgaac   1560

catgtttaat gtgcaattag gatgatcgag ctttgtatct gttgtttgat gttaaatttg   1620

gtactcaaat atctagtgaa atatttagag atgagtttat cgtataatta gggagcttat   1680

ctctaagttt tatttcactt tatttttaaa gggtatcaaa ttattaaaat aaatatctag   1740

tgccagttga ctagaggtgg gtgtaagaag agagtggctt aagaaggctt tatgtatctt   1800

taaattgtaa aatgtaaatt actgtaatgt aatgcatgca tttttcttct tg            1852


<210> SEQ ID NO 34
```

<211> LENGTH: 1554
<212> TYPE: DNA
<213> ORGANISM: Sorghum bicolor

<400> SEQUENCE: 34

```
atggtgctca ccatggccac cggccaagag gactccctcc tcctgctcct cctccccacc     60
acctccccac tcccgcccct catggccgtg ttcatcctag ccgccgtcct cctgtggctc    120
tcccccggtg gtcctgcgtg ggcgctctcc cgctgccgcc gcccgccgtc cggcccaacg    180
ggcgtggtca ccgcgctctc aagccccgtg gcgcaccgca ccctggcggc gctgtcccac    240
gccgtagacg gcggcaaagc actgatggcc ttctcggtcg ggctcacccg cctcgtcgtg    300
tcgagccagc ccgacacggc gcgagagatc ctcgtcaacc ccgcgttcag cgaccgcccc    360
atcaaggacg cggctcgcca cctgctcttc caccgcgcca tgggcttcgc gccctccgga    420
gacgcgcact ggcgcgggct ccgccgcctc gccgccaacc acctgttcgg cccgcgccgc    480
gtggcggcgg ccgcgcacca ccgcgtctcc atcggcgagg ccatggtcgc cgacgtcgcc    540
gctgccatgg cccgccacgg cgaggtctcc ctgaagcgcg tgctgcatat cgcgtctctc    600
aaccacatca tggccaccgt cttcggcaag cactacgaca tggacagcca agagggcgtc    660
cttctggaag agatggtcac cgagggctac gacctcctgg gcacgttcaa ctgggctgac    720
cacctgccgt tgatcaagca tctcgacctc cagggcgtgc gccgccggtg caacaggtta    780
gtccaaaagg ttgaagtgtt cgttggaaag atcatccagg agcacagggc gaggcgcgcg    840
aatggaggag tcgacgatga gtacatgggt gacttcgtcg acgtccttct tgacctcgag    900
ggagaggaga agctgtccga atccgacatg atcgctgttc tttgggagat gatcttcaga    960
ggcgccgaca ctgtggcgat cttgatggag tggatcatgg cgaggatggc gctgcaccct   1020
gaaatccagt ccaaggccca ggcggagctg gacggcgtcg tcgtgggcgg cgtggcggac   1080
gccgacgtgg gcaacctccc ctacatccag tgcatcgtga aggagacgct gcggatgcac   1140
cctccgggcc cgctcctgtc gtgggcgcgc ctcgccatcc acgacgcgca cgtcggcggc   1200
cacctggtcc ccgccggcac cacggccatg gtgaacatgt ggtccatcgc gcatgacccc   1260
gccatctggg cagagccgga gaagttccgc cccgagcgct tccaggagga ggacgtgagc   1320
gtcctcggga gcgacctccg cctggccccg ttcggcgccg gacgccgcgt ctgccccggc   1380
aagatgctgg ccctcgccac cacacacctc tggatcgccc agctgctgca cgagttcgag   1440
tgggcacccg cggccgccaa cggcggcgtc gacctgtccg agcgcctcaa catgtcgctg   1500
gagatggcca cgccgctggt gtgcaaggcc gtccccaggg cccagctggc ctaa          1554
```

<210> SEQ ID NO 35
<211> LENGTH: 1882
<212> TYPE: DNA
<213> ORGANISM: Sorghum bicolor

<400> SEQUENCE: 35

```
cgcaacgcaa cagctagcag caagctctga aagtcgcaat ggagagctca gttgagagct     60
ggtgggtgct tcccatgacc ttgatcccgg ccatctccgg ccagcagcac gagaacatgg    120
ccaccatagc cactagcttc gtctacctcg ccatcttcgc atgccttgca tgggcaggcg    180
cgtccctgct ctactgggct cacccaggcg gccctgcgtg gggcaagtac tggagggcga    240
aggggaagcc gtcgtcgacg atcccggggc ccaaggggct cccggtcgtc ggcagcctcg    300
gcctcatgtc cgggctggcg cactgctcgc tggccgacga ggcgtcgcgc cggccggggg    360
ccaagcggct catggcgctg tcgctcggcc ccgtccgcgc ggtggtcacg tcccacccgg    420
```

```
acgtggccaa ggagatcctc gacaacccgg cgttcgccga ccgccccctc aaccacgccg    480

cgtacggcct catgttccac cgctccatcg gcttcgccga gcacggcccg tactggcgcg    540

cgctccggcg cgtcgccgcg ggacacctgt tcggcccgag gcaggtcgag gccttcgcgc    600

cgtaccgtgc cgccgtcggg gaagggatcg tcgcggccct gcacggcgcc ggcggcggcg    660

tcgtccaggt gcgcggcctc ctgcgccgag cttcgctcta ctacatcatg cggttcgtgt    720

tcggcaagga gtacgacgtg tcgcgcgccg tgccggcgtc cgggaaggag gaggtggagg    780

agctgctcga gatggtgcac gaggggtacg agctcctggg catggagaac tggtgcgact    840

acttcccggg gctcgccgcc ctcgacccgc agggcgtcgg agcacggtgc gccgagctca    900

tgccacgggt gaaccggttc gtgcatggca tcatccagga gcgccgtgcc aaggcgatcg    960

ccggaggaga cgcgcgtgac ttcgttgaca tcttgctctc cctgcaggag agcgagaggc   1020

tcgccgacgc cgacatagcc gctgtgctct gggagatgat cttcagagga acggacgcca   1080

tggccgtgct catggagtgg accctagctc gcctcgtcct ccaccgtgac gtccaagcca   1140

aggcgcaccg tgagctcgac gaggtcgtcg gcgggaacag ccaggtcgtc accgagtcgg   1200

cagcggcgcc gtcgctgcct tacctgcagg cgttgctaaa ggaggctctc cggatgcacc   1260

cgccggggcc cctcctgtcg tggcgccaca gggcgatatc cgacacgtac gtcgacgggc   1320

acctcgtccc ggcaggcacc accgccatgg tgaaccagtg ggcaatcagc cgcgaccccg   1380

aggtgtggga cgcgccgctc gagttccggc ccgagcggtt cctccctggc ggcgagggcc   1440

aggacgtgtc cgtgctcggc gccgacggcc gcctcgtgcc gttcgggtcc ggtcggagga   1500

gctgccccgg caagtccctg gctatgacca ccgtgaccac ctggatggcc accctgctga   1560

acgagttcga gtggctgccg gcgtcagacg atacaggcgg cgacgtcgac ctctcggagg   1620

tgctccgtct gtcctgcgag atggctgtgc cgctggaggt ccgcgtgcgc ccgaggagcg   1680

gcatgtgaat gaagtatctg ccgatagcca tggcaccccc attgtgcaat gtgtagcagt   1740

aaccctaagc gttgtgttag taaactgtga ataagcagca gctggtgagg actgtgcata   1800

ccagctcagc tcagttcagt atttggttca gggtttcaac ttgcctatgt atcatatata   1860

tagtgtgacc gtgagtacaa gt                                            1882
```

<210> SEQ ID NO 36
<211> LENGTH: 2085
<212> TYPE: DNA
<213> ORGANISM: Sorghum bicolor

<400> SEQUENCE: 36

```
gtgcccactt cttccaactt ataatccaag caaccaacta tagctcaaca catctctcct     60

tgtgttctca tctatagcca tctaagtagc aattgcatta gcaaccatag tagcacctgc    120

tatgcactag tcagtaatca gtaccacaca tagtttacac acacacaaca cacacaaacg    180

cacacacaaa aaagacttta cacacttagg ttaactatac atatagccat gaagactgaa    240

gtaatcacca ccatgatctc cttggtcttc ctcgtgcatt tcgctatcac catcagccct    300

aacgcacaac cttcatggct cttctctctc atgtctctct cccttgccgt ggtggcggtc    360

atagtgccat tagtagtcac caccacttgc catgcacgta agaataccga cgctaccacc    420

accatcccgg ggccacgagg gtggccgctg gtaggctccc tgctggtcgt gtcgggccca    480

ctcatgcacc gtcgcctagc cgcgctggcc gacgcgcata gcgcacgtcg cctcatgtcg    540

ctcaccctcg gtgccacccc cgtggtgatc agcagccacc cagaaacggc gcgagacatc    600
```

```
ctctcaggtg ccgccttcgt ggaccgcccg cctaaggccg cagcccggga actcatgttt    660

tgccgtgcca tcgggtttgc cccactggg gagtattggc gtcgcctccg tcgcatcacg    720

ggcgctggca tgctctcccc gcgtcgcatg gccatgctca ggggtcttcg ctgccgtgtt    780

gccgacagca tgatccagcg tgtcgcggac cagatggaga ggtccgggga ggtggccatg    840

agagccttgc tccaaagggc ctccctagag agcatggtgg gtagcgtgct aggcctcgag    900

ggtgacgctg tttgtgagga gctgggtgag atggtgaggg aagggtatga gctcgtgggc    960

atgttcaacc tagaagacca ctactacaag acatcatggg gcccgttgat ggacctttgg   1020

ggggtgaggc ccatgtgcag ggagctggct gctatggtta gagggtattt tgggaagatc   1080

attcaggaga ggaggctggc aggggactgc cacgagaggg ccgacttgct tagctatatg   1140

ctttcacttc cagaggagga gaagttggag gactctgatg tgattgctgt gctgtgggag   1200

atgattttcc gtggcgtgga cgtcgtggcg attctcctgg agtgggccat ggcccgcatg   1260

tcactgcacc cagacatcca atccaaggcc caggaggaga tggacgcagc ggtgggcgtc   1320

cgtcgtcgtc gtgccatcac cgactccgac gtccccaacc ttgccttcct ccaatggatc   1380

ctcaaggaga cgctccggat gcacccgccg ggcccgctgc tctcctgggc gcgcctggcg   1440

gtgcaggacg cgcgggtggg caagcacgtg gtgccggcgg ggacgacggc catggtgaac   1500

atgtgggcca tctcgcacga cgaggccatc tggggagacc cctgggtgtt ccggccggag   1560

aggttcgcgg cggcggcggc cggggaggag gtgagcgtgc tcgggtccga cctcaggctg   1620

gcgccgttcg ggtccggccg gagggtgtgc cctggcagga tgatgggcct cgccaccgcg   1680

cagctctggc tcggacgcct cctgcaggag taccggtggc tgccgccgcc ggccaataag   1740

cccgtcgagc tcgccgagtg cctccgcctg tccatggaga tgaagacgcc cctcgtctgc   1800

cgcgcggttc ctcgtcgtcg cggaggacgg cctcctgctg cagcttgatg ggccactgtg   1860

atgatgagct ccttcggtgc tgtggccact gttgggcacc agtgtaaaat taaatccttg   1920

tgtgtttgcc tactactcgt ttacagtgtt gtttgtacgt acaatcaaag attattgtat   1980

gtatgtgatg tgatgtgatg tatctgtgcc cggccggcct atagctacgt ggctagacac   2040

atgagtatag tttgcactac tctgatatat atatatgtgt tatac                   2085
```

<210> SEQ ID NO 37
<211> LENGTH: 1500
<212> TYPE: DNA
<213> ORGANISM: Oryza sativa

<400> SEQUENCE: 37

```
atggcggtcg tcgccttgcc gccgcttctt gcgaaacgcc atggacatgc acgccgggtt      60

aatggcggcg gcgctgccat tcccgggccg cgggggtggc cgctgctggg gtcgctcccg     120

gtggtgtccg gtccgctcat gcaccgccgc ctcgccgcgc tggccgacgc gcacggcggc     180

ggcgcgcggc gcctgatgtc gctgacgctc ggcgcgacgc ccgtggtggt gagcagccac     240

ccggacacgg tgcgggagat cctcgccggc gccgcgttcc gcgaccgtcc cgccagggcc     300

gcggcgcggg agctcatgtt cctccgcgcc gtcggcttcg ccccggcctc cggagacgac     360

ggcggcgcct actggcgccg cctccgccgc gccgcgggcg cgggcatgct ctccccgcgc     420

cgcgccgccg cgctcgccgc gctgcgcgcc cgcgtcgcgc gccgcacgtc cgaggccgtg     480

tcccgcggca tggccgtgcc gcccggccgc gtcgccatgc gcgccctcct ccacgccgcc     540

tccctcgaca acatggttgg cagcgtgcta gggctcgaac accatgacca ccatggcggc     600

gtcatcagcg acatgggtga catggtgagg gaagggtacg agctggttgg caagttcaac     660
```

```
ctaggagact actacagtac tacacagtac cagtgcctgt gggggttgct ggatttccat    720
ggggtggggc ccaggtgtca gaggctggca gctagggtta gggagcagtt tgggagggtg    780
atggaggaga ggaggaaggt gagtgacctg cacaagaggg atgatcttct tagctacatg    840
ctctccatgc cacaggagga gaggattgag gactctgatg tcattgctgt cctctgggag    900
atgatctttc gtgggacaga tgtagttgca atactcctgg aatgggccat ggcccggatg    960
gtactccacc cagacatcca gtccaaggtg caagaagaac tagatagggc ggtgggccac   1020
cggcccatga ccgactcgga catccccaac cttcgcttcc tccattgtgt catcaaggaa   1080
accctccgca tgcacccgcc tggcccactt ctctcatggg cccgcttggc ggtgcatgat   1140
acctatgtgg gcaagcacct agtacccgca gggactacgg caatggtgaa tatgtgggcc   1200
atatcccatg atgagacgat atggggtgac ccatgggtgt ttcgacccga aaggtttatg   1260
gaagaggata tcaatgtgtt gggatcagat ttaaggttgg caccgtttgg atcaggtcgt   1320
cgggtgtgcc ctggacggat gatgggtctc tccactgcct atctatggtt tggccggatg   1380
ttgcaagagt ataagtgggc agcggctcag ccggttaaac ttacggagtg cctccgtctt   1440
tctatggaga tgaagaaacc tttggtttgt catgcagttc ctcgtagcaa aactggctaa   1500
```

<210> SEQ ID NO 38
<211> LENGTH: 1668
<212> TYPE: DNA
<213> ORGANISM: Oryza sativa

<400> SEQUENCE: 38

```
atggcaatgg ccaccgccac cgcctcctcc tgcgtcgacg ccacgtggtg ggcgtacgcc     60
ctcccggcgc tcctcggcgc cgacaccctc tgcgcccacc cggcgctgct cgccggcgcc    120
gtcctcctgg ccttcgccac cgccgcggtg ctcgcctggg ccgcgtcccc cggcgggccg    180
gcgtgggcgc acggccgcgg ccgcctcggc gcgacgccca tcgaggggcc ccgggggctc    240
cccgtgttcg gcagcatctt cgcgctctcc cggggcctcc cgcaccgcgc gctcgacgcg    300
atgtcgcgcg acgcggcggc gccacgggcg agggagctca tggcgttctc cgtcggggag    360
acgccggcgg tggtgtcgtc gtgcccggcg acggcgaggg aggtgctcgc gcacccgtcg    420
ttcgccgacc gcccgctgaa gcgctcggcg cgggagctgc tgttcgcgcg cgccatcggg    480
ttcgccccca gcggcgagta ctggcgcctc ctccgccgca tcgcctccac ccacctcttc    540
tcccctcgcc gcgtcgccgc gcacgagccg gggcgccagg ccgacgccac ggcgatgctg    600
tccgccatgg ccgccgagca gtccgccacc ggcgccgtcg tgctccgccc ccacctccag    660
gccgccgcgc tcaacaacat catgggcagc gtgttcggcc ggcgctacga cgtctcctcc    720
tcctccggcg ccgccgccga cgaggccgag cagctcaaga gcatggtgcg cgaggggttc    780
gagctcctcg gcgcgttcaa ctggtccgac cacctcccat ggctcgccca cctctacgac    840
cccaaccacg tcgcccgccg ctgcgccgcg ctcgtccccc gcgtccaggc gttcgtccgc    900
ggcgtcatcc gcgaccaccg cctccgccgc gactcctcct ccaccgccgc cgacaatgcc    960
gacttcgtcg acgtcctcct ctccctcgag gcccacgaga acctcgccga ggacgacatg   1020
gtcgccgtcc tctgggagat gatatttcgt gggacggaca cgacggcgtt ggtgacggag   1080
tggtgcatgg cggaggtggt gaggaacccg gcggtgcagg cgaggctgag ggcggaggtg   1140
gacgcggcgg tgggcggcga cgggtgtccc agcgacggcg acgtggcgcg gatgccgtac   1200
ctgcaggcgg tggtgaagga gacgctgagg gcgcacccgc cggggccgct gctgagctgg   1260
```

gcgcggctgg ccaccgccga cgtggggctc gccaacggca tggtggtgcc ggcgggcacg 1320
acggcgatgg tgaacatgtg ggccatcacc cacgacggcg aggtgtgggc cgacccggag 1380
gcgttcgcgc cggagcggtt catcccgtcg gagggcggcg ccgacgtcga cgtccgcggc 1440
ggcgacctcc gcctggcgcc gttcggcgcc gggcgccgcg tctgccccgg caagaacctc 1500
ggcctcgcca ccgtcaccct ctgggtcgcc cgcctcgtcc acgccttcga ctggttcctc 1560
cccgacggct cgccgccggt gtccctcgac gaggtcctca agctctccct cgagatgaag 1620
acccctctcg ccgccgccgc cacccccgc cgccgccgcg ccgcctga 1668

<210> SEQ ID NO 39
<211> LENGTH: 525
<212> TYPE: DNA
<213> ORGANISM: Sorghum bicolor

<400> SEQUENCE: 39
cgtgacggac gccgacgtgg cgaacctccc ctacgtgcag agcgtcgtga aggagacgct 60
gcgcatgcac ccgccagggc ccgctgctgt cgtgggcgcg cctggccatc cacgacgcgc 120
acgtcggcgg ccaccctggt ccccgccggc accacggcca tggtgaacat gtgggcgatc 180
gcgcacgacc ccgccatctg ggcggagccg gaggagttcc gccccgagcg gttccaggag 240
gaggaggagg acgtgagcgt cctcggcggc gacctccgcc tggccccctt cggtgccggc 300
cgccgcgtat gccccgacaa gatgctcgcc ctcgccacca cccacctctg ggtcgcccag 360
ctgctgcacc ggttcgagtg ggcccctgcg ggcgccgcca gcagcggcgg cggcggcgtc 420
gacctgtcgg agcgcctcaa catgtcgctg gagatggcca cgccgctggt gtgcaaggcc 480
gtgcccaggt cagcccccca gctgcatgca ggcctagcta gctaa 525

<210> SEQ ID NO 40
<211> LENGTH: 2076
<212> TYPE: DNA
<213> ORGANISM: Sorghum bicolor

<400> SEQUENCE: 40
atggcgatgg cctccgcagt ttcgtcgtgc acggacagca cgtggtgggt gtacgcgctc 60
ccgacgctgc tcggctcgga caccctgtgc gcccacccgg ccctcctggc cggcctgctc 120
ttcctgacca ccgtcacggc ggctctgctg gcgtgggccg cgtcgccggg agggcctgcg 180
tgggcgcacg gccgcggccg cctcggcgcc actcctatcg tgggtccccg gggtctcccc 240
gtgttcggca gcatcttcgc gctctcccgc ggtctgccgc accgtaccct cgccgcgatg 300
gcccgcgcgg cggggccccg ggccaaggag ctcatggcgt tctccgtcgg ggacacgccg 360
gcggtcgtgt cgtcgtgccc ggccacggcg cgtgaggtgc tcgcgcaccc gtccttcgcc 420
gaccgccccg tgaagcggtc ggcgcgggag ctcatgttcg cgcgcgccat cgggttcgcg 480
cccaacggcg agtactggcg ccgcctccgc cgcgtcgcgt ccacgcacct cttctccccg 540
cgccgcgtcg ccgcgcacga gccgggacgc cagggcgacg cggaggccat gctccgctcc 600
gtcgccgccg agcagtccgc ctcgggcacc gtcgtcctcc gcccgcacct ccaggccgcc 660
gctctcaaca acatcatggg cagcgtcttc ggcacgcgat acgacgtcac atccggcgcc 720
accgccggcg ccgcggaggc cgagcagctc aagagcatgg tgcgcgaggg gttcgagctc 780
ctcggcgcct tcaactggtc cgaccacctc ccctggctcg cccacctgta cgaccccagc 840
aacgtcaccc gccgctgcgc cgcgctcgtc ccgcgcgtcc agaccttcgt ccgtggcgtc 900
atcgacgagc accggcgccg ccgccaaaac tccgccgccc tcgacctcaa cgacaatgct 960

```
gacttcgtct acgtgctcct ctccctcgac ggcgacgaga agctccgcga cgacgacatg   1020

gtcgccatcc tctgggagat gatcttccgc ggtacggaca cgacggcgct tctgacggag   1080

tggtgcatgg cggagctggt gcgccacccg gcggtgcagg cgaggctgcg ggccgaggtg   1140

gacgcagctg tcggcgccgg cggtcgcccc accgacgccg acgtggcgcg catgccgtac   1200

ctgcaggcgg tcgtgaagga gacgctgcga gcgcacccgc ctggcccgct gctgagctgg   1260

gcgcgcctcg ccaccgccga cgtgcccctc tccaacggca tggtggtccc ggccggcacc   1320

acggcgatgg tgaacatgtg ggccatcacc cacgacgccg gcgtgtgggc cgacccggac   1380

gcgttcgcgc cggagcggtt cctgccctcc gagggcggcg ccgacgtgga cgtccgcggc   1440

gtcgacctcc gcctggcacc gttcggcgcc gggcgccgcg tctgccccgg caagaacctg   1500

gggctcacca ccgtgggcct ctgggtcgcc cgcctcgtgc acgccttcga gtgggcgctg   1560

cctgatggcg cgccgcccgt ctgcctcgac gaggtcctca agctctccct ggagatgaag   1620

acgccgctcg ccgccgcggc catcccgcgc accgcatgat ccatcctgcc gctgccgccg   1680

acgcgtgcaa caagaaccga ttatgctttg tcacgtcacg tcacgcgttc tttgtctgtg   1740

tgtgtgtggt tctaagctag tgtgcttctt cttgtcgatc gtcggttcgt tctcgtgcct   1800

gcctttgcct agggtttcgt ttcttgcaaa gtagtgacag tgtctccctt agagtcatca   1860

acggggctcc aattttggaa aggtgcgtgt taggagttaa cccctagaca tgtctgcgtc   1920

tcgatcacca cctactatgt cattatcagc gcagcaccta tatatagatc agtgtctgtc   1980

gatcagtcat ggaagtcgat cgtgtgctca agtctgctgt attatatata atgtattgta   2040

atgtgattat caagaaccgt gctatctata tgttgc                             2076
```

<210> SEQ ID NO 41
<211> LENGTH: 1937
<212> TYPE: DNA
<213> ORGANISM: Brachypodium distachyon

<400> SEQUENCE: 41

```
atggagagct cagtcgagag cagctggtgg gtgctgcccc tgaccttgat tcctgccatc     60

tccggccagc agcagcagca cgatcaaagc acggccgccg ccatagccac cagcttcgtc    120

tacctcgcca tcctcgcctg cctcgcctgg gcggccaagt ccctgctcta ctgggctcac    180

ccgggcgggc ctgcatgggg ccggcggtac tggacgagcc cgtgcgcgaa gacggctccg    240

gctccggcgc cgatccccgg gccgagaggg ctcccggtgg tgggcagcct gggcctgatg    300

tccggactag cccacagcac gctggccgcc gaggcggcaa ggacgccggg cgcgaagcgg    360

ctcatggcgc tgtctctcgg cccagtcccc gccgtcgtca cggcccaccc ggacgtggcc    420

aaggagatcc tcgacaaccc ggcgttcgcg gaccggcccg tgaaccacgc cgcctacggc    480

ctcatgttcc accgctccat cggcttcgcg gagcacggcc cctactggcg cgcgctccgg    540

cgcgtggcat cggcgcacct gttcgcgccc aggcaggtcg acgccttcgc cccttaccgc    600

gcgcgcgtcg gggaagacgt cgtggccgcg ctccgccatg ccgggggcgg cgtcgtgaac    660

gtgcgcggcg tgctccggcg cgcgtcgctc tactacatca tgcgcttcgt gttcgggaaa    720

gagtacgacg tgtcgtcgga ctcggggaag aaggatcagg gggaagtgga ggagctgctg    780

gagatggtgc atgagggtta tgagctgctg gggaaggaga actggtgcga ctacttcccg    840

gggctggcgg ggttcgaccc gcagggcgtc ggggcgcggt gcgccgagct catgccgcgg    900

gtgaaccgct tcgtgcacgg catcatcgat gagcaccgcg gcaaggcgat gatagccgga    960
```

```
ggagaaggag aggcgcagcc gctggacttt gtggacatac tgctttcgtt gcaggagagc   1020

gaggggctcg ccgacgccga catcgccgcc gtgctctggg agatgatctt cagaggaaca   1080

gacgccatgg cggtgctgat ggagtggacc atggcacgcc tcgtcctgca ccccggcgtc   1140

caagccaacg tgcacaagga gctggacgag gtggtcggca agagcagcca cgtcaccgag   1200

tcagccgtgc tctcactgcc ttacctgcag gcgctgctca aggaggcgct ccgcgtgcac   1260

ccgccggggc cgctgctgtc gtggcgccac agggccatgt gggacaccta cgtggacggc   1320

cacctggtcc cggcgggcac cacggccatg gtgaaccagt gggccatgag ccgggacccg   1380

gaggtttggg ccgagccgct cgagttccgg cccgaacggt tcctcccggg cggcgaggcc   1440

ggcccgggag tctccgtgct cggctcggac ggccggctcg tgccgttcgg gtctggacgg   1500

aggagctgcc ccgggaagaa cctggccatg accaccgtca cggcgtggat ggccacgctg   1560

atgcacgagt tcgagtggat gccggccaag accggcgccc ccgtcgacat gtcggaggtg   1620

ctccgcctgt catgcgagat ggcgacgccg ctccaggtcc gggtgcgccc caggcgcggc   1680

gtttgaaagt ctgaggctgc tttcgacggc catatatgac ttcaccgtgt agtttctttc   1740

ttactagccg tgaccctggg ttgtgcttcc tgtttgtgaa taagctggct gggatgaaca   1800

aaagtgtgca ccggctcagc ttcagtgttt ggttcagagt tttctttttg aacttcgtca   1860

gaagtatcat caggtgtgag cttgaggttc cacgttggtg tacagattgc aagaagaaaa   1920

tctataaagg attgtgc                                                  1937
```

<210> SEQ ID NO 42
<211> LENGTH: 530
<212> TYPE: PRT
<213> ORGANISM: Arabidopsis thaliana

<400> SEQUENCE: 42

```
Met Ala Thr Lys Leu Glu Ser Ser Leu Ile Phe Ala Leu Leu Ser Lys
1               5                   10                  15

Cys Ser Val Leu Ser Gln Thr Asn Leu Ala Phe Ser Leu Leu Ala Val
            20                  25                  30

Thr Ile Ile Trp Leu Ala Ile Ser Leu Phe Leu Trp Thr Tyr Pro Gly
        35                  40                  45

Gly Pro Ala Trp Gly Lys Tyr Leu Phe Gly Arg Leu Ile Ser Gly Ser
    50                  55                  60

Tyr Lys Thr Gly Asn Val Ile Pro Gly Pro Lys Gly Phe Pro Leu Val
65                  70                  75                  80

Gly Ser Met Ser Leu Met Ser Ser Thr Leu Ala His Arg Arg Ile Ala
                85                  90                  95

Asp Ala Ala Glu Lys Phe Gly Ala Lys Arg Leu Met Ala Phe Ser Leu
            100                 105                 110

Gly Glu Thr Arg Val Ile Val Thr Cys Asn Pro Asp Val Ala Lys Glu
        115                 120                 125

Ile Leu Asn Ser Pro Val Phe Ala Asp Arg Pro Val Lys Glu Ser Ala
    130                 135                 140

Tyr Ser Leu Met Phe Asn Arg Ala Ile Gly Phe Ala Pro His Gly Val
145                 150                 155                 160

Tyr Trp Arg Thr Leu Arg Arg Ile Ala Ser Asn His Leu Phe Ser Thr
                165                 170                 175

Lys Gln Ile Arg Arg Ala Glu Thr Gln Arg Arg Val Ile Ser Ser Gln
            180                 185                 190

Met Val Glu Phe Leu Glu Lys Gln Ser Ser Asn Glu Pro Cys Phe Val
```

```
        195                 200                 205

Arg Glu Leu Leu Lys Thr Ala Ser Leu Asn Asn Met Met Cys Ser Val
    210                 215                 220

Phe Gly Gln Glu Tyr Glu Leu Glu Lys Asn His Val Glu Leu Arg Glu
225                 230                 235                 240

Met Val Glu Glu Gly Tyr Asp Leu Leu Gly Thr Leu Asn Trp Thr Asp
                245                 250                 255

His Leu Pro Trp Leu Ser Glu Phe Asp Pro Gln Arg Leu Arg Ser Arg
            260                 265                 270

Cys Ser Thr Leu Val Pro Lys Val Asn Arg Phe Val Ser Arg Ile Ile
        275                 280                 285

Ser Glu His Arg Asn Gln Thr Gly Asp Leu Pro Arg Asp Phe Val Asp
    290                 295                 300

Val Leu Leu Ser Leu His Gly Ser Asp Lys Leu Ser Asp Pro Asp Ile
305                 310                 315                 320

Ile Ala Val Leu Trp Glu Met Ile Phe Arg Gly Thr Asp Thr Val Ala
                325                 330                 335

Val Leu Ile Glu Trp Ile Leu Ala Arg Met Val Leu His Pro Asp Met
            340                 345                 350

Gln Ser Thr Val Gln Asn Glu Leu Asp Gln Val Val Gly Lys Ser Arg
        355                 360                 365

Ala Leu Asp Glu Ser Asp Leu Ala Ser Leu Pro Tyr Leu Thr Ala Val
    370                 375                 380

Val Lys Glu Val Leu Arg Leu His Pro Pro Gly Pro Leu Leu Ser Trp
385                 390                 395                 400

Ala Arg Leu Ala Ile Thr Asp Thr Ile Val Asp Gly Arg Leu Val Pro
                405                 410                 415

Ala Gly Thr Thr Ala Met Val Asn Met Trp Ala Val Ser His Asp Pro
            420                 425                 430

His Val Trp Val Asp Pro Leu Glu Phe Lys Pro Glu Arg Phe Val Ala
        435                 440                 445

Lys Glu Gly Glu Val Glu Phe Ser Val Leu Gly Ser Asp Leu Arg Leu
    450                 455                 460

Ala Pro Phe Gly Ser Gly Arg Arg Ile Cys Pro Gly Lys Asn Leu Gly
465                 470                 475                 480

Phe Thr Thr Val Met Phe Trp Thr Ala Met Met Leu His Glu Phe Glu
                485                 490                 495

Trp Gly Pro Ser Asp Gly Asn Gly Val Asp Leu Ser Glu Lys Leu Arg
            500                 505                 510

Leu Ser Cys Glu Met Ala Asn Pro Leu Pro Ala Lys Leu Arg Arg Arg
        515                 520                 525

Arg Ser
    530


<210> SEQ ID NO 43
<211> LENGTH: 534
<212> TYPE: PRT
<213> ORGANISM: Arabidopsis thaliana

<400> SEQUENCE: 43

Met Ala Thr Lys Leu Asp Thr Ser Ser Leu Leu Leu Ala Leu Leu Ser
1               5                   10                  15

Lys Cys Ser Leu Leu Thr Gln Thr Asn Leu Ala Leu Ser Leu Leu Val
            20                  25                  30
```

```
Ala Ser Leu Ala Ser Leu Ala Leu Ser Leu Phe Phe Trp Ser His Pro
        35                  40                  45

Gly Gly Pro Ala Trp Gly Lys Tyr Phe Leu His Arg Arg Arg Gln Thr
    50                  55                  60

Thr Val Ile Pro Gly Pro Arg Gly Leu Pro Phe Val Gly Ser Met Ser
65                  70                  75                  80

Leu Met Ser Asn Thr Leu Ala His Arg Cys Ile Ala Ala Thr Ala Glu
                85                  90                  95

Lys Phe Arg Ala Glu Arg Leu Met Ala Phe Ser Leu Gly Glu Thr Arg
            100                 105                 110

Val Ile Val Thr Cys Asn Pro Asp Val Ala Lys Glu Ile Leu Asn Ser
        115                 120                 125

Pro Val Phe Ala Asp Arg Pro Val Lys Glu Ser Ala Tyr Ser Leu Met
    130                 135                 140

Phe Asn Arg Ala Ile Gly Phe Ala Pro Tyr Gly Val Tyr Trp Arg Thr
145                 150                 155                 160

Leu Arg Lys Ile Ala Ser Asn His Leu Phe Ser Pro Lys Gln Ile Lys
                165                 170                 175

Arg Ser Glu Thr Gln Arg Ser Val Ile Ala Asn Gln Ile Val Lys Cys
            180                 185                 190

Leu Thr Lys Gln Ser Asn Thr Lys Gly Leu Cys Phe Ala Arg Asp Leu
        195                 200                 205

Ile Lys Thr Ala Ser Leu Asn Asn Met Met Cys Ser Val Phe Gly Lys
    210                 215                 220

Glu Tyr Glu Leu Glu Glu Glu His Glu Glu Val Ser Glu Leu Arg Glu
225                 230                 235                 240

Leu Val Glu Glu Gly Tyr Asp Leu Leu Gly Thr Leu Asn Trp Thr Asp
                245                 250                 255

His Leu Pro Trp Leu Ser Glu Phe Asp Pro Gln Arg Ile Arg Ser Arg
            260                 265                 270

Cys Ser Asn Leu Val Pro Lys Val Asn Arg Phe Val Asn Arg Ile Ile
        275                 280                 285

Ser Asp His Arg Glu Gln Thr Arg Asp Ser Pro Ser Asp Phe Val Asp
    290                 295                 300

Val Leu Leu Ser Leu Asp Gly Pro Asp Lys Leu Ser Asp Pro Asp Ile
305                 310                 315                 320

Ile Ala Val Leu Trp Glu Met Ile Phe Arg Gly Thr Asp Thr Val Ala
                325                 330                 335

Val Leu Ile Glu Trp Ile Leu Ala Arg Met Val Leu His Pro Asp Ile
            340                 345                 350

Gln Ser Thr Val His Asn Glu Leu Asp Gln Ile Val Gly Arg Ser Arg
        355                 360                 365

Ala Val Glu Glu Ser Asp Val Val Ser Leu Val Tyr Leu Thr Ala Val
    370                 375                 380

Val Lys Glu Val Leu Arg Leu His Pro Pro Gly Pro Leu Leu Ser Trp
385                 390                 395                 400

Ala Arg Leu Ala Ile Thr Asp Thr Ile Ile Asp Gly Arg Arg Val Pro
                405                 410                 415

Ala Gly Thr Thr Ala Met Val Asn Met Trp Ala Ile Ala His Asp Pro
            420                 425                 430

His Val Trp Glu Asn Pro Leu Glu Phe Lys Pro Glu Arg Phe Val Ala
        435                 440                 445

Lys Glu Gly Glu Val Glu Phe Ser Val Leu Gly Ser Asp Leu Arg Leu
```

```
    450                 455                 460

Ala Pro Phe Gly Ser Gly Arg Arg Val Cys Pro Gly Lys Asn Leu Gly
465                 470                 475                 480

Leu Thr Thr Val Thr Phe Trp Thr Ala Thr Leu Leu His Glu Phe Glu
                485                 490                 495

Trp Leu Thr Pro Ser Asp Glu Lys Thr Val Asp Leu Ser Glu Lys Leu
            500                 505                 510

Arg Leu Ser Cys Glu Met Ala Asn Pro Leu Ala Ala Lys Leu Arg Pro
        515                 520                 525

Arg Arg Ser Phe Ser Val
    530


<210> SEQ ID NO 44
<211> LENGTH: 535
<212> TYPE: PRT
<213> ORGANISM: Arabidopsis thaliana

<400> SEQUENCE: 44

Met Arg Thr Glu Ile Glu Ser Leu Trp Val Phe Ala Leu Ala Ser Lys
1               5                   10                  15

Phe Asn Ile Tyr Met Gln Gln His Phe Ala Ser Leu Leu Val Ala Ile
            20                  25                  30

Ala Ile Thr Trp Phe Thr Ile Thr Ile Val Phe Trp Ser Thr Pro Gly
        35                  40                  45

Gly Pro Ala Trp Gly Lys Tyr Phe Phe Thr Arg Arg Phe Ile Ser Leu
    50                  55                  60

Asp Tyr Asn Arg Lys Tyr Lys Asn Leu Ile Pro Gly Pro Arg Gly Phe
65                  70                  75                  80

Pro Leu Val Gly Ser Met Ser Leu Arg Ser Ser His Val Ala His Gln
                85                  90                  95

Arg Ile Ala Ser Val Ala Glu Met Ser Asn Ala Lys Arg Leu Met Ala
            100                 105                 110

Phe Ser Leu Gly Asp Thr Lys Val Val Val Thr Cys His Pro Ala Val
        115                 120                 125

Ala Lys Glu Ile Leu Asn Ser Ser Val Phe Ala Asp Arg Pro Val Asp
    130                 135                 140

Glu Thr Ala Tyr Gly Leu Met Phe Asn Arg Ala Met Gly Phe Ala Pro
145                 150                 155                 160

Asn Gly Thr Tyr Trp Arg Thr Leu Arg Arg Leu Gly Ser Asn His Leu
                165                 170                 175

Phe Asn Pro Lys Gln Ile Lys Gln Ser Glu Asp Gln Arg Arg Val Ile
            180                 185                 190

Ala Thr Gln Met Val Asn Ala Phe Ala Arg Asn Pro Lys Ser Ala Cys
        195                 200                 205

Ala Val Arg Asp Leu Leu Lys Thr Ala Ser Leu Cys Asn Met Met Gly
    210                 215                 220

Leu Val Phe Gly Arg Glu Tyr Glu Leu Glu Ser Asn Asn Asn Leu Glu
225                 230                 235                 240

Ser Glu Cys Leu Lys Gly Leu Val Glu Glu Gly Tyr Asp Leu Leu Gly
                245                 250                 255

Thr Leu Asn Trp Thr Asp His Leu Pro Trp Leu Ala Gly Leu Asp Phe
            260                 265                 270

Gln Gln Ile Arg Phe Arg Cys Ser Gln Leu Val Pro Lys Val Asn Leu
        275                 280                 285
```

```
Leu Leu Ser Arg Ile Ile His Glu Gln Arg Ala Ala Thr Gly Asn Phe
    290                 295                 300

Leu Asp Met Leu Leu Ser Leu Gln Gly Ser Glu Lys Leu Ser Glu Ser
305                 310                 315                 320

Asp Met Val Ala Val Leu Trp Glu Met Ile Phe Arg Gly Thr Asp Thr
                325                 330                 335

Val Ala Val Leu Val Glu Trp Val Leu Ala Arg Ile Val Met His Pro
            340                 345                 350

Lys Val Gln Leu Thr Val His Asp Glu Leu Asp Arg Val Val Gly Arg
        355                 360                 365

Ser Arg Thr Val Asp Glu Ser Asp Leu Pro Ser Leu Thr Tyr Leu Thr
    370                 375                 380

Ala Met Ile Lys Glu Val Leu Arg Leu His Pro Pro Gly Pro Leu Leu
385                 390                 395                 400

Ser Trp Ala Arg Leu Ser Ile Thr Asp Thr Ser Val Asp Gly Tyr His
                405                 410                 415

Val Pro Ala Gly Thr Thr Ala Met Val Asn Met Trp Ala Ile Ala Arg
            420                 425                 430

Asp Pro His Val Trp Glu Asp Pro Leu Glu Phe Lys Pro Glu Arg Phe
        435                 440                 445

Val Ala Lys Glu Gly Glu Ala Glu Phe Ser Val Phe Gly Ser Asp Leu
    450                 455                 460

Arg Leu Ala Pro Phe Gly Ser Gly Lys Arg Val Cys Pro Gly Lys Asn
465                 470                 475                 480

Leu Gly Leu Thr Thr Val Ser Phe Trp Val Ala Thr Leu Leu His Glu
                485                 490                 495

Phe Glu Trp Leu Pro Ser Val Glu Ala Asn Pro Pro Asp Leu Ser Glu
            500                 505                 510

Val Leu Arg Leu Ser Cys Glu Met Ala Cys Pro Leu Ile Val Asn Val
        515                 520                 525

Ser Ser Arg Arg Lys Ile Met
    530                 535


<210> SEQ ID NO 45
<211> LENGTH: 536
<212> TYPE: PRT
<213> ORGANISM: Arabidopsis thaliana

<400> SEQUENCE: 45

Met Glu Leu Met Asn Leu Ala Ser Lys Glu Thr Ser Tyr Trp Met Ile
1               5                   10                  15

Ala Leu Pro Ala Gly Phe Gly Ser Gln Asn Leu His Asp Val Ser Thr
            20                  25                  30

Leu Gly Tyr Leu Phe Leu Ala Val Val Phe Leu Ser Ile Val Thr Trp
        35                  40                  45

Ala Leu Ala Gly Gly Gly Gly Val Ala Trp Lys Asn Gly Arg Asn Arg
    50                  55                  60

Leu Gly Arg Val Ala Ile Pro Gly Pro Arg Gly Ile Pro Val Phe Gly
65                  70                  75                  80

Ser Leu Phe Thr Leu Ser Arg Gly Leu Ala His Arg Thr Leu Ala Ala
                85                  90                  95

Met Ala Trp Ser Arg Ala Asn Thr Glu Ile Met Ala Phe Ser Leu Gly
            100                 105                 110

Ser Thr Pro Val Ile Val Ala Ser Glu Pro Asn Ile Ala Arg Glu Ile
        115                 120                 125
```

```
Leu Met Ser Pro His Phe Ala Asp Arg Pro Val Lys Gln Ser Ala Lys
    130                 135                 140

Ser Leu Met Phe Ser Arg Ala Ile Gly Phe Ala Pro Asn Gly Thr Tyr
145                 150                 155                 160

Trp Arg Met Leu Arg Arg Ile Ala Ser Thr His Leu Phe Ala Pro Arg
                165                 170                 175

Arg Ile Leu Ala His Glu Ala Gly Arg Gln Leu Asp Cys Ala Glu Met
            180                 185                 190

Val Lys Ala Val Ser Val Glu Gln Asn Gly Ala Gly Ser Val Val Leu
        195                 200                 205

Arg Lys His Leu Gln Leu Ala Ala Leu Asn Asn Ile Met Gly Ser Val
    210                 215                 220

Phe Gly Arg Arg Tyr Asp Pro Leu Ala Gln Lys Glu Asp Leu Asp Glu
225                 230                 235                 240

Leu Thr Ser Met Val Arg Glu Gly Phe Glu Leu Leu Gly Ala Phe Asn
                245                 250                 255

Trp Ser Asp Tyr Leu Pro Trp Leu Gly Tyr Phe Tyr Asp Ser Ile Arg
            260                 265                 270

Leu Asn Gln Arg Cys Ser Asp Leu Val Pro Arg Ile Arg Thr Leu Val
        275                 280                 285

Lys Lys Ile Ile Asp Glu His Arg Val Ser Asn Ser Glu Lys Lys Arg
    290                 295                 300

Asp Ile Gly Asp Phe Val Asp Val Leu Leu Ser Leu Asp Gly Asp Glu
305                 310                 315                 320

Lys Leu Gln Glu Asp Asp Met Ile Ala Val Leu Trp Glu Met Ile Phe
                325                 330                 335

Arg Gly Thr Asp Thr Thr Ala Leu Leu Thr Glu Trp Thr Met Ala Glu
            340                 345                 350

Leu Val Leu Asn Pro Asn Val Gln Thr Lys Leu Arg Asp Glu Ile Leu
        355                 360                 365

Thr Ala Val Gly Asp Gly Ala Asp Gly Asp Val Ala Asp Ala Asp Leu
    370                 375                 380

Ala Lys Leu Pro Tyr Leu Asn Ala Val Val Lys Glu Thr Leu Arg Leu
385                 390                 395                 400

His Pro Pro Gly Pro Leu Leu Ser Trp Ala Arg Leu Ser Thr Ser Asp
                405                 410                 415

Val Gln Leu Ser Asn Gly Met Val Ile Pro Lys Gly Thr Thr Ala Met
            420                 425                 430

Val Asn Met Trp Ala Ile Thr His Asp Gln Thr Val Trp Ser Asp Pro
        435                 440                 445

Leu Lys Phe Asp Pro Glu Arg Phe Thr Gly Asn Ala Asp Met Asp Ile
    450                 455                 460

Arg Gly Gly Asp Leu Arg Leu Ala Pro Phe Gly Ala Gly Arg Arg Val
465                 470                 475                 480

Cys Pro Gly Lys Asn Met Gly Leu Ala Thr Val Thr Arg Trp Val Ala
                485                 490                 495

Glu Leu Val Arg Arg Phe Glu Trp Gly Gln Asp Gln Thr Glu Pro Val
            500                 505                 510

Asp Leu Gly Glu Val Leu Lys Leu Ser Cys Glu Met Glu His Pro Leu
        515                 520                 525

Arg Ala Val Val Thr Glu Ile Phe
    530                 535
```

<210> SEQ ID NO 46
<211> LENGTH: 517
<212> TYPE: PRT
<213> ORGANISM: Arabidopsis thaliana

<400> SEQUENCE: 46

```
Met Ser Pro Glu Ala Tyr Val Leu Phe Phe Asn Ser Phe Asn Leu Val
1               5                   10                  15

Thr Phe Glu Ala Phe Ala Ser Val Ser Leu Ile Ile Ala Thr Val Ala
            20                  25                  30

Phe Leu Leu Ser Pro Gly Gly Leu Ala Trp Ala Trp Thr Gly Ser Ser
        35                  40                  45

Lys Ser Arg Val Ser Ile Pro Gly Pro Ser Gly Ser Leu Ser Val Phe
    50                  55                  60

Ser Gly Ser Asn Pro His Arg Val Leu Ala Ala Leu Ala Lys Arg Phe
65                  70                  75                  80

Lys Ala Ser Pro Leu Met Ala Phe Ser Val Gly Phe Ser Arg Phe Val
                85                  90                  95

Ile Ser Ser Glu Pro Glu Thr Ala Lys Glu Ile Leu Ser Ser Ser Ala
            100                 105                 110

Phe Ala Asp Arg Pro Val Lys Glu Ser Ala Tyr Glu Leu Leu Phe His
        115                 120                 125

Arg Ala Met Gly Phe Ala Pro Tyr Gly Glu Tyr Trp Arg Asn Leu Arg
    130                 135                 140

Arg Ile Ser Ser Thr His Leu Phe Ser Pro Arg Arg Ile Ala Ser Phe
145                 150                 155                 160

Glu Gly Val Arg Val Gly Ile Gly Met Lys Met Val Lys Lys Ile Lys
                165                 170                 175

Ser Leu Val Thr Ser Asp Ala Cys Gly Glu Val Glu Val Lys Lys Ile
            180                 185                 190

Val His Phe Gly Ser Leu Asn Asn Val Met Thr Thr Val Phe Gly Glu
        195                 200                 205

Ser Tyr Asp Phe Asp Glu Val Asn Gly Lys Gly Cys Phe Leu Glu Arg
    210                 215                 220

Leu Val Ser Glu Gly Tyr Glu Leu Leu Gly Ile Phe Asn Trp Ser Asp
225                 230                 235                 240

His Phe Trp Phe Leu Arg Trp Phe Asp Phe Gln Gly Val Arg Lys Arg
                245                 250                 255

Cys Arg Ala Leu Val Ser Glu Val Asn Thr Phe Val Gly Gly Ile Ile
            260                 265                 270

Glu Lys His Lys Met Lys Lys Gly Asn Asn Leu Asn Gly Glu Glu Asn
        275                 280                 285

Asp Phe Val Asp Val Leu Leu Gly Leu Gln Lys Asp Glu Lys Leu Ser
    290                 295                 300

Asp Ser Asp Met Ile Ala Val Leu Trp Glu Met Ile Phe Arg Gly Thr
305                 310                 315                 320

Asp Thr Val Ala Ile Leu Val Glu Trp Val Leu Ala Arg Met Val Leu
                325                 330                 335

His Gln Asp Ile Gln Asp Lys Leu Tyr Arg Glu Ile Ala Ser Ala Thr
            340                 345                 350

Ser Asn Asn Ile Arg Ser Leu Ser Asp Ser Asp Ile Pro Lys Leu Pro
        355                 360                 365

Tyr Leu Gln Ala Ile Val Lys Glu Thr Leu Arg Leu His Pro Pro Gly
    370                 375                 380
```

```
Pro Leu Leu Ser Trp Ala Arg Leu Ala Ile His Asp Val His Val Gly
385                 390                 395                 400

Pro Asn Leu Val Pro Ala Gly Thr Ile Ala Met Val Asn Met Trp Ser
                405                 410                 415

Ile Thr His Asn Ala Lys Ile Trp Thr Asp Pro Glu Ala Phe Met Pro
            420                 425                 430

Glu Arg Phe Ile Ser Glu Asp Val Ser Ile Met Gly Ser Asp Leu Arg
        435                 440                 445

Leu Ala Pro Phe Gly Ser Gly Arg Arg Val Cys Pro Gly Lys Ala Met
    450                 455                 460

Gly Leu Ala Thr Val His Leu Trp Ile Gly Gln Leu Ile Gln Asn Phe
465                 470                 475                 480

Glu Trp Val Lys Gly Ser Cys Asp Val Glu Leu Ala Glu Val Leu Lys
                485                 490                 495

Leu Ser Met Glu Met Lys Asn Pro Leu Lys Cys Lys Ala Val Pro Arg
            500                 505                 510

Asn Val Gly Phe Ala
        515


<210> SEQ ID NO 47
<211> LENGTH: 537
<212> TYPE: PRT
<213> ORGANISM: Arabidopsis thaliana

<400> SEQUENCE: 47

Met Thr Ile Asp Met Tyr Leu Ser Phe Ala Ser Arg Ser Gly Ser Ser
1               5                   10                  15

Pro Phe Pro Ser Leu Glu Leu Cys Leu Ser Ile Phe Leu Phe Ile Ser
            20                  25                  30

Leu Phe Val Phe Trp Leu Thr Pro Gly Gly Phe Ala Trp Ala Leu Tyr
        35                  40                  45

Lys Ala Arg Phe His Thr Arg Pro Glu Ser Lys Thr Gly Pro Ala Ile
    50                  55                  60

Pro Gly Pro Ser Gly Leu Pro Ile Phe Gly Leu Leu Leu Ala Phe Val
65                  70                  75                  80

Asn Asn Ala Leu Thr His Arg Ile Leu Ala Asn Ile Ala Asp Thr Cys
                85                  90                  95

Lys Ala Lys Ala Leu Met Ala Phe Ser Val Gly Ser Thr Arg Phe Val
            100                 105                 110

Ile Thr Ser Glu Pro Glu Thr Ala Lys Glu Leu Leu Asn Ser Ser Ala
        115                 120                 125

Phe Ala Asp Arg Pro Val Lys Glu Ser Ala Tyr Glu Leu Leu Phe Asp
    130                 135                 140

Arg Ala Met Gly Phe Ala Pro Phe Gly Asp Tyr Trp Arg Glu Leu Arg
145                 150                 155                 160

Arg Ile Ser Ser Thr His Leu Phe Ser Pro Lys Arg Ile Phe Ser Ser
                165                 170                 175

Gly Glu Ser Arg Arg Lys Ile Gly Gln Asn Met Val Gly Glu Ile Lys
            180                 185                 190

Asn Ala Met Glu Cys Tyr Gly Glu Val His Ile Lys Lys Ile Leu His
        195                 200                 205

Phe Gly Ser Leu Asn Asn Val Met Ser Ser Val Phe Gly Lys Thr Tyr
    210                 215                 220

Asn Phe Asn Glu Gly Ile Val Tyr Ser Lys Glu Ser Asn Glu Leu Glu
```

```
225                 230                 235                 240

His Leu Val Ser Glu Gly Tyr Glu Leu Leu Gly Ile Phe Asn Trp Ser
                245                 250                 255

Asp His Phe Pro Gly Met Arg Trp Leu Asp Leu Gln Gly Val Arg Arg
            260                 265                 270

Arg Cys Arg Ser Leu Val Gly Arg Val Asn Val Phe Val Gly Lys Ile
        275                 280                 285

Ile Asn Asp His Lys Ser Lys Arg Ser Leu Arg Asp Asn Pro Glu Glu
    290                 295                 300

Ser Thr Tyr Asp Asp Asp Phe Val Asp Val Leu Leu Gly Met His Gly
305                 310                 315                 320

Asn Ser Lys Leu Ser Asp Ser Asp Met Ile Ala Val Leu Trp Glu Met
                325                 330                 335

Ile Phe Arg Gly Thr Asp Thr Val Ala Ile Leu Leu Glu Trp Ile Leu
            340                 345                 350

Ala Arg Met Val Leu His Pro Asp Ile Gln Ala Lys Ala Gln Ala Glu
        355                 360                 365

Ile Asp Cys Ile Val Gly Asp Ser Gly Arg Gln Val Thr Asp Ser Asp
    370                 375                 380

Leu Pro Lys Leu Pro Tyr Val Arg Ala Ile Val Lys Glu Thr Leu Arg
385                 390                 395                 400

Met His Pro Pro Gly Pro Leu Leu Ser Trp Ala Arg Leu Ser Ile His
                405                 410                 415

Asp Thr Gln Ile Gly Thr His Phe Ile Pro Ala Gly Thr Thr Ala Met
            420                 425                 430

Val Asn Met Trp Ala Ile Thr His Asp Glu Lys Val Trp Pro Glu Ala
        435                 440                 445

His Glu Tyr Lys Pro Glu Arg Phe Leu Gly Ala Gln Glu Ser Asn Asn
    450                 455                 460

Phe Pro Ile Met Gly Ser Asp Leu Arg Leu Ala Pro Phe Gly Ala Gly
465                 470                 475                 480

Arg Arg Val Cys Pro Gly Lys Ser Met Gly Leu Ala Thr Val Glu Leu
                485                 490                 495

Trp Leu Ala Gln Leu Leu Gly Ser Tyr Lys Trp Val Ser Cys Gly Glu
            500                 505                 510

Val Asp Leu Ser Glu Thr Leu Lys Leu Ser Leu Glu Met Lys Asn Thr
        515                 520                 525

Leu Val Cys Lys Ala Ile Pro Arg Gly
    530                 535


<210> SEQ ID NO 48
<211> LENGTH: 555
<212> TYPE: PRT
<213> ORGANISM: Oryza sativa

<400> SEQUENCE: 48

Met Ala Met Ala Thr Ala Thr Ala Ser Ser Cys Val Asp Ala Thr Trp
1               5                   10                  15

Trp Ala Tyr Ala Leu Pro Ala Leu Leu Gly Ala Asp Thr Leu Cys Ala
            20                  25                  30

His Pro Ala Leu Leu Ala Gly Ala Val Leu Leu Ala Phe Ala Thr Ala
        35                  40                  45

Ala Val Leu Ala Trp Ala Ala Ser Pro Gly Gly Pro Ala Trp Ala His
    50                  55                  60
```

```
Gly Arg Gly Arg Leu Gly Ala Thr Pro Ile Glu Gly Pro Arg Gly Leu
65                  70                  75                  80

Pro Val Phe Gly Ser Ile Phe Ala Leu Ser Arg Gly Leu Pro His Arg
                85                  90                  95

Ala Leu Asp Ala Met Ser Arg Asp Ala Ala Ala Pro Arg Ala Arg Glu
            100                 105                 110

Leu Met Ala Phe Ser Val Gly Glu Thr Pro Ala Val Val Ser Ser Cys
        115                 120                 125

Pro Ala Thr Ala Arg Glu Val Leu Ala His Pro Ser Phe Ala Asp Arg
    130                 135                 140

Pro Leu Lys Arg Ser Ala Arg Glu Leu Leu Phe Ala Arg Ala Ile Gly
145                 150                 155                 160

Phe Ala Pro Ser Gly Glu Tyr Trp Arg Leu Leu Arg Arg Ile Ala Ser
                165                 170                 175

Thr His Leu Phe Ser Pro Arg Arg Val Ala Ala His Glu Pro Gly Arg
            180                 185                 190

Gln Ala Asp Ala Thr Ala Met Leu Ser Ala Met Ala Ala Glu Gln Ser
        195                 200                 205

Ala Thr Gly Ala Val Val Leu Arg Pro His Leu Gln Ala Ala Ala Leu
    210                 215                 220

Asn Asn Ile Met Gly Ser Val Phe Gly Arg Arg Tyr Asp Val Ser Ser
225                 230                 235                 240

Ser Ser Gly Ala Ala Ala Asp Glu Ala Glu Gln Leu Lys Ser Met Val
                245                 250                 255

Arg Glu Gly Phe Glu Leu Leu Gly Ala Phe Asn Trp Ser Asp His Leu
            260                 265                 270

Pro Trp Leu Ala His Leu Tyr Asp Pro Asn His Val Ala Arg Arg Cys
        275                 280                 285

Ala Ala Leu Val Pro Arg Val Gln Ala Phe Val Arg Gly Val Ile Arg
    290                 295                 300

Asp His Arg Leu Arg Arg Asp Ser Ser Ser Thr Ala Ala Asp Asn Ala
305                 310                 315                 320

Asp Phe Val Asp Val Leu Leu Ser Leu Glu Ala His Glu Asn Leu Ala
                325                 330                 335

Glu Asp Asp Met Val Ala Val Leu Trp Glu Met Ile Phe Arg Gly Thr
            340                 345                 350

Asp Thr Thr Ala Leu Val Thr Glu Trp Cys Met Ala Glu Val Val Arg
        355                 360                 365

Asn Pro Ala Val Gln Ala Arg Leu Arg Ala Glu Val Asp Ala Ala Val
    370                 375                 380

Gly Gly Asp Gly Cys Pro Ser Asp Gly Asp Val Ala Arg Met Pro Tyr
385                 390                 395                 400

Leu Gln Ala Val Val Lys Glu Thr Leu Arg Ala His Pro Pro Gly Pro
                405                 410                 415

Leu Leu Ser Trp Ala Arg Leu Ala Thr Ala Asp Val Gly Leu Ala Asn
            420                 425                 430

Gly Met Val Val Pro Ala Gly Thr Thr Ala Met Val Asn Met Trp Ala
        435                 440                 445

Ile Thr His Asp Gly Glu Val Trp Ala Asp Pro Glu Ala Phe Ala Pro
    450                 455                 460

Glu Arg Phe Ile Pro Ser Glu Gly Gly Ala Asp Val Asp Val Arg Asp
465                 470                 475                 480

Gly Asp Leu Arg Leu Ala Pro Phe Gly Ala Gly Arg Arg Val Cys Pro
```

```
                485                 490                 495

Gly Lys Asn Leu Gly Leu Ala Thr Val Ser Leu Trp Val Ala Arg Leu
            500                 505                 510

Val His Ala Phe Asp Trp Phe Leu Pro Asp Gly Ser Pro Pro Val Ser
        515                 520                 525

Leu Asp Glu Val Leu Lys Leu Ser Leu Glu Met Lys Thr Pro Leu Ala
    530                 535                 540

Ala Ala Ala Thr Pro Arg Arg Arg Arg Ala Ala
545                 550                 555


<210> SEQ ID NO 49
<211> LENGTH: 547
<212> TYPE: PRT
<213> ORGANISM: Zea mays

<400> SEQUENCE: 49

Met Ala Met Ala Ser Ala Ala Cys Ser Cys Thr Asp Gly Thr Trp Trp
1               5                   10                  15

Val Tyr Ala Leu Pro Ala Leu Leu Gly Ser Asp Thr Leu Cys Ala His
            20                  25                  30

Pro Ala Leu Leu Ala Gly Leu Ile Phe Leu Ala Thr Val Ser Val Ala
        35                  40                  45

Leu Leu Ala Trp Ala Thr Ser Pro Gly Gly Pro Ala Trp Thr Asn Gly
    50                  55                  60

Arg Gly Ala Ser Ala Ser Leu Leu Ser Trp Asp Pro Val Val Cys Pro
65                  70                  75                  80

Cys Ser Ala Ala Ser Ser Arg Cys Pro Gly Ala Ala Ala Pro Arg Pro
                85                  90                  95

Arg Arg Asp Gly Pro Arg Arg Arg Pro Arg Ala Lys Glu Leu Met Ala
            100                 105                 110

Phe Ser Val Gly Asp Thr Pro Ala Val Val Ser Ser Cys Pro Ala Thr
        115                 120                 125

Ala Arg Glu Val Leu Ala His Pro Ser Phe Ala Asp Arg Pro Val Lys
    130                 135                 140

Arg Ser Ala Arg Glu Leu Met Phe Ala Arg Ala Ile Gly Phe Ala Pro
145                 150                 155                 160

Asn Gly Glu Tyr Trp Arg Arg Leu Arg Arg Val Ala Ser Thr His Leu
                165                 170                 175

Phe Ser Pro Arg Arg Val Ala Ser His Glu Pro Gly Arg Gln Gly Asp
            180                 185                 190

Ala Glu Ala Met Leu Arg Ser Ile Ala Ala Glu Gln Ser Ala Ser Gly
        195                 200                 205

Ala Val Ala Leu Arg Pro His Leu Gln Ala Ala Ala Leu Asn Asn Ile
    210                 215                 220

Met Gly Ser Val Phe Gly Thr Arg Tyr Asp Val Thr Ser Gly Ala Gly
225                 230                 235                 240

Ala Ala Glu Ala Glu His Leu Lys Ser Met Val Arg Glu Gly Phe Glu
                245                 250                 255

Leu Leu Gly Ala Phe Asn Trp Ser Asp His Leu Pro Trp Leu Ala His
            260                 265                 270

Leu Tyr Asp Pro Ser Asn Val Thr Arg Arg Cys Ala Ala Leu Val Pro
        275                 280                 285

Arg Val Gln Thr Phe Val Arg Gly Val Ile Asp Glu His Arg Arg Arg
    290                 295                 300
```

```
Arg Gln Asn Ser Ala Ala Leu Asn Asp Asn Ala Asp Phe Val Asp Val
305                 310                 315                 320

Leu Leu Ser Leu Glu Gly Asp Glu Lys Leu Gly Asp Asp Asp Met Val
                325                 330                 335

Ala Ile Leu Trp Glu Met Val Phe Arg Gly Thr Asp Thr Thr Ala Leu
            340                 345                 350

Leu Thr Glu Trp Cys Met Ala Glu Leu Val Arg His Pro Ala Val Gln
        355                 360                 365

Ala Arg Val Arg Ala Glu Val Asp Ala Ala Val Gly Ala Gly Gly Cys
    370                 375                 380

Pro Thr Asp Ala Asp Val Ala Arg Met Pro Tyr Leu Gln Ala Val Val
385                 390                 395                 400

Lys Glu Thr Leu Arg Ala His Pro Pro Gly Pro Leu Leu Ser Trp Ala
                405                 410                 415

Arg Leu Ala Thr Ala Asp Val Pro Leu Cys Asn Gly Met Val Val Pro
            420                 425                 430

Ala Gly Thr Thr Ala Met Val Asn Met Trp Ala Ile Thr His Asp Ala
        435                 440                 445

Ala Val Trp Ala Asp Pro Asp Ala Phe Ala Pro Glu Arg Phe Leu Pro
    450                 455                 460

Ser Glu Gly Gly Ala Asp Val Asp Val Arg Gly Val Asp Leu Arg Leu
465                 470                 475                 480

Ala Pro Phe Gly Ala Gly Arg Arg Val Cys Pro Gly Lys Asn Leu Gly
                485                 490                 495

Leu Thr Thr Val Gly Leu Trp Val Ala Arg Leu Val His Ala Phe Gln
            500                 505                 510

Trp Ala Leu Pro Asp Gly Ala Ala Ala Val Cys Leu Asp Glu Val Leu
        515                 520                 525

Lys Leu Ser Leu Glu Met Lys Thr Pro Leu Val Ala Ala Ala Ile Pro
    530                 535                 540

Arg Thr Ala
545
```

<210> SEQ ID NO 50
<211> LENGTH: 426
<212> TYPE: PRT
<213> ORGANISM: Phalaenopsis sp. SM9108

<400> SEQUENCE: 50

```
Met Ala Phe Ser Val Gly Leu Thr Arg Phe Ile Val Ser Ser His Pro
1               5                   10                  15

Lys Thr Ala Lys Glu Ile Leu Ser Ser Pro Ala Phe Ala Asp Arg Pro
            20                  25                  30

Ile Lys Glu Ser Ala Tyr Glu Leu Leu Phe Asn Arg Ala Met Gly Phe
        35                  40                  45

Ala Pro Phe Gly Asp Tyr Trp Arg Asn Leu Arg Arg Ile Ser Ser Thr
    50                  55                  60

Tyr Leu Phe Ser Pro Arg Arg Val Ser Ser Phe Glu Lys Gln Arg Ser
65                  70                  75                  80

Glu Ile Gly Glu Gly Met Val Arg Asp Met Lys Arg Met Met Glu Arg
                85                  90                  95

Asn Gly Val Val Glu Val Arg Arg Met Leu His Tyr Gly Ser Leu Asn
            100                 105                 110

Asn Ile Met Leu Thr Val Phe Gly Lys Lys Phe Asp Phe Ala Lys Asp
        115                 120                 125
```

```
Glu Gly Leu Glu Leu Glu Leu Ile Leu Lys Glu Gly Tyr Glu Leu Leu
    130                 135                 140

Gly Ile Phe Asn Trp Gly Asp His Leu Pro Leu Leu Gly Trp Leu Asp
145                 150                 155                 160

Leu Gln Gly Val Arg Arg Arg Cys Arg Thr Leu Val Ala Lys Val Asn
                165                 170                 175

Val Phe Val Lys Lys Ile Ile Asp Glu His Lys Arg Arg Ala Asn Gly
            180                 185                 190

Val Gly Ile Asp Glu Gly Glu Gly Glu Asp Phe Val Asp Val Leu Leu
        195                 200                 205

Gly Leu Glu Glu Lys Asp Arg Leu Ser Glu Ser Asp Met Val Ala Val
    210                 215                 220

Leu Trp Glu Met Ile Phe Arg Gly Thr Asp Thr Val Ala Ile Leu Leu
225                 230                 235                 240

Glu Trp Thr Leu Ala Arg Met Val Leu His Pro Asp Ile Gln Ser Lys
                245                 250                 255

Ala Gln Val Glu Ile Asp Ser Val Val Asp Ser Ser Arg Pro Val Leu
            260                 265                 270

Asp Ser Asp Ile Gln Arg Leu Pro Tyr Leu Gln Ser Ile Val Lys Glu
        275                 280                 285

Thr Leu Arg Met His Pro Pro Gly Pro Leu Leu Ser Trp Ala Arg Leu
    290                 295                 300

Ala Ile His Asp Val Pro Val Asp Gly His Met Ile Pro Ala Gly Thr
305                 310                 315                 320

Thr Ala Met Val Asn Met Trp Ala Ile Thr His Asp Glu Cys Asn Trp
                325                 330                 335

Ala Glu Pro Asn Lys Phe Asn Pro Asp Arg Phe Ile Asp Glu Asp Val
            340                 345                 350

Asn Ile Leu Gly Ser Asp Leu Arg Leu Ala Pro Phe Gly Ser Gly Lys
        355                 360                 365

Arg Val Cys Pro Gly Lys Thr Met Ala Leu Ala Ala Val His Leu Trp
    370                 375                 380

Leu Ala Gln Leu Leu Lys Ser Phe Lys Leu Leu Pro Ser Arg Asn Gly
385                 390                 395                 400

Val Asp Leu Ser Glu Cys Leu Lys Met Ser Leu Glu Met Lys Asn Pro
                405                 410                 415

Leu Val Cys Val Ala Val Pro Arg Phe Glu
            420                 425
```

<210> SEQ ID NO 51
<211> LENGTH: 523
<212> TYPE: PRT
<213> ORGANISM: Glycine max

<400> SEQUENCE: 51

```
Met Thr Ser His Ile Asp Asp Asn Leu Trp Ile Ile Ala Leu Thr Ser
1               5                   10                  15

Lys Cys Thr Gln Glu Asn Leu Ala Trp Val Leu Leu Ile Met Gly Ser
            20                  25                  30

Leu Trp Leu Thr Met Thr Phe Tyr Tyr Trp Ser His Pro Gly Gly Pro
        35                  40                  45

Ala Trp Gly Lys Tyr Tyr Thr Tyr Ser Pro Pro Leu Ser Ile Ile Pro
    50                  55                  60

Gly Pro Lys Gly Phe Pro Leu Ile Gly Ser Met Gly Leu Met Thr Ser
```

```
65                  70                  75                  80

Leu Ala His His Arg Ile Ala Ala Ala Ala Ala Thr Cys Arg Ala Lys
                85                  90                  95

Arg Leu Met Ala Phe Ser Leu Gly Asp Thr Arg Val Ile Val Thr Cys
            100                 105                 110

His Pro Asp Val Ala Lys Glu Ile Leu Asn Ser Ser Val Phe Ala Asp
        115                 120                 125

Arg Pro Val Lys Glu Ser Ala Tyr Ser Leu Met Phe Asn Arg Ala Ile
    130                 135                 140

Gly Phe Ala Ser Tyr Gly Val Tyr Trp Arg Ser Leu Arg Arg Ile Ala
145                 150                 155                 160

Ser Asn His Leu Phe Cys Pro Arg Gln Ile Lys Ala Ser Glu Leu Gln
                165                 170                 175

Arg Ser Gln Ile Ala Ala Gln Met Val His Ile Leu Asn Asn Lys Arg
            180                 185                 190

His Arg Ser Leu Arg Val Arg Gln Val Leu Lys Lys Ala Ser Leu Ser
        195                 200                 205

Asn Met Met Cys Ser Val Phe Gly Gln Glu Tyr Lys Leu His Asp Pro
    210                 215                 220

Asn Ser Gly Met Glu Asp Leu Gly Ile Leu Val Asp Gln Gly Tyr Asp
225                 230                 235                 240

Leu Leu Gly Leu Phe Asn Trp Ala Asp His Leu Pro Phe Leu Ala His
                245                 250                 255

Phe Asp Ala Gln Asn Ile Arg Phe Arg Cys Ser Asn Leu Val Pro Met
            260                 265                 270

Val Asn Arg Phe Val Gly Thr Ile Ile Ala Glu His Arg Ala Ser Lys
        275                 280                 285

Thr Glu Thr Asn Arg Asp Phe Val Asp Val Leu Leu Ser Leu Pro Glu
    290                 295                 300

Pro Asp Gln Leu Ser Asp Ser Asp Met Ile Ala Val Leu Trp Glu Met
305                 310                 315                 320

Ile Phe Arg Gly Thr Asp Thr Val Ala Val Leu Ile Glu Trp Ile Leu
                325                 330                 335

Ala Arg Met Ala Leu His Pro His Val Gln Ser Lys Val Gln Glu Glu
            340                 345                 350

Leu Asp Ala Val Val Gly Lys Ala Arg Ala Val Ala Glu Asp Asp Val
        355                 360                 365

Ala Val Met Thr Tyr Leu Pro Ala Val Val Lys Glu Val Leu Arg Leu
    370                 375                 380

His Pro Pro Gly Pro Leu Leu Ser Trp Ala Arg Leu Ser Ile Asn Asp
385                 390                 395                 400

Thr Thr Ile Asp Gly Tyr His Val Pro Ala Gly Thr Thr Ala Met Val
                405                 410                 415

Asn Thr Trp Ala Ile Cys Arg Asp Pro His Val Trp Lys Asp Pro Leu
            420                 425                 430

Glu Phe Met Pro Glu Arg Phe Val Thr Ala Gly Gly Asp Ala Glu Phe
        435                 440                 445

Ser Ile Leu Gly Ser Asp Pro Arg Leu Ala Pro Phe Gly Ser Gly Arg
    450                 455                 460

Arg Ala Cys Pro Gly Lys Thr Leu Gly Trp Ala Thr Val Asn Phe Trp
465                 470                 475                 480

Val Ala Ser Leu Leu His Glu Phe Glu Trp Val Pro Ser Asp Glu Lys
                485                 490                 495
```

```
Gly Val Asp Leu Thr Glu Val Leu Lys Leu Ser Ser Glu Met Ala Asn
            500                 505                 510

Pro Leu Thr Val Lys Val Arg Pro Arg Arg Gly
        515                 520
```

<210> SEQ ID NO 52
<211> LENGTH: 553
<212> TYPE: PRT
<213> ORGANISM: Pinus radiata

<400> SEQUENCE: 52

```
Met Glu Asn Arg Arg Ser Ser Gly Gly Ser Gly Trp Trp Val Cys Val
1               5                   10                  15

Leu Pro Leu Phe Thr Lys Asp Gly Pro Ala Tyr Phe Leu His Ser Ser
            20                  25                  30

Ser Asp Asp Val Ser Ala Trp Arg Gln Trp Pro Leu Tyr Ile Ala Leu
        35                  40                  45

Leu Ile Val Ala Val Cys Ala Val Leu Val Ser Trp Leu Ser Pro Gly
    50                  55                  60

Gly Cys Ala Trp Ala Gly Arg His Lys Arg Gly Arg Val Ala Ile Pro
65                  70                  75                  80

Gly Pro Lys Gly Trp Pro Ile Ile Gly Ser Leu Met Asp Met Ser Val
                85                  90                  95

Gly Leu Pro His Arg Lys Leu Glu Ser Leu Ala Arg Leu His Gly Ala
            100                 105                 110

Lys Gln Leu Met Ser Phe Ser Leu Gly Cys Thr Pro Ala Val Ile Thr
        115                 120                 125

Ser Asp Pro Glu Val Ala Arg Glu Leu Leu Thr Ser Pro His Phe Ala
    130                 135                 140

Asn Arg Pro Leu Lys Gln Ser Ala Gln Gln Leu Leu Phe Gly Arg Ala
145                 150                 155                 160

Ile Gly Phe Ala Pro Asn Gly Gly Tyr Trp Arg Leu Leu Arg Arg Ile
                165                 170                 175

Ala Ser Ala His Leu Phe Ala Pro Arg Arg Ile Ala Ala His Glu Ala
            180                 185                 190

Gly Arg Gln Ala Asp Val Val Ala Met Leu Asp Asp Ile Gln Lys Glu
        195                 200                 205

Tyr His Ser Lys Gly Val Val Arg Val Arg Arg His Leu Gln Gly Ala
    210                 215                 220

Ala Leu Asn Asn Ile Met Gly Ser Val Phe Gly Arg Arg Phe Asp Met
225                 230                 235                 240

Ser His Glu Asn Glu Glu Val Lys Lys Leu Arg Glu Met Val Asp Glu
                245                 250                 255

Gly Phe Gln Leu Leu Gly Ala Phe Asn Trp Ala Asp His Leu Pro Trp
            260                 265                 270

Leu Arg Pro Leu Asp Pro Leu Arg Ile His Ala Arg Cys Ala Arg Leu
        275                 280                 285

Val Pro Arg Val Thr Thr Phe Val Ser Asn Ile Ile Glu Gln His Arg
    290                 295                 300

Arg Glu Glu Gln Arg Arg Glu Ser Gly Asp Gln Cys Asp Phe Val Asp
305                 310                 315                 320

Val Leu Leu Ser Leu Gln Gly Glu Asp Lys Leu Asp Glu Glu Asp Met
                325                 330                 335

Ile Ala Val Leu Trp Glu Met Ile Phe Arg Gly Thr Asp Thr Thr Ala
```

```
            340                 345                 350

Leu Leu Thr Glu Trp Thr Met Ala Glu Leu Val Leu His Pro Glu Ala
        355                 360                 365

Gln Lys Lys Ala Gln Ala Glu Leu Asp Ala Val Val Gly His Asp Arg
    370                 375                 380

Ser Val Lys Asp Ser Asp Ile Pro Lys Leu Pro Tyr Ile Gln Ala Val
385                 390                 395                 400

Val Lys Glu Ala Leu Arg Met His Pro Pro Gly Pro Leu Leu Ser Trp
                405                 410                 415

Ala Arg Leu Ser Thr Glu Asp Val Asn Met Gly Asp Gly Met Cys Val
            420                 425                 430

Pro Ala Gly Thr Thr Ala Met Val Asn Met Trp Ser Ile Thr His Asp
        435                 440                 445

Pro Asn Ile Trp Glu Ser Pro Tyr Glu Phe Arg Pro Glu Arg Phe Val
    450                 455                 460

Val Phe Glu Gly Gly Glu Glu Val Asp Val Arg Gly Asn Asp Leu Arg
465                 470                 475                 480

Leu Ala Pro Phe Gly Ala Gly Arg Arg Val Cys Pro Gly Lys Ala Leu
                485                 490                 495

Gly Leu Ala Thr Val Asn Leu Trp Val Ala Lys Leu Leu His His Phe
            500                 505                 510

Glu Trp Leu Pro His Ala Glu His Pro Val Asp Leu Ser Glu Val Leu
        515                 520                 525

Lys Leu Ser Cys Glu Met Ala Arg Pro Leu His Cys Val Pro Val Thr
    530                 535                 540

Arg Val Pro Phe Ala Lys Phe Ser Asp
545                 550


<210> SEQ ID NO 53
<211> LENGTH: 523
<212> TYPE: PRT
<213> ORGANISM: Glycine max

<400> SEQUENCE: 53

Met Thr Ser His Ile Asp Asp Asn Leu Trp Ile Ile Ala Leu Thr Ser
1               5                   10                  15

Lys Cys Thr Gln Glu Asn Leu Ala Trp Val Leu Leu Ile Met Gly Ser
            20                  25                  30

Leu Trp Leu Thr Met Thr Phe Tyr Tyr Trp Ser His Pro Gly Gly Pro
        35                  40                  45

Ala Trp Gly Lys Tyr Tyr Thr Tyr Ser Pro Pro Leu Ser Ile Ile Pro
    50                  55                  60

Gly Pro Lys Gly Phe Pro Leu Ile Gly Ser Met Gly Leu Met Ile Ser
65                  70                  75                  80

Leu Ala His His Arg Ile Ala Ala Ala Ala Ala Thr Cys Arg Ala Lys
                85                  90                  95

Arg Leu Met Ala Phe Ser Leu Gly Asp Thr Arg Val Ile Val Thr Cys
            100                 105                 110

His Pro Asp Val Ala Lys Glu Ile Leu Asn Ser Ser Val Phe Ala Asp
        115                 120                 125

Arg Pro Val Lys Glu Ser Ala Tyr Ser Leu Met Phe Asn Arg Ala Ile
    130                 135                 140

Gly Phe Ala Ser Tyr Gly Val Tyr Trp Arg Ser Leu Arg Arg Ile Ala
145                 150                 155                 160
```

```
Ser Asn His Phe Phe Cys Pro Arg Gln Ile Lys Ala Ser Glu Leu Gln
                165                 170                 175

Arg Ser Gln Ile Ala Ala Gln Met Val His Ile Leu Asn Asn Lys Arg
            180                 185                 190

His Arg Ser Leu Arg Val Arg Gln Val Leu Lys Lys Ala Ser Leu Ser
        195                 200                 205

Asn Met Met Cys Ser Val Phe Gly Gln Glu Tyr Lys Leu His Asp Pro
    210                 215                 220

Asn Ser Gly Met Glu Asp Leu Gly Ile Leu Val Asp Gln Gly Tyr Asp
225                 230                 235                 240

Leu Leu Gly Leu Phe Asn Trp Ala Asp His Leu Pro Phe Leu Ala His
                245                 250                 255

Phe Asp Ala Gln Asn Ile Arg Phe Arg Cys Ser Asn Leu Val Pro Met
            260                 265                 270

Val Asn Arg Phe Val Gly Thr Ile Ile Ala Glu His Arg Ala Ser Lys
        275                 280                 285

Thr Glu Thr Asn Arg Asp Phe Val Asp Val Leu Leu Ser Leu Pro Glu
    290                 295                 300

Pro Asp Gln Leu Ser Asp Ser Asp Met Ile Ala Val Leu Trp Glu Met
305                 310                 315                 320

Ile Phe Arg Gly Thr Asp Thr Val Ala Val Leu Ile Glu Trp Ile Leu
                325                 330                 335

Ala Arg Met Ala Leu His Pro His Val Gln Ser Lys Val Gln Glu Glu
            340                 345                 350

Leu Asp Ala Val Val Gly Lys Ala Arg Ala Val Ala Glu Asp Asp Val
        355                 360                 365

Ala Val Met Thr Tyr Leu Pro Ala Val Val Lys Glu Val Leu Arg Leu
    370                 375                 380

His Pro Pro Gly Pro Leu Leu Ser Trp Ala Arg Leu Ser Ile Asn Asp
385                 390                 395                 400

Thr Thr Ile Asp Gly Tyr His Val Pro Ala Gly Thr Thr Ala Met Val
                405                 410                 415

Asn Met Trp Ala Ile Cys Arg Asp Pro His Val Trp Lys Asp Pro Leu
            420                 425                 430

Glu Phe Met Pro Glu Arg Phe Val Thr Ala Gly Gly Asp Ala Glu Phe
        435                 440                 445

Ser Ile Leu Gly Ser Asp Pro Arg Leu Ala Pro Phe Gly Ser Gly Arg
    450                 455                 460

Arg Ala Cys Pro Gly Lys Thr Leu Gly Trp Ala Thr Val Asn Phe Trp
465                 470                 475                 480

Val Ala Ser Leu Leu His Glu Phe Glu Trp Val Pro Ser Asp Glu Lys
                485                 490                 495

Gly Val Asp Leu Thr Glu Val Leu Lys Leu Ser Ser Glu Met Ala Asn
            500                 505                 510

Pro Leu Thr Val Lys Val Arg Pro Arg Arg Gly
        515                 520
```

<210> SEQ ID NO 54
<211> LENGTH: 536
<212> TYPE: PRT
<213> ORGANISM: Glycine max

<400> SEQUENCE: 54

```
Met Ser Thr His Ile Glu Ser Leu Trp Val Leu Ala Leu Ala Ser Lys
1               5                   10                  15
```

```
Cys Ile Gln Glu Asn Ile Ala Trp Ser Leu Leu Ile Ile Met Val Thr
            20                  25                  30

Leu Trp Leu Thr Met Thr Phe Phe Tyr Trp Ser His Pro Gly Gly Pro
        35                  40                  45

Ala Trp Gly Lys Tyr Tyr Tyr Phe Asn Tyr Trp Lys Lys Thr Thr Ser
    50                  55                  60

Thr Asn Thr Asn Ile Asn Leu Lys Met Ile Ile Pro Gly Pro Arg Gly
65                  70                  75                  80

Tyr Pro Phe Ile Gly Ser Met Ser Leu Met Thr Ser Leu Ala His His
                85                  90                  95

Arg Ile Ala Ala Ala Gly Glu Ala Cys Asn Ala Thr Arg Leu Met Ala
            100                 105                 110

Phe Ser Met Gly Asp Thr Arg Ala Ile Val Thr Cys Asn Pro Asp Val
        115                 120                 125

Ala Lys Glu Ile Leu Asn Ser Ser Thr Phe Ala Asp Arg Pro Ile Lys
    130                 135                 140

Glu Ser Ala Tyr Ser Leu Met Phe Asn Arg Ala Ile Gly Phe Ala Pro
145                 150                 155                 160

Tyr Gly Val Tyr Trp Arg Thr Leu Arg Arg Ile Ala Ala Thr His Leu
                165                 170                 175

Phe Cys Pro Lys Gln Ile Lys Ala Ser Glu Leu Gln Arg Ala Glu Ile
            180                 185                 190

Ala Ala Gln Met Thr Asn Ser Phe Arg Asn His Arg Cys Ser Gly Gly
        195                 200                 205

Phe Gly Ile Arg Ser Val Leu Lys Arg Ala Ser Leu Asn Asn Met Met
    210                 215                 220

Trp Ser Val Phe Gly Gln Lys Tyr Asn Leu Asp Glu Ile Asn Thr Ala
225                 230                 235                 240

Met Asp Glu Leu Ser Met Leu Val Glu Gln Gly Tyr Asp Leu Leu Gly
                245                 250                 255

Thr Leu Asn Trp Gly Asp His Ile Pro Phe Leu Lys Asp Phe Asp Leu
            260                 265                 270

Gln Lys Ile Arg Phe Thr Cys Ser Lys Leu Val Pro Gln Val Asn Arg
        275                 280                 285

Phe Val Gly Ser Ile Ile Ala Asp His Gln Ala Asp Thr Thr Gln Thr
    290                 295                 300

Asn Arg Asp Phe Val His Val Leu Leu Ser Leu Gln Gly Pro Asp Lys
305                 310                 315                 320

Leu Ser His Ser Asp Met Ile Ala Val Leu Trp Glu Met Ile Phe Arg
                325                 330                 335

Gly Thr Asp Thr Val Ala Val Leu Ile Glu Trp Ile Leu Ala Arg Met
            340                 345                 350

Val Leu His Pro Glu Val Gln Arg Lys Val Gln Glu Glu Leu Asp Ala
        355                 360                 365

Val Val Arg Gly Gly Ala Leu Thr Glu Glu Val Val Ala Ala Thr Ala
    370                 375                 380

Tyr Leu Ala Ala Val Val Lys Glu Val Leu Arg Leu His Pro Pro Gly
385                 390                 395                 400

Pro Leu Leu Ser Trp Ala Arg Leu Ala Ile Thr Asp Thr Thr Ile Asp
                405                 410                 415

Gly Tyr His Val Pro Ala Gly Thr Thr Ala Met Val Asn Met Trp Ala
            420                 425                 430
```

```
Ile Ala Arg Asp Pro Glu Val Trp Leu Asp Pro Leu Glu Phe Lys Pro
        435                 440                 445

Glu Arg Phe Met Gly Leu Glu Asn Glu Phe Ser Val Phe Gly Ser Asp
    450                 455                 460

Leu Arg Leu Ala Pro Phe Gly Ser Gly Arg Arg Thr Cys Pro Gly Lys
465                 470                 475                 480

Thr Leu Gly Leu Ser Thr Val Thr Phe Trp Val Ala Trp Leu Leu His
                485                 490                 495

Glu Phe Glu Trp Leu Pro Ser Asp Glu Ala Lys Val Asp Leu Thr Glu
            500                 505                 510

Val Leu Arg Leu Ser Cys Glu Met Ala Asn Pro Leu Ile Val Lys Val
        515                 520                 525

Arg Pro Arg His Gly Leu Ser Thr
    530                 535


<210> SEQ ID NO 55
<211> LENGTH: 551
<212> TYPE: PRT
<213> ORGANISM: Oryza sativa

<400> SEQUENCE: 55

Met Asp Met Asp Ser Ser Pro Ser Thr Gln Asp Cys Gly Gly Trp Leu
1               5                   10                  15

Leu Tyr Val Ser Leu Ala Ala Lys Cys Gly Gly Asp Pro Cys Arg Val
            20                  25                  30

Val Gly Phe Val Ala Val Ala Val Val Ala Phe Ala Val Thr Ser Leu
        35                  40                  45

Leu His Trp Leu Ser Pro Gly Gly Pro Ala Trp Gly Arg Tyr Trp Trp
    50                  55                  60

Asn Arg Arg Gly Gly Leu Gly Ile Ala Ala Ala Ile Pro Gly Pro Arg
65                  70                  75                  80

Gly Leu Pro Val Leu Gly Ser Met Ser Leu Met Ala Gly Leu Ala His
                85                  90                  95

Arg Lys Leu Ala Ala Ala Ala Gly Gly Ser Pro Ala Arg Arg Arg Leu
            100                 105                 110

Met Ala Leu Ser Leu Gly Glu Thr Arg Val Val Val Thr Ala Asp Pro
        115                 120                 125

Gly Val Ala Arg Glu Leu Leu Ala Ser Ala Ala Phe Ala Asp Arg Pro
    130                 135                 140

Val Lys Glu Ser Ala Tyr Gly Met Leu Phe His Arg Ala Ile Gly Phe
145                 150                 155                 160

Ala Pro Tyr Gly Thr Tyr Trp Arg Ala Leu Arg Arg Val Ala Ser Thr
                165                 170                 175

His Leu Phe Ser Pro Arg Gln Val Ser Ala Ser Ala Ala Gln Arg Ala
            180                 185                 190

Val Ile Ala Arg Gln Met Val Glu Ala Met Arg Ser Ala Ala Ala Ala
        195                 200                 205

Ala Ala Gly Gly Gly Val Ala Ala Arg Pro Phe Leu Lys Arg Ala Ser
    210                 215                 220

Leu His Asn Val Met Trp Ser Val Phe Gly Arg Lys Tyr Glu Leu Ala
225                 230                 235                 240

Ala Pro Glu Ser Glu Glu Thr Ala Glu Leu Arg Ser Met Val Asp Glu
                245                 250                 255

Gly Tyr Asp Leu Leu Gly Gln Leu Asn Trp Ser Asp His Leu Pro Trp
            260                 265                 270
```

```
Leu Ala Pro Phe Asp Leu Lys Lys Thr Arg Ser Arg Cys Ser Ser Leu
        275                 280                 285

Val Pro Arg Val Asn Arg Phe Val Thr Arg Ile Ile Asp Glu His Arg
    290                 295                 300

Ala Arg Leu Ser Leu Ala Val Asp Ala Ala Val Asp Phe Thr Asp Val
305                 310                 315                 320

Leu Leu Ser Leu His Gly Gly Asp Lys Leu Ser Asp Ala Asp Met Val
                325                 330                 335

Ala Val Leu Trp Glu Met Ile Phe Arg Gly Thr Asp Thr Val Ala Val
            340                 345                 350

Leu Ile Glu Trp Val Ala Ala Arg Leu Val Leu His Gln Asp Val Gln
        355                 360                 365

Ala Arg Val His Asp Glu Leu Asp Arg Val Val Gly Ser Asp Arg Ala
    370                 375                 380

Val Thr Glu Ser Asp Ala Ser Lys Leu Val Tyr Leu Gln Ala Val Ile
385                 390                 395                 400

Lys Glu Val Leu Arg Leu His Pro Pro Gly Pro Leu Leu Ser Trp Ala
                405                 410                 415

Arg Leu Ala Thr Ser Asp Val His Val Gly Gly Phe Leu Ile Pro Ser
            420                 425                 430

Gly Thr Thr Ala Met Val Asn Met Trp Ala Ile Thr His Asp Pro Ala
        435                 440                 445

Val Trp Pro Asp Pro Asn Glu Phe Lys Pro Glu Arg Phe Val Ala Gly
    450                 455                 460

Pro Ser Ser Asp Gln Ala Thr Glu Phe Pro Ile Met Gly Ser Asp Leu
465                 470                 475                 480

Arg Leu Ala Pro Phe Gly Ser Gly Arg Arg Ser Cys Pro Gly Lys Ser
                485                 490                 495

Leu Ala Ile Ala Thr Val Gly Phe Trp Val Ala Thr Leu Leu His Glu
            500                 505                 510

Phe Asp Trp Leu Pro Leu Ser Asp Lys Ser Arg Gly Val Asp Leu Ser
        515                 520                 525

Glu Val Leu Lys Leu Ser Cys Glu Met Ala Thr Pro Leu Glu Ala Arg
    530                 535                 540

Leu Arg Pro Arg Arg Lys Val
545                 550


<210> SEQ ID NO 56
<211> LENGTH: 536
<212> TYPE: PRT
<213> ORGANISM: Brachypodium distachyon

<400> SEQUENCE: 56

Met Ala Thr Pro Glu Asp Cys Gly Ser Trp Leu Leu Tyr Leu Ser Leu
1               5                   10                  15

Ala Ala Lys Cys Gly Gly Asp Gly Asp His Pro Arg Arg Leu Ala Gly
            20                  25                  30

Leu Leu Ala Val Cys Ala Ala Ala Phe Leu Val Thr Cys Leu Leu His
        35                  40                  45

Trp Cys Phe Pro Gly Gly Pro Ala Trp Gly Arg Trp Trp Trp Thr Arg
    50                  55                  60

Arg Gly Leu Gly Arg Gly Pro Val Val Pro Gly Pro Arg Gly Leu Pro
65                  70                  75                  80

Val Ile Gly Ser Met Trp Leu Met Thr Gly Leu Ala His Arg Lys Leu
```

```
                85                  90                  95

Ala Ala Glu Ala Ala Arg Leu Arg Gly Gly Gly Arg Arg Leu Met Ala
            100                 105                 110

Phe Ser Leu Gly Glu Thr Arg Val Val Val Ala Gly His Pro Asp Val
        115                 120                 125

Ala Arg Glu Ile Leu Thr Ser Pro Ala Phe Ala Asp Arg Pro Val Lys
    130                 135                 140

Glu Ser Ala Tyr Gly Leu Met Phe His Arg Ala Ile Gly Phe Ala Arg
145                 150                 155                 160

His Gly Ala Tyr Trp Arg Ala Leu Arg Arg Val Ala Ser Thr His Leu
                165                 170                 175

Phe Ser Pro Trp Gln Val Ala Ala Ser Gly Ala Gln Arg Ala Val Ile
            180                 185                 190

Ala Arg Gln Met Val Ala Ala Leu Ala Gly Gly Ala Glu Val Arg Arg
        195                 200                 205

Val Leu Arg Arg Ala Ser Leu His Asn Val Met Trp Ser Val Phe Gly
    210                 215                 220

Arg Arg Tyr Asp Leu Glu Leu Asp Pro Gly Lys Glu Val Arg Glu Leu
225                 230                 235                 240

Gly Gln Leu Val Asp Glu Gly Tyr Asp Leu Leu Gly Gln Leu Asn Trp
                245                 250                 255

Ser Asp His Leu Pro Trp Leu Ala Arg Phe Asp Leu Gln Gly Thr Arg
            260                 265                 270

Ala Arg Cys Ala Ser Leu Val Pro Arg Val Asn Arg Phe Val Gly Gly
        275                 280                 285

Ile Ile Asp Asp His Arg Val Lys Ala Pro Ser Ala Val Lys Asp Phe
    290                 295                 300

Thr Asp Val Leu Leu Gly Leu Gln Gly Gly Asp Arg Leu Ala Asp Ser
305                 310                 315                 320

Asp Met Val Ala Val Leu Trp Glu Met Val Phe Arg Gly Thr Asp Thr
                325                 330                 335

Val Ala Val Leu Met Glu Trp Val Leu Ala Arg Leu Val Leu His Gln
            340                 345                 350

Asp Val Gln Ala Arg Val His Glu Glu Leu Asp Arg Val Val Gly Arg
        355                 360                 365

Asp Arg Ala Val Ala Glu Ser Asp Ala Ala Ser Leu Ala Tyr Leu His
    370                 375                 380

Ala Val Val Lys Glu Val Leu Arg Leu His Pro Pro Gly Pro Leu Leu
385                 390                 395                 400

Ser Trp Ala Arg Leu Ala Thr Ser Asp Val His Val Asp Gly Phe Leu
                405                 410                 415

Ile Pro Ala Gly Thr Thr Ala Met Val Asn Met Trp Ala Ile Thr His
            420                 425                 430

Asp Gly Asp Val Trp Ala Glu Pro Met Glu Phe Arg Pro Glu Arg Phe
        435                 440                 445

Val Gly Pro Gly Ala Glu Glu Phe Ser Val Met Gly Ser Asp Leu Arg
    450                 455                 460

Leu Ala Pro Phe Gly Ala Gly Arg Arg Ser Cys Pro Gly Lys Ser Leu
465                 470                 475                 480

Ala Met Ala Thr Val Ala Phe Trp Leu Ala Thr Leu Leu His Glu Phe
                485                 490                 495

Asp Leu Leu Pro Ser Ser Asp Pro Ala Arg Gly Val Gln Leu Ser Glu
            500                 505                 510
```

```
Thr Leu Arg Leu Ser Cys Glu Met Ala Thr Pro Leu Ala Leu Thr Pro
        515                 520                 525

Arg Ala Arg Arg Arg Pro Ala Val
    530                 535


<210> SEQ ID NO 57
<211> LENGTH: 542
<212> TYPE: PRT
<213> ORGANISM: Glycine max

<400> SEQUENCE: 57

Met Thr Thr His Ile Asp Asn Leu Trp Val Leu Ala Leu Val Ser Lys
1               5                   10                  15

Cys Thr Gln Glu Asn Ile Ala Trp Ser Leu Leu Thr Ile Met Val Thr
            20                  25                  30

Leu Trp Leu Ser Met Thr Phe Phe Cys Trp Ser His Pro Gly Gly Pro
        35                  40                  45

Ala Trp Gly Lys Tyr Tyr Ser Phe His Tyr Trp Lys Lys Thr Thr Thr
    50                  55                  60

Thr Thr Thr Ser Thr Ser Asn Asn Thr Asn Ser Asn Asn Leu Lys Met
65                  70                  75                  80

Ile Pro Gly Pro Lys Gly Tyr Pro Phe Ile Gly Ser Met Ser Leu Met
                85                  90                  95

Thr Ser Leu Ala His His Arg Ile Ala Ala Ala Ala Gln Ala Cys Lys
            100                 105                 110

Ala Thr Arg Leu Met Ala Phe Ser Met Gly Asp Thr Arg Val Ile Val
        115                 120                 125

Thr Cys His Pro His Val Ala Lys Glu Ile Leu Asn Ser Ser Val Phe
    130                 135                 140

Ala Asp Arg Pro Ile Lys Glu Ser Ala Tyr Ser Leu Met Phe Asn Arg
145                 150                 155                 160

Ala Ile Gly Phe Ala Pro Tyr Gly Val Tyr Trp Arg Thr Leu Arg Arg
                165                 170                 175

Ile Ala Ala Thr His Leu Phe Cys Pro Lys Gln Ile Lys Ala Ser Glu
            180                 185                 190

Leu Gln Arg Ala Glu Ile Ala Ala Gln Met Thr His Ser Phe Arg Asn
        195                 200                 205

Arg Arg Gly Gly Phe Gly Ile Arg Ser Val Leu Lys Arg Ala Ser Leu
    210                 215                 220

Asn Asn Met Met Trp Ser Val Phe Gly Gln Arg Tyr Asp Leu Asp Glu
225                 230                 235                 240

Thr Asn Thr Ser Val Asp Glu Leu Ser Arg Leu Val Glu Gln Gly Tyr
                245                 250                 255

Asp Leu Leu Gly Thr Leu Asn Trp Gly Asp His Ile Pro Phe Leu Lys
            260                 265                 270

Asp Phe Asp Leu Gln Lys Ile Arg Phe Thr Cys Ser Lys Leu Val Pro
        275                 280                 285

Gln Val Asn Arg Phe Val Gly Ser Ile Ile Ala Asp His Gln Thr Asp
    290                 295                 300

Thr Thr Gln Thr Asn Arg Asp Phe Val His Val Leu Leu Ser Leu Gln
305                 310                 315                 320

Gly Pro Asp Lys Leu Ser His Ser Asp Met Ile Ala Val Leu Trp Glu
                325                 330                 335

Met Ile Phe Arg Gly Thr Asp Thr Val Ala Val Leu Ile Glu Trp Ile
```

```
            340                 345                 350

Met Ala Arg Met Val Leu His Pro Glu Val Gln Arg Arg Val Gln Glu
        355                 360                 365

Glu Leu Asp Ala Val Val Gly Gly Gly Ala Arg Ala Leu Lys Glu Glu
    370                 375                 380

Asp Val Ala Ala Thr Ala Tyr Leu Leu Ala Val Val Lys Glu Val Leu
385                 390                 395                 400

Arg Leu His Pro Pro Gly Pro Leu Leu Ser Trp Ala Arg Leu Ala Ile
                405                 410                 415

Thr Asp Thr Thr Ile Asp Gly Tyr Asn Val Pro Ala Gly Thr Thr Ala
            420                 425                 430

Met Val Asn Met Trp Ala Ile Gly Arg Asp Pro Glu Val Trp Leu Asp
        435                 440                 445

Pro Leu Asp Phe Lys Pro Glu Arg Phe Met Gly Leu Glu Ala Glu Phe
    450                 455                 460

Ser Val Leu Gly Ser Asp Leu Arg Leu Ala Pro Phe Gly Ser Gly Arg
465                 470                 475                 480

Arg Thr Cys Pro Gly Lys Thr Leu Gly Leu Ser Thr Val Thr Phe Trp
                485                 490                 495

Val Ala Arg Leu Leu His Glu Phe Glu Trp Leu Pro Ser Asp Glu Gly
            500                 505                 510

Lys Val Asp Leu Thr Glu Val Leu Arg Leu Ser Cys Glu Met Ala Asn
        515                 520                 525

Pro Leu Tyr Val Lys Val Arg Pro Arg Arg Gly Leu Ser Thr
    530                 535                 540


<210> SEQ ID NO 58
<211> LENGTH: 553
<212> TYPE: PRT
<213> ORGANISM: Oryza sativa

<400> SEQUENCE: 58

Met Ala Thr Pro Glu Asp Thr Gly Ser Trp Leu Leu Tyr Leu Ser Leu
1               5                   10                  15

Ala Ala Lys Cys Ser Gly Asp Gly Asp Gly Gln Pro His Arg Leu Leu
            20                  25                  30

Gly Phe Val Val Val Cys Ala Val Ala Gly Leu Val Thr Cys Leu Leu
        35                  40                  45

His Trp Ser Phe Pro Gly Gly Pro Ala Trp Gly Arg Trp Trp Trp Thr
    50                  55                  60

Arg Arg Arg Arg Arg Gly Ser Pro Cys Gly Val Ala Ala Val Pro Gly
65                  70                  75                  80

Leu Arg Gly Leu Pro Val Ile Gly Ser Met Trp Leu Met Thr Gly Leu
                85                  90                  95

Ala His Arg Lys Leu Ala Ala Ala Ala Glu Ala Ala Gly Ala Gly Arg
            100                 105                 110

Leu Met Ala Leu Ser Leu Gly Glu Thr Arg Val Val Val Ala Ala His
        115                 120                 125

Pro Asp Val Ala Arg Glu Ile Leu His Gly Ala Ala Phe Ala Asp Arg
    130                 135                 140

Pro Val Lys Glu Ser Ala Tyr Gly Leu Leu Phe His Arg Ala Ile Gly
145                 150                 155                 160

Phe Ala Pro His Gly Ala Tyr Trp Arg Ala Leu Arg Arg Val Ala Ser
                165                 170                 175
```

```
Thr His Leu Phe Ser Pro Trp Gln Val Ala Ala Ser Ala Pro Gln Arg
            180                 185                 190

Ala Val Ile Ala Arg Gln Met Val Arg Ala Ile Lys Leu Gln Gln Arg
        195                 200                 205

Ser Arg Ser Gly Asp Ser Ala Ala Gly Ala Ala Val Glu Val Arg Arg
    210                 215                 220

Val Leu Arg Arg Ala Ser Leu His Asn Val Met Trp Ser Val Phe Gly
225                 230                 235                 240

Arg Arg Tyr Glu Leu Gln Leu Asp Pro Gly Lys Glu Ser Asp Glu Val
                245                 250                 255

Arg Glu Leu Arg Ala Leu Val Asp Glu Gly Tyr Asp Leu Leu Gly Gln
            260                 265                 270

Leu Asn Trp Ser Asp His Leu Pro Trp Leu Ala Arg Phe Asp Leu Gln
        275                 280                 285

Ser Thr Arg Ala Arg Cys Ser Arg Leu Val Pro Arg Val Asn Arg Phe
    290                 295                 300

Val Thr Arg Ile Ile Asp Glu His Arg Ser Ser Ala Pro Val Ala Ala
305                 310                 315                 320

Ala Ile Asp Phe Thr Asp Val Leu Leu Ser Leu Gln Gly Ser Asp Lys
                325                 330                 335

Leu Ala Asp Ser Asp Met Val Ala Val Leu Trp Glu Met Val Phe Arg
            340                 345                 350

Gly Thr Asp Thr Val Ala Val Leu Ile Glu Trp Val Leu Ala Arg Leu
        355                 360                 365

Val Leu Gln Gln Asp Val Gln Ala Arg Val His Asp Glu Leu Gly Arg
    370                 375                 380

Val Val Gly Leu Asp Arg Asp Val Thr Glu Ser Asp Thr Ala Ser Leu
385                 390                 395                 400

Val Tyr Leu His Ala Val Ile Lys Glu Thr Leu Arg Leu His Pro Pro
                405                 410                 415

Gly Pro Leu Leu Ser Trp Ala Arg Leu Ala Thr Ser Asp Val His Val
            420                 425                 430

Asp Gly Tyr Leu Ile Pro Ala Gly Thr Thr Ala Met Val Asn Met Trp
        435                 440                 445

Ala Ile Ala His Asp Pro Asp Val Trp Ala Glu Pro Met Glu Phe Arg
    450                 455                 460

Pro Glu Arg Phe Ile Gly Lys Ala Ala Glu Phe Ser Val Met Gly Ser
465                 470                 475                 480

Asp Leu Arg Leu Ala Pro Phe Gly Ser Gly Arg Arg Ser Cys Pro Gly
                485                 490                 495

Lys Ser Leu Ala Met Ala Thr Val Ala Phe Trp Leu Ala Thr Leu Leu
            500                 505                 510

His Glu Phe Ala Leu Leu Pro Ser Pro Asp Pro Ala His Gly Val Asp
        515                 520                 525

Leu Ser Glu Val Leu Arg Leu Ser Cys Glu Met Ala Thr Pro Leu Ala
    530                 535                 540

Val Thr Ala Trp Pro Arg Arg Val Val
545                 550
```

<210> SEQ ID NO 59
<211> LENGTH: 516
<212> TYPE: PRT
<213> ORGANISM: Glycine max

<400> SEQUENCE: 59

```
Met Ser Pro Asp Phe Thr Leu Leu Phe Phe Pro Glu Leu Met Gln Ser
1               5                   10                  15

Pro Met Ile Thr Phe Gln Ala Thr Leu Cys Val Leu Leu Phe Thr Leu
            20                  25                  30

Met Phe Thr Leu Leu Phe Thr Pro Gly Gly Leu Pro Trp Ala Trp Ala
        35                  40                  45

Arg Pro Arg Pro Ile Ile Pro Gly Pro Val Thr Ala Leu Leu Gly Ile
    50                  55                  60

Phe Thr Gly Ser Thr Pro His Arg Ala Leu Ser Lys Leu Ala Arg Asn
65                  70                  75                  80

Tyr His Ala Glu Lys Leu Met Ala Phe Ser Ile Gly Leu Thr Arg Phe
                85                  90                  95

Val Ile Ser Ser Glu Pro Glu Thr Ala Lys Glu Ile Leu Gly Ser Pro
            100                 105                 110

Ser Phe Ala Asp Arg Pro Val Lys Glu Ser Ala Tyr Glu Leu Leu Phe
        115                 120                 125

His Arg Ala Met Gly Phe Ala Pro Tyr Gly Glu Tyr Trp Arg Asn Leu
    130                 135                 140

Arg Arg Ile Ser Ala Leu His Leu Phe Ser Pro Lys Arg Ile Thr Gly
145                 150                 155                 160

Ser Glu Ser Phe Arg Ser Glu Val Gly Leu Lys Met Val Glu Gln Val
                165                 170                 175

Lys Lys Thr Met Ser Glu Asn Gln His Val Glu Val Lys Lys Ile Leu
            180                 185                 190

His Phe Ser Ser Leu Asn Asn Val Met Met Thr Val Phe Gly Lys Ser
        195                 200                 205

Tyr Glu Phe Tyr Glu Gly Glu Gly Leu Glu Leu Glu Gly Leu Val Ser
    210                 215                 220

Glu Gly Tyr Glu Leu Leu Gly Val Phe Asn Trp Ser Asp His Phe Pro
225                 230                 235                 240

Val Leu Gly Trp Leu Asp Leu Gln Gly Val Arg Lys Arg Cys Arg Cys
                245                 250                 255

Leu Val Glu Lys Val Asn Val Phe Val Gly Gly Val Ile Lys Glu His
            260                 265                 270

Arg Val Lys Arg Glu Arg Gly Glu Cys Val Lys Asp Glu Gly Thr Gly
        275                 280                 285

Asp Phe Val Asp Val Leu Leu Asp Leu Glu Lys Glu Asn Arg Leu Ser
    290                 295                 300

Glu Ala Asp Met Ile Ala Val Leu Trp Glu Met Ile Phe Arg Gly Thr
305                 310                 315                 320

Asp Thr Val Ala Ile Leu Leu Glu Trp Thr Leu Ala Arg Met Val Leu
                325                 330                 335

His Pro Glu Ile Gln Ala Lys Ala Gln Arg Glu Ile Asp Phe Val Cys
            340                 345                 350

Gly Ser Ser Arg Pro Val Ser Glu Ala Asp Ile Pro Asn Leu Arg Tyr
        355                 360                 365

Leu Gln Cys Ile Val Lys Glu Thr Leu Arg Val His Pro Pro Gly Pro
    370                 375                 380

Leu Leu Ser Trp Ala Arg Leu Ala Val His Asp Val Thr Val Gly Gly
385                 390                 395                 400

Lys His Val Ile Pro Lys Gly Thr Thr Ala Met Val Asn Met Trp Ala
                405                 410                 415
```

```
Ile Thr His Asp Glu Arg Val Trp Ala Glu Pro Glu Lys Phe Arg Pro
            420                 425                 430

Glu Arg Phe Val Glu Glu Asp Val Ser Ile Met Gly Ser Asp Leu Arg
        435                 440                 445

Leu Ala Pro Phe Gly Ser Gly Arg Arg Val Cys Pro Gly Lys Ala Leu
    450                 455                 460

Gly Leu Ala Ser Val His Leu Trp Leu Ala Gln Leu Leu Gln Asn Phe
465                 470                 475                 480

His Trp Val Ser Ser Asp Gly Val Ser Val Glu Leu Asp Glu Phe Leu
                485                 490                 495

Lys Leu Ser Met Glu Met Lys Lys Pro Leu Ser Cys Lys Ala Val Pro
            500                 505                 510

Arg Val Ser Val
        515


<210> SEQ ID NO 60
<211> LENGTH: 516
<212> TYPE: PRT
<213> ORGANISM: Glycine max

<400> SEQUENCE: 60

Met Ser Pro Asp Phe Thr Leu Leu Phe Ser Pro Glu Leu Met Gln Ser
1               5                   10                  15

Pro Ile Ile Thr Phe Gln Ala Thr Phe Cys Val Leu Leu Phe Thr Leu
            20                  25                  30

Met Phe Thr Pro Phe Phe Thr Pro Gly Gly Leu Pro Trp Ala Trp Ala
        35                  40                  45

Arg Pro Arg Thr Ile Ile Pro Gly Pro Val Thr Ala Leu Leu Gly Val
    50                  55                  60

Phe Thr Gly Ser Thr Pro His Ser Ala Leu Ser Lys Leu Ala Arg Thr
65                  70                  75                  80

Tyr His Ala Glu Lys Leu Met Ala Phe Ser Ile Gly Leu Thr Arg Phe
                85                  90                  95

Val Ile Ser Ser Glu Pro Glu Thr Ala Lys Glu Ile Leu Gly Ser Pro
            100                 105                 110

Gly Phe Ala Asp Arg Pro Val Lys Glu Ser Ala Tyr Glu Leu Leu Phe
        115                 120                 125

His Arg Ala Met Gly Phe Ala Pro Tyr Gly Glu Tyr Trp Arg Asn Leu
    130                 135                 140

Arg Arg Ile Ser Ala Leu His Leu Phe Ser Pro Lys Arg Ile Thr Ser
145                 150                 155                 160

Ser Glu Ser Phe Arg Ser Lys Val Gly Leu Lys Met Val Glu Gln Val
                165                 170                 175

Lys Lys Thr Met Ser Glu Asn Gln His Val Glu Val Lys Lys Ile Leu
            180                 185                 190

His Phe Ser Ser Leu Asn Asn Val Met Met Thr Val Phe Gly Lys Cys
        195                 200                 205

Tyr Glu Phe Tyr Glu Gly Glu Gly Leu Glu Leu Glu Gly Leu Val Ser
    210                 215                 220

Glu Gly Tyr Glu Leu Leu Gly Val Phe Asn Trp Ser Asp His Phe Pro
225                 230                 235                 240

Val Leu Gly Trp Leu Asp Leu Gln Gly Val Arg Lys Arg Cys Arg Cys
                245                 250                 255

Leu Val Glu Lys Val Asn Val Phe Val Gly Gly Val Ile Lys Glu His
            260                 265                 270
```

```
Arg Val Lys Arg Glu Arg Gly Asp Cys Val Lys Asp Glu Gly Ala Glu
        275                 280                 285

Asp Phe Val Asp Val Leu Leu Asp Leu Glu Lys Glu Asn Arg Leu Ser
    290                 295                 300

Glu Ala Asp Met Ile Ala Val Leu Trp Glu Met Ile Phe Arg Gly Thr
305                 310                 315                 320

Asp Thr Val Ala Ile Leu Leu Glu Trp Ile Leu Ala Arg Met Val Leu
                325                 330                 335

His Pro Glu Ile Gln Ala Lys Ala Gln Arg Glu Ile Asp Phe Val Cys
            340                 345                 350

Gly Ser Ser Arg Leu Val Ser Glu Ala Asp Ile Pro Asn Leu Arg Tyr
        355                 360                 365

Leu Gln Cys Ile Val Lys Glu Thr Leu Arg Val His Pro Pro Gly Pro
    370                 375                 380

Leu Leu Ser Trp Ala Arg Leu Ala Val His Asp Val Thr Val Gly Gly
385                 390                 395                 400

Lys His Val Ile Pro Lys Gly Thr Thr Ala Met Val Asn Met Trp Ala
                405                 410                 415

Ile Thr His Asp Glu Arg Val Trp Ala Glu Pro Glu Lys Phe Arg Pro
            420                 425                 430

Glu Arg Phe Val Glu Glu Asp Val Ser Ile Met Gly Ser Asp Leu Arg
        435                 440                 445

Leu Ala Pro Phe Gly Ser Gly Arg Arg Val Cys Pro Gly Lys Ala Leu
    450                 455                 460

Gly Leu Ala Ser Val His Leu Trp Leu Ala Gln Leu Leu Gln Asn Phe
465                 470                 475                 480

His Trp Val Ser Ser Asp Gly Val Ser Val Glu Leu Asp Glu Phe Leu
                485                 490                 495

Lys Leu Ser Met Glu Met Lys Lys Pro Leu Ser Cys Lys Ala Val Pro
            500                 505                 510

Arg Val Ser Val
        515


<210> SEQ ID NO 61
<211> LENGTH: 543
<212> TYPE: PRT
<213> ORGANISM: Zea mays

<400> SEQUENCE: 61

Met Ala Pro Pro Thr Glu Asp Cys Gly Trp Leu Leu Tyr Leu Ser Leu
1               5                   10                  15

Ala Ala Lys Cys Gly Asp Pro Gln Arg Leu Leu Gly Phe Ala Ala Val
            20                  25                  30

Phe Val Ala Ala Cys Val Val Thr Ser Leu Leu His Trp Ala Ser Pro
        35                  40                  45

Gly Gly Pro Ala Trp Gly Trp Tyr Trp Trp Thr Arg Arg Ala Gly Leu
    50                  55                  60

Gly Ile Val Arg Ala Ala Ile Pro Gly Pro Arg Gly Leu Pro Val Val
65                  70                  75                  80

Gly Ser Met Gly Leu Met Thr Gly Leu Ala His Arg Lys Leu Ser Ala
                85                  90                  95

Ala Ala Glu Arg Gln Ala Ser Arg Arg Arg Leu Met Ala Phe Ser Leu
            100                 105                 110

Gly Glu Thr Arg Val Val Val Thr Ala Asp Pro Asp Val Ala Arg Glu
```

```
        115                 120                 125

Leu Leu Ala Ser Ala Ala Phe Ala Asp Arg Pro Val Lys Glu Ser Ala
    130                 135                 140

Tyr Gly Leu Leu Phe His Arg Ala Ile Gly Phe Ala Pro His Gly Ala
145                 150                 155                 160

Tyr Trp Arg Ala Leu Arg Arg Val Ala Ser Ala His Leu Phe Ser Pro
                165                 170                 175

Arg Gln Ile Ala Ala Ser Ala Ala Gln Arg Ala Ala Ile Ala Arg Gln
            180                 185                 190

Met Val Asp Ala Thr Thr Thr Ala Ala Ala His Ala Pro Val Val Val
        195                 200                 205

Ala Arg Arg Phe Leu Lys Arg Ala Ser Leu His Asn Val Met Trp Ser
    210                 215                 220

Val Phe Gly Arg Arg Tyr Asp Leu Met Ala Asp Ser Arg Glu Ala Glu
225                 230                 235                 240

Glu Leu Lys Ala Leu Val Asp Glu Gly Tyr Asp Leu Leu Gly Gln Leu
                245                 250                 255

Asn Trp Ser Asp His Leu Pro Trp Leu Ala Arg Phe Asp Leu Gln Lys
            260                 265                 270

Thr Arg Ala Arg Cys Cys Ala Leu Val Pro Arg Val Asn Arg Phe Val
        275                 280                 285

Gly Asn Ile Ile Gly Glu His Arg Ala Arg Leu Gly Arg Gly Val Asp
    290                 295                 300

Thr Ala Val Met Asp Phe Thr Asp Val Leu Leu Ser Leu Gln Gly Asp
305                 310                 315                 320

Asp Lys Leu Ser Asp Ala Asp Met Ile Ala Val Leu Trp Glu Met Ile
                325                 330                 335

Phe Arg Gly Thr Asp Thr Val Ala Val Leu Ile Glu Trp Val Leu Ala
            340                 345                 350

Arg Leu Val Leu His Gln Asp Val Gln Ser Lys Val Gln Glu Glu Leu
        355                 360                 365

Asp Arg Val Val Gly Leu Gly Gln Ala Val Thr Glu Ser Asp Thr Ala
    370                 375                 380

Ser Leu Pro Tyr Leu Gln Ala Val Ile Lys Glu Val Leu Arg Leu His
385                 390                 395                 400

Pro Pro Gly Pro Leu Leu Ser Trp Ala Arg Leu Ala Thr Ser Asp Val
                405                 410                 415

His Val Gly Gly Tyr Leu Val Pro Ala Gly Thr Thr Ala Met Val Asn
            420                 425                 430

Met Trp Ala Ile Thr His Asp Pro Ser Leu Trp Pro Glu Pro Met Glu
        435                 440                 445

Phe Arg Pro Glu Arg Phe Met Gly Pro Ala Ala Glu Asp Val Pro Ile
    450                 455                 460

Met Gly Ser Asp Leu Arg Leu Ala Pro Phe Gly Ser Gly Arg Arg Ser
465                 470                 475                 480

Cys Pro Gly Lys Ser Leu Ala Val Ala Thr Val Gly Phe Trp Val Ala
                485                 490                 495

Thr Leu Leu Tyr Glu Phe Lys Trp Leu Pro Pro Ser Asp Glu Pro Arg
            500                 505                 510

Gly Gly Gly Val Asp Leu Ser Glu Val Leu Arg Leu Ser Cys Glu Met
        515                 520                 525

Ala Ala Pro Leu Glu Ala Arg Val Val Pro Arg His Ala Val Cys
    530                 535                 540
```

<210> SEQ ID NO 62
<211> LENGTH: 551
<212> TYPE: PRT
<213> ORGANISM: Sorghum bicolor

<400> SEQUENCE: 62

```
Met Ala Val Ala Ala Thr Pro Asp Asp Cys Gly Ser Trp Leu Leu Tyr
1               5                   10                  15

Leu Ser Leu Ala Ala Lys Cys Ala Gly Gly Asp Gln Pro His Arg Leu
            20                  25                  30

Ala Gly Phe Leu Ala Val Cys Ala Val Ala Phe Val Val Thr Cys Leu
        35                  40                  45

Leu His Trp Cys Phe Pro Gly Gly Pro Ala Trp Gly Arg Trp Trp Trp
    50                  55                  60

Thr Thr Gln Ala Arg Arg Val Ala Ala Ala Ala Val Pro Gly Pro Arg
65                  70                  75                  80

Gly Leu Pro Val Val Gly Ser Met Trp Leu Met Thr Gly Leu Ala His
                85                  90                  95

Arg Lys Leu Ala Ala Ala Ala Asp Ser Leu Arg Ala Arg Arg Leu Met
            100                 105                 110

Ala Phe Ser Leu Gly Gly Thr Arg Val Val Val Ala Ala His Pro Asp
        115                 120                 125

Val Ala Arg Glu Ile Leu Asn Ser Pro Ala Phe Ala Asp Arg Pro Ile
    130                 135                 140

Lys Glu Ser Ala Tyr Gly Leu Leu Phe His Arg Ala Ile Gly Phe Ala
145                 150                 155                 160

Pro Tyr Gly Ala Tyr Trp Arg Ala Leu Arg Arg Val Ala Ser Thr His
                165                 170                 175

Leu Phe Ser Pro Trp Gln Val Ala Ala Ser Ala Ala Gln Arg Ala Val
            180                 185                 190

Ile Ala Arg Gln Met Val Ala Ala Met Lys Gln Glu Leu Ser Ser Ser
        195                 200                 205

Ser Ser Ala Ser Ala Gly Phe Glu Val Arg Arg Val Leu Arg Arg Gly
    210                 215                 220

Ser Leu His Asn Val Met Trp Ser Val Phe Gly Arg Arg Tyr Asp Leu
225                 230                 235                 240

Glu Leu Asp Pro Ala Lys Glu Ser Pro Glu Thr Arg Glu Leu Arg Ser
                245                 250                 255

Leu Val Asp Glu Gly Tyr Asp Leu Leu Gly Gln Leu Asn Trp Ser Asp
            260                 265                 270

His Leu Pro Trp Leu Ala Arg Phe Asp Leu Gln Ser Thr Arg Ser Arg
        275                 280                 285

Cys Asp Arg Leu Val Pro Leu Val Asn Arg Phe Val Gly Gly Ile Ile
    290                 295                 300

Asp Ala His Arg Ala Arg Asn Asp Leu Arg Ser Ala Pro Pro His Ala
305                 310                 315                 320

Val Met Asp Phe Thr Asp Val Leu Leu Ser Leu Pro Ala Asp Asp Arg
                325                 330                 335

Leu Thr Asp Ser Asp Met Ile Ala Val Leu Trp Glu Met Val Phe Arg
            340                 345                 350

Gly Thr Asp Thr Val Ala Val Leu Ile Glu Trp Val Leu Ala Arg Leu
        355                 360                 365

Val Leu His Pro Asp Val Gln Ala Arg Val His Asp Glu Leu Asp Arg
```

```
    370                 375                 380

Val Val Gly Arg Asp Arg Ala Val Thr Glu Ser Asp Ser Gly Ser Leu
385                 390                 395                 400

Val Tyr Leu His Ala Val Ile Lys Glu Val Leu Arg Met His Pro Pro
                405                 410                 415

Gly Pro Leu Leu Ser Trp Ala Arg Leu Ala Thr Ser Asp Val Gln Val
            420                 425                 430

Asp Gly His Leu Ile Pro Ala Gly Thr Thr Ala Met Val Asn Met Trp
        435                 440                 445

Ala Ile Thr His Asp Pro Asp Val Trp Ala Glu Pro Ala Glu Phe Gln
    450                 455                 460

Pro Glu Arg Phe Met Gly Ser Thr Thr Gly Gly Glu Phe Pro Ile Met
465                 470                 475                 480

Gly Ser Asp Leu Arg Leu Ala Pro Phe Gly Ala Gly Arg Arg Ser Cys
                485                 490                 495

Pro Gly Lys Ser Leu Ala Met Ala Thr Val Ala Leu Trp Leu Ala Thr
            500                 505                 510

Leu Leu His Glu Phe Glu Leu Leu Pro Ala Arg Gly Val Tyr Leu Ser
        515                 520                 525

Glu Val Leu Lys Leu Ser Cys Glu Met Ala Val Pro Leu Ala Val Thr
    530                 535                 540

Ala Arg Pro Arg Gln Ala Val
545                 550


<210> SEQ ID NO 63
<211> LENGTH: 528
<212> TYPE: PRT
<213> ORGANISM: Glycine max

<400> SEQUENCE: 63

Met Ser Ser Ser Glu Leu Ser Ser Phe Phe Leu Leu Arg Leu Ser Asp
1               5                   10                  15

Ile Leu Ser Phe Asp Val Leu Leu Gly Val Met Phe Leu Val Ala Val
            20                  25                  30

Phe Gly Tyr Trp Leu Val Pro Gly Gly Leu Ala Trp Ala Phe Ser Lys
        35                  40                  45

Phe Lys Pro Ala Ile Pro Gly Pro Ser Gly Tyr Pro Val Val Gly Leu
    50                  55                  60

Val Trp Ala Phe Ile Gly Pro Leu Thr His Arg Val Leu Ala Lys Leu
65                  70                  75                  80

Ala Glu Thr Phe Asp Ala Lys Pro Leu Met Ala Phe Ser Val Gly Phe
                85                  90                  95

Thr Arg Phe Ile Ile Ser Ser His Pro Asp Thr Ala Lys Glu Ile Leu
            100                 105                 110

Asn Ser Ser Ala Phe Ala Asp Arg Pro Val Lys Glu Ser Ala Tyr Glu
        115                 120                 125

Leu Leu Phe His Arg Ala Met Gly Phe Ala Pro Tyr Gly Glu Tyr Trp
    130                 135                 140

Arg Asn Leu Arg Arg Ile Ser Ala Thr His Met Phe Ser Pro Arg Arg
145                 150                 155                 160

Ile Ala Ala Gln Gly Val Phe Arg Ala Arg Ile Gly Ala Gln Met Val
                165                 170                 175

Arg Asp Ile Val Gly Leu Met Gly Arg Asp Gly Val Val Glu Val Arg
            180                 185                 190
```

```
Lys Val Leu His Phe Gly Ser Leu Asn Asn Val Met Lys Ser Val Phe
        195                 200                 205

Gly Arg Ser Tyr Val Phe Gly Glu Gly Gly Asp Gly Cys Glu Leu Glu
    210                 215                 220

Gly Leu Val Ser Glu Gly Tyr His Leu Leu Gly Val Phe Asn Trp Ser
225                 230                 235                 240

Asp His Phe Pro Leu Leu Gly Trp Leu Asp Leu Gln Gly Val Arg Lys
                245                 250                 255

Ser Cys Arg Ser Leu Val Asp Arg Val Asn Val Tyr Val Gly Lys Ile
            260                 265                 270

Ile Leu Glu His Arg Val Lys Arg Val Ala Gln Gly Glu Asp Asn Lys
        275                 280                 285

Ala Ile Asp Thr Asp Ser Ser Gly Asp Phe Val Asp Val Leu Leu Asp
    290                 295                 300

Leu Glu Lys Glu Asn Arg Leu Asn His Ser Asp Met Val Ala Val Leu
305                 310                 315                 320

Trp Glu Met Ile Phe Arg Gly Thr Asp Thr Val Ala Ile Leu Leu Glu
                325                 330                 335

Trp Ile Leu Ala Arg Met Val Leu His Pro Glu Ile Gln Ala Lys Ala
            340                 345                 350

Gln Ser Glu Ile Asp Ser Val Val Gly Ser Gly Arg Ser Val Ser Asp
        355                 360                 365

Asp Asp Leu Pro Asn Leu Pro Tyr Val Arg Ala Ile Val Lys Glu Thr
    370                 375                 380

Leu Arg Met His Pro Pro Gly Pro Leu Leu Ser Trp Ala Arg Leu Ser
385                 390                 395                 400

Ile His Asp Thr Gln Ile Gly Asn His Phe Val Pro Ala Gly Thr Thr
                405                 410                 415

Ala Met Val Asn Met Trp Ala Ile Thr His Asp Gln Glu Val Trp Tyr
            420                 425                 430

Glu Pro Lys Gln Phe Lys Pro Glu Arg Phe Leu Lys Asp Glu Asp Val
        435                 440                 445

Pro Ile Met Gly Ser Asp Leu Arg Leu Ala Pro Phe Gly Ser Gly Arg
    450                 455                 460

Arg Val Cys Pro Gly Lys Ala Met Gly Leu Ala Thr Val Glu Leu Trp
465                 470                 475                 480

Leu Ala Met Phe Leu Gln Lys Phe Lys Trp Met Pro Cys Asp Asp Ser
                485                 490                 495

Gly Val Asp Leu Ser Glu Cys Leu Lys Leu Ser Met Glu Met Lys His
            500                 505                 510

Ser Leu Lys Thr Lys Val Val Ala Arg Pro Val Val Ser Leu Ala Met
        515                 520                 525


<210> SEQ ID NO 64
<211> LENGTH: 557
<212> TYPE: PRT
<213> ORGANISM: Zea mays

<400> SEQUENCE: 64

Met Ala Ala Pro Pro Thr Glu Asp Cys Gly Trp Leu Leu Tyr Leu Ser
1               5                   10                  15

Leu Ala Ala Lys Cys Gly Asp Pro Ser Arg Leu Leu Gly Leu Ala Ala
            20                  25                  30

Val Phe Val Gly Ala Cys Val Val Thr Ser Leu Leu His Trp Ala Cys
        35                  40                  45
```

```
Pro Gly Gly Pro Ala Trp Gly Arg Tyr Trp Trp Thr Arg Arg Gly Gly
    50                  55                  60

Leu Gly Ile Val Arg Ala Ala Ile Pro Gly Pro Arg Gly Leu Pro Val
65                  70                  75                  80

Val Gly Ser Met Gly Leu Met Thr Gly Leu Ala His Arg Lys Leu Ala
                85                  90                  95

Ala Ala Ala Ala Ala Ala Gly Gly Gln Gly Ser Ser Arg Arg Arg Arg
            100                 105                 110

Leu Met Ala Leu Ser Leu Gly Glu Thr Arg Ala Val Val Thr Gly Asp
        115                 120                 125

Pro Asp Val Ala Arg Glu Leu Leu Gly Ser Ala Ala Phe Ala Asp Arg
    130                 135                 140

Pro Val Lys Glu Ser Ala Tyr Gly Leu Leu Phe His Arg Ala Ile Gly
145                 150                 155                 160

Phe Ala Pro His Gly Ala Tyr Trp Arg Ala Leu Arg Arg Val Ala Ser
                165                 170                 175

Ala His Leu Phe Ser Pro Arg Gln Val Ala Ala Ser Ser Ala Gln Arg
            180                 185                 190

Ala Val Ile Ala Arg Gln Met Val Asp Ala Val Thr Thr Ala Ala Pro
        195                 200                 205

Ala Pro Ala Pro Ala Val Val Val Ala Arg Arg Phe Leu Lys Arg Ala
    210                 215                 220

Ser Leu His Asn Val Met Trp Ser Val Phe Gly Arg Arg Tyr Asp Leu
225                 230                 235                 240

Leu Leu Leu Ala Ala Asp Gly Glu Glu Leu Lys Ala Leu Val Asp Glu
                245                 250                 255

Gly Tyr Asp Leu Leu Gly Gln Leu Asn Trp Ser Asp His Leu Pro Trp
            260                 265                 270

Leu Ala Arg Phe Asp Leu Gln Arg Thr Arg Ala Arg Cys Ser Ala Leu
        275                 280                 285

Val Pro Arg Val Asn Arg Phe Val Gly Asn Ile Ile Asp Glu His Arg
    290                 295                 300

Ala Arg Leu Gly Leu Gly Asp Thr Gly Gly Val Thr Asp Phe Thr Asp
305                 310                 315                 320

Val Leu Leu Ser Leu Gln Gly Val Asp Lys Leu Ser Asp Ala Asp Met
                325                 330                 335

Val Ala Val Leu Trp Glu Met Ile Phe Arg Gly Thr Asp Thr Val Ala
            340                 345                 350

Val Leu Met Glu Trp Val Leu Ala Arg Leu Val Leu His Gln Asp Val
        355                 360                 365

Gln Ser Lys Val Gln Glu Glu Leu Asp Arg Val Val Gly Pro Pro Gly
    370                 375                 380

Gln Ala Ala Ser Val Thr Glu Ser Asp Thr Ala Ser Leu Val Tyr Leu
385                 390                 395                 400

Gln Ala Val Ile Lys Glu Val Leu Arg Leu His Pro Pro Gly Pro Leu
                405                 410                 415

Leu Ser Trp Ala Arg Leu Ala Thr Ser Asp Ala Arg Val Gly Gly Tyr
            420                 425                 430

His Val Pro Ala Gly Thr Thr Ala Met Val Asn Met Trp Ala Ile Thr
        435                 440                 445

His Asp Pro Ser Val Trp Ala Glu Pro Thr Glu Phe Arg Pro Glu Arg
    450                 455                 460
```

```
Phe Val Gly Ala Ser Ala Gly Ala Gly Ala Gly Ala Gly Ala Glu Asp
465                 470                 475                 480

Val Pro Met Ile Met Gly Ser Asp Leu Arg Leu Ala Pro Phe Gly Ser
                485                 490                 495

Gly Arg Arg Ser Cys Pro Gly Lys Ser Leu Ala Leu Ala Thr Val Gly
            500                 505                 510

Phe Trp Val Ala Thr Leu Leu His Glu Phe Lys Trp Leu Pro Pro Cys
        515                 520                 525

Arg Gly Val Asp Leu Ser Glu Val Leu Arg Leu Ser Cys Glu Met Ala
    530                 535                 540

Ala Pro Leu Glu Ala Arg Val Val Pro Arg His Ala Val
545                 550                 555


<210> SEQ ID NO 65
<211> LENGTH: 572
<212> TYPE: PRT
<213> ORGANISM: Brachypodium distachyon

<400> SEQUENCE: 65

Met Ala Pro Ala Thr Ser Ala Ser Glu Asp Cys Ala Gly Trp Leu Leu
1               5                   10                  15

Tyr Ala Ser Leu Ala Ala Arg Cys Asn Asp Gly Gly Glu Ala Tyr Arg
            20                  25                  30

Ala Ala Val Phe Ala Met Ala Leu Leu Ala Thr Ser Phe Ile Leu Thr
        35                  40                  45

Ser Leu Leu His Trp Ala Ser Thr Pro Gly Gly Pro Ala Trp Gly Arg
    50                  55                  60

Tyr Arg Trp Thr Ser Thr Thr Ser Arg Ala Ala Ile Ser Thr Ser Pro
65                  70                  75                  80

Arg Ile Pro Gly Pro Arg Gly Leu Pro Val Val Gly Ser Met Gly Leu
                85                  90                  95

Met Thr Gly Leu Ala His Arg Lys Leu Ala Ala Ala Val Ala Ala Gly
            100                 105                 110

Gly Asp Asp Glu Glu Glu Arg Ser Gln Arg Arg Arg Leu Met Ala Phe
        115                 120                 125

Ser Met Gly Glu Thr Arg Ala Val Val Ser Ser Asp Pro Ala Val Ala
    130                 135                 140

Arg Glu Leu Leu Ser Ser Pro Ala Phe Ala Asp Arg Pro Val Lys Glu
145                 150                 155                 160

Ser Ala Tyr Gly Leu Leu Phe His Arg Ala Ile Gly Phe Ala Pro His
                165                 170                 175

Gly Ala Tyr Trp Arg Ser Leu Arg Arg Val Ala Ser Ala His Leu Phe
            180                 185                 190

Ser Pro Arg Gln Val Ala Ala Ser Ala Ala His Arg Ala Ala Ile Ala
        195                 200                 205

Arg Ser Met Val Gly Ser Val Ser Ala Ile Ala Met Gly Ser Gly Glu
    210                 215                 220

Val Glu Val Arg Arg Phe Leu Lys Arg Ala Ala Leu His Gly Val Met
225                 230                 235                 240

Trp Ser Val Phe Gly Arg Arg Tyr Asp Gly Thr Ala Ala Pro Glu Leu
                245                 250                 255

Gly Lys Lys Glu Glu Glu Glu Leu Arg Ser Met Val Glu Glu Gly Tyr
            260                 265                 270

Glu Leu Leu Gly Lys Leu Asn Trp Ala Asp His Leu Pro Trp Leu Ala
        275                 280                 285
```

```
Arg Phe Asp Leu Gln Gly Ile Arg Ala Arg Cys Ala Ala Leu Val Pro
    290                 295                 300

Arg Val Asn Arg Phe Val Gly Lys Ile Val Asp Asp His Arg Ala Ala
305                 310                 315                 320

Ala Ala Ala Asp Ala Gly Asp Arg Val Val Asp Phe Thr Asp Val Leu
                325                 330                 335

Leu Ser Leu Gln Gly Ala Asp Lys Leu Ser Asp Ala Asp Met Ile Ala
            340                 345                 350

Val Leu Trp Glu Met Val Phe Arg Gly Thr Asp Thr Met Ala Val Val
        355                 360                 365

Met Glu Trp Val Leu Ala Arg Leu Val Met His Gln Asp Val Gln Ala
    370                 375                 380

Arg Val Gln Glu Glu Leu Asp Arg Val Val Gly Pro Gly Gln Ala Val
385                 390                 395                 400

Ser Glu Ser Asp Ala Ala Arg Leu Val Tyr Leu Gln Ala Val Ile Lys
                405                 410                 415

Glu Thr Met Arg Leu His Pro Pro Gly Pro Leu Leu Ser Trp Ala Arg
            420                 425                 430

Leu Ala Thr Ser Asp Val His Val Gly Gly Phe Leu Val Pro Ala Gly
        435                 440                 445

Thr Thr Ala Met Val Asn Met Trp Ala Ile Thr His Asp Pro Thr Val
    450                 455                 460

Trp Ala Asp Pro Leu Glu Phe Asn Pro Asp Arg Phe Ile Val Gly Ala
465                 470                 475                 480

Val Pro Leu Ser Glu Gly His His Asn Ala Val Pro Gly Ala Glu Phe
                485                 490                 495

Ser Ile Met Gly Ser Asp Leu Arg Leu Ala Pro Phe Gly Ser Gly Arg
            500                 505                 510

Arg Ile Cys Pro Gly Lys Pro Leu Ala Met Ala Ser Ile Gly Phe Trp
        515                 520                 525

Val Ala Thr Leu Leu His Glu Phe Lys Trp Thr Ser Ala Pro Arg Gly
    530                 535                 540

Asp Val Asp Leu Ser Glu Val Leu Arg Leu Ser Cys Glu Met Ala Ala
545                 550                 555                 560

Pro Leu Lys Ala Arg Leu Thr Pro Arg Arg Pro Val
                565                 570
```

```
<210> SEQ ID NO 66
<211> LENGTH: 517
<212> TYPE: PRT
<213> ORGANISM: Glycine max

<400> SEQUENCE: 66

Met Ser Ser Ser Glu Leu Ser Ser Phe Phe Leu Leu Pro Leu Ser Ala
1               5                   10                  15

Ile Leu Ser Phe Asp Ala Leu Leu Gly Val Met Phe Leu Val Ala Val
            20                  25                  30

Phe Gly Tyr Trp Leu Val Pro Gly Gly Leu Ala Trp Ala Leu Ser Lys
        35                  40                  45

Phe Lys Pro Ala Ile Pro Gly Pro Cys Gly Tyr Pro Val Val Gly Leu
    50                  55                  60

Val Trp Ala Phe Ile Gly Pro Leu Thr His Arg Val Leu Ala Lys Leu
65                  70                  75                  80

Ala Glu Thr Phe Asp Ala Lys Pro Leu Met Ala Phe Ser Val Gly Phe
```

```
                85                  90                  95

Thr Arg Phe Ile Ile Ser Ser His Pro Asp Thr Ala Lys Glu Ile Leu
            100                 105                 110

Asn Ser Ser Ala Phe Ala Asp Arg Pro Val Lys Glu Ser Ala Tyr Glu
        115                 120                 125

Leu Leu Phe His Arg Ala Met Gly Phe Ala Pro Tyr Gly Glu Tyr Trp
    130                 135                 140

Arg Asn Leu Arg Arg Ile Ser Ala Thr His Met Phe Ser Pro Lys Arg
145                 150                 155                 160

Ile Ala Ala Gln Gly Val Phe Arg Ala Arg Val Gly Ala Gln Met Val
                165                 170                 175

Arg Glu Ile Val Gly Leu Met Gly Lys Asn Asp Val Val Glu Val Arg
            180                 185                 190

Lys Val Leu His Phe Gly Ser Leu Asn Asn Val Met Lys Ser Val Phe
        195                 200                 205

Gly Arg Ser Tyr Val Phe Gly Glu Gly Gly Asp Gly Cys Glu Leu Glu
    210                 215                 220

Glu Leu Val Ser Glu Gly Tyr Asp Leu Leu Gly Leu Phe Asn Trp Ser
225                 230                 235                 240

Asp His Phe Pro Leu Leu Gly Trp Leu Asp Phe Gln Gly Val Arg Lys
                245                 250                 255

Arg Cys Arg Ser Leu Val Asp Arg Val Asn Val Phe Val Gly Lys Ile
            260                 265                 270

Ile Met Glu His Arg Val Lys Arg Asp Ala Glu Ser Gly Asp Phe Val
        275                 280                 285

Asp Val Leu Leu Asp Leu Glu Lys Glu Asp Arg Leu Asn His Ser Asp
    290                 295                 300

Met Val Ala Val Leu Trp Glu Met Ile Phe Arg Gly Thr Asp Thr Val
305                 310                 315                 320

Ala Ile Leu Leu Glu Trp Ile Leu Ala Arg Met Val Leu His Pro Glu
                325                 330                 335

Ile Gln Ala Lys Ala Gln Cys Glu Ile Asp Ser Val Val Gly Ser Gly
            340                 345                 350

Cys Ser Val Thr Asp Asp Asp Leu Pro Asn Leu Pro Tyr Val Arg Ala
        355                 360                 365

Ile Val Lys Glu Thr Leu Arg Met His Pro Pro Gly Pro Leu Leu Ser
    370                 375                 380

Trp Ala Arg Leu Ser Ile His Glu Thr Gln Ile Gly Asn His Phe Val
385                 390                 395                 400

Pro Ala Gly Thr Thr Ala Met Val Asn Leu Trp Ala Ile Thr His Asp
                405                 410                 415

Gln Gln Val Trp Ser Glu Pro Glu Gln Phe Lys Pro Glu Arg Phe Leu
            420                 425                 430

Lys Asp Glu Asp Val Pro Ile Met Gly Ser Asp Leu Arg Leu Ala Pro
        435                 440                 445

Phe Gly Ala Gly Arg Arg Val Cys Pro Gly Lys Ala Met Gly Leu Ala
    450                 455                 460

Thr Val Glu Leu Trp Leu Ala Val Phe Leu Gln Lys Phe Lys Trp Met
465                 470                 475                 480

Pro Cys Asp Asp Ser Gly Val Asp Leu Ser Glu Cys Leu Lys Leu Ser
                485                 490                 495

Met Glu Met Lys His Ser Leu Ile Thr Lys Ala Val Ala Arg Pro Thr
            500                 505                 510
```

```
Ser Ser Leu Ala Met
        515


<210> SEQ ID NO 67
<211> LENGTH: 525
<212> TYPE: PRT
<213> ORGANISM: Oryza sativa

<400> SEQUENCE: 67

Met Ala Leu Ser Ser Met Ala Ala Ala Gln Glu Ser Ser Leu Leu Leu
1               5                   10                  15

Phe Leu Leu Pro Thr Ser Ala Ala Ser Val Phe Pro Pro Leu Ile Ser
            20                  25                  30

Val Val Val Leu Ala Ala Leu Leu Leu Trp Leu Ser Pro Gly Gly Pro
        35                  40                  45

Ala Trp Ala Leu Ser Arg Cys Arg Gly Thr Pro Pro Pro Pro Gly Val
    50                  55                  60

Ala Gly Gly Ala Ala Ser Ala Leu Ser Gly Pro Ala Ala His Arg Val
65                  70                  75                  80

Leu Ala Gly Ile Ser Arg Ala Val Glu Gly Gly Ala Ala Val Met Ser
                85                  90                  95

Leu Ser Val Gly Leu Thr Arg Leu Val Val Ala Ser Arg Pro Glu Thr
            100                 105                 110

Ala Arg Glu Ile Leu Val Ser Pro Ala Phe Gly Asp Arg Pro Val Lys
        115                 120                 125

Asp Ala Ala Arg Gln Leu Leu Phe His Arg Ala Met Gly Phe Ala Pro
    130                 135                 140

Ser Gly Asp Ala His Trp Arg Gly Leu Arg Arg Ala Ser Ala Ala His
145                 150                 155                 160

Leu Phe Gly Pro Arg Arg Val Ala Gly Ser Ala Pro Glu Arg Glu Ala
                165                 170                 175

Ile Gly Ala Arg Ile Val Gly Asp Val Ala Ser Leu Met Ser Arg Arg
            180                 185                 190

Gly Glu Val Pro Leu Arg Arg Val Leu His Ala Ala Ser Leu Gly His
        195                 200                 205

Val Met Ala Thr Val Phe Gly Lys Arg His Gly Asp Ile Ser Ile Gln
    210                 215                 220

Asp Gly Glu Leu Leu Glu Glu Met Val Thr Glu Gly Tyr Asp Leu Leu
225                 230                 235                 240

Gly Lys Phe Asn Trp Ala Asp His Leu Pro Leu Leu Arg Trp Leu Asp
                245                 250                 255

Leu Gln Gly Ile Arg Arg Arg Cys Asn Arg Leu Val Gln Lys Val Glu
            260                 265                 270

Val Phe Val Gly Lys Ile Ile Gln Glu His Lys Ala Lys Arg Ala Ala
        275                 280                 285

Gly Gly Val Ala Val Ala Asp Gly Val Leu Gly Asp Phe Val Asp Val
    290                 295                 300

Leu Leu Asp Leu Gln Gly Glu Glu Lys Met Ser Asp Ser Asp Met Ile
305                 310                 315                 320

Ala Val Leu Trp Glu Met Ile Phe Arg Gly Thr Asp Thr Val Ala Ile
                325                 330                 335

Leu Met Glu Trp Val Met Ala Arg Met Val Met His Pro Glu Ile Gln
            340                 345                 350

Ala Lys Ala Gln Ala Glu Val Asp Ala Ala Val Gly Gly Arg Arg Gly
```

```
        355                 360                 365

Arg Val Ala Asp Gly Asp Val Ala Ser Leu Pro Tyr Ile Gln Ser Ile
    370                 375                 380

Val Lys Glu Thr Leu Arg Met His Pro Pro Gly Pro Leu Leu Ser Trp
385                 390                 395                 400

Ala Arg Leu Ala Val His Asp Ala Arg Val Gly Gly His Ala Val Pro
                405                 410                 415

Ala Gly Thr Thr Ala Met Val Asn Met Trp Ala Ile Ala His Asp Ala
            420                 425                 430

Ala Val Trp Pro Glu Pro Asp Ala Phe Arg Pro Glu Arg Phe Ser Glu
        435                 440                 445

Gly Glu Asp Val Gly Val Leu Gly Gly Asp Leu Arg Leu Ala Pro Phe
    450                 455                 460

Gly Ala Gly Arg Arg Val Cys Pro Gly Arg Met Leu Ala Leu Ala Thr
465                 470                 475                 480

Ala His Leu Trp Leu Ala Gln Leu Leu His Ala Phe Asp Trp Ser Pro
                485                 490                 495

Thr Ala Ala Gly Val Asp Leu Ser Glu Arg Leu Gly Met Ser Leu Glu
            500                 505                 510

Met Ala Ala Pro Leu Val Cys Lys Ala Val Ala Arg Ala
        515                 520                 525


<210> SEQ ID NO 68
<211> LENGTH: 520
<212> TYPE: PRT
<213> ORGANISM: Glycine max

<400> SEQUENCE: 68

Met Ser Pro Asp Phe Thr Leu Leu Phe Phe Pro Glu Leu Ile Gln Pro
1               5                   10                  15

Pro Ile Val Thr Leu Gln Ala Ala Leu Cys Ile Leu Leu Leu Thr Phe
            20                  25                  30

Leu Leu Thr Phe Phe Leu Thr Pro Gly Gly Leu Ala Trp Ala Trp Ala
        35                  40                  45

Thr Lys Ser Ser Thr Arg Pro Ile Ile Pro Gly Pro Val Met Ala Leu
    50                  55                  60

Leu Ser Val Phe Thr Gly Ser Thr Pro His Arg Arg Leu Ser Met Leu
65                  70                  75                  80

Ala Arg Ser Tyr His Ala Glu Lys Leu Met Ala Phe Ser Ile Gly Leu
                85                  90                  95

Thr Arg Phe Val Ile Ser Ser Glu Pro Glu Thr Ala Lys Glu Ile Leu
            100                 105                 110

Gly Ser Pro Gly Phe Ala Asp Arg Pro Val Lys Glu Ser Ala Tyr Gln
        115                 120                 125

Leu Leu Phe His Arg Ala Met Gly Phe Ala Pro Tyr Gly Glu Tyr Trp
    130                 135                 140

Arg Asn Leu Arg Arg Ile Ser Ala Leu His Leu Phe Ser Pro Lys Arg
145                 150                 155                 160

Ile Thr Gly Ser Glu Ala Phe Arg Asn Glu Val Gly Leu Lys Met Val
                165                 170                 175

Asp Glu Val Lys Lys Val Met Lys Asp Asn Arg His Val Glu Val Lys
            180                 185                 190

Arg Ile Leu His Tyr Gly Ser Leu Asn Asn Val Met Met Thr Val Phe
        195                 200                 205
```

```
Gly Lys Cys Tyr Glu Phe Tyr Glu Gly Glu Gly Val Glu Leu Glu Ala
    210                 215                 220

Leu Val Ser Glu Gly Tyr Glu Leu Leu Gly Val Phe Asn Trp Ser Asp
225                 230                 235                 240

His Phe Pro Val Leu Gly Trp Leu Asp Leu Gln Gly Val Arg Lys Arg
                245                 250                 255

Cys Arg Cys Leu Val Glu Lys Val Asn Ala Phe Val Gly Gly Val Ile
            260                 265                 270

Glu Glu His Arg Val Lys Arg Val Arg Gly Gly Cys Val Lys Asp Glu
        275                 280                 285

Gly Thr Gly Asp Phe Val Asp Val Leu Leu Asp Leu Glu Asn Glu Asn
    290                 295                 300

Lys Leu Ser Glu Ala Asp Met Ile Ala Val Leu Trp Glu Met Ile Phe
305                 310                 315                 320

Arg Gly Thr Asp Thr Val Ala Ile Leu Leu Glu Trp Ile Leu Ala Arg
                325                 330                 335

Met Val Leu His Pro Asp Ile Gln Ala Lys Ala Gln Arg Glu Ile Asp
            340                 345                 350

Ser Val Cys Gly Pro Tyr Arg Leu Val Ser Glu Ala Asp Met Pro Asn
        355                 360                 365

Leu Arg Tyr Leu Gln Gly Ile Val Lys Glu Thr Leu Arg Val His Pro
    370                 375                 380

Pro Gly Pro Leu Leu Ser Trp Ala Arg Leu Ala Val His Asp Val Thr
385                 390                 395                 400

Val Gly Gly Lys His Val Ile Pro Lys Gly Thr Thr Ala Met Val Asn
                405                 410                 415

Met Trp Ala Ile Thr His Asp Glu Arg Phe Trp Ala Glu Pro Glu Arg
            420                 425                 430

Phe Arg Pro Glu Arg Phe Val Glu Glu Glu Asp Val Asn Ile Met Gly
        435                 440                 445

Ser Asp Leu Arg Leu Ala Pro Phe Gly Ser Gly Arg Arg Val Cys Pro
    450                 455                 460

Gly Lys Ala Leu Gly Leu Ala Ser Val His Leu Trp Leu Ala Gln Leu
465                 470                 475                 480

Leu Gln Asn Phe His Trp Val Gln Phe Asp Gly Val Ser Val Glu Leu
                485                 490                 495

Asp Glu Cys Leu Lys Leu Ser Met Glu Met Lys Lys Pro Leu Ala Cys
            500                 505                 510

Lys Ala Val Pro Arg Val Ala Val
        515                 520


<210> SEQ ID NO 69
<211> LENGTH: 445
<212> TYPE: PRT
<213> ORGANISM: Sorghum bicolor

<400> SEQUENCE: 69

Met Asp Ala Thr Thr Gln Asp Ser Leu Leu Phe Leu Phe Pro Ala Ala
1               5                   10                  15

Ala Thr Phe Leu Ser Pro Leu Leu Ala Val Leu Leu Val Ala Leu Ser
            20                  25                  30

Leu Leu Trp Leu Val Pro Gly Gly Pro Ala Trp Ala Leu Ile Ser Thr
        35                  40                  45

Ser Arg Ser Arg Ala Thr Pro Pro Pro Gly Ala Pro Gly Val Val Thr
    50                  55                  60
```

```
Ala Leu Ser Gly Pro Ala Ala His Arg Ala Leu Ala Ser Leu Ser Arg
65                  70                  75                  80

Ser Leu Pro Gly Gly Ala Ala Leu Ser Ala Phe Ser Val Gly Leu Thr
                85                  90                  95

Arg Leu Val Val Ala Ser Gln Pro Asp Thr Ala Arg Glu Leu Leu Ala
            100                 105                 110

Ser Ala Ala Phe Ala Asp Arg Pro Val Lys Asp Ala Ala Arg Gly Leu
        115                 120                 125

Leu Phe His Arg Ala Met Gly Phe Ala Pro Ser Gly Asp Tyr Trp Arg
    130                 135                 140

Ala Leu Cys Arg Ile Ser Ser Ala Tyr Leu Phe Ser Pro Arg Ser Glu
145                 150                 155                 160

Ser Ala Thr Ala Pro Arg Arg Val Thr Ile Gly Glu Arg Met Leu Arg
                165                 170                 175

Asp Leu Ser Asp Ala Ile Gly Arg Leu Arg Arg Ser Leu Val Ser Arg
            180                 185                 190

Val Asn Val Phe Val Ala Arg Ile Ile Glu Glu His Arg Gln Lys Lys
        195                 200                 205

Lys Asp Asp Val Ala Asn Asn Gly Glu Ser Ala Ala Gly Asp Phe Val
    210                 215                 220

Asp Val Leu Leu Gly Leu Glu Gly Glu Glu Lys Leu Ser Asp Ser Asp
225                 230                 235                 240

Met Ile Ala Val Leu Trp Glu Met Ile Phe Arg Gly Thr Asp Thr Val
                245                 250                 255

Ala Ile Leu Leu Glu Trp Val Met Ala Arg Met Val Leu His Pro Gly
            260                 265                 270

Ile Gln Ser Lys Ala Gln Ala Glu Leu Asp Ala Val Val Gly Arg Gly
        275                 280                 285

Gly Ala Val Ser Asp Ala Asp Val Ser Arg Leu Pro Tyr Leu Gln Arg
    290                 295                 300

Val Val Lys Glu Thr Leu Arg Val His Pro Pro Gly Pro Leu Leu Ser
305                 310                 315                 320

Trp Ala Arg Leu Ala Val His Asp Ala Val Val Gly Gly His Leu Val
                325                 330                 335

Pro Ala Gly Thr Thr Ala Met Val Asn Met Trp Ala Ile Ala Arg Asp
            340                 345                 350

Pro Ala Val Trp Ala Asp Pro Thr Ala Phe Arg Pro Glu Arg Phe Glu
        355                 360                 365

Glu Glu Asp Val Ser Val Leu Gly Gly Asp Leu Arg Leu Ala Pro Phe
    370                 375                 380

Gly Ala Gly Arg Arg Val Cys Pro Gly Lys Thr Leu Ala Leu Ala Thr
385                 390                 395                 400

Val His Leu Trp Leu Ala Gln Leu Leu His Arg Phe Gln Trp Ala Pro
                405                 410                 415

Ala Asp Gly Gly Val Asp Leu Ala Glu Arg Leu Gly Met Ser Leu Glu
            420                 425                 430

Met Glu Lys Pro Leu Val Cys Lys Pro Thr Pro Arg Trp
        435                 440                 445
```

<210> SEQ ID NO 70
<211> LENGTH: 548
<212> TYPE: PRT
<213> ORGANISM: Oryza sativa

<400> SEQUENCE: 70

```
Met Asp Ala Thr Leu Gly Ala Ser Thr Thr His Gly Tyr Leu Leu Leu
1               5                   10                  15

Leu Pro Ala Asn Ser Thr Thr Phe Phe Ser Pro Leu Leu Ala Ala Leu
            20                  25                  30

Leu Ala Val Thr Ser Leu Leu Trp Leu Val Pro Gly Gly Pro Ala Trp
        35                  40                  45

Ala Leu Ser Arg Cys Arg Arg Pro Pro Pro Gly Ala Pro Gly Ala Leu
    50                  55                  60

Ala Ala Leu Ala Gly Pro Ala Ala His Arg Ala Leu Ala Ala Met Ser
65                  70                  75                  80

Arg Ser Val Pro Gly Gly Ala Ala Leu Ala Ser Phe Ser Val Gly Leu
                85                  90                  95

Thr Arg Phe Val Val Ala Ser Arg Pro Asp Thr Ala Arg Glu Leu Leu
            100                 105                 110

Ser Ser Ala Ala Phe Ala Asp Arg Pro Val Lys Asp Ala Ala Arg Gly
        115                 120                 125

Leu Leu Phe His Arg Ala Met Gly Phe Ala Pro Ser Gly Asp Tyr Trp
    130                 135                 140

Arg Ala Leu Arg Arg Val Ser Ala Asn His Leu Phe Thr Pro Arg Arg
145                 150                 155                 160

Val Ala Ala Ser Ala Pro Arg Arg Leu Ala Ile Gly Glu Arg Met Leu
                165                 170                 175

Asp Arg Leu Ser Ala Leu Ala Gly Gly Glu Ile Gly Met Arg Arg Val
            180                 185                 190

Leu His Ala Ala Ser Leu Asp His Val Met Asp Thr Val Phe Gly Thr
        195                 200                 205

Arg Tyr Asp Gly Asp Ser Gln Glu Gly Ala Glu Leu Glu Ala Met Val
    210                 215                 220

Lys Glu Gly Tyr Asp Leu Leu Gly Met Phe Asn Trp Gly Asp His Leu
225                 230                 235                 240

Pro Leu Leu Lys Trp Leu Asp Leu Gln Gly Val Arg Arg Arg Cys Arg
                245                 250                 255

Thr Leu Val Gln Arg Val Asp Val Phe Val Arg Ser Ile Ile Asp Glu
            260                 265                 270

His Arg Gln Arg Lys Arg Arg Thr Gly Gly Asn Gly Gly Gly Glu Glu
        275                 280                 285

Leu Pro Gly Asp Phe Val Asp Val Leu Leu Gly Leu Gln Gly Glu Glu
    290                 295                 300

Lys Met Thr Glu Ser Asp Met Val Ala Val Leu Trp Val Thr Lys Asp
305                 310                 315                 320

Pro Ser Asp Met His Ala Ser Ile Arg Ser Ile Leu Cys Ile Ala Ile
                325                 330                 335

Asn Gly Phe Met Asp Ile Phe Asp Leu Ala Arg Val Gln Glu Met Ile
            340                 345                 350

Phe Arg Gly Thr Asp Thr Val Ala Ile Leu Leu Glu Trp Ile Met Ala
        355                 360                 365

Arg Met Val Leu His Pro Asp Ile Gln Ala Lys Ala Gln Ala Glu Leu
    370                 375                 380

Asp Ala Val Val Gly Arg Gly Arg Ala Val Ser Asp Gly Asp Val Ala
385                 390                 395                 400

Gly Leu Arg Tyr Leu Gln Cys Val Val Lys Glu Ala Leu Arg Val His
                405                 410                 415
```

```
Pro Pro Gly Pro Leu Leu Ser Trp Ala Arg Leu Ala Val Arg Asp Ala
            420                 425                 430

His Val Gly Gly His Val Val Pro Ala Gly Thr Thr Ala Met Val Asn
        435                 440                 445

Met Trp Ala Ile Ala His Asp Pro Glu Leu Trp Pro Glu Pro Asp Glu
    450                 455                 460

Phe Arg Pro Glu Arg Phe Ala Glu Glu Asp Val Ser Val Leu Gly Gly
465                 470                 475                 480

Asp Leu Arg Leu Ala Pro Phe Gly Ala Gly Arg Arg Ala Cys Pro Gly
                485                 490                 495

Lys Thr Leu Ala Leu Ala Thr Val His Leu Trp Leu Ala Gln Leu Leu
            500                 505                 510

His Arg Phe Glu Trp Ala Pro Val Gly Gly Gly Val His Leu Leu Glu
        515                 520                 525

Arg Leu Asn Met Ser Leu Glu Met Glu Lys Pro Leu Val Cys Lys Ala
    530                 535                 540

Lys Pro Arg Trp
545


<210> SEQ ID NO 71
<211> LENGTH: 522
<212> TYPE: PRT
<213> ORGANISM: Glycine max

<400> SEQUENCE: 71

Met Ile Pro Thr Leu Val Cys Ile Gly Thr Thr Ile Phe Gln Ser Thr
1               5                   10                  15

Leu Ser Ser Tyr Ser Leu Ser Phe Ile Ser Leu Phe Leu Ser Thr Ser
            20                  25                  30

Leu Ala Leu Leu Ala Ile Ser Leu Asn Tyr Trp Leu Val Pro Gly Gly
        35                  40                  45

Phe Ala Trp Arg Lys Tyr His Ser Arg Tyr Lys Gly His Ala Lys Val
    50                  55                  60

Ser Gly Pro Met Gly Trp Pro Ile Leu Gly Thr Leu Pro Ala Met Gly
65                  70                  75                  80

Pro Leu Ala His Arg Lys Leu Ala Ala Met Ala Thr Ser Pro Lys Ala
                85                  90                  95

Lys Lys Leu Met Thr Leu Ser Leu Gly Thr Asn Pro Val Val Ile Ser
            100                 105                 110

Ser His Pro Glu Thr Ala Arg Glu Ile Leu Cys Gly Ser Asn Phe Ala
        115                 120                 125

Asp Arg Pro Val Lys Glu Ser Ala Arg Met Leu Met Phe Glu Arg Ala
    130                 135                 140

Ile Gly Phe Ala Pro Tyr Gly Thr Tyr Trp Arg His Leu Arg Lys Val
145                 150                 155                 160

Ala Ile Thr His Met Phe Ser Pro Arg Arg Ile Ser Asp Leu Glu Ser
                165                 170                 175

Leu Arg Gln His Val Val Gly Glu Met Val Met Arg Ile Trp Lys Glu
            180                 185                 190

Met Gly Asp Lys Gly Val Val Glu Val Arg Gly Ile Leu Tyr Glu Gly
        195                 200                 205

Ser Leu Ser His Met Leu Glu Cys Val Phe Gly Ile Asn Asn Ser Leu
    210                 215                 220

Gly Ser Gln Thr Lys Glu Ala Leu Gly Asp Met Val Glu Glu Gly Tyr
```

-continued

```
225                 230                 235                 240

Asp Leu Ile Ala Lys Phe Asn Trp Ala Asp Tyr Phe Pro Phe Gly Phe
                245                 250                 255

Leu Asp Phe His Gly Val Lys Arg Arg Cys His Lys Leu Ala Thr Lys
            260                 265                 270

Val Asn Ser Val Val Gly Lys Ile Val Glu Glu Arg Lys Asn Ser Gly
        275                 280                 285

Lys Tyr Val Gly Gln Asn Asp Phe Leu Ser Ala Leu Leu Leu Leu Pro
    290                 295                 300

Lys Glu Glu Ser Ile Gly Asp Ser Asp Val Val Ala Ile Leu Trp Glu
305                 310                 315                 320

Met Ile Phe Arg Gly Thr Asp Thr Ile Ala Ile Leu Leu Glu Trp Ile
                325                 330                 335

Met Ala Met Met Val Leu His Gln Asp Val Gln Met Lys Ala Arg Gln
            340                 345                 350

Glu Ile Asp Ser Cys Ile Lys Gln Asn Gly Tyr Met Arg Asp Ser Asp
        355                 360                 365

Ile Pro Asn Leu Pro Tyr Leu Gln Ala Ile Val Lys Glu Val Leu Arg
    370                 375                 380

Leu His Pro Pro Gly Pro Leu Leu Ser Trp Ala Arg Leu Ala Ile His
385                 390                 395                 400

Asp Val His Val Asp Lys Val Ile Val Pro Ala Gly Thr Thr Ala Met
                405                 410                 415

Val Asn Met Trp Ala Ile Ser His Asp Ser Ser Ile Trp Glu Asp Pro
            420                 425                 430

Trp Ala Phe Lys Pro Glu Arg Phe Met Lys Glu Asp Val Ser Ile Met
        435                 440                 445

Gly Ser Asp Met Arg Leu Ala Pro Phe Gly Ala Gly Arg Arg Val Cys
    450                 455                 460

Pro Gly Lys Thr Leu Gly Leu Ala Thr Val His Leu Trp Leu Ala Gln
465                 470                 475                 480

Leu Leu His His Phe Ile Trp Ile Pro Val Gln Pro Val Asp Leu Ser
                485                 490                 495

Glu Cys Leu Lys Leu Ser Leu Glu Met Lys Lys Pro Leu Arg Cys Gln
            500                 505                 510

Val Ile Arg Arg Phe Asn Thr Ile Ser Ser
        515                 520


<210> SEQ ID NO 72
<211> LENGTH: 534
<212> TYPE: PRT
<213> ORGANISM: Zea mays

<400> SEQUENCE: 72

Met Thr Leu Ile Pro Ala Ile Ser Gly Glu Gln His Gly Asn Met Ala
1               5                   10                  15

Thr Val Ala Thr Ser Phe Ala Tyr Leu Ala Ile Phe Ala Cys Leu Ala
            20                  25                  30

Trp Val Gly Ala Ser Leu Leu Tyr Trp Ala His Pro Gly Gly Pro Ala
        35                  40                  45

Trp Gly Lys Tyr Trp Arg Ala Arg Gly Lys Lys Pro Ser Ala Ala Ile
    50                  55                  60

Pro Gly Pro Lys Gly Leu Pro Val Val Gly Ser Leu Gly Leu Met Ser
65                  70                  75                  80
```

```
Gly Leu Ala His Arg Ser Leu Ala Asp Glu Ala Ser Arg Arg Pro Gly
                85                  90                  95

Ala Lys Arg Leu Met Ala Leu Ser Leu Gly Pro Val Arg Ala Val Val
            100                 105                 110

Thr Ser His Pro Asp Val Ala Lys Glu Ile Leu Asp Ser Pro Ala Phe
        115                 120                 125

Ala Ala Arg Pro Leu Asn His Ala Ala Tyr Gly Leu Met Phe His Arg
    130                 135                 140

Ser Ile Gly Phe Ala Glu His Gly Pro Tyr Trp Arg Ala Leu Arg Arg
145                 150                 155                 160

Val Ala Ala Gly His Leu Phe Gly Pro Arg Gln Val Glu Ala Phe Ala
                165                 170                 175

Pro Tyr Arg Ala Ala Val Ala Glu Gly Ile Val Ala Ala Leu Leu Arg
            180                 185                 190

Ala Gly Ser Gly Gly Ala Val Val Gln Val Arg Gly Leu Leu Arg Arg
        195                 200                 205

Ala Ser Leu Tyr Tyr Ile Met Arg Phe Val Phe Gly Lys Glu Tyr Asp
    210                 215                 220

Val Ser Arg Val Val Pro Pro Ser Gly Gly Glu Glu Val Glu Glu Leu
225                 230                 235                 240

Leu Glu Met Val His Glu Gly Tyr Glu Leu Leu Gly Met Glu Asn Leu
                245                 250                 255

Cys Asp Tyr Phe Pro Gly Leu Ala Ala Leu Asp Pro Gln Gly Val Gly
            260                 265                 270

Ala Arg Cys Ala Glu Leu Met Pro Arg Val Asn Arg Phe Val His Gly
        275                 280                 285

Val Ile Gln Glu His Arg Ala Lys Ala Val Ala Gly Gly Asp Ala Arg
    290                 295                 300

Asp Phe Val Asp Ile Leu Leu Ser Leu Gln Glu Ser Glu Gly Leu Ala
305                 310                 315                 320

Asp Ala Asp Ile Ala Ser Val Leu Trp Glu Met Ile Phe Arg Gly Thr
                325                 330                 335

Asp Ala Met Ala Val Leu Met Glu Trp Thr Leu Ala Arg Leu Val Leu
            340                 345                 350

His Arg Asp Val Gln Ala Lys Ala His Arg Glu Leu Asp Lys Val Val
        355                 360                 365

Gly Ala Asp Ser Gln Thr Thr Glu Ser Ala Ala Pro Tyr Leu Gln Ala
    370                 375                 380

Leu Leu Lys Glu Ala Leu Arg Met His Pro Pro Gly Pro Leu Leu Ser
385                 390                 395                 400

Trp Arg His Arg Ala Ile Ser Asp Thr Tyr Val Asp Gly His Leu Val
                405                 410                 415

Pro Ala Gly Thr Thr Ala Met Val Asn Gln Trp Ala Ile Ser Arg Asp
            420                 425                 430

Pro Glu Val Trp Asp Ala Pro Leu Glu Phe Arg Pro Glu Arg Phe Leu
        435                 440                 445

Pro Gly Gly Glu Gly Gln Asp Val Ser Val Leu Gly Ala Asp Gly Arg
    450                 455                 460

Leu Val Pro Phe Gly Ser Gly Arg Arg Ser Cys Pro Gly Lys Ser Leu
465                 470                 475                 480

Ala Met Thr Thr Val Thr Ser Trp Met Ala Thr Leu Leu His Glu Phe
                485                 490                 495

Glu Trp Leu Pro Ala Ser Asp Asp Thr Gly Asp Val Asp Leu Ser Glu
```

```
        500                 505                 510

Val Leu Arg Leu Ser Cys Glu Met Ala Val Pro Leu Glu Val Arg Val
        515                 520                 525

Arg Pro Arg Ser Ser Val
    530


<210> SEQ ID NO 73
<211> LENGTH: 514
<212> TYPE: PRT
<213> ORGANISM: Glycine max

<400> SEQUENCE: 73

Met Lys Pro Thr Ala Thr Phe Phe Phe Leu Leu Ser Thr Thr Thr Leu
1               5                   10                  15

Leu Val Cys Leu Cys Leu Gly Thr Thr Thr Phe Gln Thr Thr Leu Phe
            20                  25                  30

Ile Thr Phe Phe Thr Ile Ser Leu Asn Tyr Trp Leu Val Pro Gly Gly
        35                  40                  45

Phe Ala Trp Arg Asn Tyr His Ser Tyr His Thr Asn Glu Lys Pro Asn
    50                  55                  60

Lys Lys Leu Thr Gly Pro Met Gly Trp Pro Ile Leu Gly Ser Leu Pro
65                  70                  75                  80

Leu Met Gly Ser Leu Ala His Gln Lys Leu Ala Ala Leu Ala Ala Thr
                85                  90                  95

Leu Asn Ala Lys Arg Leu Met Ala Leu Ser Leu Gly Pro Thr Pro Val
            100                 105                 110

Val Ile Ser Ser His Pro Glu Thr Ala Arg Glu Ile Leu Leu Gly Ser
        115                 120                 125

Ser Phe Ser Asp Arg Pro Ile Lys Glu Ser Ala Arg Ala Leu Met Phe
    130                 135                 140

Glu Arg Ala Ile Gly Phe Ala Pro Ser Gly Thr Tyr Trp Arg His Leu
145                 150                 155                 160

Arg Arg Ile Ala Ala Phe His Met Phe Ser Pro Arg Arg Ile Gln Gly
                165                 170                 175

Leu Glu Gly Leu Arg Gln Arg Val Gly Asp Asp Met Val Lys Ser Ala
            180                 185                 190

Trp Lys Glu Met Glu Met Lys Gly Val Val Glu Val Arg Gly Val Phe
        195                 200                 205

Gln Glu Gly Ser Leu Cys Asn Ile Leu Glu Ser Val Phe Gly Ser Asn
    210                 215                 220

Asp Lys Ser Glu Glu Leu Gly Asp Met Val Arg Glu Gly Tyr Glu Leu
225                 230                 235                 240

Ile Ala Met Leu Asn Leu Glu Asp Tyr Phe Pro Leu Lys Phe Leu Asp
                245                 250                 255

Phe His Gly Val Lys Arg Arg Cys His Lys Leu Ala Ala Lys Val Gly
            260                 265                 270

Ser Val Val Gly Gln Ile Val Glu Asp Arg Lys Arg Glu Gly Ser Phe
        275                 280                 285

Val Val Lys Asn Asp Phe Leu Ser Thr Leu Leu Ser Leu Pro Lys Glu
    290                 295                 300

Glu Arg Leu Ala Asp Ser Asp Met Ala Ala Ile Leu Trp Glu Met Val
305                 310                 315                 320

Phe Arg Gly Thr Asp Thr Val Ala Ile Leu Leu Glu Trp Val Met Ala
                325                 330                 335
```

```
Arg Met Val Leu His Gln Asp Val Gln Lys Lys Ala Arg Glu Glu Ile
            340                 345                 350

Asp Thr Cys Ile Gly Gln Asn Ser His Val Arg Asp Ser Asp Ile Ala
        355                 360                 365

Asn Leu Pro Tyr Leu Gln Ala Ile Val Lys Glu Val Leu Arg Leu His
    370                 375                 380

Pro Pro Gly Pro Leu Leu Ser Trp Ala Arg Leu Ala Val Asn Asp Val
385                 390                 395                 400

His Val Asp Lys Val Leu Val Pro Ala Gly Thr Thr Ala Met Val Asn
                405                 410                 415

Met Trp Ala Ile Ser His Asp Ser Ser Ile Trp Glu Asp Pro Trp Ala
            420                 425                 430

Phe Lys Pro Glu Arg Phe Leu Lys Glu Asp Val Ser Ile Met Gly Ser
        435                 440                 445

Asp Leu Arg Leu Ala Pro Phe Gly Ala Gly Arg Arg Val Cys Pro Gly
    450                 455                 460

Arg Ala Leu Gly Leu Ala Thr Thr His Leu Trp Leu Ala Gln Leu Leu
465                 470                 475                 480

Arg His Phe Ile Trp Leu Pro Ala Gln Pro Val Asp Leu Ser Glu Cys
                485                 490                 495

Leu Arg Leu Ser Met Glu Met Lys Thr Pro Leu Arg Cys Leu Val Val
            500                 505                 510

Arg Arg


<210> SEQ ID NO 74
<211> LENGTH: 235
<212> TYPE: PRT
<213> ORGANISM: Sorghum bicolor

<400> SEQUENCE: 74

Met Asp Phe Thr Asp Val Leu Leu Ser Leu Asn Gly Asp Asp Lys Leu
1               5                   10                  15

Ser Asp Ala Asp Met Ile Ala Val Leu Trp Glu Met Ile Phe Arg Gly
            20                  25                  30

Thr Asp Thr Val Ala Val Leu Ile Glu Trp Val Leu Ala Arg Leu Val
        35                  40                  45

Leu His Gln Asp Val Gln Arg Lys Val His Asp Glu Leu Asp Arg Val
    50                  55                  60

Val Gly Pro Gly Glu Ala Val Thr Glu Ser Asp Thr Ala Ser Leu Val
65                  70                  75                  80

Tyr Leu Gln Ala Val Ile Lys Glu Val Leu Arg Leu His Pro Pro Gly
                85                  90                  95

Pro Leu Leu Ser Trp Ala Arg Leu Ala Thr Ser Asp Val Asn Val Gly
            100                 105                 110

Gly His Leu Val Pro Ala Gly Thr Thr Ala Met Val Asn Met Trp Ala
        115                 120                 125

Ile Thr His Asp Ala Ser Val Trp Pro Glu Pro Thr Glu Phe Arg Pro
    130                 135                 140

Glu Arg Phe Val Ala Ala Ala Gly Gly Glu Asp Val Val Pro Ile Met
145                 150                 155                 160

Gly Ser Asp Leu Arg Leu Ala Pro Phe Gly Ser Gly Arg Arg Ser Cys
                165                 170                 175

Pro Gly Lys Ser Leu Ala Val Ala Thr Val Gly Phe Trp Val Ala Thr
            180                 185                 190
```

```
Leu Leu His Glu Phe Glu Trp Leu Pro Cys Gly Gly Gly Gly Gly Val
        195                 200                 205

Asp Leu Ser Glu Val Leu Arg Leu Ser Cys Glu Met Ala Ala Pro Leu
    210                 215                 220

Glu Ala Arg Val Val Pro Arg Arg His Ala Val
225                 230                 235
```

<210> SEQ ID NO 75
<211> LENGTH: 508
<212> TYPE: PRT
<213> ORGANISM: Glycine max

<400> SEQUENCE: 75

```
Met Lys Pro Thr Ala Thr Phe Phe Phe Leu Leu Pro Ser Thr Thr Leu
1               5                   10                  15

Val Val Cys Leu Cys Leu Gly Ile Gly Thr Thr Thr Leu Phe Ile Thr
            20                  25                  30

Leu Leu Ala Ile Ser Leu Asn Tyr Trp Leu Val Pro Gly Gly Phe Ala
        35                  40                  45

Trp Arg Asn Tyr Asp Tyr Tyr Gln Thr Lys Lys Lys Leu Thr Gly Pro
    50                  55                  60

Met Gly Trp Pro Ile Leu Gly Thr Leu Pro Leu Met Gly Ser Leu Ala
65                  70                  75                  80

His Gln Lys Leu Ala Ala Leu Ala Thr Ser Leu Asn Ala Lys Arg Leu
                85                  90                  95

Met Ala Leu Ser Leu Gly Pro Thr Pro Val Val Ile Ser Ser His Pro
            100                 105                 110

Glu Thr Ala Arg Glu Ile Leu Leu Gly Ser Ser Phe Ser Asp Arg Pro
        115                 120                 125

Ile Lys Glu Ser Ala Arg Ala Leu Met Phe Glu Arg Ala Ile Gly Phe
    130                 135                 140

Ala His Ser Gly Thr Tyr Trp Arg His Leu Arg Arg Ile Ala Ala Phe
145                 150                 155                 160

His Met Phe Ser Pro Arg Arg Ile His Gly Leu Glu Gly Leu Arg Gln
                165                 170                 175

Arg Val Gly Asp Asp Met Val Lys Ser Ala Trp Arg Glu Met Gly Glu
            180                 185                 190

Lys Gly Val Val Glu Val Arg Arg Val Phe Gln Glu Gly Ser Leu Cys
        195                 200                 205

Asn Ile Leu Glu Ser Val Phe Gly Ser Asn Asp Lys Ser Glu Glu Leu
    210                 215                 220

Arg Asp Met Val Arg Glu Gly Tyr Glu Leu Ile Ala Met Phe Asn Leu
225                 230                 235                 240

Glu Asp Tyr Phe Pro Phe Lys Phe Leu Asp Phe His Gly Val Lys Arg
                245                 250                 255

Arg Cys His Lys Leu Ala Ala Lys Val Gly Ser Val Val Gly Gln Ile
            260                 265                 270

Val Glu Glu Arg Lys Arg Asp Gly Gly Phe Val Gly Lys Asn Asp Phe
        275                 280                 285

Leu Ser Thr Leu Leu Ser Leu Pro Lys Glu Glu Arg Leu Ala Asp Ser
    290                 295                 300

Asp Leu Val Ala Ile Leu Trp Glu Met Val Phe Arg Gly Thr Asp Thr
305                 310                 315                 320

Val Ala Ile Leu Leu Glu Trp Val Met Ala Arg Met Val Leu His Gln
                325                 330                 335
```

```
Asp Leu Gln Lys Lys Ala Arg Glu Glu Ile Asp Thr Cys Val Gly Gln
            340                 345                 350

Asn Ser His Val Arg Asp Ser Asp Ile Ala Asn Leu Pro Tyr Leu Gln
        355                 360                 365

Ala Ile Val Lys Glu Val Leu Arg Leu His Pro Pro Gly Pro Leu Leu
    370                 375                 380

Ser Trp Ala Arg Leu Ala Val His Asp Val His Ala Asp Lys Val Leu
385                 390                 395                 400

Val Pro Ala Gly Thr Thr Ala Met Val Asn Met Trp Ala Ile Ser His
                405                 410                 415

Asp Ser Ser Ile Trp Glu Asp Pro Trp Ala Phe Lys Pro Glu Arg Phe
            420                 425                 430

Leu Lys Glu Asp Val Ser Ile Met Gly Ser Asp Leu Arg Leu Ala Pro
        435                 440                 445

Phe Gly Ala Gly Arg Arg Val Cys Pro Gly Arg Ala Leu Gly Leu Ala
    450                 455                 460

Thr Ala His Leu Trp Leu Ala Gln Leu Leu Arg His Phe Ile Trp Leu
465                 470                 475                 480

Pro Ala Gln Thr Val Asp Leu Ser Glu Cys Leu Arg Leu Ser Met Glu
                485                 490                 495

Met Lys Thr Pro Leu Arg Cys Leu Val Val Arg Arg
            500                 505


<210> SEQ ID NO 76
<211> LENGTH: 517
<212> TYPE: PRT
<213> ORGANISM: Sorghum bicolor

<400> SEQUENCE: 76

Met Val Leu Thr Met Ala Thr Gly Gln Glu Asp Ser Leu Leu Leu Leu
1               5                   10                  15

Leu Leu Pro Thr Thr Ser Pro Leu Pro Pro Leu Met Ala Val Phe Ile
            20                  25                  30

Leu Ala Ala Val Leu Leu Trp Leu Ser Pro Gly Gly Pro Ala Trp Ala
        35                  40                  45

Leu Ser Arg Cys Arg Arg Pro Pro Ser Gly Pro Thr Gly Val Val Thr
    50                  55                  60

Ala Leu Ser Ser Pro Val Ala His Arg Thr Leu Ala Ala Leu Ser His
65                  70                  75                  80

Ala Val Asp Gly Gly Lys Ala Leu Met Ala Phe Ser Val Gly Leu Thr
                85                  90                  95

Arg Leu Val Val Ser Ser Gln Pro Asp Thr Ala Arg Glu Ile Leu Val
            100                 105                 110

Asn Pro Ala Phe Ser Asp Arg Pro Ile Lys Asp Ala Ala Arg His Leu
        115                 120                 125

Leu Phe His Arg Ala Met Gly Phe Ala Pro Ser Gly Asp Ala His Trp
    130                 135                 140

Arg Gly Leu Arg Arg Leu Ala Ala Asn His Leu Phe Gly Pro Arg Arg
145                 150                 155                 160

Val Ala Ala Ala Ala His His Arg Val Ser Ile Gly Glu Ala Met Val
                165                 170                 175

Ala Asp Val Ala Ala Ala Met Ala Arg His Gly Glu Val Ser Leu Lys
            180                 185                 190

Arg Val Leu His Ile Ala Ser Leu Asn His Ile Met Ala Thr Val Phe
```

```
        195                 200                 205

Gly Lys His Tyr Asp Met Asp Ser Gln Glu Gly Val Leu Leu Glu Glu
    210                 215                 220

Met Val Thr Glu Gly Tyr Asp Leu Leu Gly Thr Phe Asn Trp Ala Asp
225                 230                 235                 240

His Leu Pro Leu Ile Lys His Leu Asp Leu Gln Gly Val Arg Arg Arg
                245                 250                 255

Cys Asn Arg Leu Val Gln Lys Val Glu Val Phe Val Gly Lys Ile Ile
            260                 265                 270

Gln Glu His Arg Ala Arg Arg Ala Asn Gly Gly Val Asp Asp Glu Tyr
        275                 280                 285

Met Gly Asp Phe Val Asp Val Leu Leu Asp Leu Glu Gly Glu Glu Lys
    290                 295                 300

Leu Ser Glu Ser Asp Met Ile Ala Val Leu Trp Glu Met Ile Phe Arg
305                 310                 315                 320

Gly Ala Asp Thr Val Ala Ile Leu Met Glu Trp Ile Met Ala Arg Met
                325                 330                 335

Ala Leu His Pro Glu Ile Gln Ser Lys Ala Gln Ala Glu Leu Asp Gly
            340                 345                 350

Val Val Val Gly Gly Val Ala Asp Ala Asp Val Gly Asn Leu Pro Tyr
        355                 360                 365

Ile Gln Cys Ile Val Lys Glu Thr Leu Arg Met His Pro Pro Gly Pro
    370                 375                 380

Leu Leu Ser Trp Ala Arg Leu Ala Ile His Asp Ala His Val Gly Gly
385                 390                 395                 400

His Leu Val Pro Ala Gly Thr Thr Ala Met Val Asn Met Trp Ser Ile
                405                 410                 415

Ala His Asp Pro Ala Ile Trp Ala Glu Pro Glu Lys Phe Arg Pro Glu
            420                 425                 430

Arg Phe Gln Glu Glu Asp Val Ser Val Leu Gly Ser Asp Leu Arg Leu
        435                 440                 445

Ala Pro Phe Gly Ala Gly Arg Arg Val Cys Pro Gly Lys Met Leu Ala
    450                 455                 460

Leu Ala Thr Thr His Leu Trp Ile Ala Gln Leu Leu His Glu Phe Glu
465                 470                 475                 480

Trp Ala Pro Ala Ala Ala Asn Gly Gly Val Asp Leu Ser Glu Arg Leu
                485                 490                 495

Asn Met Ser Leu Glu Met Ala Thr Pro Leu Val Cys Lys Ala Val Pro
            500                 505                 510

Arg Ala Gln Leu Ala
        515


<210> SEQ ID NO 77
<211> LENGTH: 549
<212> TYPE: PRT
<213> ORGANISM: Sorghum bicolor

<400> SEQUENCE: 77

Met Glu Ser Ser Val Glu Ser Trp Trp Val Leu Pro Met Thr Leu Ile
1               5                   10                  15

Pro Ala Ile Ser Gly Gln Gln His Glu Asn Met Ala Thr Ile Ala Thr
            20                  25                  30

Ser Phe Val Tyr Leu Ala Ile Phe Ala Cys Leu Ala Trp Ala Gly Ala
        35                  40                  45
```

```
Ser Leu Leu Tyr Trp Ala His Pro Gly Gly Pro Ala Trp Gly Lys Tyr
    50                  55                  60

Trp Arg Ala Lys Gly Lys Pro Ser Ser Thr Ile Pro Gly Pro Lys Gly
65                  70                  75                  80

Leu Pro Val Val Gly Ser Leu Gly Leu Met Ser Gly Leu Ala His Cys
                85                  90                  95

Ser Leu Ala Asp Glu Ala Ser Arg Arg Pro Gly Ala Lys Arg Leu Met
            100                 105                 110

Ala Leu Ser Leu Gly Pro Val Arg Ala Val Val Thr Ser His Pro Asp
        115                 120                 125

Val Ala Lys Glu Ile Leu Asp Asn Pro Ala Phe Ala Asp Arg Pro Leu
    130                 135                 140

Asn His Ala Ala Tyr Gly Leu Met Phe His Arg Ser Ile Gly Phe Ala
145                 150                 155                 160

Glu His Gly Pro Tyr Trp Arg Ala Leu Arg Arg Val Ala Ala Gly His
                165                 170                 175

Leu Phe Gly Pro Arg Gln Val Glu Ala Phe Ala Pro Tyr Arg Ala Ala
            180                 185                 190

Val Gly Glu Gly Ile Val Ala Ala Leu His Gly Ala Gly Gly Gly Val
        195                 200                 205

Val Gln Val Arg Gly Leu Leu Arg Arg Ala Ser Leu Tyr Tyr Ile Met
    210                 215                 220

Arg Phe Val Phe Gly Lys Glu Tyr Asp Val Ser Arg Ala Val Pro Ala
225                 230                 235                 240

Ser Gly Lys Glu Glu Val Glu Glu Leu Leu Glu Met Val His Glu Gly
                245                 250                 255

Tyr Glu Leu Leu Gly Met Glu Asn Trp Cys Asp Tyr Phe Pro Gly Leu
            260                 265                 270

Ala Ala Leu Asp Pro Gln Gly Val Gly Ala Arg Cys Ala Glu Leu Met
        275                 280                 285

Pro Arg Val Asn Arg Phe Val His Gly Ile Ile Gln Glu Arg Arg Ala
    290                 295                 300

Lys Ala Ile Ala Gly Gly Asp Ala Arg Asp Phe Val Asp Ile Leu Leu
305                 310                 315                 320

Ser Leu Gln Glu Ser Glu Arg Leu Ala Asp Ala Asp Ile Ala Ala Val
                325                 330                 335

Leu Trp Glu Met Ile Phe Arg Gly Thr Asp Ala Met Ala Val Leu Met
            340                 345                 350

Glu Trp Thr Leu Ala Arg Leu Val Leu His Arg Asp Val Gln Ala Lys
        355                 360                 365

Ala His Arg Glu Leu Asp Glu Val Val Gly Gly Asn Ser Gln Val Val
    370                 375                 380

Thr Glu Ser Ala Ala Ala Pro Ser Leu Pro Tyr Leu Gln Ala Leu Leu
385                 390                 395                 400

Lys Glu Ala Leu Arg Met His Pro Pro Gly Pro Leu Leu Ser Trp Arg
                405                 410                 415

His Arg Ala Ile Ser Asp Thr Tyr Val Asp Gly His Leu Val Pro Ala
            420                 425                 430

Gly Thr Thr Ala Met Val Asn Gln Trp Ala Ile Ser Arg Asp Pro Glu
        435                 440                 445

Val Trp Asp Ala Pro Leu Glu Phe Arg Pro Glu Arg Phe Leu Pro Gly
    450                 455                 460

Gly Glu Gly Gln Asp Val Ser Val Leu Gly Ala Asp Gly Arg Leu Val
```

```
465                 470                 475                 480

Pro Phe Gly Ser Gly Arg Arg Ser Cys Pro Gly Lys Ser Leu Ala Met
                485                 490                 495

Thr Thr Val Thr Thr Trp Met Ala Thr Leu Leu Asn Glu Phe Glu Trp
            500                 505                 510

Leu Pro Ala Ser Asp Asp Thr Gly Gly Asp Val Asp Leu Ser Glu Val
        515                 520                 525

Leu Arg Leu Ser Cys Glu Met Ala Val Pro Leu Glu Val Arg Val Arg
    530                 535                 540

Pro Arg Ser Gly Met
545


<210> SEQ ID NO 78
<211> LENGTH: 539
<212> TYPE: PRT
<213> ORGANISM: Sorghum bicolor

<400> SEQUENCE: 78

Met Lys Thr Glu Val Ile Thr Thr Met Ile Ser Leu Val Phe Leu Val
1               5                   10                  15

His Phe Ala Ile Thr Ile Ser Pro Asn Ala Gln Pro Ser Trp Leu Phe
            20                  25                  30

Ser Leu Met Ser Leu Ser Leu Ala Val Val Ala Val Ile Val Pro Leu
        35                  40                  45

Val Val Thr Thr Thr Cys His Ala Arg Lys Asn Thr Asp Ala Thr Thr
    50                  55                  60

Thr Ile Pro Gly Pro Arg Gly Trp Pro Leu Val Gly Ser Leu Leu Val
65                  70                  75                  80

Val Ser Gly Pro Leu Met His Arg Arg Leu Ala Ala Leu Ala Asp Ala
                85                  90                  95

His Ser Ala Arg Arg Leu Met Ser Leu Thr Leu Gly Ala Thr Pro Val
            100                 105                 110

Val Ile Ser Ser His Pro Glu Thr Ala Arg Asp Ile Leu Ser Gly Ala
        115                 120                 125

Ala Phe Val Asp Arg Pro Pro Lys Ala Ala Ala Arg Glu Leu Met Phe
    130                 135                 140

Cys Arg Ala Ile Gly Phe Ala Pro Thr Gly Glu Tyr Trp Arg Arg Leu
145                 150                 155                 160

Arg Arg Ile Thr Gly Ala Gly Met Leu Ser Pro Arg Arg Met Ala Met
                165                 170                 175

Leu Arg Gly Leu Arg Cys Arg Val Ala Asp Ser Met Ile Gln Arg Val
            180                 185                 190

Ala Asp Gln Met Glu Arg Ser Gly Glu Val Ala Met Arg Ala Leu Leu
        195                 200                 205

Gln Arg Ala Ser Leu Glu Ser Met Val Gly Ser Val Leu Gly Leu Glu
    210                 215                 220

Gly Asp Ala Val Cys Glu Glu Leu Gly Glu Met Val Arg Glu Gly Tyr
225                 230                 235                 240

Glu Leu Val Gly Met Phe Asn Leu Glu Asp His Tyr Tyr Lys Thr Ser
                245                 250                 255

Trp Gly Pro Leu Met Asp Leu Trp Gly Val Arg Pro Met Cys Arg Glu
            260                 265                 270

Leu Ala Ala Met Val Arg Gly Tyr Phe Gly Lys Ile Ile Gln Glu Arg
        275                 280                 285
```

```
Arg Leu Ala Gly Asp Cys His Glu Arg Ala Asp Leu Leu Ser Tyr Met
    290                 295                 300

Leu Ser Leu Pro Glu Glu Glu Lys Leu Glu Asp Ser Asp Val Ile Ala
305                 310                 315                 320

Val Leu Trp Glu Met Ile Phe Arg Gly Val Asp Val Val Ala Ile Leu
                325                 330                 335

Leu Glu Trp Ala Met Ala Arg Met Ser Leu His Pro Asp Ile Gln Ser
            340                 345                 350

Lys Ala Gln Glu Glu Met Asp Ala Ala Val Gly Val Arg Arg Arg Arg
        355                 360                 365

Ala Ile Thr Asp Ser Asp Val Pro Asn Leu Ala Phe Leu Gln Trp Ile
    370                 375                 380

Leu Lys Glu Thr Leu Arg Met His Pro Pro Gly Pro Leu Leu Ser Trp
385                 390                 395                 400

Ala Arg Leu Ala Val Gln Asp Ala Arg Val Gly Lys His Val Val Pro
                405                 410                 415

Ala Gly Thr Thr Ala Met Val Asn Met Trp Ala Ile Ser His Asp Glu
            420                 425                 430

Ala Ile Trp Gly Asp Pro Trp Val Phe Arg Pro Glu Arg Phe Ala Ala
        435                 440                 445

Ala Ala Ala Gly Glu Glu Val Ser Val Leu Gly Ser Asp Leu Arg Leu
    450                 455                 460

Ala Pro Phe Gly Ser Gly Arg Arg Val Cys Pro Gly Arg Met Met Gly
465                 470                 475                 480

Leu Ala Thr Ala Gln Leu Trp Leu Gly Arg Leu Leu Gln Glu Tyr Arg
                485                 490                 495

Trp Leu Pro Pro Pro Ala Asn Lys Pro Val Glu Leu Ala Glu Cys Leu
            500                 505                 510

Arg Leu Ser Met Glu Met Lys Thr Pro Leu Val Cys Arg Ala Val Pro
        515                 520                 525

Arg Arg Arg Gly Gly Arg Pro Pro Ala Ala Ala
    530                 535


<210> SEQ ID NO 79
<211> LENGTH: 499
<212> TYPE: PRT
<213> ORGANISM: Oryza sativa

<400> SEQUENCE: 79

Met Ala Val Val Ala Leu Pro Pro Leu Leu Ala Lys Arg His Gly His
1               5                   10                  15

Ala Arg Arg Val Asn Gly Gly Gly Ala Ala Ile Pro Gly Pro Arg Gly
            20                  25                  30

Trp Pro Leu Leu Gly Ser Leu Pro Val Val Ser Gly Pro Leu Met His
        35                  40                  45

Arg Arg Leu Ala Ala Leu Ala Asp Ala His Gly Gly Gly Ala Arg Arg
    50                  55                  60

Leu Met Ser Leu Thr Leu Gly Ala Thr Pro Val Val Val Ser Ser His
65                  70                  75                  80

Pro Asp Thr Val Arg Glu Ile Leu Ala Gly Ala Ala Phe Arg Asp Arg
                85                  90                  95

Pro Ala Arg Ala Ala Ala Arg Glu Leu Met Phe Leu Arg Ala Val Gly
            100                 105                 110

Phe Ala Pro Ala Ser Gly Asp Asp Gly Gly Ala Tyr Trp Arg Arg Leu
        115                 120                 125
```

```
Arg Arg Ala Ala Gly Ala Gly Met Leu Ser Pro Arg Arg Ala Ala Ala
    130                 135                 140

Leu Ala Ala Leu Arg Ala Arg Val Ala Arg Arg Thr Ser Glu Ala Val
145                 150                 155                 160

Ser Arg Gly Met Ala Val Pro Pro Gly Arg Val Ala Met Arg Ala Leu
                165                 170                 175

Leu His Ala Ala Ser Leu Asp Asn Met Val Gly Ser Val Leu Gly Leu
            180                 185                 190

Glu His His Asp His His Gly Gly Val Ile Ser Asp Met Gly Asp Met
        195                 200                 205

Val Arg Glu Gly Tyr Glu Leu Val Gly Lys Phe Asn Leu Gly Asp Tyr
    210                 215                 220

Tyr Ser Thr Thr Gln Tyr Gln Cys Leu Trp Gly Leu Leu Asp Phe His
225                 230                 235                 240

Gly Val Gly Pro Arg Cys Gln Arg Leu Ala Ala Arg Val Arg Glu Gln
                245                 250                 255

Phe Gly Arg Val Met Glu Glu Arg Arg Lys Val Ser Asp Leu His Lys
            260                 265                 270

Arg Asp Asp Leu Leu Ser Tyr Met Leu Ser Met Pro Gln Glu Glu Arg
        275                 280                 285

Ile Glu Asp Ser Asp Val Ile Ala Val Leu Trp Glu Met Ile Phe Arg
    290                 295                 300

Gly Thr Asp Val Val Ala Ile Leu Leu Glu Trp Ala Met Ala Arg Met
305                 310                 315                 320

Val Leu His Pro Asp Ile Gln Ser Lys Val Gln Glu Glu Leu Asp Arg
                325                 330                 335

Ala Val Gly His Arg Pro Met Thr Asp Ser Asp Ile Pro Asn Leu Arg
            340                 345                 350

Phe Leu His Cys Val Ile Lys Glu Thr Leu Arg Met His Pro Pro Gly
        355                 360                 365

Pro Leu Leu Ser Trp Ala Arg Leu Ala Val His Asp Thr Tyr Val Gly
    370                 375                 380

Lys His Leu Val Pro Ala Gly Thr Thr Ala Met Val Asn Met Trp Ala
385                 390                 395                 400

Ile Ser His Asp Glu Thr Ile Trp Gly Asp Pro Trp Val Phe Arg Pro
                405                 410                 415

Glu Arg Phe Met Glu Glu Asp Ile Asn Val Leu Gly Ser Asp Leu Arg
            420                 425                 430

Leu Ala Pro Phe Gly Ser Gly Arg Arg Val Cys Pro Gly Arg Met Met
        435                 440                 445

Gly Leu Ser Thr Ala Tyr Leu Trp Phe Gly Arg Met Leu Gln Glu Tyr
    450                 455                 460

Lys Trp Ala Ala Ala Gln Pro Val Lys Leu Thr Glu Cys Leu Arg Leu
465                 470                 475                 480

Ser Met Glu Met Lys Lys Pro Leu Val Cys His Ala Val Pro Arg Ser
                485                 490                 495

Lys Thr Gly
```

<210> SEQ ID NO 80
<211> LENGTH: 555
<212> TYPE: PRT
<213> ORGANISM: Oryza sativa

<400> SEQUENCE: 80

```
Met Ala Met Ala Thr Ala Thr Ala Ser Ser Cys Val Asp Ala Thr Trp
1               5                   10                  15

Trp Ala Tyr Ala Leu Pro Ala Leu Leu Gly Ala Asp Thr Leu Cys Ala
            20                  25                  30

His Pro Ala Leu Leu Ala Gly Ala Val Leu Leu Ala Phe Ala Thr Ala
        35                  40                  45

Ala Val Leu Ala Trp Ala Ala Ser Pro Gly Gly Pro Ala Trp Ala His
    50                  55                  60

Gly Arg Gly Arg Leu Gly Ala Thr Pro Ile Glu Gly Pro Arg Gly Leu
65                  70                  75                  80

Pro Val Phe Gly Ser Ile Phe Ala Leu Ser Arg Gly Leu Pro His Arg
                85                  90                  95

Ala Leu Asp Ala Met Ser Arg Asp Ala Ala Ala Pro Arg Ala Arg Glu
            100                 105                 110

Leu Met Ala Phe Ser Val Gly Glu Thr Pro Ala Val Val Ser Ser Cys
        115                 120                 125

Pro Ala Thr Ala Arg Glu Val Leu Ala His Pro Ser Phe Ala Asp Arg
    130                 135                 140

Pro Leu Lys Arg Ser Ala Arg Glu Leu Leu Phe Ala Arg Ala Ile Gly
145                 150                 155                 160

Phe Ala Pro Ser Gly Glu Tyr Trp Arg Leu Leu Arg Arg Ile Ala Ser
                165                 170                 175

Thr His Leu Phe Ser Pro Arg Arg Val Ala Ala His Glu Pro Gly Arg
            180                 185                 190

Gln Ala Asp Ala Thr Ala Met Leu Ser Ala Met Ala Ala Glu Gln Ser
        195                 200                 205

Ala Thr Gly Ala Val Val Leu Arg Pro His Leu Gln Ala Ala Ala Leu
    210                 215                 220

Asn Asn Ile Met Gly Ser Val Phe Gly Arg Arg Tyr Asp Val Ser Ser
225                 230                 235                 240

Ser Ser Gly Ala Ala Ala Asp Glu Ala Glu Gln Leu Lys Ser Met Val
                245                 250                 255

Arg Glu Gly Phe Glu Leu Leu Gly Ala Phe Asn Trp Ser Asp His Leu
            260                 265                 270

Pro Trp Leu Ala His Leu Tyr Asp Pro Asn His Val Ala Arg Arg Cys
        275                 280                 285

Ala Ala Leu Val Pro Arg Val Gln Ala Phe Val Arg Gly Val Ile Arg
    290                 295                 300

Asp His Arg Leu Arg Arg Asp Ser Ser Ser Thr Ala Ala Asp Asn Ala
305                 310                 315                 320

Asp Phe Val Asp Val Leu Leu Ser Leu Glu Ala His Glu Asn Leu Ala
                325                 330                 335

Glu Asp Asp Met Val Ala Val Leu Trp Glu Met Ile Phe Arg Gly Thr
            340                 345                 350

Asp Thr Thr Ala Leu Val Thr Glu Trp Cys Met Ala Glu Val Val Arg
        355                 360                 365

Asn Pro Ala Val Gln Ala Arg Leu Arg Ala Glu Val Asp Ala Ala Val
    370                 375                 380

Gly Gly Asp Gly Cys Pro Ser Asp Gly Asp Val Ala Arg Met Pro Tyr
385                 390                 395                 400

Leu Gln Ala Val Val Lys Glu Thr Leu Arg Ala His Pro Pro Gly Pro
                405                 410                 415
```

```
Leu Leu Ser Trp Ala Arg Leu Ala Thr Ala Asp Val Gly Leu Ala Asn
            420                 425                 430

Gly Met Val Val Pro Ala Gly Thr Thr Ala Met Val Asn Met Trp Ala
        435                 440                 445

Ile Thr His Asp Gly Glu Val Trp Ala Asp Pro Glu Ala Phe Ala Pro
    450                 455                 460

Glu Arg Phe Ile Pro Ser Glu Gly Gly Ala Asp Val Asp Val Arg Gly
465                 470                 475                 480

Gly Asp Leu Arg Leu Ala Pro Phe Gly Ala Gly Arg Arg Val Cys Pro
                485                 490                 495

Gly Lys Asn Leu Gly Leu Ala Thr Val Thr Leu Trp Val Ala Arg Leu
            500                 505                 510

Val His Ala Phe Asp Trp Phe Leu Pro Asp Gly Ser Pro Pro Val Ser
        515                 520                 525

Leu Asp Glu Val Leu Lys Leu Ser Leu Glu Met Lys Thr Pro Leu Ala
    530                 535                 540

Ala Ala Ala Thr Pro Arg Arg Arg Arg Ala Ala
545                 550                 555


<210> SEQ ID NO 81
<211> LENGTH: 174
<212> TYPE: PRT
<213> ORGANISM: Sorghum bicolor

<400> SEQUENCE: 81

Arg Asp Gly Arg Arg Arg Gly Glu Pro Pro Leu Arg Ala Glu Arg Arg
1               5                   10                  15

Glu Gly Asp Ala Ala His Ala Pro Ala Arg Ala Arg Cys Cys Arg Gly
            20                  25                  30

Arg Ala Trp Pro Ser Thr Thr Arg Thr Ser Ala Ala Thr Leu Val Pro
        35                  40                  45

Ala Gly Thr Thr Ala Met Val Asn Met Trp Ala Ile Ala His Asp Pro
    50                  55                  60

Ala Ile Trp Ala Glu Pro Glu Glu Phe Arg Pro Glu Arg Phe Gln Glu
65                  70                  75                  80

Glu Glu Glu Asp Val Ser Val Leu Gly Gly Asp Leu Arg Leu Ala Pro
                85                  90                  95

Phe Gly Ala Gly Arg Arg Val Cys Pro Asp Lys Met Leu Ala Leu Ala
            100                 105                 110

Thr Thr His Leu Trp Val Ala Gln Leu Leu His Arg Phe Glu Trp Ala
        115                 120                 125

Pro Ala Gly Ala Ala Ser Ser Gly Gly Gly Gly Val Asp Leu Ser Glu
    130                 135                 140

Arg Leu Asn Met Ser Leu Glu Met Ala Thr Pro Leu Val Cys Lys Ala
145                 150                 155                 160

Val Pro Arg Ser Ala Pro Gln Leu His Ala Gly Leu Ala Ser
                165                 170


<210> SEQ ID NO 82
<211> LENGTH: 552
<212> TYPE: PRT
<213> ORGANISM: Sorghum bicolor

<400> SEQUENCE: 82

Met Ala Met Ala Ser Ala Val Ser Ser Cys Thr Asp Ser Thr Trp Trp
1               5                   10                  15
```

```
Val Tyr Ala Leu Pro Thr Leu Leu Gly Ser Asp Thr Leu Cys Ala His
            20                  25                  30

Pro Ala Leu Leu Ala Gly Leu Leu Phe Leu Thr Thr Val Thr Ala Ala
        35                  40                  45

Leu Leu Ala Trp Ala Ala Ser Pro Gly Gly Pro Ala Trp Ala His Gly
    50                  55                  60

Arg Gly Arg Leu Gly Ala Thr Pro Ile Val Gly Pro Arg Gly Leu Pro
65                  70                  75                  80

Val Phe Gly Ser Ile Phe Ala Leu Ser Arg Gly Leu Pro His Arg Thr
                85                  90                  95

Leu Ala Ala Met Ala Arg Ala Ala Gly Pro Arg Ala Lys Glu Leu Met
            100                 105                 110

Ala Phe Ser Val Gly Asp Thr Pro Ala Val Val Ser Ser Cys Pro Ala
        115                 120                 125

Thr Ala Arg Glu Val Leu Ala His Pro Ser Phe Ala Asp Arg Pro Val
    130                 135                 140

Lys Arg Ser Ala Arg Glu Leu Met Phe Ala Arg Ala Ile Gly Phe Ala
145                 150                 155                 160

Pro Asn Gly Glu Tyr Trp Arg Arg Leu Arg Arg Val Ala Ser Thr His
                165                 170                 175

Leu Phe Ser Pro Arg Arg Val Ala Ala His Glu Pro Gly Arg Gln Gly
            180                 185                 190

Asp Ala Glu Ala Met Leu Arg Ser Val Ala Ala Glu Gln Ser Ala Ser
        195                 200                 205

Gly Thr Val Val Leu Arg Pro His Leu Gln Ala Ala Ala Leu Asn Asn
    210                 215                 220

Ile Met Gly Ser Val Phe Gly Thr Arg Tyr Asp Val Thr Ser Gly Ala
225                 230                 235                 240

Thr Ala Gly Ala Ala Glu Ala Glu Gln Leu Lys Ser Met Val Arg Glu
                245                 250                 255

Gly Phe Glu Leu Leu Gly Ala Phe Asn Trp Ser Asp His Leu Pro Trp
            260                 265                 270

Leu Ala His Leu Tyr Asp Pro Ser Asn Val Thr Arg Arg Cys Ala Ala
        275                 280                 285

Leu Val Pro Arg Val Gln Thr Phe Val Arg Gly Val Ile Asp Glu His
    290                 295                 300

Arg Arg Arg Arg Gln Asn Ser Ala Ala Leu Asp Leu Asn Asp Asn Ala
305                 310                 315                 320

Asp Phe Val Tyr Val Leu Leu Ser Leu Asp Gly Asp Glu Lys Leu Arg
                325                 330                 335

Asp Asp Asp Met Val Ala Ile Leu Trp Glu Met Ile Phe Arg Gly Thr
            340                 345                 350

Asp Thr Thr Ala Leu Leu Thr Glu Trp Cys Met Ala Glu Leu Val Arg
        355                 360                 365

His Pro Ala Val Gln Ala Arg Leu Arg Ala Glu Val Asp Ala Ala Val
    370                 375                 380

Gly Ala Gly Gly Arg Pro Thr Asp Ala Asp Val Ala Arg Met Pro Tyr
385                 390                 395                 400

Leu Gln Ala Val Val Lys Glu Thr Leu Arg Ala His Pro Pro Gly Pro
                405                 410                 415

Leu Leu Ser Trp Ala Arg Leu Ala Thr Ala Asp Val Pro Leu Ser Asn
            420                 425                 430

Gly Met Val Val Pro Ala Gly Thr Thr Ala Met Val Asn Met Trp Ala
```

```
        435                 440                 445

Ile Thr His Asp Ala Gly Val Trp Ala Asp Pro Asp Ala Phe Ala Pro
    450                 455                 460

Glu Arg Phe Leu Pro Ser Glu Gly Gly Ala Asp Val Asp Val Arg Gly
465                 470                 475                 480

Val Asp Leu Arg Leu Ala Pro Phe Gly Ala Gly Arg Arg Val Cys Pro
                485                 490                 495

Gly Lys Asn Leu Gly Leu Thr Thr Val Gly Leu Trp Val Ala Arg Leu
            500                 505                 510

Val His Ala Phe Glu Trp Ala Leu Pro Asp Gly Ala Pro Pro Val Cys
        515                 520                 525

Leu Asp Glu Val Leu Lys Leu Ser Leu Glu Met Lys Thr Pro Leu Ala
    530                 535                 540

Ala Ala Ala Ile Pro Arg Thr Ala
545                 550


<210> SEQ ID NO 83
<211> LENGTH: 561
<212> TYPE: PRT
<213> ORGANISM: Brachypodium distachyon

<400> SEQUENCE: 83

Met Glu Ser Ser Val Glu Ser Ser Trp Trp Val Leu Pro Leu Thr Leu
1               5                   10                  15

Ile Pro Ala Ile Ser Gly Gln Gln Gln Gln His Asp Gln Ser Thr Ala
            20                  25                  30

Ala Ala Ile Ala Thr Ser Phe Val Tyr Leu Ala Ile Leu Ala Cys Leu
        35                  40                  45

Ala Trp Ala Ala Lys Ser Leu Leu Tyr Trp Ala His Pro Gly Gly Pro
    50                  55                  60

Ala Trp Gly Arg Arg Tyr Trp Thr Ser Pro Cys Ala Lys Thr Ala Pro
65                  70                  75                  80

Ala Pro Ala Pro Ile Pro Gly Pro Arg Gly Leu Pro Val Val Gly Ser
                85                  90                  95

Leu Gly Leu Met Ser Gly Leu Ala His Ser Thr Leu Ala Ala Glu Ala
            100                 105                 110

Ala Arg Thr Pro Gly Ala Lys Arg Leu Met Ala Leu Ser Leu Gly Pro
        115                 120                 125

Val Pro Ala Val Val Thr Ala His Pro Asp Val Ala Lys Glu Ile Leu
    130                 135                 140

Asp Asn Pro Ala Phe Ala Asp Arg Pro Val Asn His Ala Ala Tyr Gly
145                 150                 155                 160

Leu Met Phe His Arg Ser Ile Gly Phe Ala Glu His Gly Pro Tyr Trp
                165                 170                 175

Arg Ala Leu Arg Arg Val Ala Ser Ala His Leu Phe Ala Pro Arg Gln
            180                 185                 190

Val Asp Ala Phe Ala Pro Tyr Arg Ala Arg Val Gly Glu Asp Val Val
        195                 200                 205

Ala Ala Leu Arg His Ala Gly Gly Gly Val Val Asn Val Arg Gly Val
    210                 215                 220

Leu Arg Arg Ala Ser Leu Tyr Tyr Ile Met Arg Phe Val Phe Gly Lys
225                 230                 235                 240

Glu Tyr Asp Val Ser Ser Asp Ser Gly Lys Lys Asp Gln Gly Glu Val
                245                 250                 255
```

```
Glu Glu Leu Leu Glu Met Val His Glu Gly Tyr Glu Leu Leu Gly Lys
            260                 265                 270

Glu Asn Trp Cys Asp Tyr Phe Pro Gly Leu Ala Gly Phe Asp Pro Gln
        275                 280                 285

Gly Val Gly Ala Arg Cys Ala Glu Leu Met Pro Arg Val Asn Arg Phe
    290                 295                 300

Val His Gly Ile Ile Asp Glu His Arg Gly Lys Ala Met Ile Ala Gly
305                 310                 315                 320

Gly Glu Gly Glu Ala Gln Pro Leu Asp Phe Val Asp Ile Leu Leu Ser
                325                 330                 335

Leu Gln Glu Ser Glu Gly Leu Ala Asp Ala Asp Ile Ala Ala Val Leu
            340                 345                 350

Trp Glu Met Ile Phe Arg Gly Thr Asp Ala Met Ala Val Leu Met Glu
        355                 360                 365

Trp Thr Met Ala Arg Leu Val Leu His Pro Gly Val Gln Ala Asn Val
    370                 375                 380

His Lys Glu Leu Asp Glu Val Val Gly Lys Ser Ser His Val Thr Glu
385                 390                 395                 400

Ser Ala Val Leu Ser Leu Pro Tyr Leu Gln Ala Leu Leu Lys Glu Ala
                405                 410                 415

Leu Arg Val His Pro Pro Gly Pro Leu Leu Ser Trp Arg His Arg Ala
            420                 425                 430

Met Trp Asp Thr Tyr Val Asp Gly His Leu Val Pro Ala Gly Thr Thr
        435                 440                 445

Ala Met Val Asn Gln Trp Ala Met Ser Arg Asp Pro Glu Val Trp Ala
    450                 455                 460

Glu Pro Leu Glu Phe Arg Pro Glu Arg Phe Leu Pro Gly Gly Glu Ala
465                 470                 475                 480

Gly Pro Gly Val Ser Val Leu Gly Ser Asp Gly Arg Leu Val Pro Phe
                485                 490                 495

Gly Ser Gly Arg Arg Ser Cys Pro Gly Lys Asn Leu Ala Met Thr Thr
            500                 505                 510

Val Thr Ala Trp Met Ala Thr Leu Met His Glu Phe Glu Trp Met Pro
        515                 520                 525

Ala Lys Thr Gly Ala Pro Val Asp Met Ser Glu Val Leu Arg Leu Ser
    530                 535                 540

Cys Glu Met Ala Thr Pro Leu Gln Val Arg Val Arg Pro Arg Arg Gly
545                 550                 555                 560

Val
```

<210> SEQ ID NO 84
<211> LENGTH: 9
<212> TYPE: PRT
<213> ORGANISM: Artificial sequence
<220> FEATURE:
<223> OTHER INFORMATION: Synthetic sequence: CYP78A6-clade polypeptide amino acid sequence motif
<220> FEATURE:
<221> NAME/KEY: VARIANT
<222> LOCATION: (8)..(8)
<223> OTHER INFORMATION: Xaa is any amino acid, preferably Gly, His or Thr

<400> SEQUENCE: 84

```
Gly Gly Ala Trp Gly Lys Tyr Xaa Arg
1               5
```

```
<210> SEQ ID NO 85
<211> LENGTH: 17
<212> TYPE: PRT
<213> ORGANISM: Artificial sequence
<220> FEATURE:
<223> OTHER INFORMATION: Synthetic sequence: CYP78A6-clade polypeptide
      amino acid sequence motif
<220> FEATURE:
<221> NAME/KEY: VARIANT
<222> LOCATION: (1)..(1)
<223> OTHER INFORMATION: Xaa is any amino acid, preferably Val or Asn
<220> FEATURE:
<221> NAME/KEY: VARIANT
<222> LOCATION: (3)..(3)
<223> OTHER INFORMATION: Xaa is any amino acid, preferably Lys or Arg
<220> FEATURE:
<221> NAME/KEY: VARIANT
<222> LOCATION: (10)..(10)
<223> OTHER INFORMATION: Xaa may be present or absent. If present, Xaa
      is any amino acid, preferably Arg
<220> FEATURE:
<221> NAME/KEY: VARIANT
<222> LOCATION: (11)..(11)
<223> OTHER INFORMATION: Xaa is any amino acid, preferably Met or Ser
<220> FEATURE:
<221> NAME/KEY: VARIANT
<222> LOCATION: (13)..(13)
<223> OTHER INFORMATION: Xaa is any amino acid, preferably Ser, Asn or
      His
<220> FEATURE:
<221> NAME/KEY: VARIANT
<222> LOCATION: (14)..(14)
<223> OTHER INFORMATION: Xaa is any amino acid, preferably Thr or Val

<400> SEQUENCE: 85

Xaa Gly Xaa Gly Val Gly Ser Met Ser Xaa Xaa Ser Xaa Xaa Ala His
1               5                   10                  15

Arg


<210> SEQ ID NO 86
<211> LENGTH: 25
<212> TYPE: PRT
<213> ORGANISM: Artificial sequence
<220> FEATURE:
<223> OTHER INFORMATION: Synthetic sequence: CYP78A6-clade polypeptide
      amino acid sequence motif
<220> FEATURE:
<221> NAME/KEY: VARIANT
<222> LOCATION: (5)..(5)
<223> OTHER INFORMATION: Xaa is any amino acid, preferably Thr or Asp
<220> FEATURE:
<221> NAME/KEY: VARIANT
<222> LOCATION: (6)..(6)
<223> OTHER INFORMATION: Xaa is any amino acid, preferably Thr or Arg
<220> FEATURE:
<221> NAME/KEY: VARIANT
<222> LOCATION: (7)..(7)
<223> OTHER INFORMATION: Xaa may be present or absent. If present, Xaa
      is any amino acid, preferably Lys
<220> FEATURE:
<221> NAME/KEY: VARIANT
<222> LOCATION: (8)..(8)
<223> OTHER INFORMATION: Xaa may be present or absent. If present, Xaa
      is any amino acid, preferably Val
<220> FEATURE:
<221> NAME/KEY: VARIANT
<222> LOCATION: (13)..(13)
<223> OTHER INFORMATION: Xaa is any amino acid, preferably Asn or His
<220> FEATURE:
<221> NAME/KEY: VARIANT
<222> LOCATION: (14)..(14)
<223> OTHER INFORMATION: Xaa is any amino acid, preferably Asp or Ala
<220> FEATURE:
<221> NAME/KEY: VARIANT
<222> LOCATION: (19)..(19)
<223> OTHER INFORMATION: Xaa may be present or absent. If present, Xaa
```

is any amino acid, preferably Ser

<400> SEQUENCE: 86

```
Met Ala Ser Gly Xaa Xaa Xaa Xaa Val Val Thr Cys Xaa Xaa Val Ala
1               5                   10                  15

Lys Asn Xaa Ser Val Ala Asp Arg Val
            20                  25
```

<210> SEQ ID NO 87
<211> LENGTH: 12
<212> TYPE: PRT
<213> ORGANISM: Artificial sequence
<220> FEATURE:
<223> OTHER INFORMATION: Synthetic sequence: CYP78A6-clade polypeptide amino acid sequence motif

<400> SEQUENCE: 87

```
Val Gly Tyr Asp Gly Thr Asn Trp Thr Asp His Trp
1               5                   10
```

<210> SEQ ID NO 88
<211> LENGTH: 10
<212> TYPE: PRT
<213> ORGANISM: Artificial sequence
<220> FEATURE:
<223> OTHER INFORMATION: Synthetic sequence: CYP78A6-clade polypeptide amino acid sequence motif

<400> SEQUENCE: 88

```
Ala Val Trp Met Arg Gly Thr Asp Val Ala
1               5                   10
```

<210> SEQ ID NO 89
<211> LENGTH: 13
<212> TYPE: PRT
<213> ORGANISM: Artificial sequence
<220> FEATURE:
<223> OTHER INFORMATION: Synthetic sequence: CYP78A6-clade polypeptide amino acid sequence motif
<220> FEATURE:
<221> NAME/KEY: VARIANT
<222> LOCATION: (10)..(10)
<223> OTHER INFORMATION: Xaa is any amino acid, preferably Ala or Ser

<400> SEQUENCE: 89

```
Lys Val Arg His Gly Ser Trp Ala Arg Xaa Thr Asp Thr
1               5                   10
```

<210> SEQ ID NO 90
<211> LENGTH: 49
<212> TYPE: PRT
<213> ORGANISM: Artificial sequence
<220> FEATURE:
<223> OTHER INFORMATION: Synthetic sequence: CYP78A6-clade polypeptide amino acid sequence motif
<220> FEATURE:
<221> NAME/KEY: VARIANT
<222> LOCATION: (13)..(13)
<223> OTHER INFORMATION: Xaa is any amino acid, preferably Ala or Val
<220> FEATURE:
<221> NAME/KEY: VARIANT
<222> LOCATION: (14)..(14)
<223> OTHER INFORMATION: Xaa may be present or absent. If present, Xaa is any amino acid, preferably Ser
<220> FEATURE:
<221> NAME/KEY: VARIANT
<222> LOCATION: (15)..(15)
<223> OTHER INFORMATION: Xaa is any amino acid, preferably His or Arg
<220> FEATURE:
<221> NAME/KEY: VARIANT

```
<222> LOCATION: (20)..(20)
<223> OTHER INFORMATION: Xaa is any amino acid, preferably Val, Asn or
      Asp
<220> FEATURE:
<221> NAME/KEY: VARIANT
<222> LOCATION: (21)..(21)
<223> OTHER INFORMATION: Xaa may be present or absent. If present, Xaa
      is any amino acid, preferably Asp
<220> FEATURE:
<221> NAME/KEY: VARIANT
<222> LOCATION: (28)..(28)
<223> OTHER INFORMATION: Xaa is any amino acid, preferably Ala or Val
<220> FEATURE:
<221> NAME/KEY: VARIANT
<222> LOCATION: (39)..(39)
<223> OTHER INFORMATION: Xaa is any amino acid, preferably Arg or Lys
<220> FEATURE:
<221> NAME/KEY: VARIANT
<222> LOCATION: (41)..(41)
<223> OTHER INFORMATION: Xaa may be present or absent. If present, Xaa
      is any amino acid, preferably Val

<400> SEQUENCE: 90

Val Ala Gly Thr Thr Ala Met Val Asn Met Trp Ala Xaa Xaa Xaa Asp
1               5                   10                  15

His Val Trp Xaa Xaa Lys Arg Val Ala Lys Gly Xaa Ser Val Gly Ser
            20                  25                  30

Asp Arg Ala Gly Ser Gly Xaa Arg Xaa Cys Gly Lys Asn Gly Thr Thr
        35                  40                  45

Val


<210> SEQ ID NO 91
<211> LENGTH: 17
<212> TYPE: PRT
<213> ORGANISM: Arabidopsis thaliana

<400> SEQUENCE: 91

Gly Gly Ala Trp Gly Lys Tyr Gly Arg Ser Gly Ser Tyr Lys Thr Gly
1               5                   10                  15

Asn


<210> SEQ ID NO 92
<211> LENGTH: 16
<212> TYPE: PRT
<213> ORGANISM: Arabidopsis thaliana

<400> SEQUENCE: 92

Val Gly Lys Gly Val Gly Ser Met Ser Met Ser Ser Thr Ala His Arg
1               5                   10                  15


<210> SEQ ID NO 93
<211> LENGTH: 22
<212> TYPE: PRT
<213> ORGANISM: Arabidopsis thaliana

<400> SEQUENCE: 93

Met Ala Ser Gly Thr Arg Val Val Thr Cys Asn Asp Val Ala Lys Asn
1               5                   10                  15

Ser Val Ala Asp Arg Val
            20


<210> SEQ ID NO 94
<211> LENGTH: 13
<212> TYPE: PRT
<213> ORGANISM: Arabidopsis thaliana
```

<400> SEQUENCE: 94

Lys Val Arg His Gly Ser Trp Ala Arg Ala Thr Asp Thr
1 5 10

<210> SEQ ID NO 95
<211> LENGTH: 48
<212> TYPE: PRT
<213> ORGANISM: Arabidopsis thaliana

<400> SEQUENCE: 95

Val Ala Gly Thr Thr Ala Met Val Asn Met Trp Ala Val Ser His Asp
1 5 10 15

His Val Trp Val Asp Lys Arg Val Ala Lys Gly Val Ser Val Gly Ser
20 25 30

Asp Arg Ala Gly Ser Gly Arg Arg Cys Gly Lys Asn Gly Thr Thr Val
35 40 45

<210> SEQ ID NO 96
<211> LENGTH: 1229
<212> TYPE: DNA
<213> ORGANISM: Arabidopsis thaliana

<400> SEQUENCE: 96
acactctttc ctctctcttt cttctctctt tcttttctct ctctctcctc tgctcctccg 60
tctctcgtct acagtgccct ccgcatcacc tttttccttg tcctatgaat ttggtcgaaa 120
tgcccttctc ctcctcctcc ttccactaat ctcaaaagat atatccttcg agactctccc 180
ttgccgtctc caattgccac tcaccgctcc aactctcttc gaattagctg aaatgaatgg 240
agataataga ccagtggaag atgctcatta cacggagaca ggtttccctt atgctgctac 300
tggaagttac atggactttt atggtggtgc ggctcagggg cctcttaact acgatcatgc 360
cgcaactatg catcctcagg acaatctgta ctggaccatg aataccaatg catacaagtt 420
tgggttttca ggatcagata atgcttcttt ctatggttca tatgacatga acgatcattt 480
atcgaggatg tccataggga gaacaaattg ggactatcat cccatggtga acgttgctga 540
tgatcctgaa aacacagttg cacgttccgt ccaaatcgga gacacagatg agcactctga 600
agctgaagaa tgcattgcaa atgagcatga tcccgacagt cctcaggtat cctggcaaga 660
tgacattgat cctgatacaa tgacctatga ggaattagta gagctggggg aagcagtagg 720
aacagaaagc aggggggttgt ctcaggaact catagaaacg cttcccacta aaaagtataa 780
gtttgggagc atcttctcca ggaaaagagc tggggagagg tgtgtgatat gccagctcaa 840
gtacaagata ggggagaggc aaatgaatct gccgtgcaag catgtgtatc attctgaatg 900
catttccaaa tggctaagca tcaacaaggt ttgcccggtg tgtaacagcg aggtctttgg 960
ggagcccagc attcattgat cggcacaagg ggctcctcct cttcttttct ttttggcttt 1020
ttatatcgag gctcatcaag taattgtttt agtgtagtga aaaccccaaa aaatagtcta 1080
aaagatgtcc acactatact ctctcatgtt cagtccttct ctgtacatgt aatttttctt 1140
ctagttccat tttcgcttgt gtgtgcttta agtttaacag tcactcgtat tgtatactaa 1200
atgctaagtc aaaaacgctg aatccatat 1229

<210> SEQ ID NO 97
<211> LENGTH: 248
<212> TYPE: PRT
<213> ORGANISM: Arabidopsis thaliana

<400> SEQUENCE: 97

```
Met Asn Gly Asp Asn Arg Pro Val Glu Asp Ala His Tyr Thr Glu Thr
1               5                   10                  15

Gly Phe Pro Tyr Ala Ala Thr Gly Ser Tyr Met Asp Phe Tyr Gly Gly
            20                  25                  30

Ala Ala Gln Gly Pro Leu Asn Tyr Asp His Ala Ala Thr Met His Pro
        35                  40                  45

Gln Asp Asn Leu Tyr Trp Thr Met Asn Thr Asn Ala Tyr Lys Phe Gly
    50                  55                  60

Phe Ser Gly Ser Asp Asn Ala Ser Phe Tyr Gly Ser Tyr Asp Met Asn
65                  70                  75                  80

Asp His Leu Ser Arg Met Ser Ile Gly Arg Thr Asn Trp Asp Tyr His
                85                  90                  95

Pro Met Val Asn Val Ala Asp Asp Pro Glu Asn Thr Val Ala Arg Ser
            100                 105                 110

Val Gln Ile Gly Asp Thr Asp Glu His Ser Glu Ala Glu Glu Cys Ile
        115                 120                 125

Ala Asn Glu His Asp Pro Asp Ser Pro Gln Val Ser Trp Gln Asp Asp
    130                 135                 140

Ile Asp Pro Asp Thr Met Thr Tyr Glu Glu Leu Val Glu Leu Gly Glu
145                 150                 155                 160

Ala Val Gly Thr Glu Ser Arg Gly Leu Ser Gln Glu Leu Ile Glu Thr
                165                 170                 175

Leu Pro Thr Lys Lys Tyr Lys Phe Gly Ser Ile Phe Ser Arg Lys Arg
            180                 185                 190

Ala Gly Glu Arg Cys Val Ile Cys Gln Leu Lys Tyr Lys Ile Gly Glu
        195                 200                 205

Arg Gln Met Asn Leu Pro Cys Lys His Val Tyr His Ser Glu Cys Ile
    210                 215                 220

Ser Lys Trp Leu Ser Ile Asn Lys Val Cys Pro Val Cys Asn Ser Glu
225                 230                 235                 240

Val Phe Gly Glu Pro Ser Ile His
                245
```

<210> SEQ ID NO 98
<211> LENGTH: 22
<212> TYPE: DNA
<213> ORGANISM: Artificial sequence
<220> FEATURE:
<223> OTHER INFORMATION: Synthetic sequence: Primer for verifying T-DNA

<400> SEQUENCE: 98
ggtctaagat ttctctcgtg tc 22

<210> SEQ ID NO 99
<211> LENGTH: 22
<212> TYPE: DNA
<213> ORGANISM: Artificial sequence
<220> FEATURE:
<223> OTHER INFORMATION: Synthetic sequence: Primer for verifying T-DNA

<400> SEQUENCE: 99
cgtacgtctt ctattactcc ac 22

<210> SEQ ID NO 100
<211> LENGTH: 21
<212> TYPE: DNA
<213> ORGANISM: Artificial sequence
<220> FEATURE:

```
<223> OTHER INFORMATION: Synthetic sequence: Primer for verifying T-DNA

<400> SEQUENCE: 100

aactccaaag gatcaaccca c                                               21


<210> SEQ ID NO 101
<211> LENGTH: 21
<212> TYPE: DNA
<213> ORGANISM: Artificial sequence
<220> FEATURE:
<223> OTHER INFORMATION: Synthetic sequence: Primer for verifying T-DNA

<400> SEQUENCE: 101

ccggttaaag aatcggctta c                                               21


<210> SEQ ID NO 102
<211> LENGTH: 21
<212> TYPE: DNA
<213> ORGANISM: Artificial sequence
<220> FEATURE:
<223> OTHER INFORMATION: Synthetic sequence: Primer for verifying T-DNA

<400> SEQUENCE: 102

gacttgcaaa gatcgttcac c                                               21


<210> SEQ ID NO 103
<211> LENGTH: 21
<212> TYPE: DNA
<213> ORGANISM: Artificial sequence
<220> FEATURE:
<223> OTHER INFORMATION: Synthetic sequence: Primer for verifying T-DNA

<400> SEQUENCE: 103

actcaatgtg acgtgttgtg g                                               21


<210> SEQ ID NO 104
<211> LENGTH: 21
<212> TYPE: DNA
<213> ORGANISM: Artificial sequence
<220> FEATURE:
<223> OTHER INFORMATION: Synthetic sequence: Primer for verifying T-DNA

<400> SEQUENCE: 104

tttgatcgag tggattcttg c                                               21


<210> SEQ ID NO 105
<211> LENGTH: 21
<212> TYPE: DNA
<213> ORGANISM: Artificial sequence
<220> FEATURE:
<223> OTHER INFORMATION: Synthetic sequence: Primer for verifying T-DNA

<400> SEQUENCE: 105

atatttgctt gtaatcgggg c                                               21


<210> SEQ ID NO 106
<211> LENGTH: 21
<212> TYPE: DNA
<213> ORGANISM: Artificial sequence
<220> FEATURE:
<223> OTHER INFORMATION: Synthetic sequence: Primer for verifying T-DNA

<400> SEQUENCE: 106

taaaaccaaa cgacaccgtt c                                               21
```

<210> SEQ ID NO 107
<211> LENGTH: 21
<212> TYPE: DNA
<213> ORGANISM: Artificial sequence
<220> FEATURE:
<223> OTHER INFORMATION: Synthetic sequence: Primer for verifying T-DNA

<400> SEQUENCE: 107
tccaagtttg ttgacgattc c 21

<210> SEQ ID NO 108
<211> LENGTH: 24
<212> TYPE: DNA
<213> ORGANISM: Artificial sequence
<220> FEATURE:
<223> OTHER INFORMATION: Synthetic sequence: Primer for verifying T-DNA

<400> SEQUENCE: 108
cgagtatcaa tggaaactta accg 24

<210> SEQ ID NO 109
<211> LENGTH: 20
<212> TYPE: DNA
<213> ORGANISM: Artificial sequence
<220> FEATURE:
<223> OTHER INFORMATION: Synthetic sequence: Primer for verifying T-DNA

<400> SEQUENCE: 109
aacggagagt ggcttgagat 20

<210> SEQ ID NO 110
<211> LENGTH: 20
<212> TYPE: DNA
<213> ORGANISM: Artificial sequence
<220> FEATURE:
<223> OTHER INFORMATION: Synthetic sequence: Primer for verifying T-DNA

<400> SEQUENCE: 110
tggcccttat ggtttctgca 20

<210> SEQ ID NO 111
<211> LENGTH: 15
<212> TYPE: DNA
<213> ORGANISM: Artificial sequence
<220> FEATURE:
<223> OTHER INFORMATION: Synthetic sequence: Primer for verifying T-DNA
<220> FEATURE:
<221> NAME/KEY: misc_feature
<222> LOCATION: (1)..(1)
<223> OTHER INFORMATION: n is a or g or c or t

<400> SEQUENCE: 111
ntcgastwts gwgtt 15

<210> SEQ ID NO 112
<211> LENGTH: 22
<212> TYPE: DNA
<213> ORGANISM: Artificial sequence
<220> FEATURE:
<223> OTHER INFORMATION: Synthetic sequence: Primer for verifying T-DNA

<400> SEQUENCE: 112
tggttcacgt agtgggccat cg 22

<210> SEQ ID NO 113
<211> LENGTH: 34
<212> TYPE: DNA

<213> ORGANISM: Artificial sequence
<220> FEATURE:
<223> OTHER INFORMATION: Synthetic sequence: Primer for verifying T-DNA

<400> SEQUENCE: 113
gcttcctatt atatcttccc aaattaccaa taca 34

<210> SEQ ID NO 114
<211> LENGTH: 30
<212> TYPE: DNA
<213> ORGANISM: Artificial sequence
<220> FEATURE:
<223> OTHER INFORMATION: Synthetic sequence: Primer for constructs

<400> SEQUENCE: 114
ctgcagatgg ctacgaaact cgaaagctcc 30

<210> SEQ ID NO 115
<211> LENGTH: 30
<212> TYPE: DNA
<213> ORGANISM: Artificial sequence
<220> FEATURE:
<223> OTHER INFORMATION: Synthetic sequence: Primer for constructs

<400> SEQUENCE: 115
ctgcagttaa ctgcgcctac ggcgcaattt 30

<210> SEQ ID NO 116
<211> LENGTH: 24
<212> TYPE: DNA
<213> ORGANISM: Artificial sequence
<220> FEATURE:
<223> OTHER INFORMATION: Synthetic sequence: Primer for constructs

<400> SEQUENCE: 116
gagctctgtc tcgtggataa gtag 24

<210> SEQ ID NO 117
<211> LENGTH: 27
<212> TYPE: DNA
<213> ORGANISM: Artificial sequence
<220> FEATURE:
<223> OTHER INFORMATION: Synthetic sequence: Primer for constructs

<400> SEQUENCE: 117
ccatggggcg gatcaaagca aagtaag 27

<210> SEQ ID NO 118
<211> LENGTH: 18
<212> TYPE: DNA
<213> ORGANISM: Artificial sequence
<220> FEATURE:
<223> OTHER INFORMATION: Synthetic sequence: Primer for RT-PCR

<400> SEQUENCE: 118
accaaccttg ccttctcc 18

<210> SEQ ID NO 119
<211> LENGTH: 19
<212> TYPE: DNA
<213> ORGANISM: Artificial sequence
<220> FEATURE:
<223> OTHER INFORMATION: Synthetic sequence: Primer for RT-PCR

<400> SEQUENCE: 119
cgtctcggct cttctgatt 19

<210> SEQ ID NO 120
<211> LENGTH: 17
<212> TYPE: DNA
<213> ORGANISM: Artificial sequence
<220> FEATURE:
<223> OTHER INFORMATION: Synthetic sequence: Primer for RT-PCR

<400> SEQUENCE: 120
acaacgagca gcaacca 17

<210> SEQ ID NO 121
<211> LENGTH: 19
<212> TYPE: DNA
<213> ORGANISM: Artificial sequence
<220> FEATURE:
<223> OTHER INFORMATION: Synthetic sequence: Primer for RT-PCR

<400> SEQUENCE: 121
tcttcaaccg gaacttcat 19

<210> SEQ ID NO 122
<211> LENGTH: 18
<212> TYPE: DNA
<213> ORGANISM: Artificial sequence
<220> FEATURE:
<223> OTHER INFORMATION: Synthetic sequence: Primer for RT-PCR

<400> SEQUENCE: 122
atccttcctg atatcgac 18

<210> SEQ ID NO 123
<211> LENGTH: 18
<212> TYPE: DNA
<213> ORGANISM: Artificial sequence
<220> FEATURE:
<223> OTHER INFORMATION: Synthetic sequence: Primer for RT-PCR

<400> SEQUENCE: 123
gagaagatga ctcagatc 18

<210> SEQ ID NO 124
<211> LENGTH: 20
<212> TYPE: DNA
<213> ORGANISM: Artificial sequence
<220> FEATURE:
<223> OTHER INFORMATION: Synthetic sequence: Primer for quantitative real-time RT-PCR

<400> SEQUENCE: 124
ccggttaaag aatcggctta 20

<210> SEQ ID NO 125
<211> LENGTH: 20
<212> TYPE: DNA
<213> ORGANISM: Artificial sequence
<220> FEATURE:
<223> OTHER INFORMATION: Synthetic sequence: Primer for quantitative real-time RT-PCR

<400> SEQUENCE: 125
ttgagatcac tcgtcgttgc 20

<210> SEQ ID NO 126
<211> LENGTH: 20
<212> TYPE: DNA

```
<213> ORGANISM: Artificial sequence
<220> FEATURE:
<223> OTHER INFORMATION: Synthetic sequence: Primer for quantitative
      real-time RT-PCR

<400> SEQUENCE: 126

gaaatcacag cacttgcacc                                                  20


<210> SEQ ID NO 127
<211> LENGTH: 20
<212> TYPE: DNA
<213> ORGANISM: Artificial sequence
<220> FEATURE:
<223> OTHER INFORMATION: Synthetic sequence: Primer for quantitative
      real-time RT-PCR

<400> SEQUENCE: 127

aagcctttga tcttgagagc                                                  20


<210> SEQ ID NO 128
<211> LENGTH: 22
<212> TYPE: DNA
<213> ORGANISM: Artificial sequence
<220> FEATURE:
<223> OTHER INFORMATION: Synthetic sequence: Primer for in situ
      hybridization

<400> SEQUENCE: 128

aaagaagctc atatgagaat ta                                               22


<210> SEQ ID NO 129
<211> LENGTH: 23
<212> TYPE: DNA
<213> ORGANISM: Artificial sequence
<220> FEATURE:
<223> OTHER INFORMATION: Synthetic sequence: Primer for in situ
      hybridization

<400> SEQUENCE: 129

tggtgtaaat ataaattgaa act                                              23


<210> SEQ ID NO 130
<211> LENGTH: 24
<212> TYPE: DNA
<213> ORGANISM: Artificial sequence
<220> FEATURE:
<223> OTHER INFORMATION: Synthetic sequence: Primer for in situ
      hybridization

<400> SEQUENCE: 130

ttagtgtatg ataaggctaa ggct                                             24


<210> SEQ ID NO 131
<211> LENGTH: 22
<212> TYPE: DNA
<213> ORGANISM: Artificial sequence
<220> FEATURE:
<223> OTHER INFORMATION: Synthetic sequence: Primer for in situ
      hybridization

<400> SEQUENCE: 131

gtattaactt ttctttgtga ca                                               22
```

METHODS OF CONTROLLING SEED SIZE IN PLANTS

CROSS-REFERENCE TO RELATED APPLICATIONS

This application is a National Phase application of International Application No. PCT/GB2013/050072, filed Jan. 15, 2013, which claims priority to and the benefit of U.S. Provisional Application No. 61/588,792, filed Jan. 20, 2012 and GB Application No. GB1202258.8, filed Feb. 9, 2012, the contents of all of which applications are incorporated by reference herein in their entirety.

FIELD OF INVENTION

This invention relates to the control of the size of the seeds which are produced by plants.

BACKGROUND OF INVENTION

Seed size is a key determinant of evolutionary fitness in plants and is also an important agronomic trait during crop domestication (Orsi and Tanksley, 2009). Several studies suggest that seedlings of large-seeded plants are better able to tolerate many of the stresses encountered during seedling establishment, whereas small-seeded plants are considered to have superior colonization abilities because they produce large numbers of seeds (Westoby et al., 2002; Moles et al., 2005). At the same time, seed size is negatively associated with the number of seeds produced by a plant due to the limited resources of the mother plant (Harper et al., 1970). Scientific interest in seed size relates not only to its importance in plant fitness, but also to crop domestication. Crops domesticated for consumption of their seeds (e.g. rice and wheat) often produce seeds significantly larger than their wild ancestors (Fan et al., 2006; Song et al., 2007; Gegas et al., 2010).

A seed consists of three major components; the embryo, the endosperm and the seed coat, that originate from different cells of the ovule and possess different complements of maternal and paternal genomes. In angiosperms, seed development involves a double fertilization process in which one sperm nucleus fuses with the egg to produce the diploid embryo, while the other sperm nucleus fuses with two polar nuclei to form the triploid endosperm (Lopes and Larkins, 1993). The seed coat differentiates after fertilization from maternally derived integuments. The embryo is surrounded by the endosperm, which, in turn, is enclosed within the maternal seed coat. Therefore, the size of a seed is determined by the coordinated growth of maternal sporophytic and zygotic tissues.

The size of seeds is influenced by a variety of cellular processes. Seed size is known to be influenced by parent-of-origin effects. The cross between a diploid female parent and tetraploid male parent produces larger $F_1$ seeds, whereas the reciprocal cross generates smaller $F_1$ seeds, suggesting that maternal or paternal excess of genome has a dramatic effect on seed size (Scott et al., 1998). Similar to interploidy crosses, crosses between wild type and met1 mutant with hypomethylated genomes show that larger $F_1$ seeds are generated when the maternal parent is met1, while smaller $F_1$ seeds are produced when the paternal parent is met1 (Xiao et al., 2006), suggesting that parent-of-origin effects may involve DNA methylation. In addition, the size of seeds is affected by the maternal and/or zygotic tissues. Several factors that influence seed size by the zygotic tissues have been recently identified in *Arabidopsis*. haiku (iku) and miniseed3 (mini3) mutants form small seeds due to the reduced growth and early cellularization of the endosperm (Garcia et al., 2003; Luo et al., 2005). IKU1, IKU2 and MINI3 function in the same pathway to promote endosperm growth in *Arabidopsis* (Garcia et al., 2003; Luo et al., 2005; Wang et al., 2010). SHORT HYPOCOTYL UNDER BLUE1 (SHB1) associates with both MINI3 and IKU2 promoters in vivo and may act with other proteins that bind to MINI3 and IKU2 promoters to promote endosperm growth in the early phase of seed development (Zhou et al., 2009). Seed size is also influenced by maternal tissues. Several factors that act in maternal tissues to influence seed size have been isolated. *Arabidopsis* TRANSPARENT TESTA GLABRA 2 (TTG2) promotes seed growth by increasing cell expansion in the integuments (Garcia et al., 2005; Ohto et al., 2009). APETALA2 (AP2) may restrict seed growth by limiting cell expansion in the integuments (Jofuku et al., 2005; Ohto et al., 2005; Ohto et al., 2009). By contrast, AUXIN RESPONSE FACTOR 2 (ARF2) and the predicted ubiquitin receptor CYP78A61 limit seed size by restricting cell proliferation in the integuments (Schruff et al., 2006; Li et al., 2008). However, CYP78A5/KLU promotes seed growth by increasing cell proliferation in the integuments of ovules (Adamski et al., 2009). Therefore, the integument or seed coat plays a key role in maternal control of seed size. In addition, many quantitative trait loci (QTLs) for seed size have been mapped in *Arabidopsis* and crops (Alonso-Blanco et al., 1999; Li et al., 2004; Fan et al., 2006; Song et al., 2007; Shomura et al., 2008; Weng et al., 2008). Three grain size QTLs have been recently cloned in rice, including GS3, GW2 and qSW5/GW5 (Fan et al., 2006; Song et al., 2007; Shomura et al., 2008; Weng et al., 2008). However, it is not clear whether these three factors act in maternal and/or zygotic tissues in rice.

Despite the importance of seed size, relatively little is known about the genetic and molecular mechanisms that control seed size.

Identification of factors that control the final size of seeds will not only advance understanding of the mechanisms of size control in plants, but may also have substantial practical applications for example in improving crop yield.

SUMMARY OF INVENTION

The present inventors have identified and characterised a genetic factor which alters seed size in plants. This may be useful, for example, in modulating seed size and improving yields in crop plants.

An aspect of the invention provides a method of modulating seed size in a plant which comprises;

altering the expression of a CYP78A polypeptide within cells of said plant.

Another aspect of the invention provides a method of producing a plant with an altered seed size comprising:

incorporating a heterologous nucleic acid which alters the expression of a CYP78A polypeptide into a plant cell by means of transformation, and;

regenerating the plant from one or more transformed cells.

Other aspects of the invention relate to plant cells with altered expression of a CYP78A polypeptide relative to controls, for example plant cells produced by a method described above; plants comprising such cells, and the seeds and progeny of such plants.

The CYP78A polypeptide may be a CYP78A6 polypeptide.

The expression of two or more CYP78A polypeptides may be altered in the plant cells.

The expression of one or more other growth factors, such as DA or BB may additionally be altered in the plant cells.

BRIEF DESCRIPTION OF DRAWINGS

FIG. 1(A) shows seeds from wild-type, da1-1 and eod3-1D da1-1 plants (from left to right). FIG. 1(B) shows mature embryos of wild type, da1-1 and eod3-1D da1-1 (from left to right). FIG. 1(C) shows 10-d-old-seedlings of wild type, da1-1 and eod3-1D da1-1 (from left to right). FIG. 1(D) shows projective area of wild-type, da1-1 and eod3-1D da1-1 seeds. FIG. 1(E) shows seed weight of wild type, da1-1 and eod3-1D da1-1. FIG. 1(F) shows cotyledon area of 10-d-old wild-type, da1-1 and eod3-1D da1-1 seedlings. Values (D-F) are given as mean±SE relative to the respective wild-type values, set at 100%. Bars: A, B, 0.5 mm; C, 5 mm.

Table 1 shows phenotypes of wild-type, eod3-ko1, cyp78a9-ko1, eod3-ko1 cyp78a9-ko1 and eod3-1D plants.

Table 2 shows developmental stages of embryogenesis.

Table 3 shows primers.

DETAILED DESCRIPTION OF EMBODIMENTS OF THE INVENTION

In various aspects, the invention provides methods which relate to the modulation of CYP78A expression in plant cells. This modulation may be useful in altering, for example increasing or decreasing, seed size in plants.

CYP78A polypeptides are a sub-family of cytochrome p450 (CYP) dependent monooxygenases which are found only in plants. CYP78A polypeptides may be defined by phylogenetic analysis on the basis of overall identity and sequence conservation within domains (Chapple Annu. Rev. Plant Physiol. Plant Mol. Biol. (1998) 49:311-43)

Figure 18:
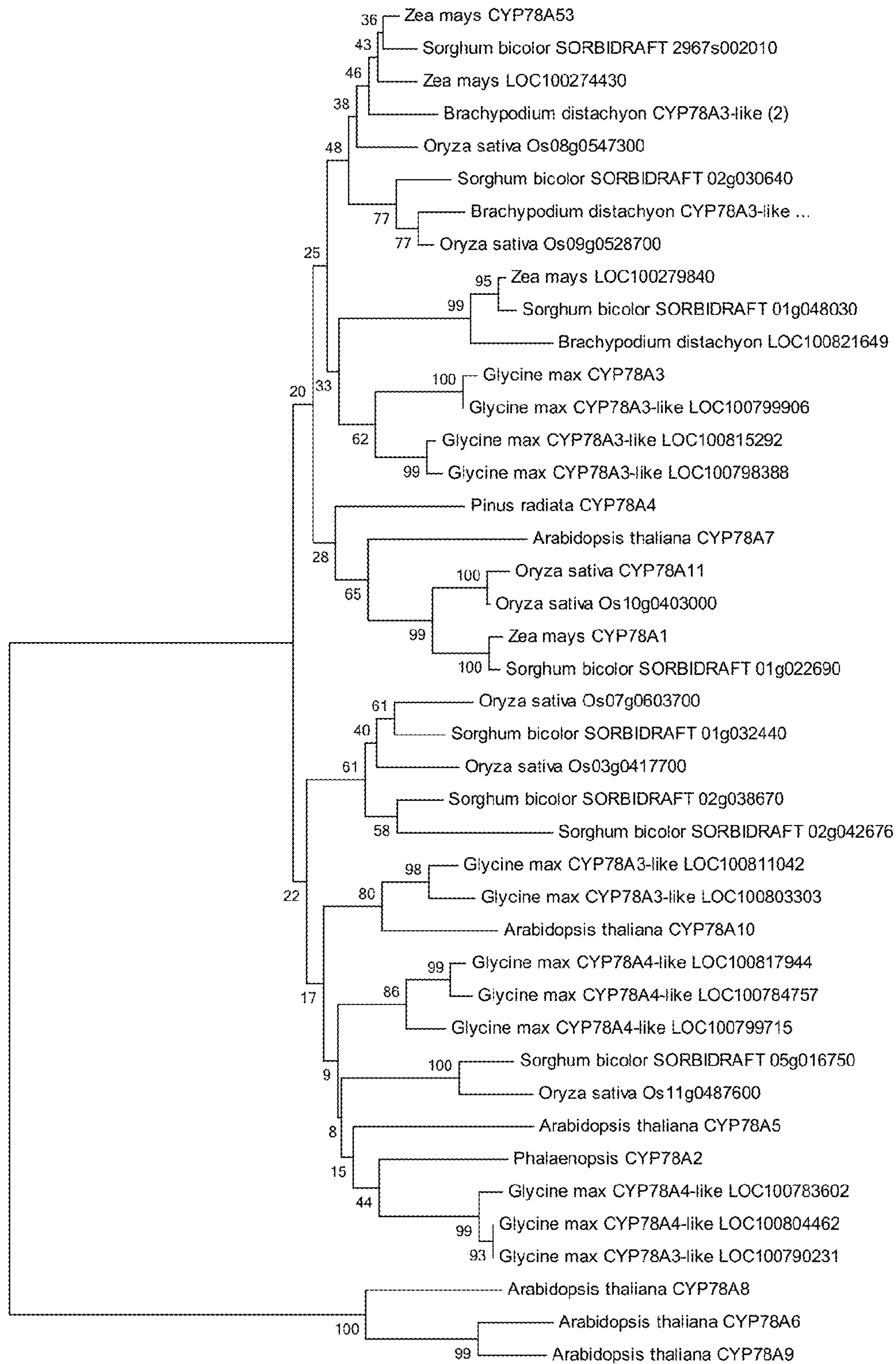
FIG. 18 shows phylogenic analysis of *Arabidopsis* CYP78A6 and its orthologues.

A CYP78A polypeptide may comprise an amino acid sequence which is shown in FIG. 18 or an amino acid sequence which is selected from the group consisting of SEQ ID NOS: 42 to 83 or an amino acid sequence which is a variant or fragment of one of these sequences which retains CYP78A activity.

Other CYP78A polypeptide sequences which include the characteristic features set out above may be identified using standard sequence analysis tools.

In some preferred embodiments, the CYP78A polypeptide may be a member of the phylogenetic grouping of CYP78A polypeptides which comprises CYP78A6, CYP78A8 and CYP78A9 and excludes CYP78A7, CYP78A5 and CYP78A10, as shown in FIG. 3E (i.e. a CYP78A6-clade polypeptide).

For example, a CYP78A6-clade polypeptide may comprise 1, 2, 3, 4, 5, 6 or all 7 of the amino acid sequence motifs of SEQ ID NOS: 84 to 90;

GGAWGKYX$_1$R (SEQ ID NO: 84), wherein $X_1$ is any amino acid, preferably G, H or T, most preferably G.

X$_2$G X$_3$GVGSMSX$_4$ X$_5$S X$_6$X$_7$AHR (SEQ ID NO: 85), wherein $X_2$ is any amino acid, preferably V or N, most preferably V; wherein $X_3$ is any amino acid, preferably K or R, most preferably K; wherein $X_4$ is absent or any amino acid, preferably absent or R, most preferably absent; wherein $X_5$ is any amino acid, preferably M or S, most preferably M; wherein $X_6$ is any amino acid, preferably S, N or H, most preferably S; and wherein $X_7$ is any amino acid, preferably T or V, most preferably T.

MASGX$_8$X$_9$X$_{10}$X$_{11}$VVTCX$_{12}$X$_{13}$VAKNX$_{14}$SVADRV (SEQ ID NO: 86), wherein $X_8$ is any amino acid, preferably T or D, most preferably T; wherein $X_9$ is any amino acid, preferably T or R, most preferably R; wherein $X_{10}$ is absent or any amino acid, preferably absent or K, most preferably absent; wherein $X_{11}$ is absent or any amino acid, preferably absent or V, most preferably absent; wherein $X_{12}$ is any amino acid, preferably N or H, most preferably N; wherein $X_{13}$ is any amino acid, preferably D or A, most preferably D; wherein $X_{14}$ is absent or any amino acid, preferably absent or S, most preferably absent.

VGYDGTNWTDHW (SEQ ID NO: 87)

AVWMRGTDVA (SEQ ID NO: 88)

KVRHGSWARX$_{15}$TDT (SEQ ID NO: 89), wherein $X_{15}$ is any amino acid, preferably A or S, most preferably A.

VAGTTAMVNMWAX$_{16}$X$_{17}$X$_{18}$DHVWX$_{19}$X$_{20}$KRVAK GX$_{21}$SVGSDRAGSGX$_{22}$RX$_{23}$CGKNGTTV (SEQ ID NO: 90); wherein independently, $X_{16}$ is any amino acid, preferably A or V, most preferably V; $X_{17}$ is absent or any amino acid, preferably absent or S, most preferably S; $X_{18}$ is any amino acid, preferably H or R, most preferably H; $X_{19}$ is any amino acid, preferably V, N or D, most preferably V; $X_{20}$ is absent or any amino acid, preferably absent or D, most preferably D; $X_{21}$ is any amino acid, preferably A or V, most preferably V; $X_{22}$ is any amino acid, preferably R or K, most preferably R; and $X_{23}$ is absent or any amino acid, preferably absent or V, most preferably absent.

For example, a CYP78A6-clade polypeptide may comprise SEQ NO:84 in combination with any 1, 2, 3, 4, 5 or all 6 of SEQ ID NOS: 85 to 90; a CYP78A6-clade polypeptide may comprise SEQ NO:85 in combination with any 1, 2, 3, 4, 5 or all 6 of SEQ ID NOS: 84 and 86 to 90; a CYP78A6-clade polypeptide may comprise SEQ NO:86 in combination with any 1, 2, 3, 4, 5 or all 6 of SEQ ID NOS: 84, 85 and 87 to 90; a CYP78A6-clade polypeptide may comprise SEQ NO:87 in combination with any 1, 2, 3, 4, 5 or all 6 of SEQ ID NOS: 84 to 86 and 88 to 90; a CYP78A6-clade polypeptide may comprise SEQ NO:88 in combination with any 1, 2, 3, 4, 5 or all 6 of SEQ ID NOS: 84 to 87, 89 or 90; a CYP78A6-clade polypeptide may comprise SEQ NO:89 in combination with any 1, 2, 3, 4, 5 or all 6 of SEQ ID NOS:

84 to 88 and 90; or a CYP78A6-clade polypeptide may comprise SEQ NO:90 in combination with any 1, 2, 3, 4, 5 or all 6 of SEQ ID NOS: 84 to 89.

In some preferred embodiments, a CYP78A6-clade polypeptide may comprise an amino acid sequence selected from the group consisting of SEQ ID NOS:42 to 44, or may be variant or a fragment of one of these sequences which retains CYP78A activity.

Preferably, the CYP78A6-clade polypeptide is a CYP78A6 polypeptide or a functional homologue thereof, as described herein. A CYP78A6 polypeptide may comprise 1, 2, 3, 4, 5, 6 or all 7 of the amino acid sequence motifs of SEQ ID NOS: 87, 88 and 91 to 95;

(SEQ ID NO: 91)
GGAWGKYGRSGSYKTGN (SEQ ID NO: 92)
VGKGVGSMSMSSTAHR (SEQ ID NO: 93)
MASGTRVVTCNDVAKNSVADRV (SEQ ID NO: 94)
KVRHGSWARATDT (SEQ ID NO: 95)
VAGTTAMVNMWAVSHDHVWVDKRVAKGVSVGSDRAGSGRRCGKNGTTV.

For example, a CYP78A6 polypeptide may comprise the amino acid sequence of *A. thaliana* CYP78A6 (At2g46660) (SEQ ID NO: 42) or may be a fragment or variant of this sequence which retains CYP78A activity. Other CYP78A6 polypeptides may comprise the amino acid sequence of any one of SEQ ID NOS: 42 to 83 or may be a fragment or variant of the sequence which retains CYP78A activity.

A CYP78A polypeptide which is a variant of a reference CYP78A sequence, such as any one of SEQ ID NOS: 42 to 83, preferably SEQ ID NOS: 42 to 44, most preferably SEQ ID NO:42, may comprise an amino acid sequence having at least 20%, at least 30%, at least 40%, at least 50%, at least 55%, at least 60%, at least 70%, at least 80%, at least 90%, at least 95%, or at least 98% sequence identity to the reference sequence.

Particular amino acid sequence variants may differ from the reference CYP78A sequence, such as any one of SEQ ID NOS: 42 to 83, by insertion, addition, substitution or deletion of 1 amino acid, 2, 3, 4, 5-10, 10-20 20-30, 30-50, or more than 50 amino acids.

Sequence similarity and identity are commonly defined with reference to the algorithm GAP (Wisconsin Package, Accelerys, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4.

Use of GAP may be preferred but other algorithms may be used, e.g. BLAST (which uses the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), or the TBLASTN program, of Altschul et al. (1990) supra, generally employing default parameters. In particular, the psi-Blast algorithm (Nucl. Acids Res. (1997) 25 3389-3402) may be used.

Sequence comparison may be made over the full-length of the relevant sequence described herein.

A CYP78A polypeptide which is a fragment of a reference CYP78A sequence, such as any one of SEQ ID NOS: 42 to 83, may consist of fewer amino acid residues than the full-length sequence. A CYP78A polypeptide fragment retains CYP78A activity and may, for example, comprise 100 or more, 150 or more, 200 or more or 250 or more amino acids.

Methods of increasing seed size in plants as described herein may comprise increasing expression of a CYP78A polypeptide in one or more cells of the plant relative to controls.

CYP78A expression may be increased by mutation. For example, a nucleic acid sequence which represses expression of a CYP78A coding sequence may be mutated. Suitable mutation methods, such as insertional activation using a heterologous nucleic acid, are well known in the art.

Alternatively, CYP78A expression may be increased by over-expression of a CYP78A coding sequence. For example, a heterologous nucleic acid encoding the CYP78A polypeptide may be expressed within the cells of a plant or a heterologous nucleic acid which promotes or increases expression of an endogenous CYP78A coding sequence may be inserted into the cells of a plant.

In some preferred embodiments, a nucleic acid encoding a CYP78A polypeptide may comprise the nucleotide sequence of SEQ ID NO: 1 or any one of SEQ ID NOS: 2 to 41 or may be a variant or fragment of this sequence which encodes a polypeptide which retains CYP78A activity.

Other nucleic acid sequences which encode CYP78A polypeptides are available on public databases.

A variant sequence may be a mutant, homologue, or allele of a reference CYP78A nucleotide sequence, such as any one of SEQ ID NOS: 1 to 41, or a reference BB sequence, such as SEQ ID NO: 96 and may differ from the reference CYP78A or BB sequence by one or more of addition, insertion, deletion or substitution of one or more nucleotides in the nucleic acid, leading to the addition, insertion, deletion or substitution of one or more amino acids in the encoded polypeptide. Of course, changes to the nucleic acid that make no difference to the encoded amino acid sequence are included. A nucleic acid encoding a CYP78A polypeptide may comprise a sequence having at least 20% or at least 30% sequence identity with the reference CYP78A nucleic acid sequence, preferably at least 40%, at least 50%, at least 60%, at least 65%, at least 70%, at least 80%, at least 90%, at least 95% or at least 98%. A nucleic acid encoding a BB polypeptide may comprise a sequence having at least 20% or at least 30% sequence identity with the reference BB nucleic acid sequence, preferably at least 40%, at least 50%, at least 60%, at least 65%, at least 70%, at least 80%, at least 90%, at least 95% or at least 98%. Sequence identity is described above.

A fragment or variant may comprise a sequence which encodes a functional CYP78A polypeptide i.e. a polypeptide which retains one or more functional characteristics of the polypeptide encoded by the wild-type CYP78A gene, for example, cytochrome p450 monooxygenase activity.

A nucleic acid comprising a nucleotide sequence which is a variant of a reference CYP78A6 nucleic acid sequence, such as any one of SEQ ID NOS: 1 to 41, may selectively hybridise under stringent conditions with this nucleic acid sequence or the complement thereof.

Stringent conditions include, e.g. for hybridization of sequences that are about 80 to 90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS. An alternative, which may be particularly appropriate with plant nucleic acid preparations, is a solution of 5×SSPE (final 0.9 M NaCl, 0.05M sodium phosphate, 0.005M EDTA pH 7.7), 5×Denhardt's solution, 0.5% SDS, at 50° C. or 65° C. overnight. Washes may be performed in 0.2×SSC/0.1% SDS at 65° C. or at 50-60° C. in 1×SSC/0.1% SDS, as required.

Nucleic acids as described herein may be wholly or partially synthetic. In particular, they may be recombinant in that nucleic acid sequences which are not found together in nature (do not run contiguously) have been ligated or otherwise combined artificially. Alternatively, they may have been synthesised directly e.g. using an automated synthesiser.

The nucleic acid may of course be double- or single-stranded, cDNA or genomic DNA, or RNA. The nucleic acid may be wholly or partially synthetic, depending on design. Naturally, the skilled person will understand that where the nucleic acid includes RNA, reference to the sequence shown should be construed as reference to the RNA equivalent, with U substituted for T.

Nucleic acid encoding a CYP78A polypeptide may be expressed in the same plant species or variety from which it was originally isolated or in a different plant species or variety (i.e. a heterologous plant).

"Heterologous" indicates that the gene/sequence of nucleotides in question or a sequence regulating the gene/sequence in question, has been introduced into said cells of the plant or an ancestor thereof, using genetic engineering or recombinant means, i.e. by human intervention. Nucleotide sequences which are heterologous to a plant cell may be non-naturally occurring in cells of that type, variety or species (i.e. exogenous or foreign) or may be sequences which are non-naturally occurring in that sub-cellular or genomic environment of the cells or may be sequences which are non-naturally regulated in the cells i.e. operably linked to a non-natural regulatory element. "Isolated" indicates that the isolated molecule (e.g. polypeptide or nucleic acid) exists in an environment which is distinct from the environment in which it occurs in nature. For example, an isolated nucleic acid may be substantially isolated with respect to the genomic environment in which it naturally occurs. An isolated nucleic acid may exist in an environment other than the environment in which it occurs in nature.

Methods of reducing seed size in plants as described herein may comprise reducing or abolishing expression of a CYP78A polypeptide in one or more cells of the plant relative to controls.

CYP78A expression may be reduced or abolished by mutation. For example, nucleic acid sequence encoding a CYP78A polypeptide within cells of said plant may be mutated, for example by insertion of a heterologous nucleic acid, within the plant cells. Alternatively, nucleic acid which regulates the expression of a CYP78A coding sequence within cells of said plant, such as a promoter or enhancer sequence, may be mutated, for example by insertion of a heterologous nucleic acid, within the plant cells.

The expression of CYP78A polypeptide may be reduced or abolished by mutating the nucleic acid sequences in the plant cell which encode the active protein and regenerating a plant from the mutated cell. The nucleic acids may be mutated by insertion or deletion of one or more nucleotides. Techniques for the inactivation or knockout of target genes are well-known in the art.

CYP78A expression may be reduced or abolished by suppression. For example, a heterologous nucleic encoding a suppressor nucleic acid which suppresses expression of a CYP78A polypeptide may be expressed within the plant cells.

The suppression of the expression of target polypeptides in plant cells is well-known in the art. Suitable suppressor nucleic acids may be copies of all or part of the target CYP78A gene inserted in antisense or sense orientation or both relative to the CYP78A gene, to achieve reduction in expression of the CYP78A gene. See, for example, van der Krol et al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020. Further refinements of this approach may be found in WO95/34668 (Biosource); Angell & Baulcombe (1997) The EMBO Journal 16, 12:3675-3684; and Voinnet & Baulcombe (1997) Nature 389: pg 553.

In some embodiments, the suppressor nucleic acids may be sense suppressors of expression of active CYP78A protein.

A suitable sense suppressor nucleic acid may be a double stranded RNA (Fire A. et al Nature, Vol 391, (1998)). dsRNA mediated silencing is gene specific and is often termed RNA interference (RNAi). RNAi is a two step process. First, dsRNA is cleaved within the cell to yield short interfering RNAs (siRNAs) of about 21-23 nt length with 5' terminal phosphate and 3' short overhangs (~2 nt). The siRNAs target the corresponding mRNA sequence specifically for destruction (Zamore P. D. Nature Structural Biology, 8, 9, 746-750, (2001)

siRNAs (sometimes called microRNAs) down-regulate gene expression by binding to complementary RNAs and either triggering mRNA elimination (RNAi) or arresting mRNA translation into protein. siRNA may be derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complementary target sequences without RNA cleavage and degrade mRNAs bearing fully complementary sequences.

Accordingly, the present invention provides the use of RNAi sequences based on the CYP78A nucleic acid sequence for suppression of the expression of the CYP78A polypeptide. For example, an RNAi sequence may correspond to a fragment of any one of SEQ ID NOS: 1 to 41 or other CYP78A nucleic acid sequence referred to above, or a variant thereof.

siRNA molecules are typically double stranded and, in order to optimise the effectiveness of RNA mediated down-regulation of the function of a target gene, it is preferred that the length and sequence of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA sequences which are transcribed from DNA, but are not translated into protein. A DNA sequence that codes for a miRNA is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed on John et al, PLoS Biology, 11(2), 1862-1879, 2004.

Typically, the RNA molecules intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design suitable siRNA and miRNA sequences, for example using one of the numerous publically available on-line siRNA finders, such as GenScript siRNA Target Finder, GenScript USA Inc. siRNA and miRNA sequences can be synthetically produced and added exogenously to cause gene downregulation or produced using expression systems (e.g. vectors). In a preferred embodiment, the siRNA is synthesized synthetically.

Longer double stranded RNAs may be processed in the cell to produce siRNAs (see for example Myers (2003) *Nature Biotechnology* 21:324-328). The longer dsRNA molecule may have symmetric 3' or 5' overhangs, e.g. of one or two (ribo) nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP (Shinagawa et al., Genes and Dev., 17, 1340-5, 2003).

Another alternative is the expression of a short hairpin RNA molecule (shRNA) in the cell. shRNAs are more stable than synthetic siRNAs. A shRNA consists of short inverted repeats separated by a small loop sequence. One inverted repeat is complementary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter. Alternatively, the shRNA may be synthesised exogenously (in vitro) by transcription from a vector. The shRNA may then be introduced directly into the cell. Preferably, the shRNA molecule comprises a partial sequence of SHR. For example, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

siRNA molecules, longer dsRNA molecules or miRNA molecules may be made recombinantly by transcription of a nucleic acid sequence, preferably contained within a vector. Preferably, the siRNA molecule, longer dsRNA molecule or miRNA molecule comprises a partial sequence of any one of SEQ ID NOS: 1 to 41 or a variant thereof, preferably any one of SEQ ID NOS: 1, 2, or 3 or a variant thereof, most preferably SEQ ID NO: 1 or a variant thereof.

In other embodiments, the suppressor nucleic acid may be an anti-sense suppressor of expression of a CYP78A6 polypeptide. In using anti-sense sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724-726; Zhang et al, (1992) *The Plant Cell* 4, 1575-1588, English et al., (1996) *The Plant Cell* 8, 179-188. Antisense technology is also reviewed in Bourque, (1995), *Plant Science* 105, 125-149, and Flavell (1994) *PNAS USA* 91, 3490-3496.

An anti-sense suppressor nucleic acid may comprise an anti-sense sequence of at least 10 nucleotides from a nucleotide sequence is a fragment of any one of SEQ ID NOS: 1 to 41 or other CYP78A sequence referred to above, or a variant thereof.

It may be preferable that there is complete sequence identity in the sequence used for down-regulation of expression of a target sequence, and the target sequence, although total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a variant of such a sequence.

The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene. Effectively, the homology should be sufficient for the down-regulation of gene expression to take place.

A nucleic acid encoding a CYP78A polypeptide or a CYP78A suppressor as described herein may be operably linked to a heterologous regulatory sequence, such as a promoter, for example a constitutive, inducible, tissue-specific or developmental specific promoter.

Many suitable regulatory sequences are known in the art and may be used in accordance with the invention. Examples of suitable regulatory sequences may be derived from a plant virus, for example the Cauliflower Mosaic Virus 35S (CaMV 35S) gene promoter that is expressed at a high level in virtually all plant tissues (Benfey et al, (1990) EMBO J 9: 1677-1684). Other suitable constitutive regulatory elements include the cauliflower mosaic virus 19S promoter; the Figwort mosaic virus promoter; and the nopaline synthase (nos) gene promoter (Singer et al., Plant Mol. Biol. 14:433 (1990); An, Plant Physiol. 81:86 (1986)).

Constructs for expression of the CYP78A genes or CYP78A suppressors under the control of a strong constitutive promoter (the 35S promoter) are exemplified below but those skilled in the art will appreciate that a wide variety of other promoters may be employed to advantage in particular contexts.

A tissue-specific promoter may be employed to express the CYP78A polypeptide or CYP78A suppressor in a specific tissue or organ.

For example, a seed-, seed-coat- or integument-specific promoter may be used to express the CYP78A polypeptide or CYP78A suppressor in seeds. Suitable promoters include, for example *Phaseolus vulgaris* phas promoter, *Vicia faba* leB4-, usp- or sbp-promoters, Soybean β-conglycinin α-subunit promoter, *Brassica* FAE1 promoter and At4g12960 promoter (AtGILTpro) (Wu et al Plant Cell Rep (2011) 30:75-80).

Alternatively, or in addition, one might select an inducible promoter. In this way, for example, the CYP78A polypeptide or suppressor may be expressed at specific times or places in order to obtain desired changes in organ growth. Inducible promoters include the alcohol inducible AlcA gene-expression system (Roslan et al., Plant Journal; 2001 Oct.; 28(2): 225-35) may be employed.

The nucleic acid encoding the CYP78A polypeptide or CYP78A suppressor may be contained on a nucleic acid construct or vector. The construct or vector is preferably suitable for transformation into and/or expression within a plant cell. A vector is, inter alia, any plasmid, cosmid, phage or *Agrobacterium* binary vector in double or single stranded linear or circular form, which may or may not be self transmissible or mobilizable, and which can transform prokaryotic or eukaryotic host, in particular a plant host, either by integration into the cellular genome or exist extrachromasomally (e.g. autonomous replicating plasmid with an origin of replication).

Specifically included are shuttle vectors by which is meant a DNA vehicle capable, naturally or by design, of replication in two different organisms, which may be selected from *Actinomyces* and related species, bacteria and eukaryotic (e.g. higher plant, mammalia, yeast or fungal) cells.

A construct or vector comprising nucleic acid as described above need not include a promoter or other regulatory sequence, particularly if the vector is to be used to introduce the nucleic acid into cells for recombination into the genome.

Constructs and vectors may further comprise selectable genetic markers consisting of genes that confer selectable phenotypes such as resistance to antibiotics such as kanamycin, hygromycin, phosphinotricin, chlorsulfuron, methotrexate, gentamycin, spectinomycin, imidazolinones, glyphosate and d-amino acids.

Those skilled in the art can construct vectors and design protocols for recombinant gene expression, for example in a microbial or plant cell. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 3rd edition, Sambrook et al, 2001, Cold Spring Harbor Laboratory Press and *Protocols in Molecular Biology*, Second Edition, Ausubel et al. eds. John Wiley & Sons, 1992. Specific procedures and vectors previously used with wide success upon plants are described by Bevan, Nucl. Acids Res. (1984) 12, 8711-8721), and Guerineau and Mullineaux, (1993) Plant transformation and expression vectors. In: Plant Molecular Biology Labfax (Croy R R D ed) Oxford, BIOS Scientific Publishers, pp 121-148.

When introducing a chosen nucleic acid construct into a cell, certain considerations must be taken into account, well known to those skilled in the art. The nucleic acid to be inserted should be assembled within a construct that contains effective regulatory elements that will drive transcription. There must be available a method of transporting the construct into the cell. Once the construct is within the cell membrane, integration into the endogenous chromosomal material either will or will not occur. Finally, the target cell type is preferably such that cells can be regenerated into whole plants.

Those skilled in the art will also appreciate that in producing constructs for achieving expression of the genes according to this invention, it is desirable to use a construct and transformation method which enhances expression of the nucleic acid encoding the CYP78A polypeptide or CYP78A suppressor. Integration of a single copy of the gene into the genome of the plant cell may be beneficial to minimize gene silencing effects. Likewise, control of the complexity of integration may be beneficial in this regard. Of particular interest in this regard is transformation of plant cells utilizing a minimal gene expression construct according to, for example, EP1407000B1, herein incorporated by reference for this purpose.

Techniques well known to those skilled in the art may be used to introduce nucleic acid constructs and vectors into plant cells to produce transgenic plants with the properties described herein.

*Agrobacterium* transformation is one method widely used by those skilled in the art to transform plant species. Production of stable, fertile transgenic plants is now routine in the art (see for example Toriyama, et al. (1988) *Bio/Technology* 6, 1072-1074; Zhang, et al. (1988) *Plant Cell Rep.* 7, 379-384; Zhang, et al. (1988) *Theor Appl Genet* 76, 835-840; Shimamoto, et al. (1989) *Nature* 338, 274-276; CYP78A6tta, et al. (1990) *Bio/Technology* 8, 736-740; Christou, et al. (1991) *Bio/Technology* 9, 957-962; Peng, et al. (1991) International Rice Research Institute, Manila, Philippines 563-574; Cao, et al. (1992) *Plant Cell Rep.* 11, 585-591; Li, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828; Nilsson, O. et al (1992) *Transgenic Research* 1, 209-220).

Other methods, such as microprojectile or particle bombardment (U.S. Pat. No. 5,100,792, EP-A-444882, EP-A-434616), electroporation (EP 290395, WO 8706614), microinjection (WO 92/09696, WO 94/00583, EP 331083, EP 175966, Green et al. (1987) *Plant Tissue and Cell Culture*, Academic Press), direct DNA uptake (DE 4005152, WO 9012096, U.S. Pat. No. 4,684,611), liposome mediated DNA uptake (e.g. Freeman et al. *Plant Cell Physiol.* 29: 1353 (1984)) or the vortexing method (e.g. Kindle, *PNAS U.S.A.* 87: 1228 (1990d)) may be preferred where *Agrobacterium* transformation is inefficient or ineffective, for example in some gymnosperm species.

Physical methods for the transformation of plant cells are reviewed in Oard, 1991, *Biotech. Adv.* 9: 1-11.

Alternatively, a combination of different techniques may be employed to enhance the efficiency of the transformation process, e.g. bombardment with *Agrobacterium* coated microparticles (EP-A-486234) or microprojectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

In some embodiments, the plant cell may further comprise altered expression of a DA protein, such as DA-1, and/or EOD1/BB protein. For example, expression of a DA and/or EOD1/BB protein may be reduced or abolished in plant cells in which CYP78A expression is increased, or dominant negative forms of DA and/or EOD1/BB proteins may be expressed. Expression of a DA and/or EOD1/BB protein may be increased in plant cells in which CYP78A expression is reduced.

DA proteins possess a characteristic domain structure comprising a LIM domain, a UIM1 domain and a UIM2 domain (Li et al Genes & Dev, 2003. 22: 1331-1336; WO2009/04752). A DA polypeptide may comprise the amino acid sequence of SEQ ID NO: 42 (AT1G19270; NP_173361.1 GI: 15221983) or may be a fragment or variant of this sequence which retains DA activity.

Big Brother (EOD1/BB) is an E3 ubiquitin ligase which is known to repress plant organ growth (Disch Curr Biol 16 272-279 (2006)). A BB protein may comprise the amino acid sequence of At3g63530 NP_001030922.1 GI: 79316205 (SEQ ID NO: 97), or may be a fragment or variant which retains BB activity or is capable of interfering with the function of BB.

A BB protein or DA protein which is a variant of a reference BB or DA sequence described above may comprise an amino acid sequence having at least 20%, at least 30%, at least 40%, at least 50%, at least 60%, at least 70%, at least 80%, at least 90%, at least 95%, or at least 98% sequence identity to the reference sequence. Sequence identity is described in more detail above.

DA proteins and EOD1/BB proteins, which may include AtDA1 (At1G19270) and AtBB (At3g63530), respectively, and variants thereof, are described and defined in detail in WO2009/04752, which is incorporated herein by reference for all purposes.

Particular amino acid sequence variants may differ from the DA polypeptide of SEQ ID NO: 42 or the BB polypeptide of SEQ ID NO: 97 (At3g63530) by insertion, addition, substitution or deletion of 1 amino acid, 2, 3, 4, 5-10, 10-20 20-30, 30-50, or more than 50 amino acids.

Plant as described herein having altered CYP78A expression in one or more cells therein, for example abolished, reduced, or increased CYP78A expression relative to controls, may be sexually or asexually propagated or off-spring or descendants may be grown.

Another aspect of the invention provides a method of producing a plant with an altered seed size comprising:

incorporating a heterologous nucleic acid which alters the expression of a CYP78A polypeptide into a plant cell by means of transformation, and;

regenerating the plant from one or more transformed cells.

As described above, the heterologous nucleic acid may encode a CYP78A polypeptide or a CYP78A suppressor molecule or may inactivate the endogenous CYP78A coding sequence of the plant or a regulatory sequence thereof, for example a repressor or enhancer.

The altered phenotype of the plant produced by the method is described in more detail above. The method may be useful, for example, in producing plants having increased yields, for example, crop plants having improved grain yield, relative to control plants.

In some embodiments, a method may further comprise reducing or abolishing the expression or activity of a DA polypeptide and/or EOD1/BB protein in the plant cell or plant.

This may be carried out before, at the same time or after the incorporation of the nucleic acid which encodes the CYP78A polypeptide. For example, in some embodiments, the expression or activity of a DA polypeptide and/or EOD1/BB protein may be abolished or reduced in one or more plant cells which already incorporate the nucleic acid encoding the CYP78A polypeptide. In other embodiments, the nucleic acid encoding the CYP78A polypeptide may be incorporated into one or more plant cells which have abolished or reduced expression of a DA polypeptide and/or EOD1/BB protein.

A plant thus produced may comprise a heterologous nucleic acid which encodes a CYP78A polypeptide and may possess abolished or reduced expression or activity of a DA polypeptide and/or EOD1/BB protein in one or more of its plant cells.

The expression or activity of a DA polypeptide and/or EOD1/BB protein may be reduced or abolished as described above. For example, a method may comprise incorporating a heterologous nucleic acid into a plant cell by means of transformation, wherein the nucleic acid encodes a suppressor nucleic acid, such as a siRNA or shRNA, which reduces the expression of a DA polypeptide and/or EOD1/BB protein.

The heterologous nucleic acids encoding the CYP78A polypeptide and Da and/or EOD1/BB suppressor nucleic acid may be on the same or different expression vectors and may be incorporated into the plant cell by conventional techniques.

CYP78A6 polypeptides and CYP78A suppressor nucleic acids are described in more detail above.

In some embodiments, the expression or activity of two or more CYP78A polypeptides, such as CYP78A6 and CYP78A9, may be abolished or reduced to produce a plant having reduced seed size.

A plant produced as described above may be sexually or asexually propagated or grown to produce off-spring or descendants. Off-spring or descendants of the plant regenerated from the one or more cells may be sexually or asexually propagated or grown. The plant or its off-spring or descendents may be crossed with other plants or with itself.

A plant suitable for use in the present methods is preferably a higher plant, for example an agricultural plant selected from the group consisting of *Lithospermum erythrorhizon, Taxus* spp, tobacco, cucurbits, carrot, vegetable *brassica*, melons, capsicums, grape vines, lettuce, strawberry, oilseed *brassica*, sugar beet, wheat, barley, maize, rice, soyabeans, peas, sorghum, sunflower, tomato, potato, pepper, *chrysanthemum*, carnation, linseed, hemp and rye.

In some embodiments, the plant may be a flowering plant (angiosperm). Flowering plants may include monocotyledons or dicotyledons, such as eudicots, in particular members of the Rosid clade, including Brasicaceae, such as broccoli, horseradish, cabbage, and cauliflower. In some embodiments, a plant may be other than *Arabidopsis thaliana.*

Another aspect of the invention provides a plant which comprises a heterologous nucleic acid which alters expression of a CYP78A polypeptide, as described above, and optionally has reduced or abolished expression of a DA polypeptide and/or EOD1/BB polypeptide.

The plant may display an altered seed size phenotype relative to controls (e.g. non-transgenic plants of the same species). For example, a plant which displays increased expression of a CYP78A polypeptide may display increased seed size relative to controls.

A plant which displays increased expression of the CYP78A6 polypeptide may also display one or more of; increased flower and leaf size, increased stem thickness, and increased height relative to control plants (e.g. identical plants which do not display increased expression of the CYP78A6 polypeptide).

A plant which displays reduced expression of a CYP78A polypeptide may display reduced seed size relative to controls.

A suitable plant with altered expression of a CYP78A polypeptide may be produced by a method described herein In some embodiments, the plant may have normal fertility relative to control plants.

In some embodiments, a plant may not display increased organ size relative to controls.

In addition to a plant comprising a heterologous nucleic acid which alters CYP78A expression, for example a nucleic acid which encodes a CYP78A polypeptide or CYP78A suppressor molecule, as described herein, the invention encompasses any clone of such a plant, seed, selfed or hybrid progeny and descendants, and any part or propagule of any of these, such as cuttings and seed, which may be used in reproduction or propagation, sexual or asexual. Also encompassed by the invention is a plant which is a sexually or asexually propagated off-spring, clone or descendant of such a plant, or any part or propagule of said plant, off-spring, clone or descendant.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Having generally described the invention above, certain aspects and embodiments of the invention will now be illustrated by way of example to extend the written description and enablement of the invention, and to ensure adequate disclosure of the best mode of practicing the invention. Those skilled in the art will appreciate, however, that the scope of this invention should not be interpreted as being limited by the specifics of these examples. Rather, variations, extensions, modifications and equivalents of these specifics and generic extensions of these details may be made without departing from the scope of the invention comprehended by this disclosure. Therefore, for an appreciation of the scope of this invention and the exclusive rights claimed herein, reference should be had to the claims appended to this disclosure, including equivalents thereof.

All documents mentioned in this specification are incorporated herein by reference in their entirety for all purposes.

The contents of all database entries mentioned in this specification are also incorporated herein by reference in their entirety. This includes the versions of any sequences which are current at the filing date of this application.

EXAMPLES

Methods

Activation Tagging Screening

The *Agrobacterium tumefaciens* strain GV3101 was transformed with the activation tagging vector pJFAT260 (Fan et al., 2009), and the resulting strain was used for floral dip transformation of *Arabidopsis* da1-1 mutant plants (Li et al., 2008). $T_1$ plants were selected by using the herbicide Basta. Seeds produced from $T_1$ plants were passed through a fine wire sieve (425 μm) (Fisher Scientific). Seeds retained by the sieve were kept for further characterization.

Plant Materials and Growth Conditions

*Arabidopsis thaliana* Columbia (Col-0) was the wild type line used. All mutants were in the Col-0 background. Plant materials and growth conditions are available in the Supporting Information.

Morphological and Cellular Analysis

Area measurements of fully expanded cotyledons, petals (stage 14), and leaves were made by flattening the organs, scanning to produce a digital image, and then calculating area by using Image J software. Embryo cell sizes were measured on the adaxial side of cotyledons from DIC images.

For analysis of whole-mount seeds, seeds were dissected from siliques and placed in a drop of clearing solution [30 ml $H_2O$, 80 g Chloral hydrate (Sigma, C8383), 10 ml 100% Glycerol (Sigma, G6279)]. Samples were photographed under a Leica microscope (LEICA DM2500) with differential interference contrast optics using a SPOT FLEX Cooled CCD Digital Imaging System.

Seed Size and Seed Mass Analysis

Average seed mass was determined by weighing mature dry seeds in batches of 500 using an electronic analytical balance (METTLER TOLEDO AL104, China). The weights of five sample batches were measured for each seed lot. The wild-type and mutant seeds were photographed under a Leica microscope (LEICA S8APO) using Leica CCD (DFC420). The length, width and projective area of wild-type and mutant seeds were measured by using Image J software.

Cloning of the EOD3 Gene

The flanking region of the T-DNA insertion of the eod3-1D mutant was isolated by the thermal asymmetric interlaced PCR (TAIL-PCR) (Liu et al., 1995). Detailed protocols are described in the Supporting Information.

Constructs and Transformation

The EOD3 CDS was subcloned into the PstI site of the binary vector 35S::pGreen to generate the transformation plasmid 35S::EOD3. The specific primers for the EOD3 CDS are EOD3CDS-F and EOD3CDS-R.

The 1878 bp EOD3 promoter was subcloned into SacI and NcoI sites of the binary vector pGreen-GUS to generate the transformation plasmid pEOD3::GUS. The specific primers for the EOD3 promoter are EOD3PROM-F and EOD3PROM-R.

GUS Staining

Samples (pEOD3::GUS) were stained in a solution of 1 mM X-gluc, 50 mM $NaPO_4$ buffer, 0.4 mM each $K_3Fe(CN)6/K_4Fe(CN)6$, 0.1% (v/v) Triton X-100 and incubated at 37° C. for 8 hrs. After GUS staining chlorophyll was removed using 70% ethanol.

RT-PCR, Quantitative Real-Time RT-PCR, and RNA In Situ Hybridization

Total RNA was extracted from *Arabidopsis* seedlings using an RNAprep pure Plant kit (TIANGEN). Reverse transcription (RT)-PCR was performed as described (Li et al., 2006). cDNA samples were standardized on actin transcript amount using the primers ACTIN7-F and ACTIN7-R. Quantitative real-time RT-PCR analysis was performed with a Lightcycler 480 machine (Roche) using the Lightcycler 480 SYBR Green I Master (Roche). ACTIN2 mRNA was used as an internal control, and relative amounts of mRNA were calculated using the comparative threshold cycle method. RNA in situ hybridization method is described in the Supporting Information. The primers used for RT-PCR, quantitative real-time RT-PCR, and RNA in situ hybridization are described herein.

Plant Materials and Growth Conditions

*Arabidopsis thaliana* Columbia (Col-0) was the wild type line used. All mutants were in the Col-0 background. eod3-1D was identified as an enhancer of da1-1 by using T-DNA activation tagging method. The eod3-ko1 (CS833552), eod3-ko2 (CS806696), cyp78a9-ko1 (SALK_121278) and ttg2-3 (SALK_148838) were identified in AtIDB (*Arabidopsis Thaliana* Integrated Database) and obtained from *Arabidopsis* Stock Centre ABRC collection. The eod3-ko1, eod3-ko2, cyp78a9-ko1 and ttg2-3 mutants were backcrossed into Col-0 for three times. T-DNA insertions were confirmed by PCR and sequencing by using the primers described in Supplementary Table 3. Seeds were surface-sterilized with 100% isopropanol for 1 min and 10% (v/v) household bleach for 10 mins, washed at least five times with sterile water, stratified at 4° C. for 2d in the dark, dispersed on Murashige and Skoog medium (Sigma) supplemented with 0.9% agar and 1% glucose, and then grown at 22° C.

Cloning of the EOD3 gene

The flanking region of the T-DNA insertion of the eod3-1D mutant was isolated by the thermal asymmetric interlaced PCR (TAIL-PCR) (Liu et al., 1995). Genomic DNA was prepared by using buffer containing 50 mM Tris-HCL (pH8.0), 25 mM EDTA, 250 mM NaCl and 0.5% SDS. Approximately 100 ng of the genomic DNA of the eod3-1D da1-1 mutant was used to perform TAIL-PCR analysis according to a previously reported method (Liu et al., 1995). Briefly, TAIL-PCR utilizes three nested specific primers (OJF22, OJF23 and OJF24) within the T-DNA region of the pJFAT260 vector together with a shorter arbitrary degenerate primer (AD1) so that the relative amplification efficiencies of specific and non-specific products can be thermally controlled. The specific primers OJF22, OJF23 and OJF24 and an arbitrary degenerate (AD1) primer are described in Table S3. TAIL-PCR products were sequenced by using the primer OJF24.

Cellular Analysis

For resin sections, siliques were cut transversely into four pieces and fixed in 4% paraformaldehyde. The tissues were embedded in Technovit 7100 resin (Heraeus Kulzer, Germany), sectioned at 5 μm thickness and stained with 0.05% toluidine blue.

RNA In Situ Hybridization

In situ hybridization was performed as described (Li et al., 2003). DIG-labeled RNA transcripts were generated by transcription of EOD3 and CYP78A9 in sense or antisense orientation using SP6 or T7 RNA polymerase (Roche). After hybridization, washing and blocking, DIG-labeled RNA transcripts reacting with alkaline phosphatase-conjugated anti-DIG Fab fragment (1:3000 [v/v], Roche) were detected using 5-bromo-4-chloro-3-indolyl phosphate/nitroblue tetrazolium. The slides were observed with a microscope (LEICA DM2500) and photographed using a SPOT FLEX Cooled CCD Digital Imaging System.

Expression of *Arabidopsis* EOD3 in *Oryza sativa*

Figure 19:
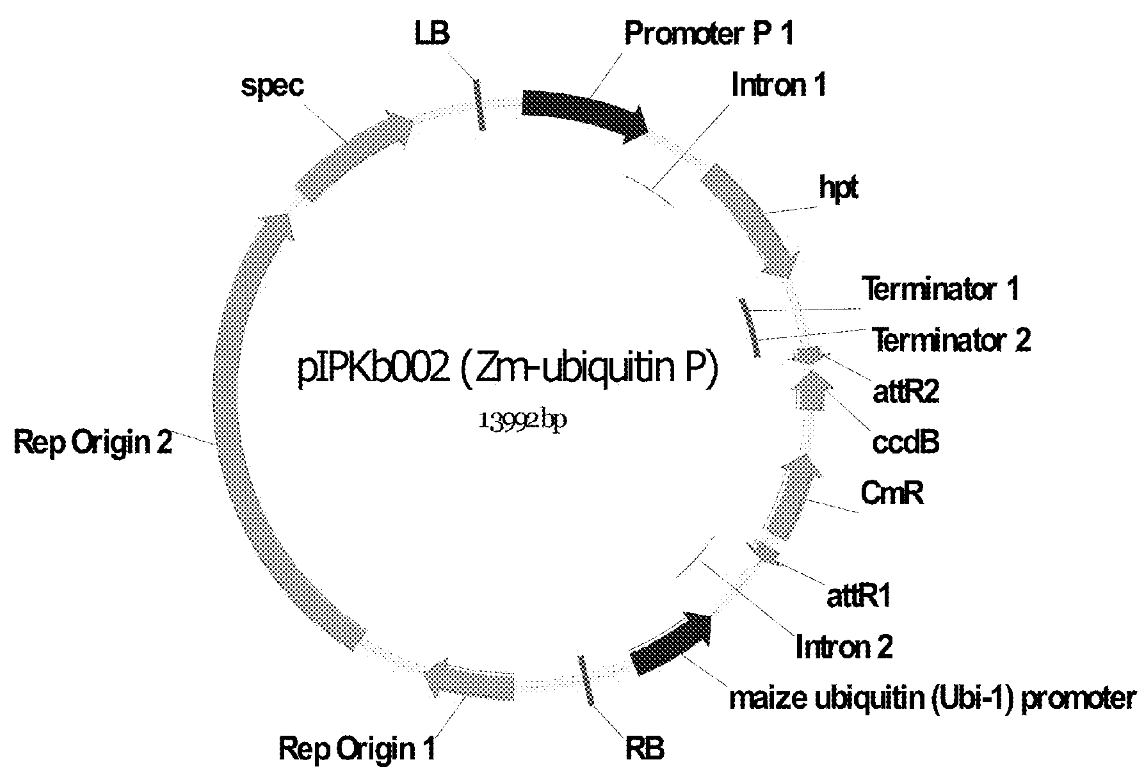
FIG. 19 shows the Gateway Binary Vector pIPKb002 containing the Zm-ubiqutin promoter used to express EOD3 in *Oryza sativa.*

For overexpression of *Arabidopsis* EOD3 in *Oryza sativa*, the full length CDS of EOD3 was subcloned into pCR8/GW/TOPO TA cloning vector (Invitrogen) using TOPO enzyme and sequenced. The EOD3 CDS was then subcloned into Gateway Binary Vector pIPKb002 containing the Zm-ubiqutin promoter (FIG. 19). The construct was then introduced into callus of *Oryza sativa L. japonica*. cv. *Nipponbare* and selected on hygromycin-containing medium. The detailed methods were described in Hiei et al (1994) Plant J 6 271-282.

The areas of 24 seeds from each line of T0 transgene plants were scanned to produce digital images, and then the average area per seed was calculated using Image J software as an indicator of seed size. The average area per seeds from each transgenic line was then determined.

Results

Figure 1:
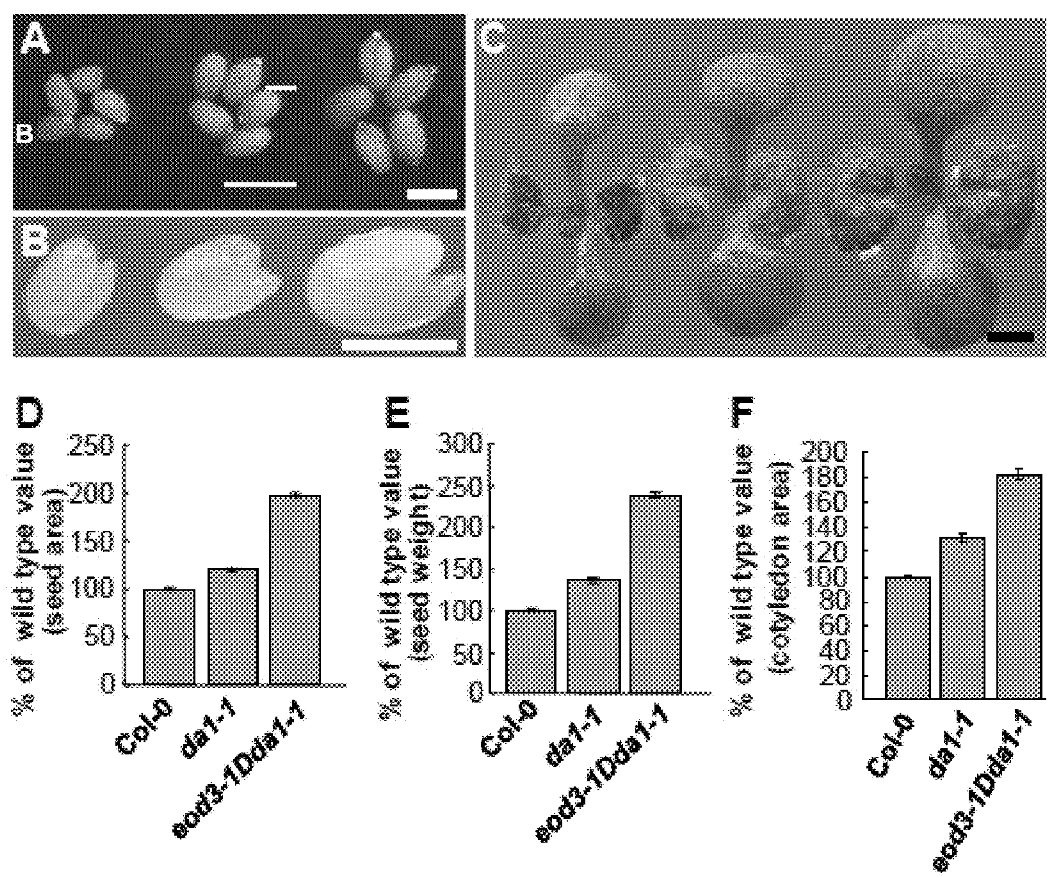
FIG. 1 shows the isolation of an enhancer of da1-1 (eod3-1D).
Figure 10:
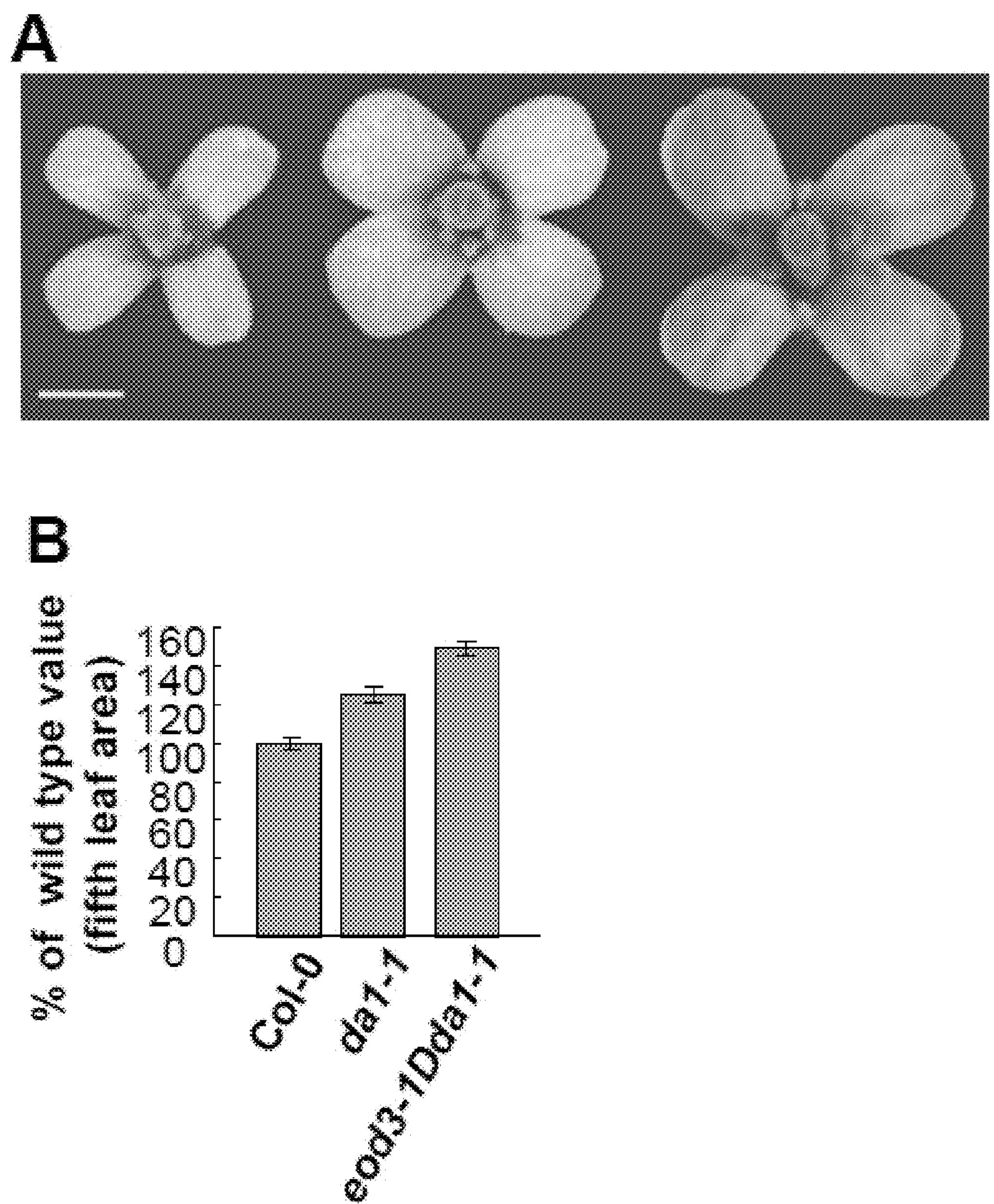
FIG. 10 shows eod3-1D enhances the organ size phenotype of da1-1. 10A shows flowers of wild type, da1-1 and eod3-1D da1-1. 10(*b*) shows area of the fifth leaves in wild type, da1-1 and eod3-1D da1-1. Values (B) are given as mean±SE relative to the respective wild-type values, set at 100%. Bar: A, 1 mm.

We previously characterized the *Arabidopsis* da1-1 mutant, which had larger seeds than wild type (Li et al., 2008). DA1, encoding a predicted ubiquitin receptor, sets final seed size by restricting cell proliferation (Li et al., 2008). To identify other components in the DA1 pathway or additional factors of seed size control, we initiated a T-DNA activation tagging screen in a da1-1 homozygous genetic background. Seeds produced from approximate 16,000 $T_1$ plants were screened for mutations affecting the seed size phenotype of da1-1. A dominant enhancer of da1-1 (eod3-1D), which enhanced the seed size phenotype of da1-1, was identified (FIGS. 1A and D). Seeds of the eod3-1D da1-1 double mutant were dramatically larger and heavier than those of the da1-1 mutant (FIGS. 1D and E). The embryo constitutes the major volume of a mature seed in *Arabidopsis*. The size of eod3-1D da1-1 embryos was substantially increased, compared with that of Col-0 and da1-1 embryos (FIG. 1B). The changes in seed size were also reflected in the size of seedlings (FIG. 1C). Cotyledons of eod3-1D da1-1 seedlings were significantly larger than those of Col-0 and da1-1 seedlings (FIGS. 1C and F). In addition, eod3-1D da1-1 double mutant had larger flowers and leaves than da1-1 (FIG. 10).

eod3-1D Sets Large Seeds

Figure 2:
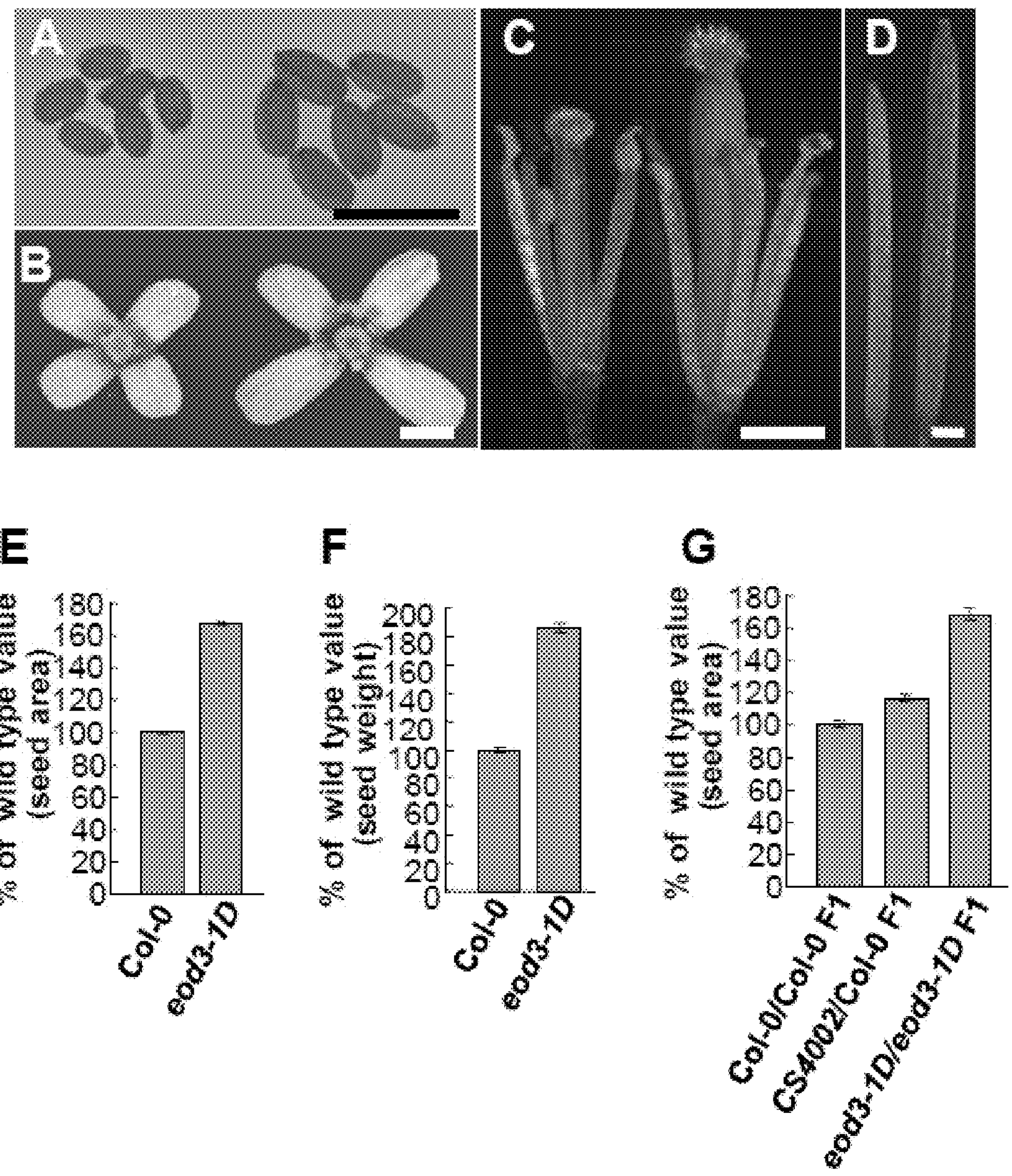
FIG. 2 shows seed and organ size in the eod3-1D mutant. 2(A-D) show seeds (A), flowers (B), stamens and carpels (C), and siliques (D) of wild type (left) and eod3-1D (right). 2(E) shows projective area of wild-type and eod3-1D seeds. 2(F) shows seed weight of wild type and eod3-1D. 2(G) shows projective area of Col-0×Col-0 $F_1$, CS4002×Col-0 $F_1$ and eod3-1D×eod3-1D $F_1$ seeds. Values (E-G) are given as mean±SE relative to the respective wild-type values, set at 100%. Bars: A, B, C, D, 1 mm.
Figure 11:
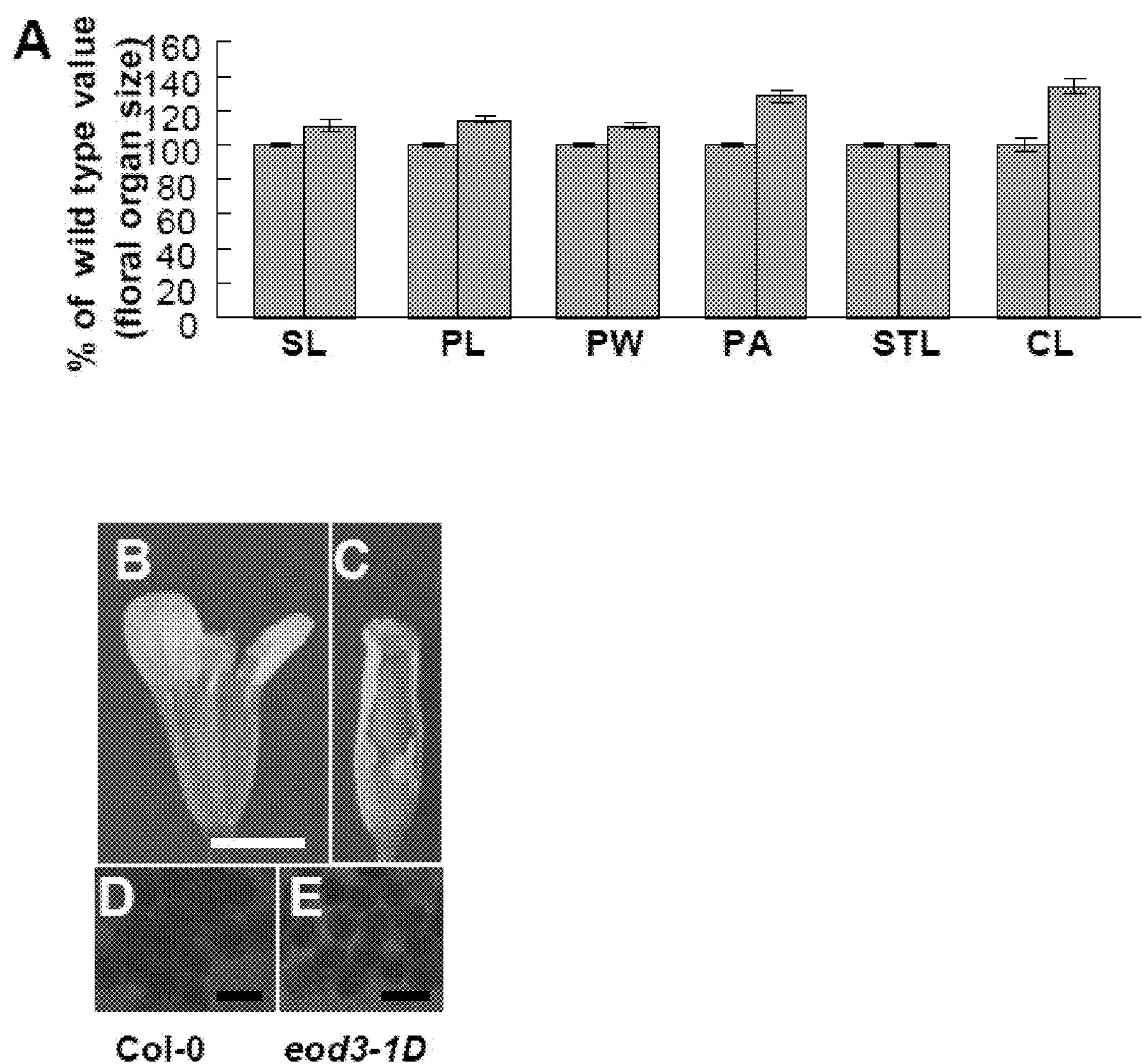
FIG. 11 shows organ size and reproductive development in eod3-1D. 11(A) shows sepal length (SL), petal length (PL), petal width (PW), petal area (PA), stamen length (STL) and carpel length (CL) of wild-type (left) and eod3-1D (right) flowers. 11(B and C) show the earliest-arising flowers on the primary inflorescences of wild type (B) and eod3-1D (C). 11(D and E) show pollens from the earliest-arising flowers were stained by using Alexander staining buffer. Values (A) are given as mean±SE relative to the respective wild-type values, set at 100%. Bars: B, C, 1 mm; D,E, 100 μm.

To determine whether the single eod3-1D mutant has the altered seed size, we identified the eod3-1D mutant among $F_2$ progeny derived from a cross between the eod3-1D da1-1 double mutant and wild type (Col-0). Seeds produced by eod3-1D were larger and heavier than the wild-type seeds (FIGS. 2A, E and F). In addition to the seed phenotype, eod3-1D plants showed larger flowers and leaves, thicker stems, and higher plants than wild type (FIG. 2B; FIG. 11A; Table 1). However, the number of rosette and cauline leaves was similar in wild type and eod3-1D, and the number of rosette and cauline branches in eod3-1D was also comparable with that in wild type (Table 1).

The eod3-1D mutation also caused defects in reproductive development. For example, eod3-1D mutant produced fewer elongated siliques than wild type (Table 1). First several flowers on the primary inflorescences of eod3-1D did not open normally (FIGS. 11B and C). Their stamens were much shorter than those of wild type (FIGS. 11B and C). The dehiscence of eod3-1D anthers was much delayed (FIG. 11C), but their pollens were functional (FIGS. 11D and E). The enlarged siliques were more frequently observed on the latest-arising flowers of old plants. In general, the enlarged siliques contained few seeds although the number of ovules per silique in eod3-1D was not reduced (Table 1). We observed that carpels of the late developing eod3-1D flowers were longer than those of wild-type flowers, whereas the length of stamens was similar to that of wild-type stamens (FIG. 2C; FIG. 11A), such that eod3-1D pollen is not able to directly reach stigmatic papillae; this could, in part, explain the decreased fertility. Fully elongated eod3-1D mutant siliques were longer and wider than wild-type siliques (FIG. 2D).

To determine whether the large seed size phenotype could result from allocation of extra resources to the few seeds produced, we hand-pollinated six flowers on primary inflorescences of wild-type plants, eod3-1D, and a male-sterile mutant (CS4002). For this set of experiments, flowers were pollinated with pollens of the same genotypes, with the exception of male-sterile plants for which wild-type pollens were used. Thus, each male-sterile plant produced only six siliques. The average seed size from male-sterile maternal plants was increased to 116% of that from wild-type maternal plants (FIG. 2G), indicating that seed size increased under condition of reduced fertility. By contrast, the average seed size from the eod3-1D mutant were approximate 170% of that from wild type (FIG. 2G), indicating that the effect of eod3-1D on seed size is not primarily due to its effect on fertility.

EOD3 Encodes a Cytochrome P450 Monooxygenase

Figure 3:
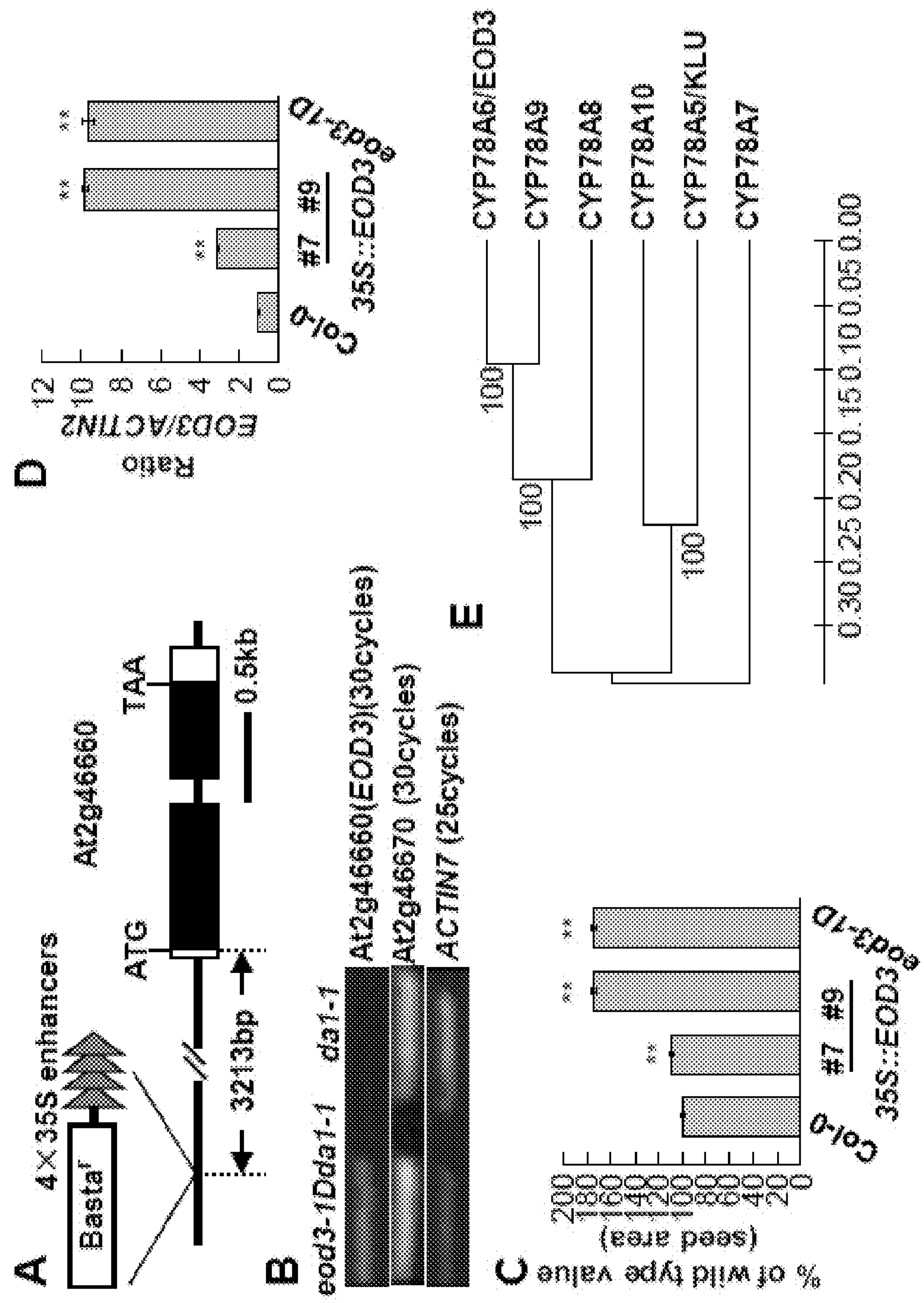
FIG. 3 shows the cloning of the EOD3 gene. 3(A) shows the structure of T-DNA insertion in the eod3-1D mutant. 3(B) shows expression levels of At2g46660 (EOD3) and At2g46670 in da1-1 and eod3-1D da1-1 seedlings. 3(C) shows projective area of wild-type, 35S::EOD3#7, 35S::EOD3#9 and eod3-1D seeds. 3(D) shows expression levels of EOD3 in wild-type, 35S::EOD3#7, 35S::EOD3#9 and eod3-1D seedlings. 3(E) shows phylogenetic tree of the CYP78A family members in *Arabidopsis thaliana*. Values (C and D) are given as mean±SE relative to the wild-type value, set at 100%. **, P<0.01 compared with the wild type (Student's t-test).

To test whether this T-DNA insertion might cause the eod3-1D phenotypes, we analyzed the genetic linkage of the mutant phenotype with Basta resistance, which is conferred by the selectable marker of the activation tagging vector (Fan et al., 2009). All 101 plants with eod3-1D da1-1 phenotypes in $T_2$ population were resistant, whereas the 36 plants with da1-1 phenotypes were sensitive, indicating that the insertion is responsible for the eod3-1D mutation. To identify the EOD3 gene, the DNA flanking the T-DNA insertion was isolated by thermal asymmetric interlaced PCR (Liu et al., 1995). Sequence analysis indicated that the insertion was in an intergenic region on chromosome II between the genes At2g46660 and At2g46670. The T-DNA had inserted approximately 3.2 kb upstream of the At2g46660 gene and about 6.5 kb downstream of the At2g46670 gene (FIG. 3A). The mRNA levels of these two genes were determined by reverse transcription-polymerase chain reaction (RT-PCR). Expression levels of the At2g46670 gene were similar in da1-1 and eod3-1D da1-1 plants (FIG. 3B), indicating that At2g46670 was unlikely to be the EOD3 gene. The mRNA of At2g46660 accumulated at a higher level in eod3-1D da1-1 than in da1-1 (FIG. 3B), strongly indicating that At2g46660 is likely to be the EOD3 gene. To demonstrate that this gene corresponded to EOD3, we overexpressed the At2g46660 gene in Col-0 wild-type plants and isolated 41 transgenic plants. Most transgenic plants showed large seeds and increased plant height (FIGS. 3C and D; FIG. 12A), as had been seen in the eod3-1D single mutant, confirming At2g46660 is the EOD3 gene. Importantly, the 35S::EOD3#7 transgenic plants exhibited normal growth and fertility, but produced significantly large seeds compared with wild type (FIG. 3 C; FIGS. 12B and C).

The EOD3 gene encodes the putative cytochrome P450 monooxygenase CYP78A6, one of six members of the CYP78A family in *Arabidopsis*. Genes in the CYP78A class belong to the group A cytochrome P450 in plants and seem to perform plant-specific functions (Zondlo and Irish, 1999; Ito and Meyerowitz, 2000; Anastasiou et al., 2007). EOD3/CYP78A6 exhibits the highest similarity to *Arabidopsis* CYP78A9 (FIG. 3E) (Ito and Meyerowitz, 2000).

EOD3/CYP78A6 Acts Redundantly with CYP78A9 to Control Seed Size

Figure 4:
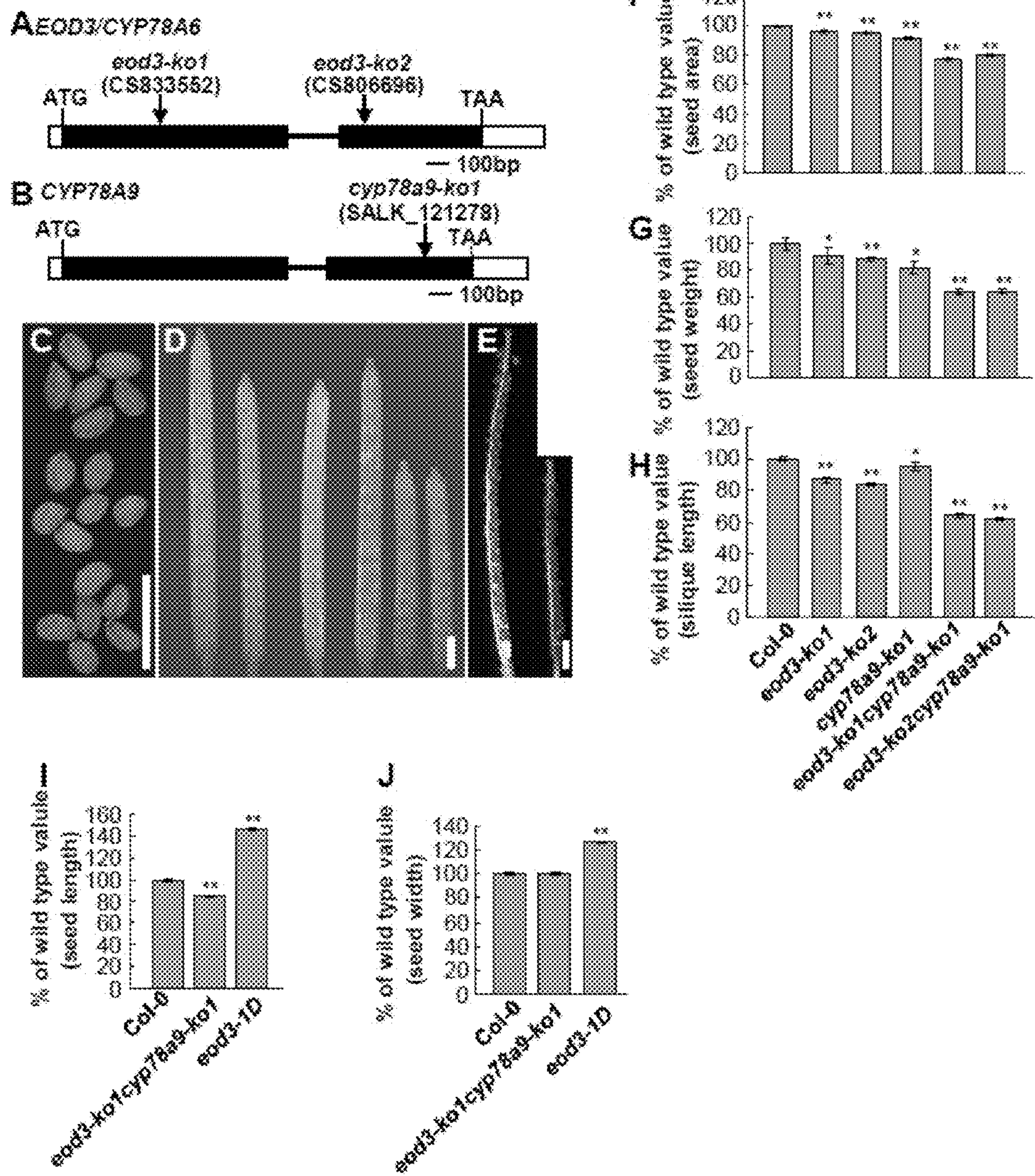
FIG. 4 shows that EOD3 acts redundantly with CYP78A9 to influence seed size. 4(A) shows EOD3 gene structure. The start codon (ATG) and the stop codon (TAA) are indicated. Closed boxes indicate the coding sequence, and the line between boxes indicates intron. T-DNA insertion sites (eod3-ko1 and eod3-ko2) in the EOD3 gene were shown. 4(B) shows CYP78A9 gene structure. The start codon (ATG) and the stop codon (TAA) are indicated. Closed boxes indicate the coding sequence, and the line between boxes indicates intron. The T-DNA insertion site (cyp78a9-ko1) in the CYP78A9 gene was shown. 4(C) shows seeds from wild-type, eod3-ko1 cyp78a9-ko1 and eod3-ko2 cyp78a9-ko1 plants (from top to bottom). 4(D) Siliques from wild-type, eod3-ko1, eod3-ko2, cyp78a9-ko1, eod3-ko1 cyp78a9-ko1 and eod3-ko2 cyp78a9-ko1 plants (from left to right). 4(E) shows opened siliques from wild-type and eod3-ko1 cyp78a9-ko1 plants (from left to right). 4(F) shows projective area of wild-type, eod3-ko1, eod3-ko2, cyp78a9-ko1, eod3-ko1 cyp78a9-ko1 and eod3-ko2 cyp78a9-ko1 seeds. 4(G) shows seed weight of wild type, eod3-ko1, eod3-ko2, cyp78a9-ko1, eod3-ko1 cyp78a9-ko1 and eod3-ko2 cyp78a9-ko1. 4(H) shows silique length of wild type, eod3-ko1, eod3-ko2, cyp78a9-ko1, eod3-ko1 cyp78a9-ko1 and eod3-ko2 cyp78a9-ko1. 4(I and J) show seed length (I) and seed width (J) of wild type, eod3-ko1, cyp78a9-ko1 and eod3-ko1 cyp78a9-ko1. Values (F-J) are given as mean±SE relative to the respective wild-type values, set at 100%. **, P<0.01 and *, P<0.05 compared with the wild type (Student's t-test). Bars: C, D, E, 1 mm.
Figure 13:
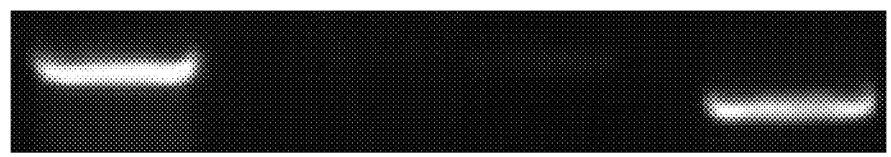
FIG. 13 shows identification of eod3-ko1, eod3-ko2 and cyp78a9-ko1 mutants. 13(A-C) show PCR identification of T-DNA insertions in eod3-ko1 (A), eod3-ko2 (B), cyp78a9-ko1 (C) mutants with T-DNA specific primers and flanking primers.
Figure 13:
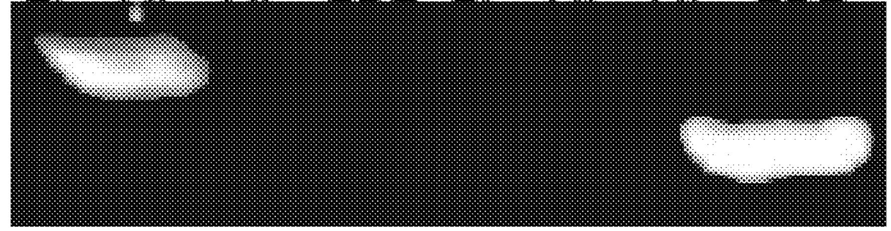
Figure 13:
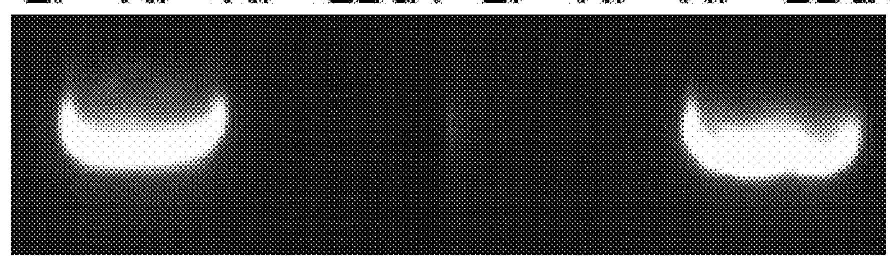

In order to further understand the function of EOD3, we isolated T-DNA inserted loss-of-function mutants for EOD3/CYP78A6 and CYP78A9, the most closely related family member. eod3-ko1 and eod3-ko2 were identified with T-DNA insertions in the first and second exons of the EOD3/CYP78A6 gene, respectively (FIG. 4A). cyp78a9-ko1 had T-DNA insertion in the second exon of CYP78A9 (FIG. 4B). The T-DNA insertion sites were confirmed by PCR using T-DNA specific and flanking primers and sequencing PCR products (FIG. 13). The eod3-ko1, eod3-ko2 and cyp78a9-ko1 mutants were further backcrossed into Col-0 for three times.

Seeds from eod3-ko1, eod3-ko2 and cyp78a9-ko1 mutants were smaller and lighter than seeds from wild-type plants (FIGS. 4F and G). Silique length in eod3-ko1, eod3-ko2 and cyp78a9-ko1 was reduced, compared with that in wild type (FIGS. 4D and H). By contrast, the size of leaves and petals, stem thickness and plant height in eod3-ko1 and cyp78a9-ko1 were comparable with those in wild type (Table 1). In addition, the number of rosette and cauline leaves, rosette and cauline branches, siliques per plant and ovules per silique in eod3-ko1 and cyp78a9-ko1 was similar to that in wild type (Table 1). As EOD3/CYP78A6 shows the highest similarity to the *Arabidopsis* CYP78A9, we postulated that EOD3 may act redundantly with CYP78A9 to control seed size. To test this, we generated the double knockout mutants, eod3-ko1 cyp78a9-ko1 and eod3-ko2 cyp78a9-ko1. The seed size and weight phenotype of eod3-ko mutants was synergistically enhanced by the disruption of CYP78A9 (FIGS. 4F and G), indicating that EOD3 functions redundantly with CYP78A9 to control seed growth. The eod3-ko cyp78a9-ko mutations also caused a significant change in seed shape (FIG. 4C). eod3-ko cyp78a9-ko seeds were shorter than wild-type seeds, whereas seed width was comparable with that of wild type (FIGS. 4C, I and J), indicating that eod3-ko cyp78a9-ko seeds are more round in shape than wild type. eod3-ko cyp78a9-ko produced fewer siliques per plant than wild type (Table 1). The length of siliques in eod3-ko cyp78a9-ko was dramatically reduced, compared with their parental lines (FIGS. 4D and H). Surprisingly, the number of ovules per silique in eod3-ko1 cyp78a9-ko1 was similar to that in wild type, resulting in a higher density of seeds within siliques (FIG. 4E; Table 1). In addition, the primary inflorescence stem of eod3-ko1 cyp78a9-ko1 was shorter than that of wild type, and the size of petals and leaves was slightly reduced compared with wild type (Table 1). However, the number of leaves and branches in eod3-ko1 cyp78a9-ko1 was comparable with that observed in wild type (Table 1).

EOD3 Acts Maternally to Influence Seed Size

Figure 14:
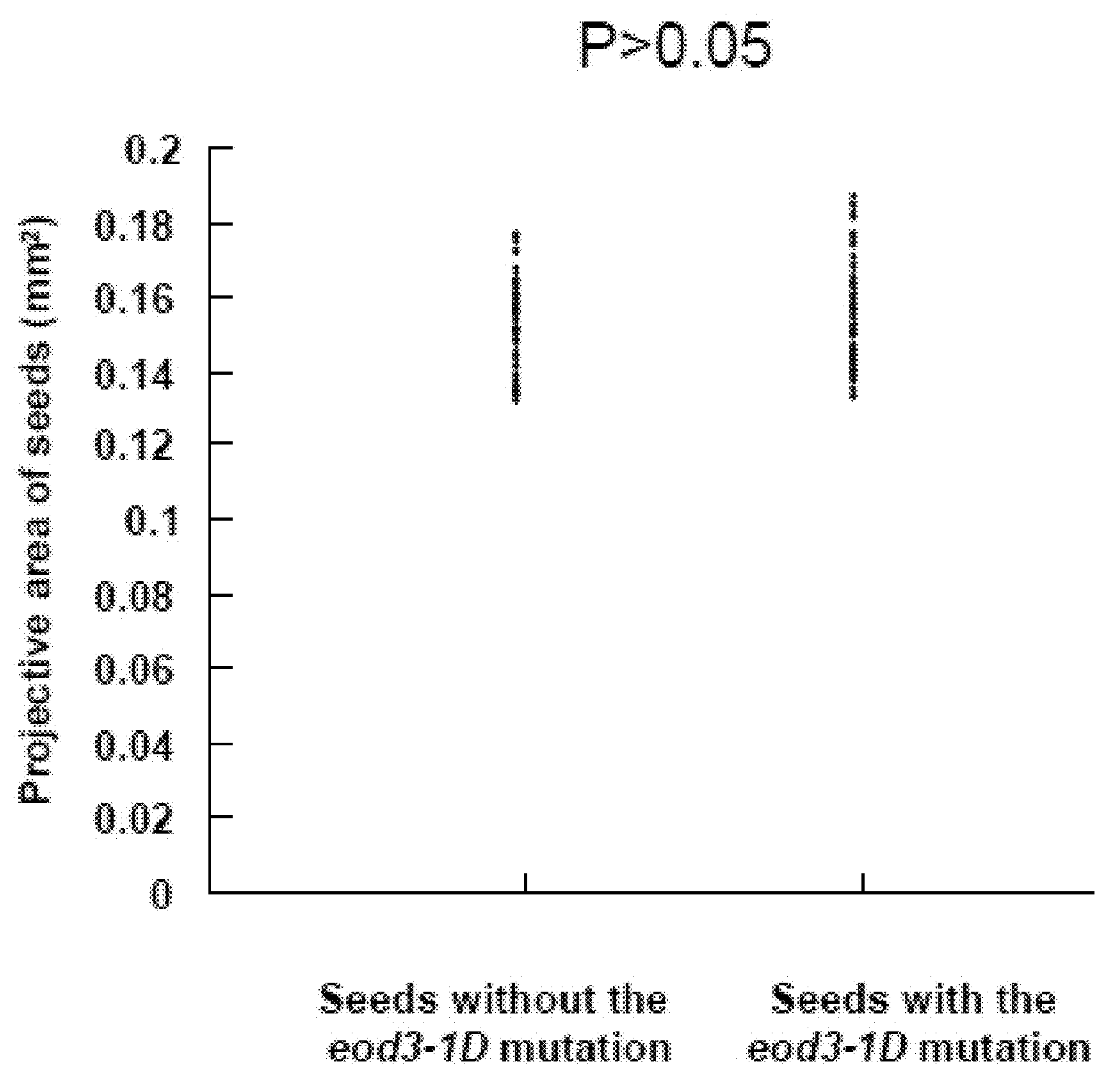
FIG. 14 shows EOD3 acts maternally to influence seed size. Projective area of individual seeds from eod3-1D/+ plants fertilized with wild-type pollen was measured. These seeds were further genotyped for the eod3-1D mutation. The data shows that the eod3-1D mutation is not associated with variation in the size of these seeds ($P>0.05$, Student's t-test).
Figure 15:
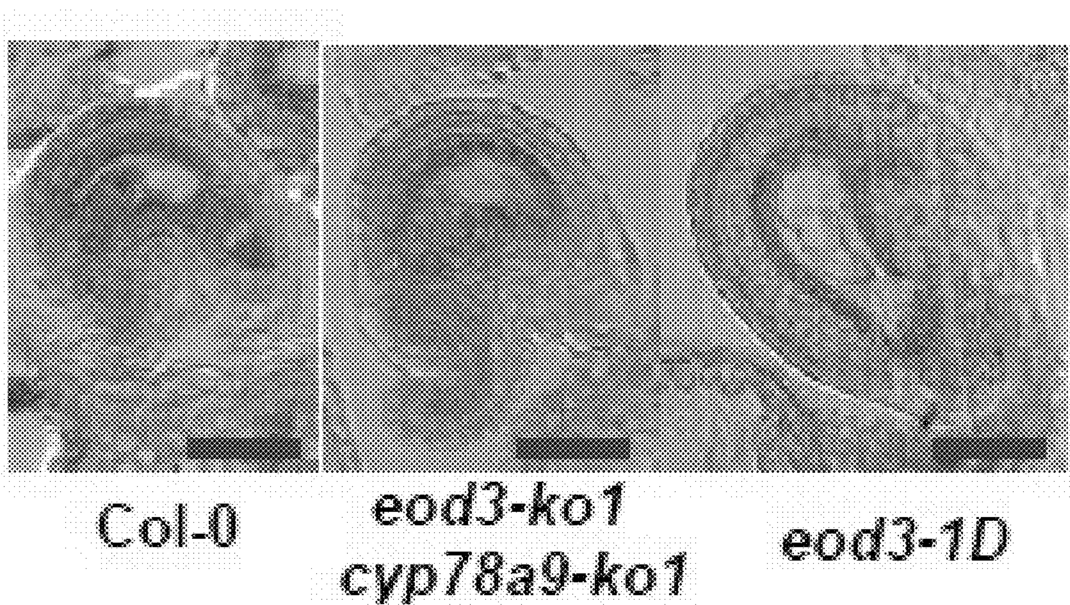
FIG. 15 shows mature ovules from Col-0, eod3-ko1 cyp78a9-ko1 and eod3-1D plants. Bars: A, B, C, 50 μm.
Figure 16:
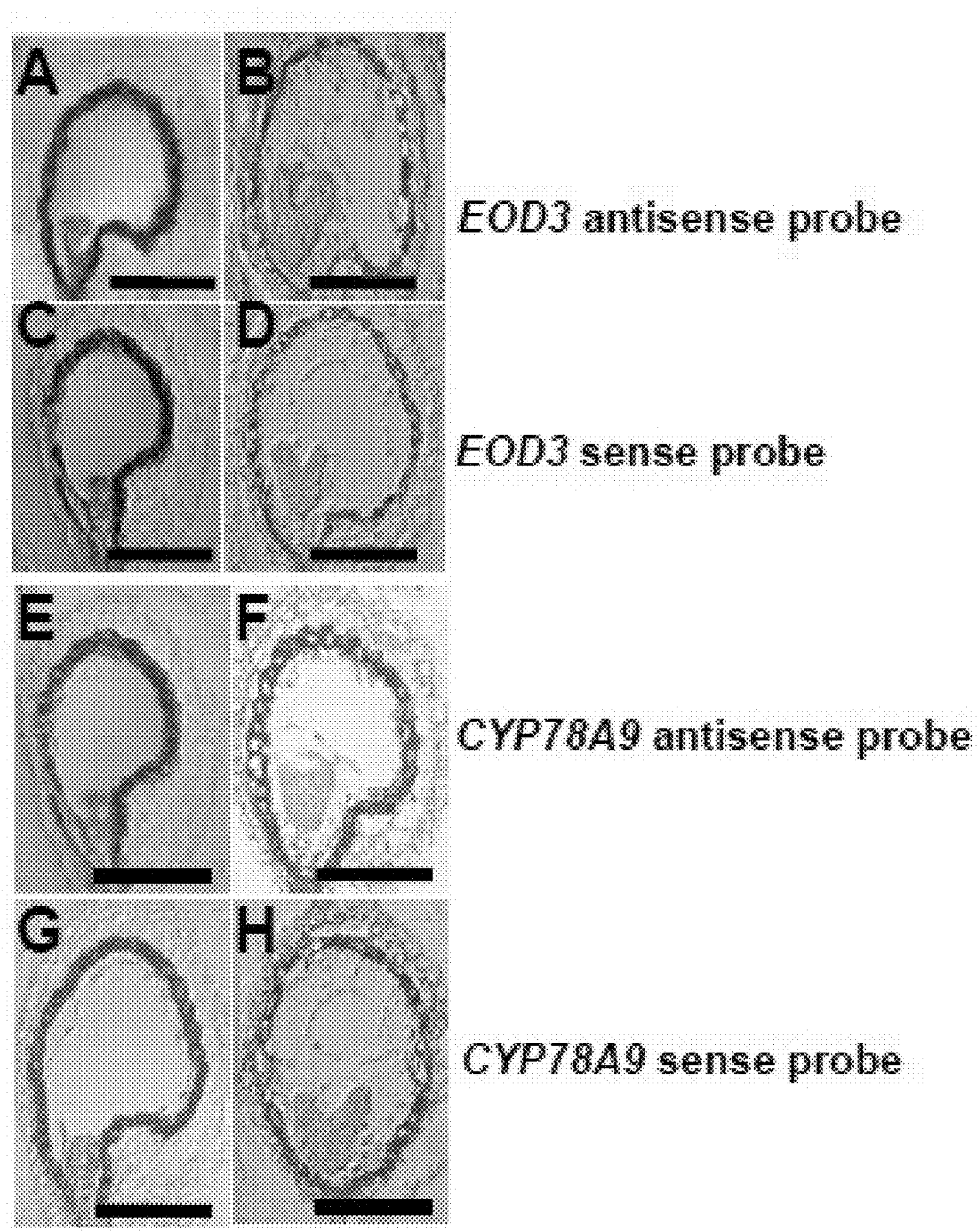
FIG. 16 shows EOD3 and CYP78A9 expression in developing seeds. 16(A and B) show results of in situ hybridization with EOD3 antisense probe. 16(C and D) show results of in situ hybridization with EOD3 sense probe. 16(E and F) show results of in situ hybridization with CYP78A9 antisense probe. 16(G and H) show results of in situ hybridization with CYP78A9 sense probe. Bars: A, B, C, D, E, F, G, H, 50 μm.

To obtain clues about the genetic control of seed size, we asked whether EOD3 functions maternally or zygotically. Reciprocal cross experiments between wild type and eod3-ko1 cyp78a9-ko1 were performed. The effect of eod3-ko1 cyp78a9-ko1 on seed size was observed only when maternal plants are eod3-ko1 cyp78a9-ko1 mutant. Seeds produced by an eod3-ko1 cyp78a9-ko1 mother, regardless of the genotype of the pollen donor, were consistently smaller than those produced by maternal wild-type plants, and eod3-ko1 cyp78a9-ko1 mutant pollen in a wild-type mother produced seeds with wild-type size (FIG. 5A). This indicates that eod3-ko1 cyp78a9-ko1 can act maternally to control seed size. We further did reciprocal cross experiments between wild type and eod3-1D. Pollinating wild-type plants with eod3-1D pollen leads to the development of eod3-1D/+ embryos within a wild-type seed coat. However, the size of the resulting seeds was comparable with that of self-pollinated wild type seeds (FIG. 5B). In contrast, we could not observed the wild-type sized seeds from eod3-1D/+ plants fertilized with wild-type pollen, although half of them contained wild-type embryos. We further measured the size of individual seeds from eod3-1D/+ plants fertilized with wild-type pollen and genotyped the eod3-1D mutation. Our results show that the eod3-1D mutation is not associated with variation in the size of these seeds (FIG. 14). Together, these analyses indicate that the embryo and endosperm genotype for EOD3 do not influence seed size, and EOD3 is required in the sporophytic tissue of the mother plant to promote seed growth.

eod3-ko1 cyp78a9-ko1 Reduces Cell Expansion in the Integuments of Developing Seeds The reciprocal crosses indicate that EOD3 acts maternally to influence seed growth. The integuments surrounding the ovule form the seed coat after fertilization, which may physically restrict seed growth. The integument size of ovules is known to influence seed size (Garcia et al., 2005; Schruff et al., 2006). We therefore asked whether EOD3 functions through the maternal integument to affect seed size. To test this, we characterized mature ovules from wild type and eod3-ko1 cyp78a9-ko1 at 2 days after emasculation. Surprisingly, the size of eod3-ko1 cyp78a9-ko1 ovules was not significantly altered, compared with that of wild-type ovules (FIG. 6A and FIG. 15). We further investigated the outer integument length of wild-type and eod3-ko1 cyp78a9-ko1 seeds at specific times after pollination. The size of wild-type and eod3-ko1 cyp78a9-ko1 outer integuments showed a significant difference at 2 days after pollination (DAP) and subsequent time points (FIG. 6B). Previous study showed that the integument of a developing seed could completely stop cell division at 4 d after pollination (Garcia et al., 2005). To assess the contribution of cell proliferation and cell expansion in the integuments of developing seeds to eod3-ko1 cyp78a9-ko1, we measured outer integument cell number and cell size at 6 DAP. Outer integument cell number in eod3-ko1 cyp78a9-ko1 was similar to that in wild type (FIG. 6C), whereas cells in eod3-ko1 cyp78a9-ko1 outer integuments were significantly smaller than those in wild-type outer integuments (FIG. 6D). These results indicate that eod3-ko1 cyp78a9-ko1 restricts cell expansion in the integuments of developing seeds.

eod3-1D Promotes Both Cell Proliferation and Cell Expansion in the Integuments

As the gain-of-function eod3-1D mutant had large seeds, we further asked whether eod3-1D mutant affects the integument size of ovules and developing seeds. The size of eod3-1D ovules was significantly larger than wild-type ovules (FIG. 6A and FIG. S6). eod3-1D also had dramatically larger outer integuments than wild type during the whole process of seed development (FIG. 6B). We further investigated outer integument cell number and cell size of developing seeds at 6 DAP and found that eod3-1D had more and larger outer integument cells than wild type (FIGS. 6C and D).

Effects of eod3-ko1 cyp78a9-ko1 and eod3-1D Mutations on Embryo Development eod3-ko1 cyp78a9-ko1 and eod3-1D had smaller and larger seed coats, respectively. The maternal integument or seed coat acts as a physical constraint on embryo growth. We therefore investigated whether eod3-ko1 cyp78a9-ko1 and eod3-1D integuments could indirectly influence embryo development. To test this, we manually pollinated wild-type, eod3-ko1 cyp78a9-ko1 and eod3-1D plants with their own pollen grains and examined developing embryos at specific times after pollination. In the siliques of wild-type plants, the majority of embryos reached the globular stage at 2DAP, the heart and torpedo stages at 4DAP, the bent-cotyledon stage at 6 DAP, and the stage of the fully filled seed cavity from 10 DAP onward (Table 2). Developmental progresses of eod3-ko1 cyp78a9-ko1 embryos were almost similar to those of wild type. However, morphological development of eod3-1D embryos was slightly slower than wild type at 4 DAP. At 6 DAP, most embryos reached the bent-cotyledon stage, as seen in wild-type plants (Table 2). This phenomenon of embryo development has also been observed in other *Arabidopsis* mutants (Schruff et al., 2006; Ohto et al., 2009; Zhou et al., 2009). Interestingly, the majority of wild-type embryos fully filled the seed cavity at 12 DAP, while most eod3-1D embryos completely filled the seed cavity at 14 DAP. It is plausible that eod3-1D forms a larger seed cavity than wild type; therefore eod3-1D embryos need to grow for a longer period of time to fill the large seed cavity than wild-type embryos.

Figure 5:
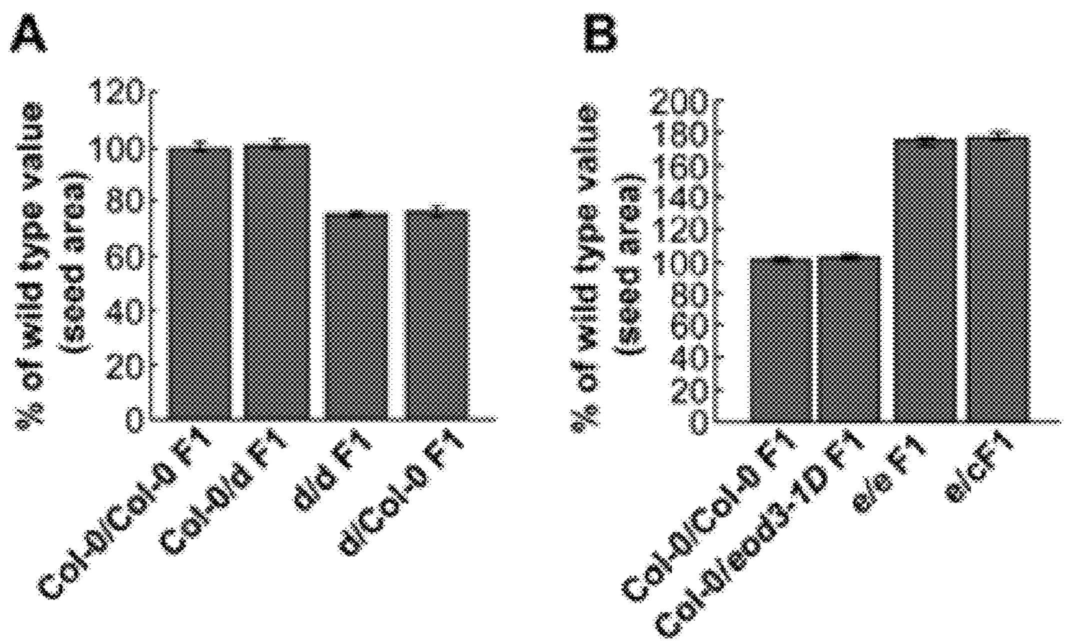
FIG. 5 shows EOD3 acts maternally to control seed size. 5(A) shows projective area of Col-0×Col-0 $F_1$, Col-0×eod3-ko1 cyp78a9-ko1(d) $F_1$, eod3-ko1 cyp78a9-ko1 (d)×eod3-ko1 cyp78a9-ko1 (d) $F_1$ and eod3-ko1 cyp78a9-ko1(d)×Col-0 $F_1$ seeds. 5(B) shows projective area of Col-0×Col-0 $F_1$, Col-0×eod3-1D $F_1$, eod3-1D/+×eod3-1D/+(e/e) $F_1$, eod3-1D/+×Col-0 (e/c) $F_1$ seeds. Values (A and B) are given as mean±SE relative to the respective wild-type values, set at 100%.

Effects of eod3-ko1 cyp78a9-ko1 and eod3-1D Mutations on Embryo Cell Number and Cell Size We isolated and visualized embryos from mature eod3-ko1 cyp78a9-ko1 and eod3-1D seeds. eod3-ko1 cyp78a9-ko1 embryos were significantly smaller than those of wild type, whereas eod3-1D produced large mature embryos compared with wild type (FIG. 7A). The average cotyledon area of eod3-ko1 cyp78a9-ko1 and eod3-1D embryos was about 72% and 196% that of wild-type embryos, respectively (FIG. 7B). The size of embryos is determined by both cell number and cell size. We measured palisade cells in the central regions of wild-type, eod3-ko1 cyp78a9-ko1 and eod3-1D cotyledons to learn which parameter is affected. The average size of eod3-ko1 cyp78a9-ko1 cotyledon cells was 79% that of wild-type cotyledon cells, while the average size of eod3-1D cotyledon cells was 1.36-fold that of the wild-type cotyledon cells (FIG. 7C). The magnitude of the changes in the areas of eod3-ko1 cyp78a9-ko1 and wild-type cotyledons (0.72 times) closely parallels the differences in the areas of cotyledon cells (0.79 times), indicating that eod3-ko1 cyp78a9-ko1 mainly affects embryo cell expansion. Given differences in the areas of eod3-1D and wild-type cotyledons (1.96 times) and cells (1.36 times), we conclude that eod3-1D had approximate 1.44 times more cells than wild type (1.96/1.36=1.44). These results indicate that eod3-ko1 cyp78a9-ko1 formed small embryos as a result of the reduced embryo cell expansion, and eod3-1D had large embryos due to increases in both embryo cell proliferation and cell expansion. Thus, EOD3 could act maternally to influence embryo cell proliferation and cell expansion because EOD3 is solely required in the sporophytic tissue of the mother plant to control seed growth (FIG. 5).

Expression Pattern of EOD3/CYP78A6

Figure 8:
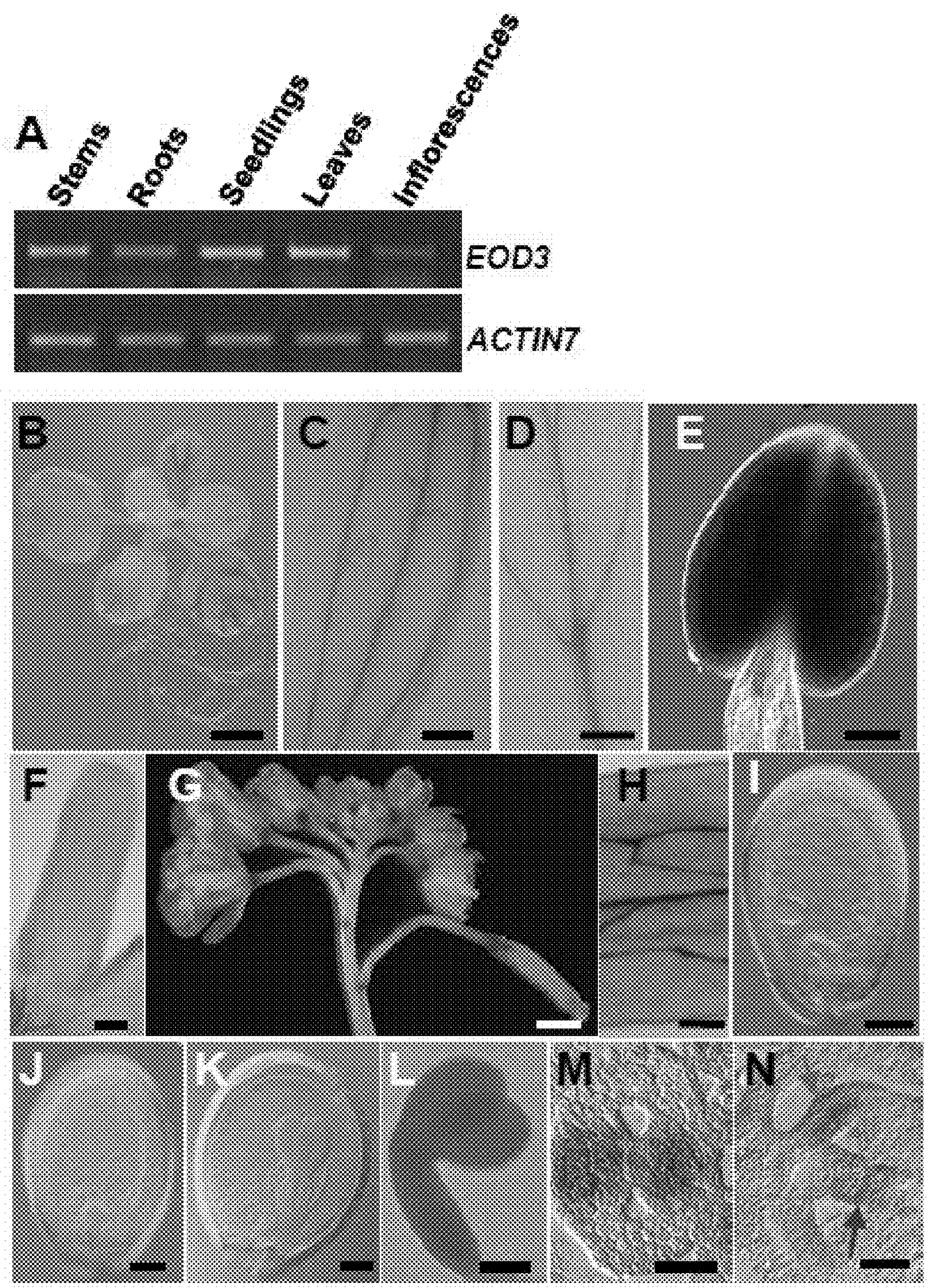
FIG. 8 shows the expression pattern of EOD3. 8(A) shows RT-PCR analysis of the EOD3 gene expression. Total RNA was isolated from stems, roots, 10-d-old seedlings, leaves and inflorescences. 8(B-L) show EOD3 expression activity monitored by pEOD3::GUS transgene expression. Three GUS-expressing lines were observed and all showed a similar pattern, although they differed slightly in the intensity of the staining. Histochemical analysis of GUS activity in a 14-d-old seedling (B), a sepal (C), a petal (D), a stamen (E), a carpel (F), an inflorescence (G), the valve of a silique (H) and embryos (I-L). No GUS activity was detected in developing seeds. 8(M and N) show results of in situ hybridization with EOD3 antisense probe. Cross-section of the carpel of a stage 8 flower (M). Cross-section of the carpel of a stage 12 flower (N). The blue arrow indicates the central region of the septum, and the red arrow shows the funiculus. Bars: B, 2 mm; G, 1 mm; C, E, F, I, J, K, L, 100 μm; D, M, N, 50 μm. H, 200 μm.
Figure 17:
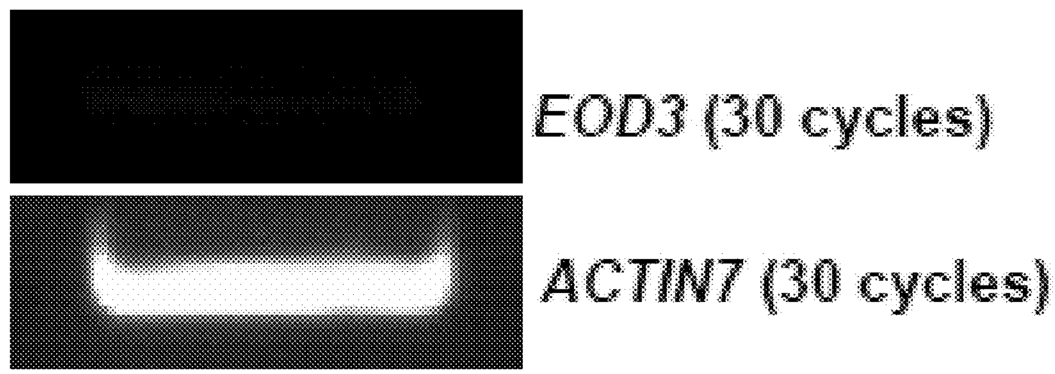
FIG. 17 shows expression of EOD3 in developing seeds using RT-PCR analysis of the EOD3 gene expression. Total RNA was isolated from developing seeds within elongated siliques.

To examine the expression pattern of EOD3, RT-PCR were performed with total RNA from various tissues with EOD3-specific primers, including roots, stems, leaves, seedlings and inflorescences. EOD3 mRNA can be detected in all plant organs tested (FIG. 8A). To monitor EOD3 expression pattern during development, the pEOD3::GUS vector was constructed and transformed to wild-type plants. Tissues at different development stages were stained with GUS solution. In 14-d-old seedlings, GUS activity was detected in leaves. Relatively high GUS activity was observed in old leaves than in young ones (FIG. 8B). In flowers, GUS expression was detected in sepals, petals, stamens and carpels (FIG. 8C-H). Surprisingly, there was no EOD3 expression during the development of seeds (FIG. 8I-L; FIG. 17). We further performed in situ hybridization experiments to investigate expression of EOD3. EOD3 accumulated in the medial gynoecial domains at stage 8 (FIG. 8M). During stage 12, the EOD3 transcript was found within the central region of the septum (FIG. 8N). Expression was also seen in the funiculus (FIG. 8N). However, EOD3 expression was not detected in integuments, embryos, and endosperms during seed development (FIG. 16A-D), consistent with the GUS staining results. Similarly, CYP78A9 was also not observed in developing seeds (FIG. 16E-H). These analyses indicate that EOD3 is a temporally and spatially expressed gene.

Figure 9:
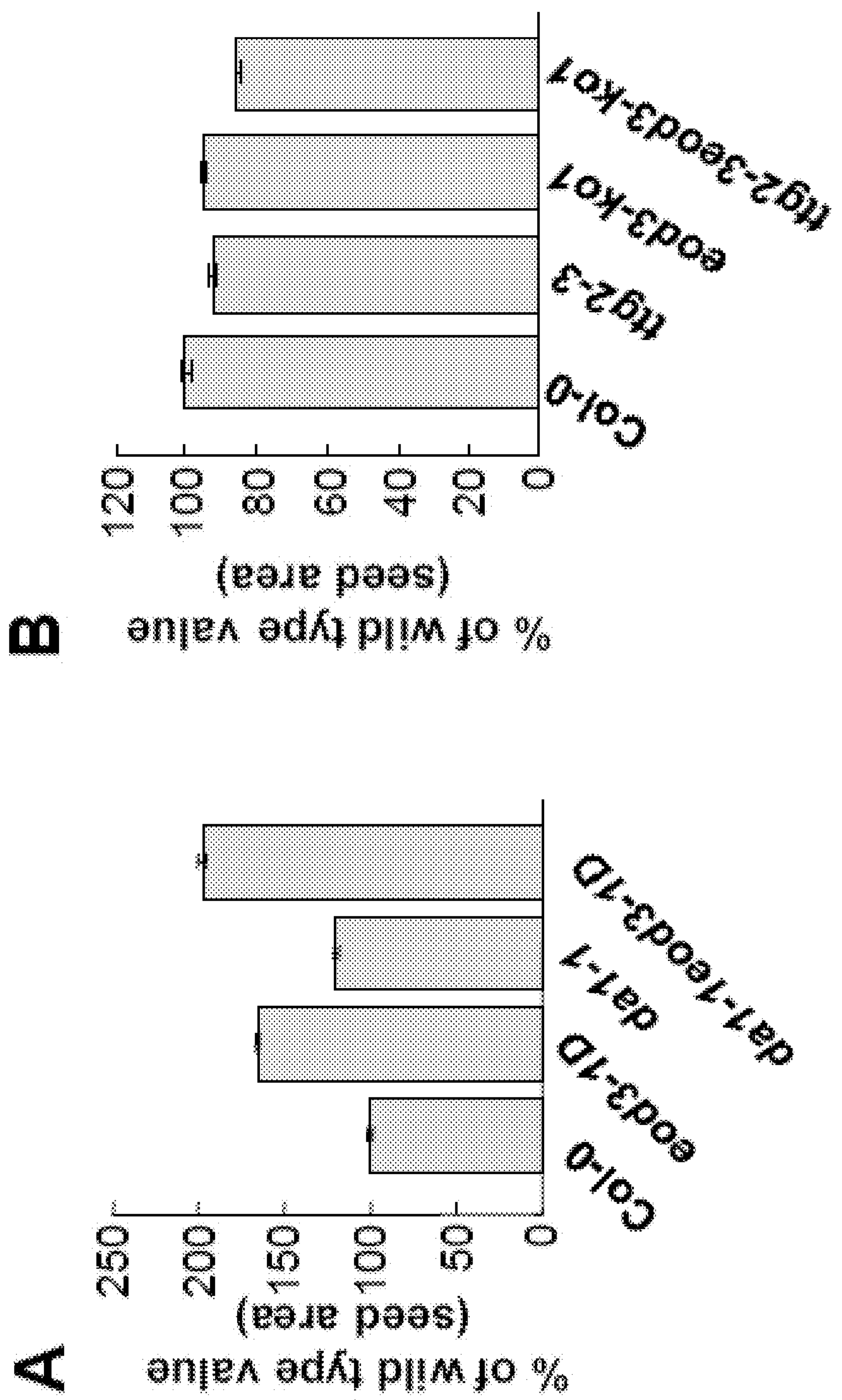
FIG. 9 shows genetic interactions of eod3 with da1-1 and ttg2-3 mutants. 9(A) shows the projective area of wild-type, eod3-1D, da1-1 and da1-1 eod3-1D seeds. 9(B) shows projective area of wild-type, ttg2-3, eod3-ko1 and ttg2-3 eod3-ko1 seeds. Values (A-B) are given as mean±SE relative to the respective wild-type values, set at 100%.

EOD3 May Function Independently of DA1 and TTG2 to Influence Seed Size da1-1 mutant had large seeds due to the increased cell proliferation in maternal integuments (Li et al., 2008), while eod3-ko mutants produced small seeds as a result of the reduced cell expansion in the integuments after fertilization, providing indication that EOD3 and DA1 might function in different pathways. However, the gain-of-function eod3-1D mutant promotes both cell proliferation and cell expansion in the integuments. We therefore asked whether there are any genetic interactions between eod3-1D and da1-1. To test this, we measured the size of seeds in wild-type, da1-1, eod3-1D and eod3-1D da1-1 plants. The genetic interaction between eod3-1D and da1-1 was essentially additive for seed size, compared with their parental lines (FIG. 9A), further indicating that EOD3 might function independently of DA1 to control seed size.

The TTG2 gene acts maternally to promote cell expansion in the integuments. ttg2 mutants produced small seeds as a result of the reduced cell elongation in the integuments (Garcia et al., 2005). To determine the genetic interaction between EOD3 and TTG2, we generated ttg2-3 eod3-ko1 double mutant. The genetic interaction between eod3-ko1 and ttg2-3 was additive for seed size, compared with their parental lines (FIG. 9B), providing indication that EOD3 functions to control seed growth separately from TTG2.

EOD3 Promotes Seed Growth by Increasing Maternal Integument Size

In this study, we identified the role of EOD3/CYP78A6 in seed size control. eod3-1D gain-of-function mutant formed larger seeds, while eod3-ko loss-of-function mutants exhibited smaller seeds. In addition, mutations in its most closely related family member CYP78A9 synergistically enhanced the seed size phenotype of eod3-ko mutants (FIGS. 4C, F and G), indicating that EOD3/CYP78A6 acts redundantly with CYP78A9 to influence seed growth. However, the eod3-1D mutant exhibited partial sterility although eod3-ko mutants had normal fertility. The tradeoff between seed number and size in many species (Harper et al., 1970), including *Arabidopsis* (Alonso-Blanco et al., 1999), has been observed. Our results show that the effect of eod3-1D on seed size is not primarily due to its effect on fertility. Similarly, recent studies show that ap2 and arf2 mutations increase seed size partly because of reduced fertility but also through a separate maternal effect on seed growth (Jofuku et al., 2005; Ohto et al., 2005; Schruff et al., 2006).

Reciprocal cross experiments show that EOD3 acts maternally to affect seed growth. The integuments surrounding the ovule are maternal tissues and form the seed coat after fertilization. Altered maternal integument size such as those seen in arf2, da1-1 and klu ovules is known to contribute to changes in seed size (Schruff et al., 2006; Li et al., 2008; Adamski et al., 2009). However, the size of mature eod3-ko1 cyp78a9-ko1 ovules was similar to that of wild-type ovules, indicating that the size difference between the wild-type and eod3-ko1 cyp78a9-ko1 seeds happens after fertilization. Consistent with this idea, eod3-ko1 cyp78a9-ko1 integuments were smaller than wild-type integuments from 2DAP onward (FIG. 6B). By contrast, eod3-1D formed large integuments in mature ovules and developing seeds (FIGS. 6A and B). Thus, a general theme emerging from these studies is that the control of maternal integument size is one of critical mechanisms for determining final seed size.

Figure 6:
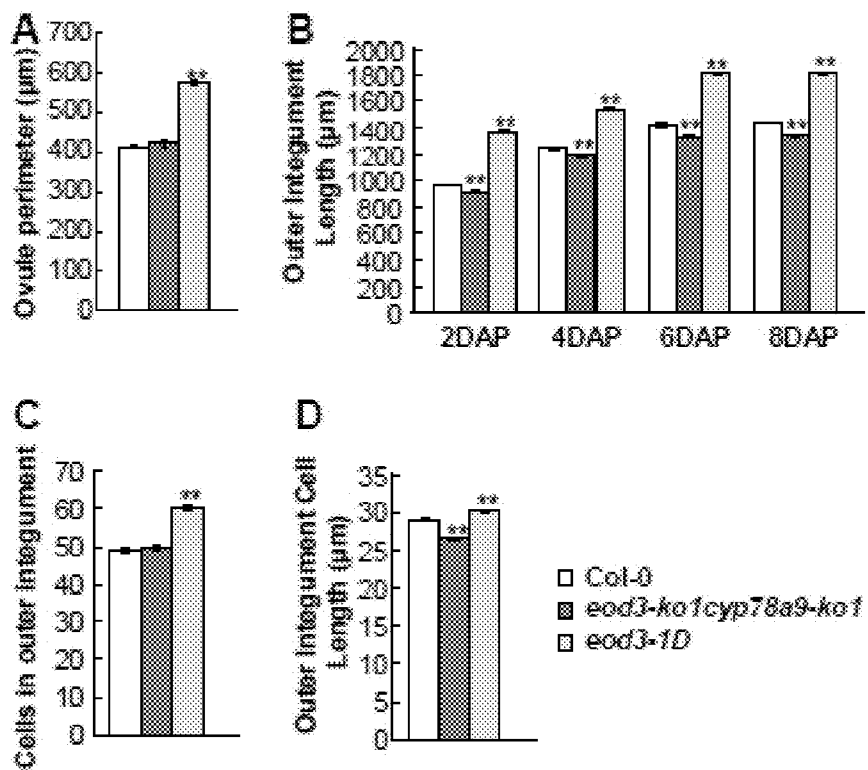
FIG. 6 shows cell size and cell number in the integuments of wild-type, eod3-ko1 cyp78a9-ko1 and eod3-1D developing seeds. 6(A) shows mature ovule perimeter. 6(B) shows the outer integument length at specific times after pollination, as measured from the insertion point at the funiculus to the tip at the micropyle. 6(C) shows the number of cells in the outer integument at 6DAP. 6(D) shows the average length of cells in the outer integument at 6DAP calculated from the outer integument length and cell number for individual seeds. Values (A-D) are given as mean±SE. **, P<0.01 compared with the wild type (Student's t-test).
Figure 7:
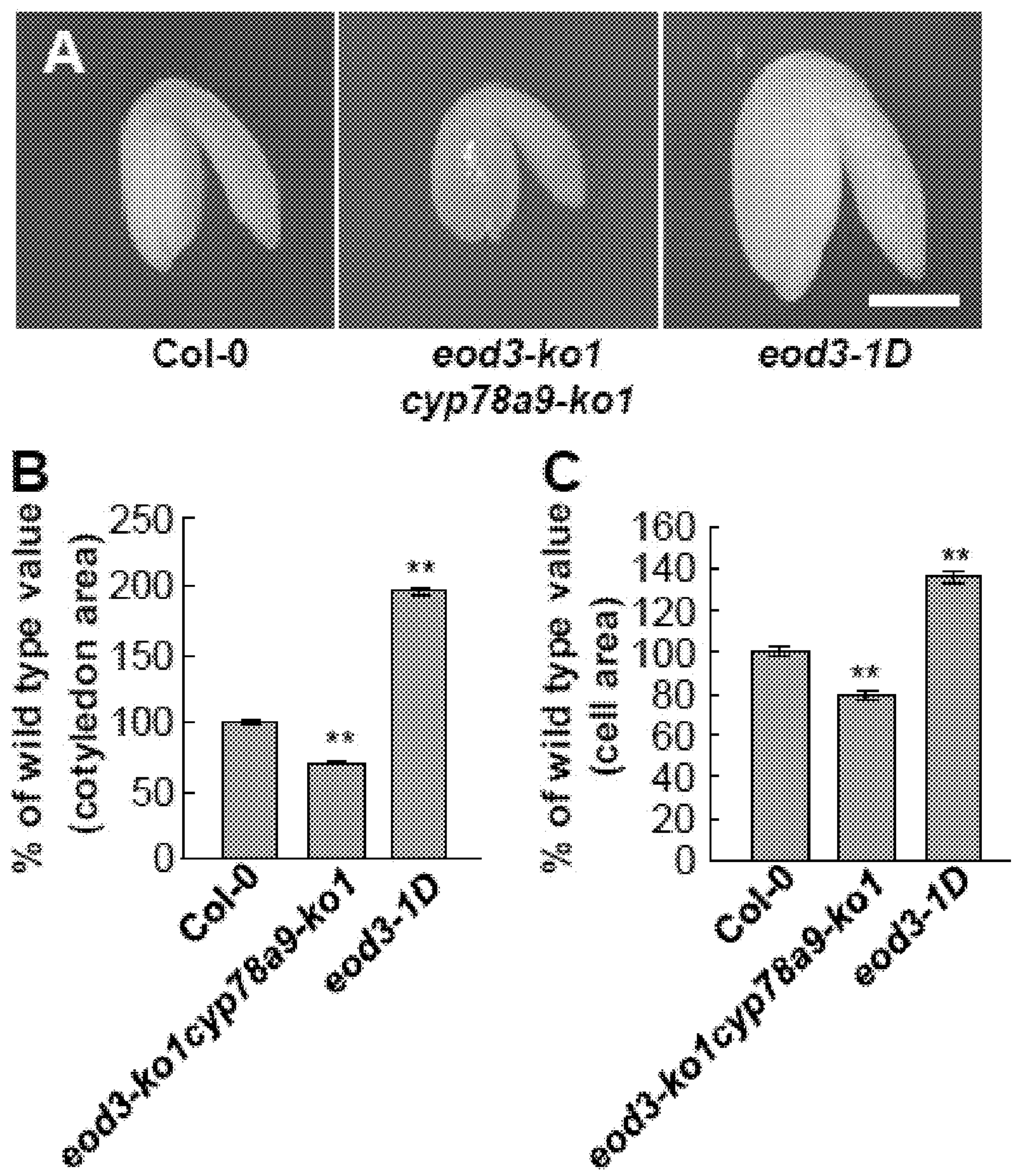
FIG. 7 shows cell size and cell number in cotyledons of mature wild-type, eod3-ko1 cyp78a9-ko1 and eod3-1D embryos. 7(A) shows mature embryos of wild type, eod3-ko1 cyp78a9-ko1 and eod3-1D. 7(B) shows cotyledon area of wild-type, eod3-ko1 cyp78a9-ko1 and eod3-1D embryos. 7(C) Average area of palisade cells in cotyledons of wild-type, eod3-ko1 cyp78a9-ko1 and eod3-1D embryos. Values (B and C) are given as mean±SE relative to the respective wild-type values, set at 100%. **, P<0.01 compared with the wild type (Student's t-test). Bar: A, 0.25 mm.

The size of the integument or seed coat is determined by cell proliferation and cell expansion. The cell number in the integuments of the mature ovule sets the growth potential of the seed coat after fertilization. For example, arf2 and da1-1 mutants had large ovules with more cells, resulting in large seeds (Schruff et al., 2006; Li et al., 2008), whereas klu mutants formed small ovules with less cells, leading to small seeds (Adamski et al., 2009). After fertilization, cells in integuments mainly undergo expansion. Our results indicate that eod3-ko1 cyp78a9-ko1 mutant formed normal-sized ovules, but smaller developing seeds as a result of the reduced cell expansion in the integuments after fertilization (FIG. 6). However, eod3-1D promoted both cell proliferation and cell elongation in the integuments of developing seeds, resulting in large volume of a seed cavity. Therefore, integument growth is driven by both cell proliferation and cell expansion; these two processes are assumed to be coordinated. In addition, our reciprocal cross experiments provide a demonstration of maternal sporophytic control of embryo growth (FIG. 5; FIG. 7; FIG. 14). The maternal integument or seed coat, which acts as a physical constraint on embryo and endosperm growth, may set an upper limit to final seed size.

The CYP78A Family Members have Overlapping and Distinct Functions in Seed Growth EOD3 encodes a cytochrome P450 CYP78A6, one of the CYP78A family members. The other CYP78A subfamily member genes have been isolated as growth regulators. Overexpression of CYP78A9, which is most closely related to EOD3/CYP78A6, induced large and seedless silique in *Arabidopsis* (Ito and Meyerowitz, 2000). To a certain extent, plants overexpressing EOD3/CYP78A6 and CYP78A9 exhibited similar growth phenotypes, such as large siliques and short stamens (FIGS. 2C and D) (Ito and Meyerowitz, 2000), indicating that these two genes might affect the same or related metabolic network. In line with this idea, our genetic analyses demonstrate that the cyp78a9-ko1 mutation synergistically enhanced the seed size phenotype of eod3-ko mutants (FIGS. 4C and F). This provides indication that EOD3 and CYP78A9 may have overlapping functions in seed size control.

Another CYP78A subfamily member KLU/CYP78A5 also affects seed size by promoting cell proliferation in the integuments of ovules (Adamski et al., 2009). klu mutants produced smaller seeds than wild type due to small ovules with less cells (Adamski et al., 2009). By contrast, eod3-ko1 cyp78a9-ko1 mutants did not significantly affect the size of ovules, but restricted cell expansion in the integuments of developing seeds. These findings provide indication that KLU may act in the cell proliferation phase at the early stages of integument development, and EOD3 mainly functions in the cell expansion phase at the later stages of integument growth.

EOD3 and CYP78A9 May Control Seed Growth in a Non-Cell-Autonomous Manner

Figure 12:
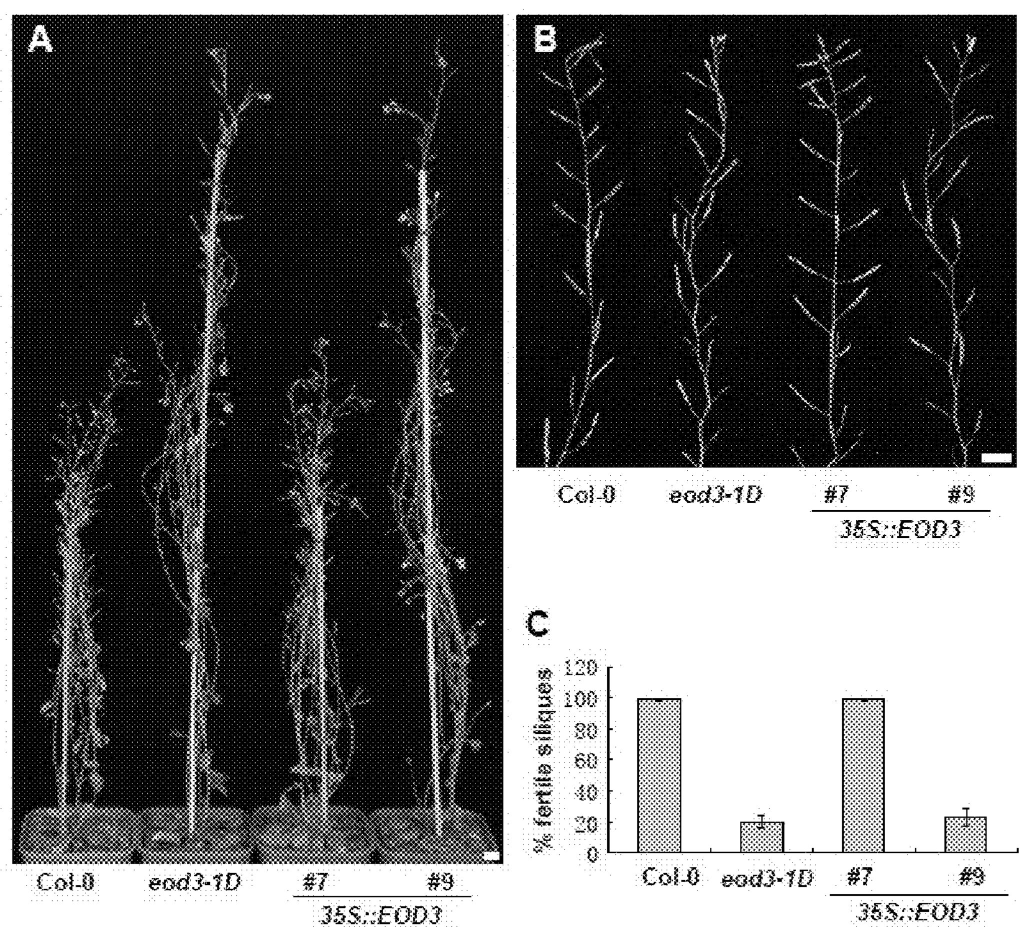
FIG. 12 shows phenotypes of wild-type, eod3-1D and 35S::EOD3 plants. 12A shows 56-d-old wild-type, eod3-1D, 35S::EOD3#7 and 35S::EOD3#9 plants. 12B shows primary inflorescence stems of wild-type, eod3-1D, 35S::EOD3#7 and 35S::EOD3#9 plants. 12C shows percent of fertile siliques on the primary inflorescence. Values (C) are given as mean±SE. Bars: A, B, 1 cm.

Another interesting feature of the CYP78A subfamily members is to generate mobile factors mediating organ growth (Miyoshi et al., 2004; Anastasiou et al., 2007). Rice PLA1/CYP78A11 affected cell division in the shoot apical meristem (SAM), but CYP78A11 expression was not detected in the shoot apical meristem, suggesting that CYP78A11 most likely acts through its non-cell-autonomous function (Miyoshi et al., 2004). *Arabidopsis* CYP78A5 has been proposed to be involved in generating a mobile signal distinct from the classical phytohormones (Anastasiou et al., 2007). However, mobile growth substances remain to be discovered. Interestingly, EOD3 and CYP78A9 were not detected in the maternal integuments of developing seeds (FIG. S7) (Ito and Meyerowitz, 2000), but eod3-ko, cyp78a9-ko and eod3-ko cyp78a9-ko mutants produced small seeds (FIGS. 4C and F). This suggests that EOD3 and CYP78A9 might control seed growth in a non-cell-autonomous manner, as proposed for other CYP78A subfamily members (Miyoshi et al., 2004; Anastasiou et al., 2007). However, EOD3 expression was detected in other organs, such as leaves and carpels (FIGS. 8B and F), providing indication that EOD3 might promote leaf and carpel growth in a cell-autonomous manner. Several *Arabidopsis* mutants with large organs also exhibited large seeds (Schruff et al., 2006; Li et al., 2008), suggesting a possible link between organ size and seed growth. By contrast, several other mutants with large organs produced normal-sized seeds (Szecsi et al., 2006; White, 2006), indicating that organ size is not always positively related to seed growth. 35S::EOD3#7 plants exhibited normal growth and fertility, but produced significantly larger seeds than wild type (FIGS. 3C and D; FIG. 12), providing indication that the effect of EOD3 on seed size might not be due to its effect on organ size. CYP78A9 has been suggested to be involved in producing an undiscovered plant growth substance (Ito and Meyerowitz, 2000). One of the functions of EOD3 might be production of a signal that promotes integument growth. Eventually, the elucidation of the biochemical function of these gene products may lead to the discovery of one or more new plant growth substances with use in control of seed size.

EOD3 Controls Seed Growth in *Oryza sativa*

The *Arabidopsis* EOD3 coding sequence was sub-cloned and overexpressed in *Oryza sativa*. The areas of the seeds from T0 transgenic *Oryza sativa* plants were then determined.

Figure 20:
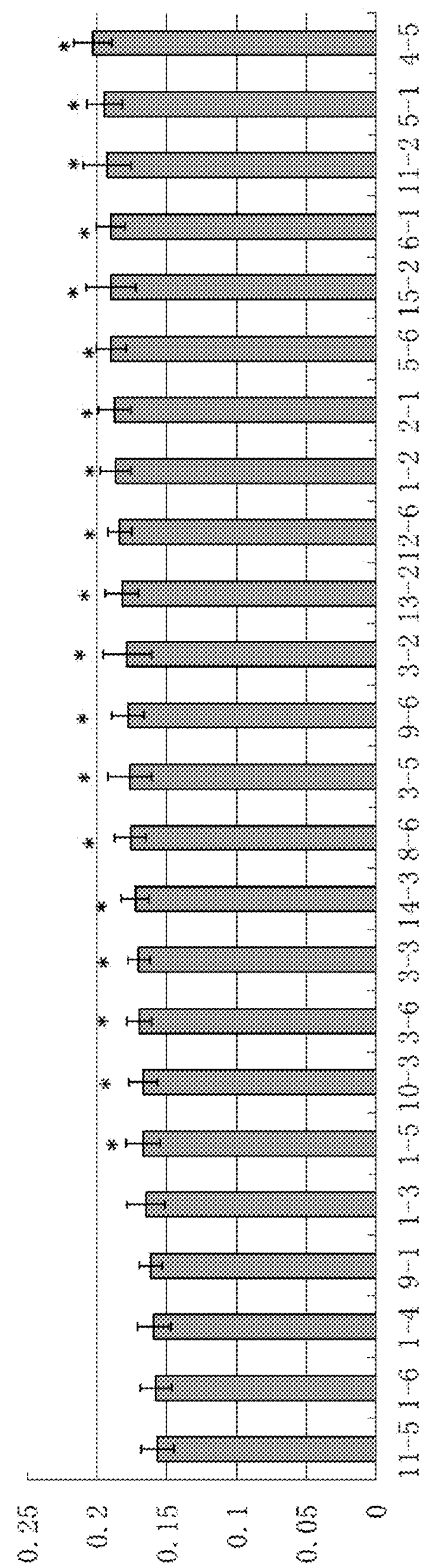
FIG. 20 shows seed size in T0 transgenic *Oryza sativa* overexpressing EOD3. * represents $p<0.01$ in t-test with the smallest seed line (11-5).

The transgenic rice plant lines (To) showed a range of different average seed sizes (FIG. 20), as expected from variations in insertion site, expression levels and other factors. However, statistically significant differences in seed size were found between a number of the To lines and the smallest seed line (11-5) (FIG. 20; P<0.01). These statistically significant differences show that that Eod3 overexpression increases seed size in rice.

REFERENCES

Adamski, N. M. et al. (2009) *Proc Natl Acad Sci USA,* 106, 20115-20120

Alonso-Blanco, C. et al (1999) *Proc Natl Acad Sci USA,* 96, 4710-4717

Anastasiou, E. et al (2007) *Dev Cell,* 13, 843-856.

Fan, C. et al (2006) *Theor Appl Genet,* 112, 1164-1171.

Fan, J. et al (2009) *Plant Physiol,* 150, 1750-1761.

Garcia, D. et al 2003) *Plant Physiol,* 131, 1661-1670.

Garcia, D. et al (2005) *Plant Cell,* 17, 52-60.

Gegas, V. C. et al (2010). *Plant Cell,* 22, 1046-1056.

Harper, J. L. et al (1970) *Annual Review of Ecology and Systematics,* 1, 327-356

Ito, T. et al (2000) *Plant Cell,* 12, 1541-1550.

Jofuku, K. D. et al (2005). *Proc Natl Acad Sci USA,* 102, 3117-3122.

Li, J. et al (2004). *Genetics,* 168, 2187-2195.

Li, Y. et al (2006). *Genome Res,* 16, 414-427.

Li, Y., Zheng et al (2008) *Genes Dev,* 22, 1331-1336.

Li, Y. et al (2003). *Plant Cell,* 15, 2020-2031.

Liu, Y. G. et al (1995) *Plant J,* 8, 457-463.

Lopes, M. A et al (1993). *Plant Cell,* 5, 1383-1399.

Luo, M. et al (2005) *Proc Natl Acad Sci USA,* 102, 17531-17536.

Miyoshi, K. et al (2004) *Proc Natl Acad Sci USA,* 101, 875-880.

Moles, A. T. et al (2005) *Science,* 307, 576-580.

Ohto, M. A. et al (2005) *Proc Natl Acad Sci USA,* 102, 3123-3128.

Ohto, M. A. et al (2009) *Sex Plant Reprod,* 22, 277-289.

Orsi, C. H. et al (2009) *PLoS Genet,* 5, e1000347.

Schruff, M. C. et al (2006) 133, 251-261.

Scott, R. J. et al (1998). *Development,* 125, 3329-3341.

Shomura, A. et al (2008) *Nat Genet,* 40, 1023-1028.

Song, X. J. et al (2007) *Nat Genet,* 39, 623-630.

Szecsi, J. et al (2006) *Embo J,* 25, 3912-3920.

Wang, A. et al (2010) *Plant J,* 64, 670-679.

Weng, J. et al (2008) *Cell Res,* 18, 1199-1209.

Westoby, M. et al (2002) *Annual Review of Ecology and Systematics,* 33, 125-159.

White, D. W. (2006) *Proc Natl Acad Sci USA,* 103, 13238-13243.

Xiao, W. et al (2006) *Plant Physiol,* 142, 1160-1168.

Zhou, Y. et al. (2009) *Plant Cell,* 21, 106-117.

Zondlo, S. C. et al (1999) *Plant J,* 19, 259-268.

Phenotypes of Wild-Type, eod3-ko1, cyp78a9-ko1, eod3-ko1 cyp78a9-ko1 and eod3-1D plants

TABLE 1

| | Col-0 | eod3-ko1 | cyp78a9-ko1 | eod3-ko1cyp78a9-ko1 | eod3-1D |
|---|---|---|---|---|---|
| Petal area ($mm^2$) | 1.99 ± 0.11 | 1.99 ± 0.09 | 1.95 ± 0.10 | 1.86 ± 0.09** | 2.48 ± 0.16** |
| Petal length (mm) | 3.08 ± 0.10 | 3.08 ± 0.09 | 3.05 ± 0.12 | 3.02 ± 0.08** | 3.32 ± 0.11** |
| Petal width (mm) | 1.03 ± 0.04 | 1.03 ± 0.04 | 1.02 ± 0.04 | 1.01 ± 0.03** | 1.18 ± 0.05** |
| Leaf area ($cm^2$) | 1.02 ± 0.07 | 1.01 ± 0.07 | 0.99 ± 0.08 | 0.91 ± 0.08** | 1.34 ± 0.11** |
| Leaf length (cm) | 1.29 ± 0.05 | 1.28 ± 0.04 | 1.27 ± 0.05 | 1.24 ± 0.07* | 1.40 ± 0.09** |
| Leaf width (cm) | 1.01 ± 0.05 | 1.00 ± 0.04 | 0.99 ± 0.03 | 0.92 ± 0.04** | 1.16 ± 0.05** |
| Plant height (cm) | 36.8 ± 1.9 | 36.7 ± 1.7 | 36.6 ± 1.5 | 33.5 ± 1.8** | 64.8 ± 3.0** |
| Stem thickness (mm) | 0.88 ± 0.03 | 0.87 ± 0.03 | 0.87 ± 0.02 | 0.87 ± 0.04 | 0.99 ± 0.03** |
| Number of RI | 3.0 ± 0.7 | 3.0 ± 0.6 | 2.9 ± 0.6 | 2.9 ± 0.6 | 3.0 ± 0.6 |
| Number of RII | 4.0 ± 1.3 | 4.0 ± 0.9 | 3.9 ± 1.3 | 3.9 ± 1.1 | 4.0 ± 0.9 |
| Number of CI | 2.5 ± 0.5 | 2.5 ± 0.5 | 2.4 ± 0.5 | 2.4 ± 0.5 | 2.5 ± 0.5 |
| Number of CII | 5.0 ± 0.8 | 5.0 ± 1.0 | 4.9 ± 1.0 | 4.9 ± 1.1 | 5.0 ± 0.8 |
| Leaf number | 12.7 ± 0.8 | 12.6 ± 0.7 | 12.6 ± 0.7 | 12.6 ± 0.5 | 12.8 ± 0.7 |
| Elongated siliques | 328 ± 28 | 326 ± 32 | 324 ± 34 | 269 ± 22** | 87 ± 18** |
| % fertile siliques | 99.1 ± 1.6 | 99.0 ± 1.5 | 98.9 ± 1.7 | 99.0 ± 1.8 | 21.1 ± 11.8** |

TABLE 1-continued

| | Col-0 | eod3-ko1 | cyp78a9-ko1 | eod3-ko1cyp78a9-ko1 | eod3-1D |
|---|---|---|---|---|---|
| Ovule number per silique | 53.9 ± 2.3 | 53.7 ± 2.6 | 53.4 ± 2.3 | 52.9 ± 2.1 | 53.1 ± 2.9 |
| Silique fertility | 98.4 ± 4.2% | 98.2 ± 4.8% | 98.2 ± 4.3% | 98.1 ± 3.9% | 51.8 ± 26.0%** |

Number of primary rosette branches (RI), second rosette branches (RII), primary cauline branches (CI), and second cauline branches (CII) were counted at 30 d after bolting. Primary rosette branches (RI) are axillary branches from rosette leaves, and second rosette branches (RII) are axillary branches from RI. Similarly, primary cauline branches (CI) are axillary branches from cauline leaves, and second cauline branches (CII) are axillary branches from CI. Opened flowers on the primary inflorescence were used to investigate ovules per silique. The elongated siliques on the primary inflorescence were used to investigate fertility. All values are given as mean ± SD.

**$P < 0.01$ and

*$P < 0.05$ compared with the wild type (Student's t-test).

Developmental Stages of Embryogenesis

TABLE 2

| DAP | Genotype | Quadrant or octant | Dermatogen | Globular | Transition | Heart | Torpedo | Bent cotyledon | The stage of the fully filled seed cavity |
|---|---|---|---|---|---|---|---|---|---|
| 2 | Col-0 | 9 | 23 | 67 | | | | | |
| | e3a9 | 8 | 21 | 65 | | | | | |
| | eod3-1D | 14 | 29 | 52 | | | | | |
| 4 | Col-0 | | | | 5 | 36 | 72 | | |
| | e3a9 | | | | 9 | 39 | 62 | | |
| | eod3-1D | | | 17 | 28 | 40 | 13 | | |
| 6 | Col-0 | | | | | | 41 | 88 | |
| | e3a9 | | | | | | 29 | 97 | |
| | eod3-1D | | | | | | 34 | 86 | |
| 8 | Col-0 | | | | | | 7 | 70 | |
| | e3a9 | | | | | | 4 | 72 | |
| | eod3-1D | | | | | | 18 | 80 | |
| 10 | Col-0 | | | | | | | 80 | 28 |
| | e3a9 | | | | | | | 77 | 13 |
| | eod3-1D | | | | | | | 98 | |
| 12 | Col-0 | | | | | | | 10 | 90 |
| | e3a9 | | | | | | | 17 | 70 |
| | eod3-1D | | | | | | | 89 | |
| 14 | Col-0 | | | | | | | | 96 |
| | e3a9 | | | | | | | | 124 |
| | eod3-1D | | | | | | | 26 | 68 |

Siliques from the wild-type (Col-0), eod3-ko1cyp78a9-ko1 (e3a9) and eod3-1D plants were dissected. The number of embryos at each developmental stage was recorded.

TABLE 3

| Name | Primers |
|---|---|
| | Primers for verifying T-DNA |
| eod3-1D-LP | GGTCTAAGATTTCTCTCGTGTC (SEQ ID NO: 98) |
| eod3-1D-RP | CGTACGTCTTCTATTACTCCAC (SEQ ID NO: 99) |
| CS833552LP | AACTCCAAAGGATCAACCCAC (SEQ ID NO: 100) |
| CS833552RP | CCGGTTAAAGAATCGGCTTAC (SEQ ID NO: 101) |
| CS806696LP | GACTTGCAAAGATCGTTCACC (SEQ ID NO: 102) |
| CS806696RP | ACTCAATGTGACGTGTTGTGG (SEQ ID NO: 103) |
| SALK121278LP | TTTGATCGAGTGGATTCTTGC (SEQ ID NO: 104) |
| SALK121278RP | ATATTTGCTTGTAATCGGGGC (SEQ ID NO: 105) |
| SALK148838LP(TTG2) | TAAAACCAAACGACACCGTTC (SEQ ID NO: 106) |
| SALK148838RP(TTG2) | TCCAAGTTTGTTGACGATTCC (SEQ ID NO: 107) |
| OJF22 | CGAGTATCAATGGAAACTTAACCG (SEQ ID NO: 108) |
| OJF23 | AACGGAGAGTGGCTTGAGAT (SEQ ID NO: 109) |

TABLE 3-continued

| Name | Primers |
|---|---|
| OJF24 | TGGCCCTTATGGTTTCTGCA (SEQ ID NO: 110) |
| AD1 | NTCGA(G/C)T(A/T)T(G/C)G(A/T)GTT (SEQ ID NO: 111) |
| SALK_LBa1 | TGGTTCACGTAGTGGGCCATCG (SEQ ID NO: 112) |
| SAIL_LB2 | GCTTCCTATTATATCTTCCCAAATTACCAATACA (SEQ ID NO: 113) |
| Primers for constructs | |
| EOD3CDS-F | CTGCAGATGGCTACGAAACTCGAAAGCTCC (SEQ ID NO: 114) |
| EOD3CDS-R | CTGCAGTTAACTGCGCCTACGGCGCAATTT (SEQ ID NO: 115) |
| EOD3PROM-F | GAGCTCTGTCTCGTGGATAAGTAG (SEQ ID NO: 116) |
| EOD3PROM-R | CCATGGGGCGGATCAAAGCAAAGTAAG (SEQ ID NO: 117) |
| Primers for RT-PCR | |
| EOD3RT-F | ACCAACCTTGCCTTCTCC (SEQ ID NO: 118) |
| EOD3RT-R | CGTCTCGGCTCTTCTGATT (SEQ ID NO: 119) |
| AT2G46670RT-F | ACAACGAGCAGCAACCA (SEQ ID NO: 120) |
| AT2G46670RT-R | TCTTCAACCGGAACTTCAT (SEQ ID NO: 121) |
| ACTIN7-F | ATCCTTCCTGATATCGAC (SEQ ID NO: 122) |
| ACTIN7-R | GAGAAGATGACTCAGATC (SEQ ID NO: 123) |
| Primers for quantitative real-time RT-PCR | |
| EOD3QRT-F | CCGGTTAAAGAATCGGCTTA (SEQ ID NO: 124) |
| EOD3QRT-R | TTGAGATCACTCGTCGTTGC (SEQ ID NO: 125) |
| ACTIN2-F | GAAATCACAGCACTTGCACC (SEQ ID NO: 126) |
| ACTIN2-R | AAGCCTTTGATCTTGAGAGC (SEQ ID NO: 127) |
| Primers for in situ hybridization | |
| E0D3INSITU-F | AAAGAAGCTCATATGAGAATTA (SEQ ID NO: 128) |
| E0D3INSITU-R | TGGTGTAAATATAAATTGAAACT (SEQ ID NO: 129) |
| CYP78A9INSITU-F | TTAGTGTATGATAAGGCTAAGGCT (SEQ ID NO: 130) |
| CYP78A9INSITU-R | GTATTAACTTTTCTTTGTGACA (SEQ ID NO: 131) |

The invention claimed is:

1. A method of increasing seed size in a plant comprising: introducing into at least one plant or plant cell the nucleic acid molecule of SEQ ID NO: 1 or a nucleic acid molecule encoding a polypeptide having at least 95% sequence identity to SEQ ID NO: 42, wherein the nucleic acid molecule encodes a CYP78A6 polypeptide, wherein said nucleic acid molecule is operably linked to a heterologous promoter, and selecting a plant produced from said at least one plant or said plant cell having increased seed size compared to a plant not comprising said nucleic acid molecule.

2. A method of producing a plant with an increased seed size comprising:

introducing into at least one plant cell the nucleic acid molecule of SEQ ID NO: 1 or a nucleic acid molecule encoding a polypeptide having 95% sequence identity to SEQ ID NO: 42, wherein the nucleic acid molecule encodes a CYP78A6 polypeptide, wherein said nucleic acid molecule is operably linked to a heterologous promoter, wherein the introducing is by means of transformation, regenerating at least one plant from one or more transformed cells and selecting at least one plant having increased seed size compared to a plant not comprising said nucleic acid molecule.

3. The method according to claim 1, wherein the CYP78A6 polypeptide comprises the amino acid sequence encoded by SEQ ID NO: 1.

4. The method of claim 1 further comprising sexually or asexually propagating or growing off-spring or descendants of said plant and selecting any of said off-spring or descendants comprising said nucleic acid molecule.

5. The method according to claim 1 wherein the plant is a higher plant.

6. The method according to claim 1, wherein the plant is an agricultural plant selected from the group consisting of *Lithospermum erythrorhizon, Taxus* spp, tobacco, cucurbits, carrot, vegetable *brassica*, melons, capsicums, grape vines, lettuce, strawberry, oilseed *brassica*, sugar beet, wheat, barley, maize, rice, soyabeans, peas, sorghum, sunflower, tomato, potato, pepper, *chrysanthemum*, carnation, linseed, hemp and rye.

7. The method according to claim 1 wherein said plant is further selected to exhibit one or more of increased flower size, increased leaf size, increased stem thickness, and increased height relative to control plants.

8. The method of claim 1, wherein said nucleic acid molecule comprises SEQ ID NO: 1.

9. The method according to claim 1, wherein said nucleic acid molecule comprises a sequence having at least 95% identity to SEQ ID NO: 1.

* * * * *